United States Patent
Nakanishi et al.

(10) Patent No.: US 10,391,081 B2
(45) Date of Patent: Aug. 27, 2019

(54) FGFR GATEKEEPER MUTANT GENE AND DRUG TARGETING SAME

(71) Applicant: CHUGAI SEIYAKU KABUSHIKI KAISHA, Tokyo (JP)

(72) Inventors: Yoshito Nakanishi, Kanagawa (JP); Nukinori Akiyama, Kanagawa (JP); Kenji Morikami, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/108,014

(22) PCT Filed: Dec. 26, 2014

(86) PCT No.: PCT/JP2014/084521
§ 371 (c)(1),
(2) Date: Jun. 24, 2016

(87) PCT Pub. No.: WO2015/099127
PCT Pub. Date: Jul. 2, 2015

(65) Prior Publication Data
US 2016/0317499 A1 Nov. 3, 2016

(30) Foreign Application Priority Data

Dec. 27, 2013 (JP) .................................. 2013-273053

(51) Int. Cl.
| | |
|---|---|
| A61K 31/4184 | (2006.01) |
| A61K 31/437 | (2006.01) |
| C12Q 1/6804 | (2018.01) |
| C07K 16/28 | (2006.01) |
| C12N 9/12 | (2006.01) |
| C12Q 1/6886 | (2018.01) |
| G01N 33/574 | (2006.01) |
| C07K 14/71 | (2006.01) |
| C12Q 1/68 | (2018.01) |
| C12N 15/63 | (2006.01) |

(52) U.S. Cl.
CPC .......... *A61K 31/4184* (2013.01); *C07K 14/71* (2013.01); *C07K 16/2863* (2013.01); *C12N 9/12* (2013.01); *C12N 15/63* (2013.01); *C12Q 1/68* (2013.01); *C12Q 1/6886* (2013.01); *C12Y 207/10001* (2013.01); *G01N 33/574* (2013.01); *G01N 33/57492* (2013.01); *C12Q 2600/106* (2013.01); *C12Q 2600/156* (2013.01); *C12Q 2600/158* (2013.01); *G01N 2333/91205* (2013.01)

(58) Field of Classification Search
CPC . A61K 31/4184; A61K 31/437; C12Q 1/6804
See application file for complete search history.

(56) References Cited

U.S. PATENT DOCUMENTS

| | | |
|---|---|---|
| 6,316,466 B1 | 11/2001 | Goldstein et al. |
| 8,829,199 B2 | 9/2014 | Taka et al. |
| 9,102,692 B2 | 8/2015 | Taka et al. |
| 9,814,776 B2 | 11/2017 | Nihira et al. |
| 2005/0049288 A1 | 3/2005 | Fryszman et al. |
| 2009/0197866 A1 | 8/2009 | Cherrier et al. |
| 2012/0208811 A1 | 8/2012 | Taka et al. |
| 2014/0315856 A1 | 10/2014 | Taka et al. |
| 2015/0238607 A1 | 8/2015 | Nihira et al. |
| 2015/0307945 A1 | 10/2015 | Nakanishi et al. |
| 2016/0317499 A1 | 11/2016 | Nakanishi et al. |
| 2018/0362509 A1 | 12/2018 | Ebiike et al. |

FOREIGN PATENT DOCUMENTS

| | | |
|---|---|---|
| CN | 102099335 | 6/2011 |
| EP | 1 218 346 | 7/2002 |
| EP | 1 641 764 | 4/2006 |
| EP | 2 657 233 | 10/2013 |
| EP | 2902029 | 8/2015 |
| EP | 2471786 | 11/2015 |
| FR | 2831537 | 5/2003 |
| JP | 2002-513784 | 5/2002 |
| JP | 2003-50945 | 3/2003 |
| JP | 2007-521278 | 8/2007 |
| JP | 2011-528686 | 11/2011 |
| JP | 2012-180344 | 9/2012 |
| JP | 2013-144679 | 7/2013 |
| WO | WO 94/13643 | 6/1994 |
| WO | WO 99/57101 | 11/1999 |

(Continued)

OTHER PUBLICATIONS

Cappellen et al. Nature Genetics, 1999, vol. 23, pp. 18-20.*
Akiyama et al., The Japanese Association for Molecular Target Therapy of Cancer Gakujutsu Shukai Program/Shorokushu, May 2014, vol. 18th, p. 85 (with English translation).
Byron et al., "The N550K/H mutations in FGFR2 confer differential resistance to PD173074, dovitinib, and ponatinib ATP-competitive inhibitors," Neoplasia, 15(8):975-88 (Aug. 2013).

(Continued)

*Primary Examiner* — Samira J Jean-Louis
(74) *Attorney, Agent, or Firm* — Fish & Richardson P.C.

(57) ABSTRACT

The present inventors successfully identified novel gatekeeper mutations for FGFR. Further, they discovered that mutant FGFR having the mutations demonstrate resistance to known FGFR inhibitors such as AZD4547, and at the same time demonstrate sensitivity to specific compounds. Mutant polypeptides having the mutations may be used as biomarkers in cancer treatment by FGFR inhibitors to prevent the development of side effects in therapy by conventional FGFR inhibitors, and to control the therapeutic mode for receiving the best therapeutic effect, thus making individualized treatment possible.

12 Claims, 5 Drawing Sheets

Specification includes a Sequence Listing.

(56) References Cited

FOREIGN PATENT DOCUMENTS

| WO | WO 01/12600 | 2/2001 |
|---|---|---|
| WO | WO 01/21591 | 3/2001 |
| WO | WO 03/035065 | 5/2003 |
| WO | WO 2004/096792 | 11/2004 |
| WO | WO 2005/009973 | 2/2005 |
| WO | WO 2006/134318 | 12/2006 |
| WO | WO 2007/077435 | 7/2007 |
| WO | WO 2010/010017 | 1/2010 |
| WO | WO 2011/016528 | 2/2011 |
| WO | WO 2012/067831 | 5/2012 |
| WO | WO 2014/050781 | 4/2014 |
| WO | WO 2014/051022 | 4/2014 |
| WO | WO 2015/016295 | 2/2015 |
| WO | WO 2015/086635 | 6/2015 |
| WO | WO 2015/086636 | 6/2015 |
| WO | WO 2015/086642 | 6/2015 |
| WO | WO 2015/099127 | 7/2015 |
| WO | WO 2016/204261 | 12/2016 |
| WO | WO 2017/017516 | 2/2017 |
| WO | WO 2017/028816 | 2/2017 |

OTHER PUBLICATIONS

Ebiike et al., American Association for Cancer Research Annual Meeting Abstract 2014, Abstract No. 2533.
Gavine et al., "AZD4547: an orally bioavailable, potent, and selective inhibitor of the fibroblast growth factor receptor tyrosine kinase family," Cancer Res., 72(8):2045-56 (Apr. 2012).
Guagnano et al., "Discovery of 3-(2,6-dichloro-3,5-dimethoxyphenyl)-1-{6-[4-(4-ethyl-piperazin-1-yl)-phenylamino]-pyrimidin-4-yl}-1-methyl-urea (NVP-BGJ398), a potent and selective inhibitor of the fibroblast growth factor receptor family of receptor tyrosine kinase," J Med Chem., 54(20:7066-83 (Oct. 2011).
Nakanishi et al., "The fibroblast growth factor receptor genetic status as a potential predictor of the sensitivity to CH5183284/Debio 1347, a novel selective FGFR inhibitor," Mol Cancer Ther., Nov. 2014;13(11):2547-58. doi: 10.1158/1535-7163.MCT-14-0248. Epub Aug. 28, 2014.
Sakamoto, "ALK Inhibitor," Nihon Yakurigaku Zasshi, 142(1):48-50 (Jul. 2013) (with English translation).
Tan et al., "Development of covalent inhibitors that can overcome resistance to first-generation FGFR kinase inhibitors," Proc Natl Acad Sci USA. Nov. 11, 2014:111(45):E4869-77. doi:10.1073/pnas.1403438111. Epub Oct. 27, 2014.
Byron et al., "Inhibition of activated fibroblast growth factor receptor 2 in endometrial cancer cells induces cell death despite PTEN abrogation," Cancer Res., 68(17):6902-7 (2008).
Cappellen et al., "Frequent activating mutations of FGFR3 in human bladder and cervix carcinomas," Nat. Genet., 23(1):18-20 (1999).
Cheng et al., "Novel agents for the treatment of pancreatic adenocarcinoma. Highlights from the "2011 ASCO Annual Meeting," Chicago, IL, USA; Jun. 3-7, 2011," JOP, 12(4):334-338.
Elbauomy Elsheikh et al., "FGFR1 amplification in breast carcinomas: a chromogenic in situ hybridisation analysis," Breast Cancer Res., 9(2):R23 (2007).
Eswarakumar et al., "Cellular signaling by fibroblast growth factor receptors," Cytokine Growth Factor Rev., 16(2):139-49 (2005).
Fonseca et al., "Clinical and biologic implications of recurrent genomic aberrations in myeloma," Blood., 101(11):4569-75 (2003).
Golub et al., "Molecular classification of cancer: class discovery and class prediction by gene expression monitoring," Science, 286:531-537 (1999).
Heiskanen et al., "CGH, cDNA and tissue microarray analyses implicate FGFR2 amplification in a small subset of breast tumors," Anal. Cell Pathol., 22(4):229-34 (2001).

MacDonald et al., "The 8p11 myeloproliferative syndrome: a distinct clinical entity caused by constitutive activation of FGFR1," Acta. Haematol., 107(2):101-7 (2002).
Peng et al., "Alterations of chromosomal copy number during progression of diffuse-type gastric carcinomas: metaphase- and array-based comparative genomic hybridization analyses of multiple samples from individual," J. Pathol., 201(3):439-50 (2003).
Rand et al., "Sequence survey of receptor tyrosine kinases reveals mutations in glioblastomas," Proc. Natl. Acad. Sci. USA, 102(40):14344-9 (2005).
Wang et al., "Antisense targeting of basic fibroblast growth factor and fibroblast growth factor receptor-1 in human melanomas blocks intratumoral angiogenesis and tumor growth," Nat. Med., 3(8):887-93 (1997).
Zhao et al., "Homozygous deletions and chromosome amplifications in human lung carcinomas revealed by single nucleotide polymorphism array analysis," Cancer Res., 65(13):5561-70 (2005).
International Search Report for App. Ser. No. PCT/JP2010/063315, dated Sep. 7, 2010, 8 pages.
International Preliminary Report on Patentability for App. Ser. No. PCT/JP2010/063315, dated Mar. 13, 2012, 9 pages.
Supplementary European Search Report for App. Ser. No. EP 10 80 6527, dated Feb. 15, 2013, 3 pages.
Search Report and Written Opinion issued in corresponding Singapore App. Ser. No. 201200851-2, dated Apr. 17, 2013, 19 pages.
International Search Report for App. Ser. No. PCT/JP2014/084521, dated Feb. 24, 2015, 4 pages.
International Preliminary Report on Patentability for App. Ser. No. PCT/JP2014/084521, dated Jun. 28, 2016, 10 pages.
Luqmani et al., "Expression of basic fibroblast growth factor, FGFR1 and FGFR2 in normal and malignant human breast, and comparison with other normal tissues," Br. J. Cancer, Aug. 1992:66(2):273-80.
Benati et al., "Src Family Kinases as Potential Therapeutic Targets for Malignancies and Immunological Disorders," Current Medicinal Chemistry, 2008:15(12):1154-65.
U.S. Appl. No. 15/736,821, Ebiike et al.
Ebiike et al., "Discovery of [5-Amino-1-(2-methyl-3H-benzimidazol-5-yl)pyrazol-4-yl]-(1H-indol-2-yl)methanone (CHS 183284/Debio 1347), An Orally Available and Selective Fibroblast Growth Factor Receptor (FGFR) Inhibitor," Journal of Medicinal Chemistry, Dec. 8, 2016:59(23):10586-10600. Epub Nov. 29, 2016.
Gozgit et al., "Ponatinib (AP24534), a Multitargeted Pan-FGFR Inhibitor with Activity in Multiple FGFR-Amplified or Mutated Cancer Models," Molecular Cancer Therapeutics, 11(3):690-699, Mar. 2012.
Puls et al., "Current Status of Src Inhibitors in Solid Tumor Malignancies," Oncologist, 2011:16(5):566-78. doi:10.1634/theoncologist. Apr. 8, 2010. Epub Apr. 26, 2011.
Yeatman et al., "A Renaissance for SRC," Nature Reviews Cancer, Jun. 2004:4(6):470-80.
International Search Report for App. Ser. No. PCT/JP2016/068039, dated Sep. 13, 2016, 3 pages.
International Preliminary Report on Patentability for App. Ser. No. PCT/JP2016/068039, dated Dec. 28, 2016, 8 pages.
Goyal et al, "Polyclonal Secondary FGFR2 Mutations Drive Acquired Resistance to FGFR Inhibition in Patients with FGFR2 Fusion—Positive Cholangiocarcinoma," Cancer Discov, Mar. 2017, 7(3):252-263. doi: 10.1158/2159-8290.CD-16-1000. Epub Dec. 29, 2016.
USPTO Non-Final Office Action in U.S. Appl. No. 14/297,790 dated Sep. 12, 2014, 60 pages.
U.S. Appl. No. 15/736,821, Ebiike et al., filed Dec. 15, 2017.
Getlik et al., Hybrid Compound Design to Overcome the Gatekeeper T338M Mutation in cSrc, J Med Chem, Jul. 9, 2009, 52(13):3915-26. doi: 10.1021/jm9002928.

* cited by examiner

```
SEQUENCE LISTING

<160> NUMBER OF SEQ ID NOS: 54

<210> SEQ ID NO 1
<211> LENGTH: 821
<212> TYPE: PRT
<213> ORGANISM: Homo sapiens

<400> SEQUENCE: 1

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175
```

```
Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
            340                 345                 350

His Ser Ala Trp Leu Thr Val Leu Pro Ala Pro Gly Arg Glu Lys Glu
        355                 360                 365

Ile Thr Ala Ser Pro Asp Tyr Leu Glu Ile Ala Ile Tyr Cys Ile Gly
    370                 375                 380

Val Phe Leu Ile Ala Cys Met Val Val Thr Val Ile Leu Cys Arg Met
385                 390                 395                 400

Lys Asn Thr Thr Lys Lys Pro Asp Phe Ser Ser Gln Pro Ala Val His
                405                 410                 415

Lys Leu Thr Lys Arg Ile Pro Leu Arg Arg Gln Val Thr Val Ser Ala
            420                 425                 430

Glu Ser Ser Ser Ser Met Asn Ser Asn Thr Pro Leu Val Arg Ile Thr
        435                 440                 445

Thr Arg Leu Ser Ser Thr Ala Asp Thr Pro Met Leu Ala Gly Val Ser
    450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
                485                 490                 495

Met Ala Glu Ala Val Gly Ile Asp Lys Asp Lys Pro Lys Glu Ala Val
            500                 505                 510

Thr Val Ala Val Lys Met Leu Lys Asp Asp Ala Thr Glu Lys Asp Leu
        515                 520                 525

Ser Asp Leu Val Ser Glu Met Glu Met Met Lys Met Ile Gly Lys His
    530                 535                 540

Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
                565                 570                 575

Arg Ala Arg Arg Pro Pro Gly Met Glu Tyr Ser Tyr Asp Ile Asn Arg
            580                 585                 590
```

Val Pro Glu Glu Gln Met Thr Phe Lys Asp Leu Val Ser Cys Thr Tyr
            595                 600                 605

Gln Leu Ala Arg Gly Met Glu Tyr Leu Ala Ser Gln Lys Cys Ile His
        610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
            660                 665                 670

Glu Ala Leu Phe Asp Arg Val Tyr Thr His Gln Ser Asp Val Trp Ser
        675                 680                 685

Phe Gly Val Leu Met Trp Glu Ile Phe Thr Leu Gly Gly Ser Pro Tyr
690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
                725                 730                 735

Arg Asp Cys Trp His Ala Val Pro Ser Gln Arg Pro Thr Phe Lys Gln
            740                 745                 750

Leu Val Glu Asp Leu Asp Arg Ile Leu Thr Leu Thr Thr Asn Glu Glu
        755                 760                 765

Tyr Leu Asp Leu Ser Gln Pro Leu Glu Gln Tyr Ser Pro Ser Tyr Pro
        770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
            820

<210> SEQ ID NO 2
<211> LENGTH: 822
<212> TYPE: PRT
<213> ORGANISM: Homo sapiens

<400> SEQUENCE: 2

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

-continued

```
Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
            165                 170                 175

Phe Arg Cys Pro Ala Gly Gly Asn Pro Met Pro Thr Met Arg Trp Leu
        180                 185                 190

Lys Asn Gly Lys Glu Phe Lys Gln Glu His Arg Ile Gly Gly Tyr Lys
    195                 200                 205

Val Arg Asn Gln His Trp Ser Leu Ile Met Glu Ser Val Val Pro Ser
210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
            245                 250                 255

Ile Leu Gln Ala Gly Leu Pro Ala Asn Ala Ser Thr Val Val Gly Gly
        260                 265                 270

Asp Val Glu Phe Val Cys Lys Val Tyr Ser Asp Ala Gln Pro His Ile
    275                 280                 285

Gln Trp Ile Lys His Val Glu Lys Asn Gly Ser Lys Tyr Gly Pro Asp
290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
            325                 330                 335

Glu Tyr Ile Cys Lys Val Ser Asn Tyr Ile Gly Gln Ala Asn Gln Ser
        340                 345                 350

Ala Trp Leu Thr Val Leu Pro Lys Gln Gln Ala Pro Gly Arg Glu Lys
    355                 360                 365

Glu Ile Thr Ala Ser Pro Asp Tyr Leu Glu Ile Ala Ile Tyr Cys Ile
370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
            405                 410                 415

His Lys Leu Thr Lys Arg Ile Pro Leu Arg Arg Gln Val Thr Val Ser
        420                 425                 430

Ala Glu Ser Ser Ser Ser Met Asn Ser Asn Thr Pro Leu Val Arg Ile
    435                 440                 445

Thr Thr Arg Leu Ser Ser Thr Ala Asp Thr Pro Met Leu Ala Gly Val
450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
            485                 490                 495

Val Met Ala Glu Ala Val Gly Ile Asp Lys Asp Lys Pro Lys Glu Ala
        500                 505                 510

Val Thr Val Ala Val Lys Met Leu Lys Asp Asp Ala Thr Glu Lys Asp
    515                 520                 525

Leu Ser Asp Leu Val Ser Glu Met Glu Met Met Lys Met Ile Gly Lys
530                 535                 540

His Lys Asn Ile Ile Asn Leu Leu Gly Ala Cys Thr Gln Asp Gly Pro
545                 550                 555                 560
```

```
Leu Tyr Val Ile Val Glu Tyr Ala Ser Lys Gly Asn Leu Arg Glu Tyr
                565                 570                 575
Leu Arg Ala Arg Arg Pro Pro Gly Met Glu Tyr Ser Tyr Asp Ile Asn
            580                 585                 590
Arg Val Pro Glu Glu Gln Met Thr Phe Lys Asp Leu Val Ser Cys Thr
        595                 600                 605
Tyr Gln Leu Ala Arg Gly Met Glu Tyr Leu Ala Ser Gln Lys Cys Ile
    610                 615                 620
His Arg Asp Leu Ala Ala Arg Asn Val Leu Val Thr Glu Asn Asn Val
625                 630                 635                 640
Met Lys Ile Ala Asp Phe Gly Leu Ala Arg Asp Ile Asn Asn Ile Asp
                645                 650                 655
Tyr Tyr Lys Lys Thr Thr Asn Gly Arg Leu Pro Val Lys Trp Met Ala
            660                 665                 670
Pro Glu Ala Leu Phe Asp Arg Val Tyr Thr His Gln Ser Asp Val Trp
        675                 680                 685
Ser Phe Gly Val Leu Met Trp Glu Ile Phe Thr Leu Gly Gly Ser Pro
    690                 695                 700
Tyr Pro Gly Ile Pro Val Glu Glu Leu Phe Lys Leu Leu Lys Glu Gly
705                 710                 715                 720
His Arg Met Asp Lys Pro Ala Asn Cys Thr Asn Glu Leu Tyr Met Met
                725                 730                 735
Met Arg Asp Cys Trp His Ala Val Pro Ser Gln Arg Pro Thr Phe Lys
            740                 745                 750
Gln Leu Val Glu Asp Leu Asp Arg Ile Leu Thr Leu Thr Thr Asn Glu
        755                 760                 765
Glu Tyr Leu Asp Leu Ser Gln Pro Leu Glu Gln Tyr Ser Pro Ser Tyr
    770                 775                 780
Pro Asp Thr Arg Ser Ser Cys Ser Ser Gly Asp Asp Ser Val Phe Ser
785                 790                 795                 800
Pro Asp Pro Met Pro Tyr Glu Pro Cys Leu Pro Gln Tyr Pro His Ile
                805                 810                 815
Asn Gly Ser Val Lys Thr
            820

<210> SEQ ID NO 3
<211> LENGTH: 2466
<212> TYPE: DNA
<213> ORGANISM: Homo sapiens

<400> SEQUENCE: 3
atggtcagct ggggtcgttt catctgcctg gtcgtggtca ccatggcaac cttgtccctg    60
gcccggccct ccttcagttt agttgaggat accacattag agccagaaga gccaccaacc   120
aaataccaaa tctctcaacc agaagtgtac gtggctgcgc aggggagtc gctagaggtg   180
cgctgcctgt tgaaagatgc cgccgtgatc agttggacta aggatgggt gcacttgggg   240
cccaacaata ggacagtgct tattggggag tacttgcaga taaagggcgc cacgcctaga   300
gactccggcc tctatgcttg tactgccagt aggactgtag acagtgaaac ttggtacttc   360
atggtgaatg tcagatgc catctcatcc ggagatgatg aggatgacac cgatggtgcg   420
gaagattttg tcagtgagaa cagtaacaac aagagagcac catactggac caacacagaa   480
aagatggaaa agcggctcca tgctgtgcct gcggccaaca ctgtcaagtt cgctgccca   540
gccgggggga acccaatgcc aaccatgcgg tggctgaaaa acgggaagga gtttaagcag   600
```

-continued

| | |
|---|---|
| gagcatcgca ttggaggcta caaggtacga aaccagcact ggagcctcat tatggaaagt | 660 |
| gtggtcccat ctgacaaggg aaattatacc tgtgtagtgg agaatgaata cgggtccatc | 720 |
| aatcacacgt accacctgga tgttgtggag cgatcgcctc accggcccat cctccaagcc | 780 |
| ggactgccgg caaatgcctc cacagtggtc ggaggagacg tagagtttgt ctgcaaggtt | 840 |
| tacagtgatg cccagcccca catccagtgg atcaagcacg tggaaaagaa cggcagtaaa | 900 |
| tacgggcccg acgggctgcc ctacctcaag gttctcaagg ccgccggtgt aacaccacg | 960 |
| gacaaagaga ttgaggttct ctatattcgg aatgtaactt ttgaggacgc tggggaatat | 1020 |
| acgtgcttgg cgggtaattc tattgggata tcctttcact ctgcatggtt gacagttctg | 1080 |
| ccagcgcctg gaagagaaaa ggagattaca gcttccccag actacctgga gatagccatt | 1140 |
| tactgcatag gggtcttctt aatcgcctgt atggtggtaa cagtcatcct gtgccgaatg | 1200 |
| aagaacacga ccaagaagcc agacttcagc agccagccgg ctgtgcacaa gctgaccaaa | 1260 |
| cgtatccccc tgcggagaca ggtaacagtt tcggctgagt ccagctcctc catgaactcc | 1320 |
| aacacccgc tggtgaggat aacaacacgc ctctcttcaa cggcagacac ccccatgctg | 1380 |
| gcagggggtct ccgagtatga acttccagag gacccaaaat gggagtttcc aagagataag | 1440 |
| ctgacactgg caagcccct gggagaaggt tgctttgggc aagtggtcat ggcggaagca | 1500 |
| gtgggaattg acaaagacaa gcccaaggag gcggtcaccg tggccgtgaa gatgttgaaa | 1560 |
| gatgatgcca cagagaaaga cctttctgat ctggtgtcag agatggagat gatgaagatg | 1620 |
| attgggaaac acaagaatat cataaatctt cttggagcct gcacacagga tgggcctctc | 1680 |
| tatgtcatag ttgagtatgc ctctaaaggc aacctccgag aatacctccg agcccggagg | 1740 |
| ccacccggga tggagtactc ctatgacatt aaccgtgttc ctgaggagca gatgaccttc | 1800 |
| aaggacttgg tgtcatgcac ctaccagctg gccagaggca tggagtactt ggcttcccaa | 1860 |
| aaatgtattc atcgagattt agcagccaga aatgttttgg taacagaaaa caatgtgatg | 1920 |
| aaaatagcag actttggact cgccagagat atcaacaata tagactatta caaaagacc | 1980 |
| accaatgggc ggcttccagt caagtggatg gctccagaag ccctgtttga tagagtatac | 2040 |
| actcatcaga gtgatgtctg gtccttcggg gtgttaatgt gggagatctt cactttaggg | 2100 |
| ggctcgccct acccagggat tcccgtggag gaactttta agctgctgaa ggaaggacac | 2160 |
| agaatggata agccagccaa ctgcaccaac gaactgtaca tgatgatgag ggactgttgg | 2220 |
| catgcagtgc cctcccagag accaacgttc aagcagttgg tagaagactt ggatcgaatt | 2280 |
| ctcactctca caaccaatga ggaatacttg gacctcagcc aacctctcga acagtattca | 2340 |
| cctagttacc ctgacacaag aagttcttgt tcttcaggag atgattctgt tttttctcca | 2400 |
| gacccccatgc cttacgaacc atgccttcct cagtatccac acataaacgg cagtgttaaa | 2460 |
| acatga | 2466 |

<210> SEQ ID NO 4
<211> LENGTH: 2469
<212> TYPE: DNA
<213> ORGANISM: Homo sapiens

<400> SEQUENCE: 4

| | |
|---|---|
| atggtcagct ggggtcgttt catctgcctg gtcgtggtca ccatggcaac cttgtccctg | 60 |
| gcccggccct ccttcagttt agttgaggat accacattag agccagaaga gccaccaacc | 120 |
| aaataccaaa tctctcaacc agaagtgtac gtggctgcgc caggggagtc gctagaggtg | 180 |
| cgctgcctgt tgaaagatgc cgccgtgatc agttggacta aggatggggt gcacttgggg | 240 |

```
cccaacaata ggacagtgct tattggggag tacttgcaga taaagggcgc cacgcctaga    300
gactccggcc tctatgcttg tactgccagt aggactgtag acagtgaaac ttggtacttc    360
atggtgaatg tcacagatgc catctcatcc ggagatgatg aggatgacac cgatggtgcg    420
gaagattttg tcagtgagaa cagtaacaac aagagagcac catactggac caacacagaa    480
aagatggaaa agcggctcca tgctgtgcct gcggccaaca ctgtcaagtt tcgctgccca    540 gccggggga acccaatgcc aaccatgcgg tggctgaaaa acgggaagga gtttaagcag    600
gagcatcgca ttggaggcta caaggtacga aaccagcact ggagcctcat tatggaaagt    660
gtggtcccat ctgacaaggg aaattatacc tgtgtagtgg agaatgaata cgggtccatc    720
aatcacacgt accacctgga tgttgtggag cgatcgcctc accggcccat cctccaagcc    780
ggactgccgg caaatgcctc cacagtggtc ggaggagacg tagagtttgt ctgcaaggtt    840
tacagtgatg cccagcccca catccagtgg atcaagcacg tggaaaagaa cggcagtaaa    900
tacgggcccg acgggctgcc ctacctcaag gttctcaagc actcggggat aaatagttcc    960
aatgcagaag tgctggctct gttcaatgtg accgaggcgg atgctgggga atatatatgt   1020
aaggtctcca attatatagg gcaggccaac cagtctgcct ggctcactgt cctgccaaaa   1080
cagcaagcgc ctggaagaga aaaggagatt acagcttccc cagactacct ggagatagcc   1140
atttactgca taggggtctt cttaatcgcc tgtatggtgg taacagtcat cctgtgccga   1200
atgaagaaca cgaccaagaa gccagacttc agcagccagc cggctgtgca caagctgacc   1260
aaacgtatcc ccctgcggag acaggtaaca gtttcggctg agtccagctc ctccatgaac   1320
tccaacaccc cgctggtgag gataacaaca cgcctctctt caacgcagca cacccccatg   1380
ctggcagggg tctccgagta tgaacttcca gaggacccaa atggagtt tccaagagat    1440 aagctgacac tgggcaagcc cctgggagaa ggttgctttg gcaagtggt catggcggaa   1500 gcagtgggaa ttgacaaaga caagcccaag gaggcggtca ccgtggccgt gaagatgttg   1560
aaagatgatg ccacagagaa agacctttct gatctggtgt cagagatgga gatgatgaag   1620
atgattggga acacaagaa tatcataaat cttcttggag cctgcacaca ggatgggcct   1680
ctctatgtca tagttgagta tgcctctaaa ggcaacctcc gagaatacct ccgagcccgg   1740
aggccacccg gatggagta ctcctatgac attaaccgtg ttcctgagga gcagatgacc   1800
ttcaaggact tggtgtcatg cacctaccag ctggccagag gcatggagta cttggcttcc   1860
caaaaatgta ttcatcgaga tttagcagcc agaaatgttt tggtaacaga aaacaatgtg   1920
atgaaaatag cagactttgg actcgccaga gatatcaaca atatagacta ttacaaaaag   1980
accaccaatg ggcggcttcc agtcaagtgg atggctccag aagccctgtt tgatagagta   2040
tacactcatc agagtgatgt ctggtccttc ggggtgttaa tgtgggagat cttcactta    2100 ggggctcgc cctacccagg gattcccgtg gaggaacttt ttaagctgct gaaggaagga   2160
cacagaatgg ataagccagc caactgcacc aacgaactgt acatgatgat gagggactgt   2220
tggcatgcag tgccctccca gagaccaacg ttcaagcagt tggtagaaga cttggatcga   2280
attctcactc tcacaaccaa tgaggaatac ttggacctca gccaacctct cgaacagtat   2340
tcacctagtt accctgacac aagaagttct tgttcttcag gagatgattc tgttttttct   2400
ccagacccca tgccttacga accatgcctt cctcagtatc cacacataaa cggcagtgtt   2460
aaaacatga                                                            2469
```

<210> SEQ ID NO 5

<211> LENGTH: 2466
<212> TYPE: DNA
<213> ORGANISM: Homo sapiens

<400> SEQUENCE: 5

| | | | | | |
|---|---|---|---|---|---|
| atggtcagct | ggggtcgttt | catctgcctg | gtcgtggtca | ccatggcaac | cttgtccctg | 60 |
| gcccggccct | ccttcagttt | agttgaggat | accacattag | agccagaaga | gccaccaacc | 120 |
| aaataccaaa | tctctcaacc | agaagtgtac | gtggctgcgc | cagggagtc | gctagaggtg | 180 |
| cgctgcctgt | tgaaagatgc | cgccgtgatc | agttggacta | aggatggggt | gcacttgggg | 240 |
| cccaacaata | ggacagtgct | tattggggag | tacttgcaga | taaagggcgc | cacgcctaga | 300 |
| gactccggcc | tctatgcttg | tactgccagt | aggactgtag | acagtgaaac | ttggtacttc | 360 |
| atggtgaatg | tcacagatgc | catctcatcc | ggagatgatg | aggatgacac | cgatggtgcg | 420 |
| gaagattttg | tcagtgagaa | cagtaacaac | aagagagcac | catactggac | caacacagaa | 480 |
| aagatggaaa | agcggctcca | tgctgtgcct | gcggccaaca | ctgtcaagtt | tcgctgccca | 540 |
| gccggggga | acccaatgcc | aaccatgcgg | tggctgaaaa | acgggaagga | gtttaagcag | 600 |
| gagcatcgca | ttggaggcta | caaggtacga | accagcact | ggagcctcat | tatggaaagt | 660 |
| gtggtcccat | ctgacaaggg | aaattatacc | tgtgtagtgg | agaatgaata | cggtccatc | 720 |
| aatcacacgt | accacctgga | tgttgtggag | cgatcgcctc | accggcccat | cctccaagcc | 780 |
| ggactgccgg | caaatgcctc | cacagtggtc | ggaggagacg | tagagtttgt | ctgcaaggtt | 840 |
| tacagtgatg | cccagcccca | catccagtgg | atcaagcacg | tggaaaagaa | cggcagtaaa | 900 |
| tacgggcccg | acgggctgcc | ctacctcaag | gttctcaagg | ccgccggtgt | taacaccacg | 960 |
| gacaaagaga | ttgaggttct | ctatattcgg | aatgtaactt | ttgaggacgc | tggggaatat | 1020 |
| acgtgcttgg | cgggtaattc | tattgggata | tcctttcact | ctgcatggtt | gacagttctg | 1080 |
| ccagcgcctg | gaagagaaaa | ggagattaca | gcttccccag | actacctgga | gatagccatt | 1140 |
| tactgcatag | gggtcttctt | aatcgcctgt | atggtggtaa | cagtcatcct | gtgccgaatg | 1200 |
| aagaacacga | ccaagaagcc | agacttcagc | agccagccgg | ctgtgcacaa | gctgaccaaa | 1260 |
| cgtatccccc | tgcggagaca | ggtaacagtt | tcggctgagt | ccagctcctc | catgaactcc | 1320 |
| aacacccgc | tggtgaggat | aacaacacgc | ctctcttcaa | cggcagacac | ccccatgctg | 1380 |
| gcagggtct | ccgagtatga | acttccagag | gacccaaaat | gggagtttcc | aagagataag | 1440 |
| ctgacactgg | gcaagcccct | gggagaaggt | tgctttgggc | aagtggtcat | ggcggaagca | 1500 |
| gtgggaattg | acaaagacaa | gcccaaggag | gcggtcaccg | tggccgtgaa | gatgttgaaa | 1560 |
| gatgatgcca | cagagaaaga | cctttctgat | ctggtgtcag | agatggagat | gatgaagatg | 1620 |
| attgggaaac | acaagaatat | cataaatctt | cttggagcct | gcacacagga | tgggcctctc | 1680 |
| tatgtcatag | ttgagtatgc | ctctaaaggc | aacctccgag | aatacctccg | agcccggagg | 1740 |
| ccacccggga | tggagtactc | ctatgacatt | aaccgtgttc | ctgaggagca | gatgaccttc | 1800 |
| aaggacttgg | tgtcatgcac | ctaccagctg | ccagaggca | tggagtactt | ggcttcccaa | 1860 |
| aaatgtattc | atcgagattt | agcagccaga | aatgttttgg | taacagaaaa | caatgtgatg | 1920 |
| aaaatagcag | actttggact | cgccagagat | atcaacaata | tagactatta | caaaaagacc | 1980 |
| accaatgggc | ggcttccagt | caagtggatg | gctccagaag | ccctgtttga | tagagtatac | 2040 |
| actcatcaga | gtgatgtctg | gtccttcggg | gtgttaatgt | gggagatctt | cactttaggg | 2100 |
| ggctcgccct | acccagggat | tcccgtggag | gaacttttta | agctgctgaa | ggaaggacac | 2160 |
| agaatggata | agccagccaa | ctgcaccaac | gaactgtaca | tgatgatgag | ggactgttgg | 2220 |

-continued

| | |
|---|---|
| catgcagtgc cctcccagag accaacgttc aagcagttgg tagaagactt ggatcgaatt | 2280 |
| ctcactctca caaccaatga ggaatacttg gacctcagcc aacctctcga acagtattca | 2340 |
| cctagttacc ctgacacaag aagttcttgt tcttcaggag atgattctgt tttttctcca | 2400 |
| gaccccatgc cttacgaacc atgccttcct cagtatccac acataaacgg cagtgttaaa | 2460 |
| acatag | 2466 |

<210> SEQ ID NO 6
<211> LENGTH: 2466
<212> TYPE: DNA
<213> ORGANISM: Homo sapiens

<400> SEQUENCE: 6

| | |
|---|---|
| atggtcagct ggggtcgttt catctgcctg gtcgtggtca ccatggcaac cttgtccctg | 60 |
| gcccggccct ccttcagttt agttgaggat accacattag agccagaaga gccaccaacc | 120 |
| aaataccaaa tctctcaacc agaagtgtac gtggctgcgc caggggagtc gctagaggtg | 180 |
| cgctgcctgt tgaaagatgc cgccgtgatc agttggacta aggatggggt gcacttgggg | 240 |
| cccaacaata ggacagtgct tattggggag tacttgcaga taaagggcgc cacgcctaga | 300 |
| gactccggcc tctatgcttg tactgccagt aggactgtag acagtgaaac ttggtacttc | 360 |
| atggtgaatg tcacagatgc catctcatcc ggagatgatg aggatgacac cgatggtgcg | 420 |
| gaagattttg tcagtgagaa cagtaacaac aagagagcac catactggac caacacagaa | 480 |
| aagatggaaa agcggctcca tgctgtgcct gcggccaaca ctgtcaagtt tcgctgccca | 540 |
| gccgggggga acccaatgcc aaccatgcgg tggctgaaaa acgggaagga gtttaagcag | 600 |
| gagcatcgca ttgaaggcta caaggtacga aaccagcact ggagcctcat tatggaaagt | 660 |
| gtggtcccat ctgacaaggg aaattatacc tgtgtagtgg agaatgaata cgggtccatc | 720 |
| aatcacacgt accacctgga tgttgtggag cgatcgcctc accggcccat cctccaagcc | 780 |
| ggactgccgg caaatgcctc cacagtggtc ggaggagacg tagagtttgt ctgcaaggtt | 840 |
| tacagtgatg cccagccccc catccagtgg atcaagcacg tggaaaagaa cggcagtaaa | 900 |
| tacgggcccg acgggctgcc ctacctcaag gttctcaagg ccgccggtgt taacaccacg | 960 |
| gacaaagaga ttgaggttct ctatattcgg aatgtaactt ttgaggacgc tggggaatat | 1020 |
| acgtgcttgg cgggtaattc tattgggata tcctttcact ctgcatggtt gacagttctg | 1080 |
| ccagcgcctg aagagaaaaa ggagattaca gcttccccag actacctgga gatagccatt | 1140 |
| tactgcatag gggtcttctt aatcgcctgt atggtggtaa cagtcatcct gtgccgaatg | 1200 |
| aagaacacga ccaagaagcc agacttcagc agccagccgg ctgtgcacaa gctgaccaaa | 1260 |
| cgtatccccc tgcggagaca ggtaacagtt tcggctgagt ccagctcctc catgaactcc | 1320 |
| aacacccgc tggtgaggat aacaacacgc ctctcttcaa cggcagacac ccccatgctg | 1380 |
| gcagggtct ccgagtatga acttccagag acccaaaat gggagtttcc aagagataag | 1440 |
| ctgacactgg gcaagcccct gggagaaggt tgctttgggc aagtggtcat ggcggaagca | 1500 |
| gtgggaattg acaaagacaa gcccaaggag gcggtcaccg tggccgtgaa gatgttgaaa | 1560 |
| gatgatgcca cagagaaaga cctttctgat ctggtgtcag agatggagat gatgaagatg | 1620 |
| attgggaaac acaagaatat cataaatctt cttggagcct gcacacagga tgggcctctc | 1680 |
| tatgtcatat ttgagtatgc ctctaaaggc aacctccgag aatacctccg agcccggagg | 1740 |
| ccacccggga tggagtactc ctatgacatt aaccgtgttc ctgaggagca gatgaccttc | 1800 |

| | | |
|---|---|---|
| aaggacttgg tgtcatgcac ctaccagctg gccagaggca tggagtactt ggcttcccaa | 1860 | |
| aaatgtattc atcgagattt agcagccaga aatgttttgg taacagaaaa caatgtgatg | 1920 | |
| aaaatagcag actttggact cgccagagat atcaacaata tagactatta caaaaagacc | 1980 | |
| accaatgggc ggcttccagt caagtggatg gctccagaag ccctgtttga tagagtatac | 2040 | |
| actcatcaga gtgatgtctg gtccttcggg gtgttaatgt gggagatctt cactttaggg | 2100 | |
| ggctcgccct acccagggat tcccgtggag gaacttttta agctgctgaa ggaaggacac | 2160 | |
| agaatggata agccagccaa ctgcaccaac gaactgtaca tgatgatgag ggactgttgg | 2220 | |
| catgcagtgc cctcccagag accaacgttc aagcagttgg tagaagactt ggatcgaatt | 2280 | |
| ctcactctca caaccaatga ggaatacttg gacctcagcc aacctctcga acagtattca | 2340 | |
| cctagttacc ctgacacaag aagttcttgt tcttcaggag atgattctgt tttttctcca | 2400 | |
| gaccccatgc cttacgaacc atgccttcct cagtatccac ataaacgg cagtgttaaa | 2460 | |
| acatag | 2466 | |

<210> SEQ ID NO 7
<211> LENGTH: 2466
<212> TYPE: DNA
<213> ORGANISM: Homo sapiens

<400> SEQUENCE: 7

| | | |
|---|---|---|
| atggtcagct ggggtcgttt catctgcctg gtcgtggtca ccatggcaac cttgtccctg | 60 | |
| gcccggccct ccttcagttt agttgaggat accacattag agccagaaga gccaccaacc | 120 | |
| aaataccaaa tctctcaacc agaagtgtac gtggctgcgc caggggagtc gctagaggtg | 180 | |
| cgctgcctgt tgaaagatgc cgccgtgatc agttggacta aggatggggt gcacttgggg | 240 | |
| cccaacaata ggacagtgct tattgggag tacttgcaga taagggcgc cacgcctaga | 300 | |
| gactccggcc tctatgcttg tactgccagt aggactgtag acagtgaaac ttggtacttc | 360 | |
| atggtgaatg tcacagatgc catctcatcc ggagatgatg aggatgacac cgatggtgcg | 420 | |
| gaagattttg tcagtgagaa cagtaacaac aagagagcac catactggac caacacagaa | 480 | |
| aagatggaaa agcggctcca tgctgtgcct gcggccaaca ctgtcaagtt cgctgccca | 540 | |
| gccgggggga acccaatgcc aaccatgcgg tggctgaaaa acgggaagga gtttaagcag | 600 | |
| gagcatcgca ttgaggctca aaggtacga aaccagcact ggagcctcat tatggaaagt | 660 | |
| gtggtcccat ctgacaaggg aaattatacc tgtgtagtgg agaatgaata cgggtccatc | 720 | |
| aatcacacgt accacctgga tgttgtggag cgatcgcctc accggcccat cctccaagcc | 780 | |
| ggactgccgg caaatgcctc cacagtggtc ggaggagacg tagagtttgt ctgcaaggtt | 840 | |
| tacagtgatg cccagcccca catccagtgg atcaagcacg tggaaaagaa cggcagtaaa | 900 | |
| tacgggcccg acgggctgcc ctacctcaag gttctcaagg ccgccggtgt aacaccacg | 960 | |
| gacaaagaga ttgaggttct ctatattcgg aatgtaactt tgaggacgc tggggaatat | 1020 | |
| acgtgcttgg cgggtaattc tattgggata tcctttcact ctgcatggtt gacagttctg | 1080 | |
| ccagcgcctg gaagagaaaa ggagattaca gcttccccag actacctgga gatagccatt | 1140 | |
| tactgcatag gggtcttctt aatcgcctgt atggtggtaa cagtcatcct gtgccgaatg | 1200 | |
| aagaacacga ccaagaagcc agacttcagc agccagccgg ctgtgcacaa gctgaccaaa | 1260 | |
| cgtatccccc tgcggagaca ggtaacagtt tcggctgagt ccagctcctc catgaactcc | 1320 | |
| aacacccgc tggtgaggat aacaacacgc ctctcttcaa cggcagacac ccccatgctg | 1380 | |
| gcagggggtct ccgagtatga acttccagag gacccaaaaat gggagttccc aagagataag | 1440 | |

```
ctgacactgg gcaagcccct gggagaaggt tgctttgggc aagtggtcat ggcggaagca    1500
gtgggaattg acaaagacaa gcccaaggag gcggtcaccg tggccgtgaa gatgttgaaa    1560
gatgatgcca cagagaaaga cctttctgat ctggtgtcag agatggagat gatgaagatg    1620
attgggaaac acaagaatat cataaatctt cttggagcct gcacacagga tgggcctctc    1680
tatctcatag ttgagtatgc ctctaaaggc aacctccgag aatacctccg agcccggagg    1740
ccacccggga tggagtactc ctatgacatt aaccgtgttc ctgaggagca gatgaccttc    1800
aaggacttgg tgtcatgcac ctaccagctg gccagaggca tggagtactt ggcttcccaa    1860
aaatgtattc atcgagattt agcagccaga aatgttttgg taacagaaaa caatgtgatg    1920
aaaatagcag actttggact cgccagagat atcaacaata tagactatta caaaaagacc    1980
accaatgggc ggcttccagt caagtggatg gctccagaag ccctgtttga tagagtatac    2040
actcatcaga gtgatgtctg gtccttcggg gtgttaatgt gggagatctt cactttaggg    2100
ggctcgccct acccagggat tcccgtggag gaactttta agctgctgaa ggaaggacac    2160
agaatggata agccagccaa ctgcaccaac gaactgtaca tgatgatgag ggactgttgg    2220
catgcagtgc cctcccagag accaacgttc aagcagttgg tagaagactt ggatcgaatt    2280
ctcactctca caaccaatga ggaatacttg gacctcagcc aacctctcga acagtattca    2340
cctagttacc ctgacacaag aagttcttgt tcttcaggag atgattctgt tttttctcca    2400
gaccccatgc cttacgaacc atgccttcct cagtatccac acataaacgg cagtgttaaa    2460
acatag                                                              2466

<210> SEQ ID NO 8
<211> LENGTH: 821
<212> TYPE: PRT
<213> ORGANISM: Homo sapiens

<400> SEQUENCE: 8

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
```

```
                    180                 185                 190
Lys Asn Gly Lys Glu Phe Lys Gln Glu His Arg Ile Gly Gly Tyr Lys
                195                 200                 205
Val Arg Asn Gln His Trp Ser Leu Ile Met Glu Ser Val Pro Ser
    210                 215                 220
Asp Lys Gly Asn Tyr Thr Cys Val Val Glu Asn Glu Tyr Gly Ser Ile
225                 230                 235                 240
Asn His Thr Tyr His Leu Asp Val Val Glu Arg Ser Pro His Arg Pro
                245                 250                 255
Ile Leu Gln Ala Gly Leu Pro Ala Asn Ala Ser Thr Val Val Gly Gly
                260                 265                 270
Asp Val Glu Phe Val Cys Lys Val Tyr Ser Asp Ala Gln Pro His Ile
    275                 280                 285
Gln Trp Ile Lys His Val Glu Lys Asn Gly Ser Lys Tyr Gly Pro Asp
    290                 295                 300
Gly Leu Pro Tyr Leu Lys Val Leu Lys Ala Ala Gly Val Asn Thr Thr
305                 310                 315                 320
Asp Lys Glu Ile Glu Val Leu Tyr Ile Arg Asn Val Thr Phe Glu Asp
                325                 330                 335
Ala Gly Glu Tyr Thr Cys Leu Ala Gly Asn Ser Ile Gly Ile Ser Phe
                340                 345                 350
His Ser Ala Trp Leu Thr Val Leu Pro Ala Pro Gly Arg Glu Lys Glu
                355                 360                 365
Ile Thr Ala Ser Pro Asp Tyr Leu Glu Ile Ala Ile Tyr Cys Ile Gly
    370                 375                 380
Val Phe Leu Ile Ala Cys Met Val Val Thr Val Ile Leu Cys Arg Met
385                 390                 395                 400
Lys Asn Thr Thr Lys Lys Pro Asp Phe Ser Ser Gln Pro Ala Val His
                405                 410                 415
Lys Leu Thr Lys Arg Ile Pro Leu Arg Arg Gln Val Thr Val Ser Ala
                420                 425                 430
Glu Ser Ser Ser Ser Met Asn Ser Asn Thr Pro Leu Val Arg Ile Thr
                435                 440                 445
Thr Arg Leu Ser Ser Thr Ala Asp Thr Pro Met Leu Ala Gly Val Ser
    450                 455                 460
Glu Tyr Glu Leu Pro Glu Asp Pro Lys Trp Glu Phe Pro Arg Asp Lys
465                 470                 475                 480
Leu Thr Leu Gly Lys Pro Leu Gly Glu Gly Cys Phe Gly Gln Val Val
                485                 490                 495
Met Ala Glu Ala Val Gly Ile Asp Lys Asp Lys Pro Lys Glu Ala Val
                500                 505                 510
Thr Val Ala Val Lys Met Leu Lys Asp Asp Ala Thr Glu Lys Asp Leu
                515                 520                 525
Ser Asp Leu Val Ser Glu Met Glu Met Met Lys Met Ile Gly Lys His
    530                 535                 540
Lys Asn Ile Ile Asn Leu Leu Gly Ala Cys Thr Gln Asp Gly Pro Leu
545                 550                 555                 560
Tyr Val Ile Val Glu Tyr Ala Ser Lys Gly Asn Leu Arg Glu Tyr Leu
                565                 570                 575
Arg Ala Arg Arg Pro Pro Gly Met Glu Tyr Ser Tyr Asp Ile Asn Arg
                580                 585                 590
Val Pro Glu Glu Gln Met Thr Phe Lys Asp Leu Val Ser Cys Thr Tyr
    595                 600                 605
```

```
Gln Leu Ala Arg Gly Met Glu Tyr Leu Ala Ser Gln Lys Cys Ile His
    610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
            660                 665                 670

Glu Ala Leu Phe Asp Arg Val Tyr Thr His Gln Ser Asp Val Trp Ser
        675                 680                 685

Phe Gly Val Leu Met Trp Glu Ile Phe Thr Leu Gly Gly Ser Pro Tyr
    690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
                725                 730                 735

Arg Asp Cys Trp His Ala Val Pro Ser Gln Arg Pro Thr Phe Lys Gln
            740                 745                 750

Leu Val Glu Asp Leu Asp Arg Ile Leu Thr Leu Thr Thr Asn Glu Glu
        755                 760                 765

Tyr Leu Asp Leu Ser Gln Pro Leu Glu Gln Tyr Ser Pro Ser Tyr Pro
    770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
            820

<210> SEQ ID NO 9
<211> LENGTH: 821
<212> TYPE: PRT
<213> ORGANISM: Homo sapiens

<400> SEQUENCE: 9

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
```

-continued

```
                145                 150                 155                 160
Lys Met Glu Lys Arg Leu His Ala Val Pro Ala Ala Asn Thr Val Lys
                    165                 170                 175
Phe Arg Cys Pro Ala Gly Gly Asn Pro Met Pro Thr Met Arg Trp Leu
                    180                 185                 190
Lys Asn Gly Lys Glu Phe Lys Gln Glu His Arg Ile Gly Gly Tyr Lys
                    195                 200                 205
Val Arg Asn Gln His Trp Ser Leu Ile Met Glu Ser Val Val Pro Ser
                    210                 215                 220
Asp Lys Gly Asn Tyr Thr Cys Val Val Glu Asn Glu Tyr Gly Ser Ile
225                 230                 235                 240
Asn His Thr Tyr His Leu Asp Val Val Glu Arg Ser Pro His Arg Pro
                    245                 250                 255
Ile Leu Gln Ala Gly Leu Pro Ala Asn Ala Ser Thr Val Val Gly Gly
                    260                 265                 270
Asp Val Glu Phe Val Cys Lys Val Tyr Ser Asp Ala Gln Pro His Ile
                    275                 280                 285
Gln Trp Ile Lys His Val Glu Lys Asn Gly Ser Lys Tyr Gly Pro Asp
                    290                 295                 300
Gly Leu Pro Tyr Leu Lys Val Leu Lys Ala Ala Gly Val Asn Thr Thr
305                 310                 315                 320
Asp Lys Glu Ile Glu Val Leu Tyr Ile Arg Asn Val Thr Phe Glu Asp
                    325                 330                 335
Ala Gly Glu Tyr Thr Cys Leu Ala Gly Asn Ser Ile Gly Ile Ser Phe
                    340                 345                 350
His Ser Ala Trp Leu Thr Val Leu Pro Ala Pro Gly Arg Glu Lys Glu
                    355                 360                 365
Ile Thr Ala Ser Pro Asp Tyr Leu Glu Ile Ala Ile Tyr Cys Ile Gly
                    370                 375                 380
Val Phe Leu Ile Ala Cys Met Val Val Thr Val Ile Leu Cys Arg Met
385                 390                 395                 400
Lys Asn Thr Thr Lys Lys Pro Asp Phe Ser Ser Gln Pro Ala Val His
                    405                 410                 415
Lys Leu Thr Lys Arg Ile Pro Leu Arg Arg Gln Val Thr Val Ser Ala
                    420                 425                 430
Glu Ser Ser Ser Ser Met Asn Ser Asn Thr Pro Leu Val Arg Ile Thr
                    435                 440                 445
Thr Arg Leu Ser Ser Thr Ala Asp Thr Pro Met Leu Ala Gly Val Ser
                    450                 455                 460
Glu Tyr Glu Leu Pro Glu Asp Pro Lys Trp Glu Phe Pro Arg Asp Lys
465                 470                 475                 480
Leu Thr Leu Gly Lys Pro Leu Gly Glu Gly Cys Phe Gly Gln Val Val
                    485                 490                 495
Met Ala Glu Ala Val Gly Ile Asp Lys Asp Lys Pro Lys Glu Ala Val
                    500                 505                 510
Thr Val Ala Val Lys Met Leu Lys Asp Asp Ala Thr Glu Lys Asp Leu
                    515                 520                 525
Ser Asp Leu Val Ser Glu Met Glu Met Met Lys Met Ile Gly Lys His
                    530                 535                 540
Lys Asn Ile Ile Asn Leu Leu Gly Ala Cys Thr Gln Asp Gly Pro Leu
545                 550                 555                 560
Tyr Val Ile Phe Glu Tyr Ala Ser Lys Gly Asn Leu Arg Glu Tyr Leu
                    565                 570                 575
```

Arg Ala Arg Arg Pro Pro Gly Met Glu Tyr Ser Tyr Asp Ile Asn Arg
            580                 585                 590

Val Pro Glu Glu Gln Met Thr Phe Lys Asp Leu Val Ser Cys Thr Tyr
        595                 600                 605

Gln Leu Ala Arg Gly Met Glu Tyr Leu Ala Ser Gln Lys Cys Ile His
    610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
            660                 665                 670

Glu Ala Leu Phe Asp Arg Val Tyr Thr His Gln Ser Asp Val Trp Ser
        675                 680                 685

Phe Gly Val Leu Met Trp Glu Ile Phe Thr Leu Gly Gly Ser Pro Tyr
    690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
                725                 730                 735

Arg Asp Cys Trp His Ala Val Pro Ser Gln Arg Pro Thr Phe Lys Gln
            740                 745                 750

Leu Val Glu Asp Leu Asp Arg Ile Leu Thr Leu Thr Thr Asn Glu Glu
        755                 760                 765

Tyr Leu Asp Leu Ser Gln Pro Leu Glu Gln Tyr Ser Pro Ser Tyr Pro
    770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
            820

<210> SEQ ID NO 10
<211> LENGTH: 821
<212> TYPE: PRT
<213> ORGANISM: Homo sapiens

<400> SEQUENCE: 10

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile

-continued

```
                115                 120                 125
Ser Ser Gly Asp Asp Glu Asp Thr Asp Gly Ala Glu Asp Phe Val
    130                 135                 140
Ser Glu Asn Ser Asn Asn Lys Arg Ala Pro Tyr Trp Thr Asn Thr Glu
145                 150                 155                 160
Lys Met Glu Lys Arg Leu His Ala Val Pro Ala Ala Asn Thr Val Lys
                165                 170                 175
Phe Arg Cys Pro Ala Gly Gly Asn Pro Met Pro Thr Met Arg Trp Leu
            180                 185                 190
Lys Asn Gly Lys Glu Phe Lys Gln Glu His Arg Ile Gly Gly Tyr Lys
        195                 200                 205
Val Arg Asn Gln His Trp Ser Leu Ile Met Glu Ser Val Val Pro Ser
    210                 215                 220
Asp Lys Gly Asn Tyr Thr Cys Val Val Glu Asn Glu Tyr Gly Ser Ile
225                 230                 235                 240
Asn His Thr Tyr His Leu Asp Val Val Glu Arg Ser Pro His Arg Pro
                245                 250                 255
Ile Leu Gln Ala Gly Leu Pro Ala Asn Ala Ser Thr Val Val Gly Gly
            260                 265                 270
Asp Val Glu Phe Val Cys Lys Val Tyr Ser Asp Ala Gln Pro His Ile
        275                 280                 285
Gln Trp Ile Lys His Val Glu Lys Asn Gly Ser Lys Tyr Gly Pro Asp
    290                 295                 300
Gly Leu Pro Tyr Leu Lys Val Leu Lys Ala Ala Gly Val Asn Thr Thr
305                 310                 315                 320
Asp Lys Glu Ile Glu Val Leu Tyr Ile Arg Asn Val Thr Phe Glu Asp
                325                 330                 335
Ala Gly Glu Tyr Thr Cys Leu Ala Gly Asn Ser Ile Gly Ile Ser Phe
            340                 345                 350
His Ser Ala Trp Leu Thr Val Leu Pro Ala Pro Gly Arg Glu Lys Glu
        355                 360                 365
Ile Thr Ala Ser Pro Asp Tyr Leu Glu Ile Ala Ile Tyr Cys Ile Gly
    370                 375                 380
Val Phe Leu Ile Ala Cys Met Val Val Thr Val Ile Leu Cys Arg Met
385                 390                 395                 400
Lys Asn Thr Thr Lys Lys Pro Asp Phe Ser Ser Gln Pro Ala Val His
                405                 410                 415
Lys Leu Thr Lys Arg Ile Pro Leu Arg Arg Gln Val Thr Val Ser Ala
            420                 425                 430
Glu Ser Ser Ser Ser Met Asn Ser Asn Thr Pro Leu Val Arg Ile Thr
        435                 440                 445
Thr Arg Leu Ser Ser Thr Ala Asp Thr Pro Met Leu Ala Gly Val Ser
    450                 455                 460
Glu Tyr Glu Leu Pro Glu Asp Pro Lys Trp Glu Phe Pro Arg Asp Lys
465                 470                 475                 480
Leu Thr Leu Gly Lys Pro Leu Gly Glu Gly Cys Phe Gly Gln Val Val
                485                 490                 495
Met Ala Glu Ala Val Gly Ile Asp Lys Asp Lys Pro Lys Glu Ala Val
            500                 505                 510
Thr Val Ala Val Lys Met Leu Lys Asp Asp Ala Thr Glu Lys Asp Leu
        515                 520                 525
Ser Asp Leu Val Ser Glu Met Glu Met Met Lys Met Ile Gly Lys His
    530                 535                 540
```

Lys Asn Ile Ile Asn Leu Leu Gly Ala Cys Thr Gln Asp Gly Pro Leu
545                 550                 555                 560

Tyr Leu Ile Val Glu Tyr Ala Ser Lys Gly Asn Leu Arg Glu Tyr Leu
                565                 570                 575

Arg Ala Arg Arg Pro Pro Gly Met Glu Tyr Ser Tyr Asp Ile Asn Arg
            580                 585                 590

Val Pro Glu Glu Gln Met Thr Phe Lys Asp Leu Val Ser Cys Thr Tyr
        595                 600                 605

Gln Leu Ala Arg Gly Met Glu Tyr Leu Ala Ser Gln Lys Cys Ile His
    610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
            660                 665                 670

Glu Ala Leu Phe Asp Arg Val Tyr Thr His Gln Ser Asp Val Trp Ser
        675                 680                 685

Phe Gly Val Leu Met Trp Glu Ile Phe Thr Leu Gly Gly Ser Pro Tyr
    690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
                725                 730                 735

Arg Asp Cys Trp His Ala Val Pro Ser Gln Arg Pro Thr Phe Lys Gln
            740                 745                 750

Leu Val Glu Asp Leu Asp Arg Ile Leu Thr Leu Thr Thr Asn Glu Glu
        755                 760                 765

Tyr Leu Asp Leu Ser Gln Pro Leu Glu Gln Tyr Ser Pro Ser Tyr Pro
    770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
            820

<210> SEQ ID NO 11
<211> LENGTH: 1722
<212> TYPE: DNA
<213> ORGANISM: Artificial sequence
<220> FEATURE:
<223> OTHER INFORMATION: An artificially synthesized polynucleotide
      sequence

<400> SEQUENCE: 11
atgtctgaga ctcctgctca gtgtagcatt aagcaggaac gaatttcata tacacctcca     60
gagagcccag tgccgagtta cgcttcctcg acgccacttc atgttccagt gcctagagcg    120
ctcaggatgg aggaagactc gatccgcctg cctgcgcacc tgcgcttgca gccaatttac    180
tggagcaggg atgacgtagc ccagtggctc aagtgggctg aaaatgagtt ttctttaagg    240
ccaattgaca gcaacacgtt tgaaatgaat ggcaaagctc tcctgctgct gaccaaagag    300
gactttcgct atcgatctcc tcattcaggt gatgtgctct atgaactcct tcagcatatt    360
ctgaagcaga ggaaacctcg gattctttt tcaccattct tccaccctgg aaactctata    420

```
cacacacagc cggaggtcat actgcatcag aaccatgaag aagataactg tgtccagagg      480
accccaggc catccgtgga taatgtgcac cataaccctc ccaccattga actgttgcac       540
cgcgtttcgg ctgagtccag ctcctccatg aactccaaca ccccgctggt gaggataaca     600
acacgcctct cttcaacggc agacaccccc atgctggcag gggtctccga gtatgaactt     660
ccagaggacc caaaatggga gtttccaaga gataagctga cactgggcaa gcccctggga    720
gaaggttgct ttgggcaagt ggtcatggcg aagcagtgg gaattgacaa agacaagccc      780
aaggaggcgg tcaccgtggc cgtgaagatg ttgaaagatg atgccacaga gaaagacctt    840
tctgatctgg tgtcagagat ggagatgatg aagatgattg ggaaacacaa gaatatcata    900
aatcttcttg gagcctgcac acaggatggg cctctctatg tcatagttga gtatgcctct    960
aaaggcaacc tccgagaata cctccgagcc cggaggccac ccgggatgga gtactcctat   1020
gacattaacc gtgttcctga ggagcagatg accttcaagg acttggtgtc atgcacctac   1080
cagctggcca gaggcatgga gtacttggct tcccaaaaat gtattcatcg agatttagca   1140
gccagaaatg ttttggtaac agaaaacaat gtgatgaaaa tagcagactt ggactcgcc    1200
agagatatca acaatataga ctattacaaa aagaccacca atgggcggct tccagtcaag   1260
tggatggctc cagaagccct gtttgataga gtatacactc atcagagtga tgtctggtcc   1320
ttcgggggtgt taatgtggga gatcttcact ttagggggct cgccctaccc agggattccc   1380
gtggaggaac tttttaagct gctgaaggaa ggacacagaa tggataagcc agccaactgc   1440
accaacgaac tgtacatgat gatgagggac tgttggcatg cagtgccctc ccagagacca   1500
acgttcaagc agttggtaga agacttggat cgaattctca ctctcacaac caatgaggaa   1560
tacttggacc tcagccaacc tctcgaacag tattcaccta gttaccctga cacaagaagt   1620
tcttgttctt caggagatga ttctgtttt tctccagacc ccatgcctta cgaaccatgc    1680
cttcctcagt atccacacat aaacggcagt gttaaaacat ag                      1722
```

<210> SEQ ID NO 12
<211> LENGTH: 1722
<212> TYPE: DNA
<213> ORGANISM: Artificial sequence
<220> FEATURE:
<223> OTHER INFORMATION: An artificially synthesized polynucleotide
      sequence

<400> SEQUENCE: 12

```
atgtctgaga ctcctgctca gtgtagcatt aagcaggaac gaatttcata tacacctcca      60
gagagcccag tgccgagtta cgcttcctcg acgccacttc atgttccagt gcctagagcg    120
ctcaggatgg aggaagactc gatccgcctg cctgcgcacc tgcgcttgca gccaatttac    180
tggagcaggg atgacgtagc ccagtggctc aagtgggctg aaaatgagtt ttctttaagg    240
ccaattgaca gcaacacgtt tgaaatgaat ggcaaagctc tcctgctgct gaccaaagag    300
gactttcgct atcgatctcc tcattcaggt gatgtgctct atgaactcct tcagcatatt    360
ctgaagcaga ggaaaccctcg gattctttt tcaccattct tccaccctgg aaactctata    420
cacacacagc cggaggtcat actgcatcag aaccatgaag aagataactg tgtccagagg    480
accccaggc catccgtgga taatgtgcac cataaccctc ccaccattga actgttgcac    540
cgcgtttcgg ctgagtccag ctcctccatg aactccaaca ccccgctggt gaggataaca    600
acacgcctct cttcaacggc agacaccccc atgctggcag gggtctccga gtatgaactt    660
ccagaggacc caaaatggga gtttccaaga gataagctga cactgggcaa gcccctggga   720
```

```
gaaggttgct ttgggcaagt ggtcatggcg gaagcagtgg gaattgacaa agacaagccc    780
aaggaggcgg tcaccgtggc cgtgaagatg ttgaaagatg atgccacaga gaaagacctt    840
tctgatctgg tgtcagagat ggagatgatg aagatgattg ggaaacacaa gaatatcata    900
aatcttcttg gagcctgcac acaggatggg cctctctatg tcatatttga gtatgcctct    960
aaaggcaacc tccgagaata cctccgagcc cggaggccac ccgggatgga gtactcctat   1020
gacattaacc gtgttcctga ggagcagatg accttcaagg acttggtgtc atgcacctac   1080
cagctggcca gaggcatgga gtacttggct cccaaaaat gtattcatcg agatttagca    1140
gccagaaatg ttttggtaac agaaaacaat gtgatgaaaa tagcagactt tggactcgcc   1200
agagatatca acaatataga ctattacaaa aagaccacca atgggcggct tccagtcaag   1260
tggatggctc cagaagccct gtttgataga gtatacactc atcagagtga tgtctggtcc   1320
ttcggggtgt taatgtggga gatcttcact ttagggggct cgccctaccc agggattccc   1380
gtggaggaac ttttaagct gctgaaggaa ggacacagaa tggataagcc agccaactgc   1440
accaacgaac tgtacatgat gatgagggac tgttggcatg cagtgccctc ccagagacca   1500
acgttcaagc agttggtaga agacttggat cgaattctca ctctcacaac caatgaggaa   1560
tacttggacc tcagccaacc tctcgaacag tattcaccta gttaccctga cacaagaagt   1620
tcttgttctt caggagatga ttctgttttt tctccagacc ccatgcctta cgaaccatgc   1680
cttcctcagt atccacacat aaacggcagt gttaaaacat ag                     1722
```

<210> SEQ ID NO 13
<211> LENGTH: 4
<212> TYPE: PRT
<213> ORGANISM: Artificial sequence
<220> FEATURE:
<223> OTHER INFORMATION: Peptide linker sequence

<400> SEQUENCE: 13

Gly Gly Gly Ser
1

<210> SEQ ID NO 14
<211> LENGTH: 4
<212> TYPE: PRT
<213> ORGANISM: Artificial sequence
<220> FEATURE:
<223> OTHER INFORMATION: Peptide linker sequence

<400> SEQUENCE: 14

Ser Gly Gly Gly
1

<210> SEQ ID NO 15
<211> LENGTH: 5
<212> TYPE: PRT
<213> ORGANISM: Artificial sequence
<220> FEATURE:
<223> OTHER INFORMATION: Peptide linker sequence

<400> SEQUENCE: 15

Gly Gly Gly Gly Ser
1               5

<210> SEQ ID NO 16
<211> LENGTH: 5
<212> TYPE: PRT
<213> ORGANISM: Artificial sequence

```
<220> FEATURE:
<223> OTHER INFORMATION: Peptide linker sequence

<400> SEQUENCE: 16

Ser Gly Gly Gly Gly
1               5

<210> SEQ ID NO 17
<211> LENGTH: 6
<212> TYPE: PRT
<213> ORGANISM: Artificial sequence
<220> FEATURE:
<223> OTHER INFORMATION: Peptide linker sequence

<400> SEQUENCE: 17

Gly Gly Gly Gly Gly Ser
1               5

<210> SEQ ID NO 18
<211> LENGTH: 6
<212> TYPE: PRT
<213> ORGANISM: Artificial sequence
<220> FEATURE:
<223> OTHER INFORMATION: Peptide linker sequence

<400> SEQUENCE: 18

Ser Gly Gly Gly Gly Gly
1               5

<210> SEQ ID NO 19
<211> LENGTH: 7
<212> TYPE: PRT
<213> ORGANISM: Artificial sequence
<220> FEATURE:
<223> OTHER INFORMATION: Peptide linker sequence

<400> SEQUENCE: 19

Gly Gly Gly Gly Gly Gly Ser
1               5

<210> SEQ ID NO 20
<211> LENGTH: 7
<212> TYPE: PRT
<213> ORGANISM: Artificial sequence
<220> FEATURE:
<223> OTHER INFORMATION: Peptide linker sequence

<400> SEQUENCE: 20

Ser Gly Gly Gly Gly Gly Gly
1               5

<210> SEQ ID NO 21
<211> LENGTH: 820
<212> TYPE: PRT
<213> ORGANISM: Homo sapiens

<400> SEQUENCE: 21

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
        50                  55                  60
```

```
Asn Trp Leu Arg Asp Gly Val Gln Leu Ala Glu Ser Asn Arg Thr Arg
 65                  70                  75                  80

Ile Thr Gly Glu Glu Val Glu Val Gln Asp Ser Val Pro Ala Asp Ser
             85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Ser Ser Ser Glu Glu Lys Glu Thr Asp Asn Thr
130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
        275                 280                 285

Lys His Ile Glu Val Asn Gly Ser Lys Ile Gly Pro Asp Asn Leu Pro
290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Leu Ser His His Ser Ala
            340                 345                 350

Trp Leu Thr Val Leu Glu Ala Leu Glu Glu Arg Pro Ala Val Met Thr
        355                 360                 365

Ser Pro Leu Tyr Leu Glu Ile Ile Ile Tyr Cys Thr Gly Ala Phe Leu
370                 375                 380

Ile Ser Cys Met Val Gly Ser Val Ile Val Tyr Lys Met Lys Ser Gly
385                 390                 395                 400

Thr Lys Lys Ser Asp Phe His Ser Gln Met Ala Val His Lys Leu Ala
                405                 410                 415

Lys Ser Ile Pro Leu Arg Arg Gln Val Thr Val Ser Ala Asp Ser Ser
            420                 425                 430

Ala Ser Met Asn Ser Gly Val Leu Leu Val Arg Pro Ser Arg Leu Ser
        435                 440                 445

Ser Ser Gly Thr Pro Met Leu Ala Gly Val Ser Glu Tyr Glu Leu Pro
450                 455                 460

Glu Asp Pro Arg Trp Glu Leu Pro Arg Asp Arg Leu Val Leu Gly Lys
465                 470                 475                 480
```

```
Pro Leu Gly Glu Gly Cys Phe Gly Gln Val Leu Ala Glu Ala Ile
                485                 490                 495

Gly Leu Asp Lys Asp Lys Pro Asn Arg Val Thr Lys Val Ala Val Lys
            500                 505                 510

Met Leu Lys Ser Asp Ala Thr Glu Lys Asp Leu Ser Asp Leu Ile Ser
            515                 520                 525

Glu Met Glu Met Met Lys Met Ile Gly Lys His Lys Asn Ile Ile Asn
            530                 535                 540

Leu Leu Gly Ala Cys Thr Gln Asp Gly Pro Leu Tyr Val Ile Val Glu
545                 550                 555                 560

Tyr Ala Ser Lys Gly Asn Leu Arg Glu Tyr Leu Gln Ala Arg Arg Pro
                565                 570                 575

Pro Gly Leu Glu Tyr Cys Tyr Asn Pro Ser His Asn Pro Glu Glu Gln
            580                 585                 590

Leu Ser Ser Lys Asp Leu Val Ser Cys Ala Tyr Gln Val Ala Arg Gly
            595                 600                 605

Met Glu Tyr Leu Ala Ser Lys Lys Cys Ile His Arg Asp Leu Ala Ala
            610                 615                 620

Arg Asn Val Leu Val Thr Glu Asp Asn Val Met Lys Ile Ala Asp Phe
625                 630                 635                 640

Gly Leu Ala Arg Asp Ile His His Ile Asp Tyr Tyr Lys Lys Thr Thr
                645                 650                 655

Asn Gly Arg Leu Pro Val Lys Trp Met Ala Pro Glu Ala Leu Phe Asp
            660                 665                 670

Arg Ile Tyr Thr His Gln Ser Asp Val Trp Ser Phe Gly Val Leu Leu
            675                 680                 685

Trp Glu Ile Phe Thr Leu Gly Gly Ser Pro Tyr Pro Gly Val Pro Val
690                 695                 700

Glu Glu Leu Phe Lys Leu Leu Lys Glu Gly His Arg Met Asp Lys Pro
705                 710                 715                 720

Ser Asn Cys Thr Asn Glu Leu Tyr Met Met Met Arg Asp Cys Trp His
                725                 730                 735

Ala Val Pro Ser Gln Arg Pro Thr Phe Lys Gln Leu Val Glu Asp Leu
            740                 745                 750

Asp Arg Ile Val Ala Leu Thr Ser Asn Gln Glu Tyr Leu Asp Leu Ser
            755                 760                 765

Met Pro Leu Asp Gln Tyr Ser Pro Ser Phe Pro Asp Thr Arg Ser Ser
            770                 775                 780

Thr Cys Ser Ser Gly Glu Asp Ser Val Phe Ser His Glu Pro Leu Pro
785                 790                 795                 800

Glu Glu Pro Cys Leu Pro Arg His Pro Ala Gln Leu Ala Asn Gly Gly
                805                 810                 815

Leu Lys Arg Arg
                820

<210> SEQ ID NO 22
<211> LENGTH: 806
<212> TYPE: PRT
<213> ORGANISM: Homo sapiens

<400> SEQUENCE: 22

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30
```

```
Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
                100                 105                 110

Leu Thr Gln Arg Val Leu Cys His Phe Ser Val Arg Val Thr Asp Ala
            115                 120                 125

Pro Ser Ser Gly Asp Asp Glu Asp Gly Glu Asp Glu Ala Glu Asp Thr
        130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
                180                 185                 190

Arg Glu Phe Arg Gly Glu His Arg Ile Gly Gly Ile Lys Leu Arg His
            195                 200                 205

Gln Gln Trp Ser Leu Val Met Glu Ser Val Val Pro Ser Asp Arg Gly
        210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
                260                 265                 270

Phe His Cys Lys Val Tyr Ser Asp Ala Gln Pro His Ile Gln Trp Leu
            275                 280                 285

Lys His Val Glu Val Asn Gly Ser Lys Val Gly Pro Asp Gly Thr Pro
        290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
                340                 345                 350

Trp Leu Val Val Leu Pro Ala Glu Glu Glu Leu Val Glu Ala Asp Glu
            355                 360                 365

Ala Gly Ser Val Tyr Ala Gly Ile Leu Ser Tyr Gly Val Gly Phe Phe
        370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
                420                 425                 430

Ser Asn Thr Pro Leu Val Arg Ile Ala Arg Leu Ser Ser Gly Glu Gly
            435                 440                 445
```

-continued

```
Pro Thr Leu Ala Asn Val Ser Glu Leu Glu Leu Pro Ala Asp Pro Lys
    450                 455                 460
Trp Glu Leu Ser Arg Ala Arg Leu Thr Leu Gly Lys Pro Leu Gly Glu
465                 470                 475                 480
Gly Cys Phe Gly Gln Val Val Met Ala Glu Ala Ile Gly Ile Asp Lys
                485                 490                 495
Asp Arg Ala Ala Lys Pro Val Thr Val Ala Val Lys Met Leu Lys Asp
                500                 505                 510
Asp Ala Thr Asp Lys Asp Leu Ser Asp Leu Val Ser Glu Met Glu Met
                515                 520                 525
Met Lys Met Ile Gly Lys His Lys Asn Ile Ile Asn Leu Leu Gly Ala
    530                 535                 540
Cys Thr Gln Gly Gly Pro Leu Tyr Val Leu Val Glu Tyr Ala Ala Lys
545                 550                 555                 560
Gly Asn Leu Arg Glu Phe Leu Arg Ala Arg Arg Pro Pro Gly Leu Asp
                565                 570                 575
Tyr Ser Phe Asp Thr Cys Lys Pro Pro Glu Glu Gln Leu Thr Phe Lys
                580                 585                 590
Asp Leu Val Ser Cys Ala Tyr Gln Val Ala Arg Gly Met Glu Tyr Leu
                595                 600                 605
Ala Ser Gln Lys Cys Ile His Arg Asp Leu Ala Ala Arg Asn Val Leu
    610                 615                 620
Val Thr Glu Asp Asn Val Met Lys Ile Ala Asp Phe Gly Leu Ala Arg
625                 630                 635                 640
Asp Val His Asn Leu Asp Tyr Tyr Lys Lys Thr Thr Asn Gly Arg Leu
                645                 650                 655
Pro Val Lys Trp Met Ala Pro Glu Ala Leu Phe Asp Arg Val Tyr Thr
                660                 665                 670
His Gln Ser Asp Val Trp Ser Phe Gly Val Leu Leu Trp Glu Ile Phe
                675                 680                 685
Thr Leu Gly Gly Ser Pro Tyr Pro Gly Ile Pro Val Glu Glu Leu Phe
    690                 695                 700
Lys Leu Leu Lys Glu Gly His Arg Met Asp Lys Pro Ala Asn Cys Thr
705                 710                 715                 720
His Asp Leu Tyr Met Ile Met Arg Glu Cys Trp His Ala Ala Pro Ser
                725                 730                 735
Gln Arg Pro Thr Phe Lys Gln Leu Val Glu Asp Leu Asp Arg Val Leu
                740                 745                 750
Thr Val Thr Ser Thr Asp Glu Tyr Leu Asp Leu Ser Ala Pro Phe Glu
                755                 760                 765
Gln Tyr Ser Pro Gly Gly Gln Asp Thr Pro Ser Ser Ser Ser Ser Gly
    770                 775                 780
Asp Asp Ser Val Phe Ala His Asp Leu Leu Pro Pro Ala Pro Pro Ser
785                 790                 795                 800
Ser Gly Gly Ser Arg Thr
                805
```

<210> SEQ ID NO 23
<211> LENGTH: 2463
<212> TYPE: DNA
<213> ORGANISM: Homo sapiens

<400> SEQUENCE: 23
atgtggagct ggaagtgcct cctcttctgg gctgtgctgg tcacagccac actctgcacc    60

```
gctaggccgt ccccgacctt gcctgaacaa gcccagccct ggggagcccc tgtggaagtg    120
gagtccttcc tggtccaccc cggtgacctg ctgcagcttc gctgtcggct gcgggacgat    180
gtgcagagca tcaactggct gcgggacggg gtgcagctgg cggaaagcaa ccgcacccgc    240
atcacagggg aggaggtgga ggtgcaggac tccgtgcccg cagactccgg cctctatgct    300
tgcgtaacca gcagcccctc gggcagtgac accacctact tctccgtcaa tgtttcagat    360
gctctcccct cctcggagga tgatgatgat gatgatgact cctcttcaga ggagaaagaa    420
acagataaca ccaaaccaaa ccccgtagct ccatattgga catccccaga aaagatggaa    480
aagaaattgc atgcagtgcc ggctgccaag acagtgaagt tcaaatgccc ttccagtggg    540
accccaaacc ccacactgcg ctggttgaaa aatggcaaag aattcaaacc tgaccacaga    600
attggaggct acaaggtccg ttatgccacc tggagcatca taatggactc tgtggtgccc    660
tctgacaagg gcaactacac ctgcattgtg agaatgagt acggcagcat caaccacaca    720
taccagctgg atgtcgtgga gcggtcccct caccggccca tcctgcaagc agggttgccc    780
gccaacaaaa cagtggccct gggtagcaac gtggagttca tgtgtaaggt gtacagtgac    840
ccgcagccgc acatccagtg ctaaagcac atcgaggtga atgggagcaa gattggccca    900
gacaacctgc cttatgtcca gatcttgaag actgctggag ttaataccac cgacaaagag    960
atggaggtgc ttcacttaag aaatgtctcc tttgaggacg caggggagta cacgtgcttg    1020
gcgggtaact ctatcggact ctcccatcac tctgcatggt tgaccgttct ggaagccctg    1080
gaagagaggc cggcagtgat gacctcgccc ctgtacctgg agatcatcat ctattgcaca    1140
ggggccttcc tcatctcctg catggtgggg tcggtcatcg tctacaagat gaagagtggt    1200
accaagaaga gtgacttcca cagccagatg gctgtgcaca gctggccaa gagcatccct    1260 ctgcgcagac aggtaacagt gtctgctgac tccagtgcat ccatgaactc tggggttctt    1320
ctggttcggc catcacggct ctcctccagt gggactccca tgctagcagg ggtctctgag    1380
tatgagcttc ccaagaccc tcgctgggag ctgcctcggg acagactggt cttaggcaaa    1440
cccctgggag agggctgctt tgggcaggtg gtgttggcag aggctatcgg gctggacaag    1500
gacaaaccca accgtgtgac caaagtggct gtgaagatgt tgaagtcgga cgcaacagag    1560
aaagacttgt cagacctgat ctcagaaatg gagatgatga gatgatcgg gaagcataag    1620 aatatcatca acctgctggg ggcctgcacg caggatggtc ccttgtatgt catcgtggag    1680
tatgcctcca agggcaacct gcgggagtac ctgcaggccc ggaggccccc agggctggaa    1740
tactgctaca ccccagcca aacccagag gagcagctct cctccaagga cctggtgtcc    1800
tgcgcctacc aggtggcccg aggcatggag tatctggcct ccaagaagtg catacaccga    1860
gacctggcag ccaggaatgt cctggtgaca gaggacaatg tgatgaagat agcagacttt    1920
ggcctcgcac gggacattca ccacatcgac tactataaaa agacaaccaa cggccgactg    1980
cctgtgaagt ggatggcacc cgaggcatta tttgaccgga tctacaccca ccagagtgat    2040
gtgtggtctt tcggggtgct cctgtgggag atcttcactc tgggcggctc cccataccc    2100 ggtgtgcctg tggaggaact tttcaagctg ctgaaggagg tcaccgcat ggacaagccc    2160 agtaactgca ccaacgagct gtacatgatg atgcgggact gctggcatgc agtgccctca    2220
cagagaccca ccttcaagca gctggtggaa gacctggacc gcatcgtggc cttgacctcc    2280
aaccaggagt acctggacct gtccatgccc ctggaccagt actccccag ctttcccgac    2340 acccggagct ctacgtgctc ctcagggag gattccgtct tctctcatga gccgctgccc    2400
gaggagccct gcctgccccg acacccagcc cagcttgcca atggcggact caaacgccgc    2460
``` tga                                                                  2463

<210> SEQ ID NO 24
<211> LENGTH: 2421
<212> TYPE: DNA
<213> ORGANISM: Homo sapiens

<400> SEQUENCE: 24

```
atgggcgccc ctgcctgcgc cctcgcgctc tgcgtggccg tggccatcgt ggccggcgcc    60
tcctcggagt ccttggggac ggagcagcgc gtcgtggggc gagcggcaga agtcccgggc   120
ccagagcccg ccagcaggac gcagttggtc ttcggcagcg gggatgctgt ggagctgagc   180
tgtccccgc ccggggtgg tcccatgggg cccactgtct gggtcaagga tggcacaggg   240
ctggtgccct cggagcgtgt cctggtgggg cccagcggc tgcaggtgct gaatgcctcc   300
cacgaggact ccggggccta cagctgccgg cagcggctca cgcagcgcgt actgtgccac   360
ttcagtgtgc gggtgacaga cgctccatcc tcgggagatg acgaagacgg ggaggacgag   420
gctgaggaca caggtgtgga cacaggggcc ccttactgga cacggcccga gcggatggac   480
aagaagctgc tggccgtgcc ggccgccaac accgtccgct ccgctgccc agccgctggc   540
aaccccactc cctccatctc ctggctgaag aacggcaggg agttccgcgg cgagcaccgc   600
attggaggca tcaagctgcg gcatcagcag tggagcctgg tcatggaaag cgtggtgccc   660
tcggaccgcg gcaactacac ctgcgtcgtg gagaacaagt ttggcagcat ccggcagacg   720
tacacgctgg acgtgctgga cgctccccg caccggccca tcctgcaggc ggggctgccg   780
gccaaccaga cggcggtgct gggcagcgac gtggagttcc actgcaaggt gtacagtgac   840
gcacagcccc acatccagtg gctcaagcac gtggaggtga atggcagcaa ggtgggcccg   900
gacggcacac cctacgttac cgtgctcaag acggcgggcg ctaacaccac cgacaaggag   960
ctagaggttc tctccttgca caacgtcacc tttgaggacg ccggggagta cacctgcctg  1020
gcgggcaatt ctattgggtt ttctcatcac tctgcgtggc tggtggtgct gccagccgag  1080
gaggagctgg tggaggctga cgaggcgggc agtgtgtatg caggcatcct cagctacggg  1140
gtgggcttct tcctgttcat cctggtggtg gcggctgtga cgctctgccg cctgcgcagc  1200
cccccaagaa aaggcctggg ctcccccacc gtgcacaaga tctcccgctt cccgctcaag  1260
cgacaggtgt ccctggagtc caacgcgtcc atgagctcca acacaccact ggtgcgcatc  1320
gcaaggctgt cctcagggga gggccccacg ctggccaatg tctccgagct cgagctgcct  1380
gccgacccca atgggagct gtctcgggcc cggctgaccc tggcaagcc ccttggggag  1440
ggctgcttcg ccaggtggt catggcggag ccatcggca ttgacaagga ccgggccgcc  1500
aagcctgtca ccgtagccgt gaagatgctg aaagacgatg ccactgacaa ggacctgtcg  1560
gacctggtgt ctgagatgga gatgatgaag atgatcggga acacaaaaa catcatcaac  1620
ctgctgggcg cctgcacgca gggcgggccc ctgtacgtgc tggtgagta cgcggccaag  1680
ggtaacctgc gggagtttct gcgggcgcgg cggcccccgg gcctggacta ctccttcgac  1740
acctgcaagc cgcccgagga gcagctcacc ttcaaggacc tggtgtcctg tgcctaccag  1800
gtggcccggg gcatggagta cttggcctcc cagaagtgca tccacaggga cctggctgcc  1860
cgcaatgtgc tggtgaccga ggacaacgtg atgaagatcg cagacttcgg gctggcccgg  1920
gacgtgcaca acctcgacta ctacaagaag acaaccaacg gccggctgcc cgtgaagtgg  1980
atggcgcctg aggccttgtt tgaccgagtc tacactcacc agagtgacgt ctggtccttt  2040
```

-continued

```
ggggtcctgc tctgggagat cttcacgctg gggggctccc cgtaccccgg catccctgtg   2100
gaggagctct tcaagctgct gaaggagggc caccgcatgg acaagcccgc caactgcaca   2160
cacgacctgt acatgatcat gcgggagtgc tggcatgccg cgccctccca gaggcccacc   2220
ttcaagcagc tggtggagga cctggaccgt gtccttaccg tgacgtccac cgacgagtac   2280
ctggacctgt cggcgccttt cgagcagtac tccccgggtg gccaggacac ccccagctcc   2340
agctcctcag gggacgactc cgtgtttgcc cacgacctgc tgccccggc cccacccagc    2400 agtgggggct cgcggacgtg a                                              2421
```

<210> SEQ ID NO 25
<211> LENGTH: 820
<212> TYPE: PRT
<213> ORGANISM: Homo sapiens

<400> SEQUENCE: 25

```
Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
        50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
    210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
        275                 280                 285

Lys His Ile Glu Val Asn Gly Ser Lys Ile Gly Pro Asp Asn Leu Pro
    290                 295                 300
```

```
Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
            325                 330                 335

Tyr Thr Cys Leu Ala Gly Asn Ser Ile Gly Leu Ser His His Ser Ala
                340                 345                 350

Trp Leu Thr Val Leu Glu Ala Leu Glu Glu Arg Pro Ala Val Met Thr
            355                 360                 365

Ser Pro Leu Tyr Leu Glu Ile Ile Tyr Cys Thr Gly Ala Phe Leu
    370                 375                 380

Ile Ser Cys Met Val Gly Ser Val Ile Val Tyr Lys Met Lys Ser Gly
385                 390                 395                 400

Thr Lys Lys Ser Asp Phe His Ser Gln Met Ala Val His Lys Leu Ala
                405                 410                 415

Lys Ser Ile Pro Leu Arg Arg Gln Val Thr Val Ser Ala Asp Ser Ser
                420                 425                 430

Ala Ser Met Asn Ser Gly Val Leu Leu Val Arg Pro Ser Arg Leu Ser
            435                 440                 445

Ser Ser Gly Thr Pro Met Leu Ala Gly Val Ser Glu Tyr Glu Leu Pro
    450                 455                 460

Glu Asp Pro Arg Trp Glu Leu Pro Arg Asp Arg Leu Val Leu Gly Lys
465                 470                 475                 480

Pro Leu Gly Glu Gly Cys Phe Gly Gln Val Val Leu Ala Glu Ala Ile
                485                 490                 495

Gly Leu Asp Lys Asp Lys Pro Asn Arg Val Thr Lys Val Ala Val Lys
                500                 505                 510

Met Leu Lys Ser Asp Ala Thr Glu Lys Asp Leu Ser Asp Leu Ile Ser
            515                 520                 525

Glu Met Glu Met Met Lys Met Ile Gly Lys His Lys Asn Ile Ile Asn
530                 535                 540

Leu Leu Gly Ala Cys Thr Gln Asp Gly Pro Leu Tyr Val Ile Phe Glu
545                 550                 555                 560

Tyr Ala Ser Lys Gly Asn Leu Arg Glu Tyr Leu Gln Ala Arg Arg Pro
                565                 570                 575

Pro Gly Leu Glu Tyr Cys Tyr Asn Pro Ser His Asn Pro Glu Glu Gln
            580                 585                 590

Leu Ser Ser Lys Asp Leu Val Ser Cys Ala Tyr Gln Val Ala Arg Gly
            595                 600                 605

Met Glu Tyr Leu Ala Ser Lys Lys Cys Ile His Arg Asp Leu Ala Ala
    610                 615                 620

Arg Asn Val Leu Val Thr Glu Asp Asn Val Met Lys Ile Ala Asp Phe
625                 630                 635                 640

Gly Leu Ala Arg Asp Ile His His Ile Asp Tyr Tyr Lys Lys Thr Thr
                645                 650                 655

Asn Gly Arg Leu Pro Val Lys Trp Met Ala Pro Glu Ala Leu Phe Asp
            660                 665                 670

Arg Ile Tyr Thr His Gln Ser Asp Val Trp Ser Phe Gly Val Leu Leu
    675                 680                 685

Trp Glu Ile Phe Thr Leu Gly Gly Ser Pro Tyr Pro Gly Val Pro Val
    690                 695                 700

Glu Glu Leu Phe Lys Leu Leu Lys Glu Gly His Arg Met Asp Lys Pro
705                 710                 715                 720

Ser Asn Cys Thr Asn Glu Leu Tyr Met Met Met Arg Asp Cys Trp His
```

-continued

```
                725                 730                 735
Ala Val Pro Ser Gln Arg Pro Thr Phe Lys Gln Leu Val Glu Asp Leu
            740                 745                 750

Asp Arg Ile Val Ala Leu Thr Ser Asn Gln Glu Tyr Leu Asp Leu Ser
            755                 760                 765

Met Pro Leu Asp Gln Tyr Ser Pro Ser Phe Pro Asp Thr Arg Ser Ser
770                 775                 780

Thr Cys Ser Ser Gly Glu Asp Ser Val Phe Ser His Glu Pro Leu Pro
785                 790                 795                 800

Glu Glu Pro Cys Leu Pro Arg His Pro Ala Gln Leu Ala Asn Gly Gly
                805                 810                 815

Leu Lys Arg Arg
            820
```

<210> SEQ ID NO 26
<211> LENGTH: 820
<212> TYPE: PRT
<213> ORGANISM: Homo sapiens

<400> SEQUENCE: 26

```
Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
    210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
            260                 265                 270
```

-continued

```
Phe Met Cys Lys Val Tyr Ser Asp Pro Gln Pro His Ile Gln Trp Leu
            275                 280                 285
Lys His Ile Glu Val Asn Gly Ser Lys Ile Gly Pro Asp Asn Leu Pro
        290                 295                 300
Tyr Val Gln Ile Leu Lys Thr Ala Gly Val Asn Thr Thr Asp Lys Glu
305                 310                 315                 320
Met Glu Val Leu His Leu Arg Asn Val Ser Phe Glu Asp Ala Gly Glu
                325                 330                 335
Tyr Thr Cys Leu Ala Gly Asn Ser Ile Gly Leu Ser His His Ser Ala
            340                 345                 350
Trp Leu Thr Val Leu Glu Ala Leu Glu Glu Arg Pro Ala Val Met Thr
        355                 360                 365
Ser Pro Leu Tyr Leu Glu Ile Ile Ile Tyr Cys Thr Gly Ala Phe Leu
370                 375                 380
Ile Ser Cys Met Val Gly Ser Val Ile Val Tyr Lys Met Lys Ser Gly
385                 390                 395                 400
Thr Lys Lys Ser Asp Phe His Ser Gln Met Ala Val His Lys Leu Ala
                405                 410                 415
Lys Ser Ile Pro Leu Arg Arg Gln Val Thr Val Ser Ala Asp Ser Ser
            420                 425                 430
Ala Ser Met Asn Ser Gly Val Leu Leu Val Arg Pro Ser Arg Leu Ser
        435                 440                 445
Ser Ser Gly Thr Pro Met Leu Ala Gly Val Ser Glu Tyr Glu Leu Pro
450                 455                 460
Glu Asp Pro Arg Trp Glu Leu Pro Arg Asp Arg Leu Val Leu Gly Lys
465                 470                 475                 480
Pro Leu Gly Glu Gly Cys Phe Gly Gln Val Val Leu Ala Glu Ala Ile
                485                 490                 495
Gly Leu Asp Lys Asp Lys Pro Asn Arg Val Thr Lys Val Ala Val Lys
            500                 505                 510
Met Leu Lys Ser Asp Ala Thr Glu Lys Asp Leu Ser Asp Leu Ile Ser
        515                 520                 525
Glu Met Glu Met Met Lys Met Ile Gly Lys His Lys Asn Ile Ile Asn
530                 535                 540
Leu Leu Gly Ala Cys Thr Gln Asp Gly Pro Leu Tyr Leu Ile Val Glu
545                 550                 555                 560
Tyr Ala Ser Lys Gly Asn Leu Arg Glu Tyr Leu Gln Ala Arg Arg Pro
                565                 570                 575
Pro Gly Leu Glu Tyr Cys Tyr Asn Pro Ser His Asn Pro Glu Glu Gln
            580                 585                 590
Leu Ser Ser Lys Asp Leu Val Ser Cys Ala Tyr Gln Val Ala Arg Gly
        595                 600                 605
Met Glu Tyr Leu Ala Ser Lys Lys Cys Ile His Arg Asp Leu Ala Ala
610                 615                 620
Arg Asn Val Leu Val Thr Glu Asp Asn Val Met Lys Ile Ala Asp Phe
625                 630                 635                 640
Gly Leu Ala Arg Asp Ile His His Ile Asp Tyr Tyr Lys Lys Thr Thr
                645                 650                 655
Asn Gly Arg Leu Pro Val Lys Trp Met Ala Pro Glu Ala Leu Phe Asp
            660                 665                 670
Arg Ile Tyr Thr His Gln Ser Asp Val Trp Ser Phe Gly Val Leu Leu
        675                 680                 685
Trp Glu Ile Phe Thr Leu Gly Gly Ser Pro Tyr Pro Gly Val Pro Val
```

```
              690                 695                 700
Glu Glu Leu Phe Lys Leu Leu Lys Glu Gly His Arg Met Asp Lys Pro
705                 710                 715                 720

Ser Asn Cys Thr Asn Glu Leu Tyr Met Met Met Arg Asp Cys Trp His
                725                 730                 735

Ala Val Pro Ser Gln Arg Pro Thr Phe Lys Gln Leu Val Glu Asp Leu
                740                 745                 750

Asp Arg Ile Val Ala Leu Thr Ser Asn Gln Glu Tyr Leu Asp Leu Ser
                755                 760                 765

Met Pro Leu Asp Gln Tyr Ser Pro Ser Phe Pro Asp Thr Arg Ser Ser
                770                 775                 780

Thr Cys Ser Ser Gly Glu Asp Ser Val Phe Ser His Glu Pro Leu Pro
785                 790                 795                 800

Glu Glu Pro Cys Leu Pro Arg His Pro Ala Gln Leu Ala Asn Gly Gly
                805                 810                 815

Leu Lys Arg Arg
                820

<210> SEQ ID NO 27
<211> LENGTH: 806
<212> TYPE: PRT
<213> ORGANISM: Homo sapiens

<400> SEQUENCE: 27

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
        50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
                100                 105                 110

Leu Thr Gln Arg Val Leu Cys His Phe Ser Val Arg Val Thr Asp Ala
            115                 120                 125

Pro Ser Ser Gly Asp Asp Glu Asp Gly Glu Asp Glu Ala Glu Asp Thr
        130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
                180                 185                 190

Arg Glu Phe Arg Gly Glu His Arg Ile Gly Gly Ile Lys Leu Arg His
            195                 200                 205

Gln Gln Trp Ser Leu Val Met Glu Ser Val Val Pro Ser Asp Arg Gly
        210                 215                 220

Asn Tyr Thr Cys Val Val Glu Asn Lys Phe Gly Ser Ile Arg Gln Thr
225                 230                 235                 240
```

```
Tyr Thr Leu Asp Val Leu Glu Arg Ser Pro His Arg Pro Ile Leu Gln
            245                 250                 255
Ala Gly Leu Pro Ala Asn Gln Thr Ala Val Leu Gly Ser Asp Val Glu
        260                 265                 270
Phe His Cys Lys Val Tyr Ser Asp Ala Gln Pro His Ile Gln Trp Leu
    275                 280                 285
Lys His Val Glu Val Asn Gly Ser Lys Val Gly Pro Asp Gly Thr Pro
290                 295                 300
Tyr Val Thr Val Leu Lys Thr Ala Gly Ala Asn Thr Thr Asp Lys Glu
305                 310                 315                 320
Leu Glu Val Leu Ser Leu His Asn Val Thr Phe Glu Asp Ala Gly Glu
                325                 330                 335
Tyr Thr Cys Leu Ala Gly Asn Ser Ile Gly Phe Ser His His Ser Ala
            340                 345                 350
Trp Leu Val Val Leu Pro Ala Glu Glu Leu Val Glu Ala Asp Glu
        355                 360                 365
Ala Gly Ser Val Tyr Ala Gly Ile Leu Ser Tyr Gly Val Gly Phe Phe
    370                 375                 380
Leu Phe Ile Leu Val Val Ala Ala Val Thr Leu Cys Arg Leu Arg Ser
385                 390                 395                 400
Pro Pro Lys Lys Gly Leu Gly Ser Pro Thr Val His Lys Ile Ser Arg
                405                 410                 415
Phe Pro Leu Lys Arg Gln Val Ser Leu Glu Ser Asn Ala Ser Met Ser
            420                 425                 430
Ser Asn Thr Pro Leu Val Arg Ile Ala Arg Leu Ser Ser Gly Glu Gly
        435                 440                 445
Pro Thr Leu Ala Asn Val Ser Glu Leu Glu Leu Pro Ala Asp Pro Lys
    450                 455                 460
Trp Glu Leu Ser Arg Ala Arg Leu Thr Leu Gly Lys Pro Leu Gly Glu
465                 470                 475                 480
Gly Cys Phe Gly Gln Val Val Met Ala Glu Ala Ile Gly Ile Asp Lys
                485                 490                 495
Asp Arg Ala Ala Lys Pro Val Thr Val Ala Val Lys Met Leu Lys Asp
            500                 505                 510
Asp Ala Thr Asp Lys Asp Leu Ser Asp Leu Val Ser Glu Met Glu Met
        515                 520                 525
Met Lys Met Ile Gly Lys His Lys Asn Ile Ile Asn Leu Leu Gly Ala
    530                 535                 540
Cys Thr Gln Gly Gly Pro Leu Tyr Val Leu Phe Glu Tyr Ala Ala Lys
545                 550                 555                 560
Gly Asn Leu Arg Glu Phe Leu Arg Ala Arg Arg Pro Pro Gly Leu Asp
                565                 570                 575
Tyr Ser Phe Asp Thr Cys Lys Pro Pro Glu Glu Gln Leu Thr Phe Lys
            580                 585                 590
Asp Leu Val Ser Cys Ala Tyr Gln Val Ala Arg Gly Met Glu Tyr Leu
        595                 600                 605
Ala Ser Gln Lys Cys Ile His Arg Asp Leu Ala Ala Arg Asn Val Leu
    610                 615                 620
Val Thr Glu Asp Asn Val Met Lys Ile Ala Asp Phe Gly Leu Ala Arg
625                 630                 635                 640
Asp Val His Asn Leu Asp Tyr Tyr Lys Lys Thr Thr Asn Gly Arg Leu
                645                 650                 655
Pro Val Lys Trp Met Ala Pro Glu Ala Leu Phe Asp Arg Val Tyr Thr
```

```
                    660                 665                 670
His Gln Ser Asp Val Trp Ser Phe Gly Val Leu Leu Trp Glu Ile Phe
                675                 680                 685

Thr Leu Gly Gly Ser Pro Tyr Pro Gly Ile Pro Val Glu Glu Leu Phe
            690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
            755                 760                 765

Gln Tyr Ser Pro Gly Gly Gln Asp Thr Pro Ser Ser Ser Ser Ser Gly
            770                 775                 780

Asp Asp Ser Val Phe Ala His Asp Leu Leu Pro Pro Ala Pro Pro Ser
785                 790                 795                 800

Ser Gly Gly Ser Arg Thr
            805

<210> SEQ ID NO 28
<211> LENGTH: 806
<212> TYPE: PRT
<213> ORGANISM: Homo sapiens

<400> SEQUENCE: 28

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220
```

```
Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
            245                 250                 255

Ala Gly Leu Pro Ala Asn Gln Thr Ala Val Leu Gly Ser Asp Val Glu
        260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Leu Val Glu Ala Asp Glu
        355                 360                 365

Ala Gly Ser Val Tyr Ala Gly Ile Leu Ser Tyr Gly Val Gly Phe Phe
    370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
        435                 440                 445

Pro Thr Leu Ala Asn Val Ser Glu Leu Glu Leu Pro Ala Asp Pro Lys
    450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
                485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
        515                 520                 525

Met Lys Met Ile Gly Lys His Lys Asn Ile Ile Asn Leu Leu Gly Ala
    530                 535                 540

Cys Thr Gln Gly Gly Pro Leu Tyr Leu Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
        595                 600                 605

Ala Ser Gln Lys Cys Ile His Arg Asp Leu Ala Ala Arg Asn Val Leu
    610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
```

```
                      645                 650                 655
Pro Val Lys Trp Met Ala Pro Glu Ala Leu Phe Asp Arg Val Tyr Thr
                660                 665                 670

His Gln Ser Asp Val Trp Ser Phe Gly Val Leu Leu Trp Glu Ile Phe
            675                 680                 685

Thr Leu Gly Gly Ser Pro Tyr Pro Gly Ile Pro Val Glu Glu Leu Phe
        690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
        755                 760                 765

Gln Tyr Ser Pro Gly Gly Gln Asp Thr Pro Ser Ser Ser Ser Ser Gly
    770                 775                 780

Asp Asp Ser Val Phe Ala His Asp Leu Leu Pro Pro Ala Pro Pro Ser
785                 790                 795                 800

Ser Gly Gly Ser Arg Thr
                805

<210> SEQ ID NO 29
<211> LENGTH: 822
<212> TYPE: PRT
<213> ORGANISM: Homo sapiens

<400> SEQUENCE: 29

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205
```

```
Val Arg Asn Gln His Trp Ser Leu Ile Met Glu Ser Val Val Pro Ser
210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
            245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
            275                 280                 285

Gln Trp Ile Lys His Val Glu Lys Asn Gly Ser Lys Tyr Gly Pro Asp
290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
            325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Gly Arg Glu Lys
            355                 360                 365

Glu Ile Thr Ala Ser Pro Asp Tyr Leu Glu Ile Ala Ile Tyr Cys Ile
            370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
            405                 410                 415

His Lys Leu Thr Lys Arg Ile Pro Leu Arg Arg Gln Val Thr Val Ser
            420                 425                 430

Ala Glu Ser Ser Ser Ser Met Asn Ser Asn Thr Pro Leu Val Arg Ile
            435                 440                 445

Thr Thr Arg Leu Ser Ser Thr Ala Asp Thr Pro Met Leu Ala Gly Val
450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
            485                 490                 495

Val Met Ala Glu Ala Val Gly Ile Asp Lys Asp Lys Pro Lys Glu Ala
            500                 505                 510

Val Thr Val Ala Val Lys Met Leu Lys Asp Asp Ala Thr Glu Lys Asp
            515                 520                 525

Leu Ser Asp Leu Val Ser Glu Met Glu Met Met Lys Met Ile Gly Lys
530                 535                 540

His Lys Asn Ile Ile Asn Leu Leu Gly Ala Cys Thr Gln Asp Gly Pro
545                 550                 555                 560

Leu Tyr Val Ile Phe Glu Tyr Ala Ser Lys Gly Asn Leu Arg Glu Tyr
            565                 570                 575

Leu Arg Ala Arg Arg Pro Pro Gly Met Glu Tyr Ser Tyr Asp Ile Asn
            580                 585                 590

Arg Val Pro Glu Glu Gln Met Thr Phe Lys Asp Leu Val Ser Cys Thr
            595                 600                 605

Tyr Gln Leu Ala Arg Gly Met Glu Tyr Leu Ala Ser Gln Lys Cys Ile
            610                 615                 620

His Arg Asp Leu Ala Ala Arg Asn Val Leu Val Thr Glu Asn Asn Val
```

```
              625                 630                 635                 640
Met Lys Ile Ala Asp Phe Gly Leu Ala Arg Asp Ile Asn Asn Ile Asp
                    645                 650                 655

Tyr Tyr Lys Lys Thr Thr Asn Gly Arg Leu Pro Val Lys Trp Met Ala
                    660                 665                 670

Pro Glu Ala Leu Phe Asp Arg Val Tyr Thr His Gln Ser Asp Val Trp
                675                 680                 685

Ser Phe Gly Val Leu Met Trp Glu Ile Phe Thr Leu Gly Gly Ser Pro
            690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                    725                 730                 735

Met Arg Asp Cys Trp His Ala Val Pro Ser Gln Arg Pro Thr Phe Lys
                740                 745                 750

Gln Leu Val Glu Asp Leu Asp Arg Ile Leu Thr Leu Thr Thr Asn Glu
                755                 760                 765

Glu Tyr Leu Asp Leu Ser Gln Pro Leu Glu Gln Tyr Ser Pro Ser Tyr
770                 775                 780

Pro Asp Thr Arg Ser Ser Cys Ser Ser Gly Asp Asp Ser Val Phe Ser
785                 790                 795                 800

Pro Asp Pro Met Pro Tyr Glu Pro Cys Leu Pro Gln Tyr Pro His Ile
                805                 810                 815

Asn Gly Ser Val Lys Thr
                820

<210> SEQ ID NO 30
<211> LENGTH: 822
<212> TYPE: PRT
<213> ORGANISM: Homo sapiens

<400> SEQUENCE: 30

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                    85                  90                  95

Ala Thr Pro Arg Asp Ser Gly Leu Tyr Ala Cys Thr Ala Ser Arg Thr
                100                 105                 110

Val Asp Ser Glu Thr Trp Tyr Phe Met Val Asn Val Thr Asp Ala Ile
            115                 120                 125

Ser Ser Gly Asp Asp Glu Asp Asp Thr Asp Gly Ala Glu Asp Phe Val
        130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175
```

```
Phe Arg Cys Pro Ala Gly Gly Asn Pro Met Pro Thr Met Arg Trp Leu
            180                 185                 190
Lys Asn Gly Lys Glu Phe Lys Gln Glu His Arg Ile Gly Gly Tyr Lys
        195                 200                 205
Val Arg Asn Gln His Trp Ser Leu Ile Met Glu Ser Val Val Pro Ser
    210                 215                 220
Asp Lys Gly Asn Tyr Thr Cys Val Val Glu Asn Glu Tyr Gly Ser Ile
225                 230                 235                 240
Asn His Thr Tyr His Leu Asp Val Val Glu Arg Ser Pro His Arg Pro
                245                 250                 255
Ile Leu Gln Ala Gly Leu Pro Ala Asn Ala Ser Thr Val Val Gly Gly
            260                 265                 270
Asp Val Glu Phe Val Cys Lys Val Tyr Ser Asp Ala Gln Pro His Ile
        275                 280                 285
Gln Trp Ile Lys His Val Glu Lys Asn Gly Ser Lys Tyr Gly Pro Asp
    290                 295                 300
Gly Leu Pro Tyr Leu Lys Val Leu Lys His Ser Gly Ile Asn Ser Ser
305                 310                 315                 320
Asn Ala Glu Val Leu Ala Leu Phe Asn Val Thr Glu Ala Asp Ala Gly
                325                 330                 335
Glu Tyr Ile Cys Lys Val Ser Asn Tyr Ile Gly Gln Ala Asn Gln Ser
            340                 345                 350
Ala Trp Leu Thr Val Leu Pro Lys Gln Gln Ala Pro Gly Arg Glu Lys
        355                 360                 365
Glu Ile Thr Ala Ser Pro Asp Tyr Leu Glu Ile Ala Ile Tyr Cys Ile
    370                 375                 380
Gly Val Phe Leu Ile Ala Cys Met Val Val Thr Val Ile Leu Cys Arg
385                 390                 395                 400
Met Lys Asn Thr Thr Lys Lys Pro Asp Phe Ser Ser Gln Pro Ala Val
                405                 410                 415
His Lys Leu Thr Lys Arg Ile Pro Leu Arg Arg Gln Val Thr Val Ser
            420                 425                 430
Ala Glu Ser Ser Ser Ser Met Asn Ser Asn Thr Pro Leu Val Arg Ile
        435                 440                 445
Thr Thr Arg Leu Ser Ser Thr Ala Asp Thr Pro Met Leu Ala Gly Val
    450                 455                 460
Ser Glu Tyr Glu Leu Pro Glu Asp Pro Lys Trp Glu Phe Pro Arg Asp
465                 470                 475                 480
Lys Leu Thr Leu Gly Lys Pro Leu Gly Glu Gly Cys Phe Gly Gln Val
                485                 490                 495
Val Met Ala Glu Ala Val Gly Ile Asp Lys Asp Lys Pro Lys Glu Ala
            500                 505                 510
Val Thr Val Ala Val Lys Met Leu Lys Asp Asp Ala Thr Glu Lys Asp
        515                 520                 525
Leu Ser Asp Leu Val Ser Glu Met Glu Met Met Lys Met Ile Gly Lys
    530                 535                 540
His Lys Asn Ile Ile Asn Leu Leu Gly Ala Cys Thr Gln Asp Gly Pro
545                 550                 555                 560
Leu Tyr Leu Ile Val Glu Tyr Ala Ser Lys Gly Asn Leu Arg Glu Tyr
                565                 570                 575
Leu Arg Ala Arg Arg Pro Pro Gly Met Glu Tyr Ser Tyr Asp Ile Asn
            580                 585                 590
Arg Val Pro Glu Glu Gln Met Thr Phe Lys Asp Leu Val Ser Cys Thr
```

```
                        595                 600                 605
Tyr Gln Leu Ala Arg Gly Met Glu Tyr Leu Ala Ser Gln Lys Cys Ile
            610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
            675                 680                 685

Ser Phe Gly Val Leu Met Trp Glu Ile Phe Thr Leu Gly Gly Ser Pro
            690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
            755                 760                 765

Glu Tyr Leu Asp Leu Ser Gln Pro Leu Glu Gln Tyr Ser Pro Ser Tyr
            770                 775                 780

Pro Asp Thr Arg Ser Ser Cys Ser Ser Gly Asp Asp Ser Val Phe Ser
785                 790                 795                 800

Pro Asp Pro Met Pro Tyr Glu Pro Cys Leu Pro Gln Tyr Pro His Ile
                805                 810                 815

Asn Gly Ser Val Lys Thr
            820

<210> SEQ ID NO 31
<211> LENGTH: 511
<212> TYPE: PRT
<213> ORGANISM: Homo sapiens

<400> SEQUENCE: 31

Met Ser Arg Gly Pro Glu Glu Val Asn Arg Leu Thr Glu Ser Thr Tyr
1               5                   10                  15

Arg Asn Val Met Glu Gln Phe Asn Pro Gly Leu Arg Asn Leu Ile Asn
            20                  25                  30

Leu Gly Lys Asn Tyr Glu Lys Ala Val Asn Ala Met Ile Leu Ala Gly
        35                  40                  45

Lys Ala Tyr Tyr Asp Gly Val Ala Lys Ile Gly Glu Ile Ala Thr Gly
    50                  55                  60

Ser Pro Val Ser Thr Glu Leu Gly His Val Leu Ile Glu Ile Ser Ser
65                  70                  75                  80

Thr His Lys Lys Leu Asn Glu Ser Leu Asp Glu Asn Phe Lys Lys Phe
                85                  90                  95

His Lys Glu Ile Ile His Glu Leu Glu Lys Lys Ile Glu Leu Asp Val
            100                 105                 110

Lys Tyr Met Asn Ala Thr Leu Lys Arg Tyr Gln Thr Glu His Lys Asn
        115                 120                 125

Lys Leu Glu Ser Leu Glu Lys Ser Gln Ala Glu Leu Lys Lys Ile Arg
    130                 135                 140
```

-continued

```
Arg Lys Ser Gln Gly Ser Arg Asn Ala Leu Lys Tyr Glu His Lys Glu
145                 150                 155                 160

Ile Glu Tyr Val Glu Thr Val Thr Ser Arg Gln Ser Glu Ile Gln Lys
                165                 170                 175

Phe Ile Ala Asp Gly Cys Lys Glu Ala Leu Leu Glu Glu Lys Arg Arg
            180                 185                 190

Phe Cys Phe Leu Val Asp Lys His Cys Gly Phe Ala Asn His Ile His
        195                 200                 205

Tyr Tyr His Leu Gln Ser Ala Glu Leu Leu Asn Ser Lys Leu Pro Arg
210                 215                 220

Trp Gln Glu Thr Cys Val Asp Ala Ile Lys Val Pro Glu Lys Ile Met
225                 230                 235                 240

Asn Met Ile Glu Glu Ile Lys Thr Pro Ala Ser Thr Pro Val Ser Gly
                245                 250                 255

Thr Pro Gln Ala Ser Pro Met Ile Glu Arg Ser Asn Val Val Arg Lys
            260                 265                 270

Asp Tyr Asp Thr Leu Ser Lys Cys Ser Pro Lys Met Pro Pro Ala Pro
        275                 280                 285

Ser Gly Arg Ala Tyr Thr Ser Pro Leu Ile Asp Met Phe Asn Asn Pro
290                 295                 300

Ala Thr Ala Ala Pro Asn Ser Gln Arg Val Asn Asn Ser Thr Gly Thr
305                 310                 315                 320

Ser Glu Asp Pro Ser Leu Gln Arg Ser Val Ser Val Ala Thr Gly Leu
                325                 330                 335

Asn Met Met Lys Lys Gln Lys Val Lys Thr Ile Phe Pro His Thr Ala
            340                 345                 350

Gly Ser Asn Lys Thr Leu Leu Ser Phe Ala Gln Gly Asp Val Ile Thr
        355                 360                 365

Leu Leu Ile Pro Glu Glu Lys Asp Gly Trp Leu Tyr Gly Glu His Asp
370                 375                 380

Val Ser Lys Ala Arg Gly Trp Phe Pro Ser Ser Tyr Thr Lys Leu Leu
385                 390                 395                 400

Glu Glu Asn Glu Thr Glu Ala Val Thr Val Pro Thr Pro Ser Pro Thr
                405                 410                 415

Pro Val Arg Ser Ile Ser Thr Val Asn Leu Ser Glu Asn Ser Ser Val
            420                 425                 430

Val Ile Pro Pro Pro Asp Tyr Leu Glu Cys Leu Ser Met Gly Ala Ala
        435                 440                 445

Ala Asp Arg Arg Ala Asp Ser Ala Arg Thr Thr Ser Thr Phe Lys Ala
450                 455                 460

Pro Ala Ser Lys Pro Glu Thr Ala Ala Pro Asn Asp Ala Asn Gly Thr
465                 470                 475                 480

Ala Lys Pro Pro Phe Leu Ser Gly Glu Asn Pro Phe Ala Thr Val Lys
                485                 490                 495

Leu Arg Pro Thr Val Thr Asn Asp Arg Ser Ala Pro Ile Ile Arg
            500                 505                 510
```

<210> SEQ ID NO 32
<211> LENGTH: 838
<212> TYPE: PRT
<213> ORGANISM: Homo sapiens

<400> SEQUENCE: 32

```
Met Ser Leu Gln Val Leu Asn Asp Lys Asn Val Ser Asn Glu Lys Asn
1               5                   10                  15
```

```
Thr Glu Asn Cys Asp Phe Leu Phe Ser Pro Pro Val Thr Gly Arg
         20                  25                  30

Ser Ser Val Leu Arg Val Ser Gln Lys Glu Asn Val Pro Lys Asn
         35                  40                  45

Leu Ala Lys Ala Met Lys Val Thr Phe Gln Thr Pro Leu Arg Asp Pro
 50                  55                  60

Gln Thr His Arg Ile Leu Ser Pro Ser Met Ala Ser Lys Leu Glu Ala
 65                  70                  75                  80

Pro Phe Thr Gln Asp Asp Thr Leu Gly Leu Glu Asn Ser His Pro Val
             85                  90                  95

Trp Thr Gln Lys Glu Asn Gln Gln Leu Ile Lys Glu Val Asp Ala Lys
             100                 105                 110

Thr Thr His Gly Ile Leu Gln Lys Pro Val Glu Ala Asp Thr Asp Leu
         115                 120                 125

Leu Gly Asp Ala Ser Pro Ala Phe Gly Ser Gly Ser Ser Glu Ser
 130                 135                 140

Gly Pro Gly Ala Leu Ala Asp Leu Asp Cys Ser Ser Ser Gln Ser
145                  150                 155                 160

Pro Gly Ser Ser Glu Asn Gln Met Val Ser Pro Gly Lys Val Ser Gly
             165                 170                 175

Ser Pro Glu Gln Ala Val Glu Glu Asn Leu Ser Ser Tyr Ser Leu Asp
         180                 185                 190

Arg Arg Val Thr Pro Ala Ser Glu Thr Leu Glu Asp Pro Cys Arg Thr
         195                 200                 205

Glu Ser Gln His Lys Ala Glu Thr Pro His Gly Ala Glu Glu Glu Cys
         210                 215                 220

Lys Ala Glu Thr Pro His Gly Ala Glu Glu Cys Arg His Gly Gly
225                  230                 235                 240

Val Cys Ala Pro Ala Ala Val Ala Thr Ser Pro Pro Gly Ala Ile Pro
                 245                 250                 255

Lys Glu Ala Cys Gly Gly Ala Pro Leu Gln Gly Leu Pro Gly Glu Ala
             260                 265                 270

Leu Gly Cys Pro Ala Gly Val Gly Thr Pro Val Pro Ala Asp Gly Thr
         275                 280                 285

Gln Thr Leu Thr Cys Ala His Thr Ser Ala Pro Glu Ser Thr Ala Pro
 290                 295                 300

Thr Asn His Leu Val Ala Gly Arg Ala Met Thr Leu Ser Pro Gln Glu
305                  310                 315                 320

Glu Val Ala Ala Gly Gln Met Ala Ser Ser Arg Ser Gly Pro Val
                 325                 330                 335

Lys Leu Glu Phe Asp Val Ser Asp Gly Ala Thr Ser Lys Arg Ala Pro
             340                 345                 350

Pro Pro Arg Arg Leu Gly Glu Arg Ser Gly Leu Lys Pro Pro Leu Arg
         355                 360                 365

Lys Ala Ala Val Arg Gln Gln Lys Ala Pro Gln Glu Val Glu Glu Asp
         370                 375                 380

Asp Gly Arg Ser Gly Ala Gly Glu Asp Pro Pro Met Pro Ala Ser Arg
385                  390                 395                 400

Gly Ser Tyr His Leu Asp Trp Asp Lys Met Asp Asp Pro Asn Phe Ile
                 405                 410                 415

Pro Phe Gly Gly Asp Thr Lys Ser Gly Cys Ser Glu Ala Gln Pro Pro
             420                 425                 430
```

-continued

```
Glu Ser Pro Glu Thr Arg Leu Gly Gln Pro Ala Ala Glu Gln Leu His
            435                 440                 445
Ala Gly Pro Ala Thr Glu Glu Pro Gly Pro Cys Leu Ser Gln Gln Leu
450                 455                 460
His Ser Ala Ser Ala Glu Asp Thr Pro Val Val Gln Leu Ala Ala Glu
465                 470                 475                 480
Thr Pro Thr Ala Glu Ser Lys Glu Arg Ala Leu Asn Ser Ala Ser Thr
                485                 490                 495
Ser Leu Pro Thr Ser Cys Pro Gly Ser Glu Pro Val Pro Thr His Gln
            500                 505                 510
Gln Gly Gln Pro Ala Leu Glu Leu Lys Glu Glu Ser Phe Arg Asp Pro
        515                 520                 525
Ala Glu Val Leu Gly Thr Gly Ala Glu Val Asp Tyr Leu Glu Gln Phe
    530                 535                 540
Gly Thr Ser Ser Phe Lys Glu Ser Ala Leu Arg Lys Gln Ser Leu Tyr
545                 550                 555                 560
Leu Lys Phe Asp Pro Leu Leu Arg Asp Ser Pro Gly Arg Pro Val Pro
                565                 570                 575
Val Ala Thr Glu Thr Ser Ser Met His Gly Ala Asn Glu Thr Pro Ser
            580                 585                 590
Gly Arg Pro Arg Glu Ala Lys Leu Val Glu Phe Asp Phe Leu Gly Ala
        595                 600                 605
Leu Asp Ile Pro Val Pro Gly Pro Pro Pro Gly Pro Ala Pro Gly
    610                 615                 620
Gly Pro Pro Leu Ser Thr Gly Pro Ile Val Asp Leu Leu Gln Tyr Ser
625                 630                 635                 640
Gln Lys Asp Leu Asp Ala Val Val Lys Ala Thr Gln Glu Glu Asn Arg
                645                 650                 655
Glu Leu Arg Ser Arg Cys Glu Glu Leu His Gly Lys Asn Leu Glu Leu
            660                 665                 670
Gly Lys Ile Met Asp Arg Phe Glu Glu Val Val Tyr Gln Ala Met Glu
        675                 680                 685
Glu Val Gln Lys Gln Lys Glu Leu Ser Lys Ala Glu Ile Gln Lys Val
    690                 695                 700
Leu Lys Glu Lys Asp Gln Leu Thr Thr Asp Leu Asn Ser Met Glu Lys
705                 710                 715                 720
Ser Phe Ser Asp Leu Phe Lys Arg Phe Glu Lys Gln Lys Glu Val Ile
                725                 730                 735
Glu Gly Tyr Arg Lys Asn Glu Glu Ser Leu Lys Lys Cys Val Glu Asp
            740                 745                 750
Tyr Leu Ala Arg Ile Thr Gln Glu Gly Gln Arg Tyr Gln Ala Leu Lys
        755                 760                 765
Ala His Ala Glu Glu Lys Leu Gln Leu Ala Asn Glu Glu Ile Ala Gln
    770                 775                 780
Val Arg Ser Lys Ala Gln Ala Glu Ala Leu Ala Leu Gln Ala Ser Leu
785                 790                 795                 800
Arg Lys Glu Gln Met Arg Ile Gln Ser Leu Glu Lys Thr Val Glu Gln
                805                 810                 815
Lys Thr Lys Glu Asn Glu Glu Leu Thr Arg Ile Cys Asp Asp Leu Ile
            820                 825                 830
Ser Lys Met Glu Lys Ile
        835
```

```
<210> SEQ ID NO 33
<211> LENGTH: 452
<212> TYPE: PRT
<213> ORGANISM: Homo sapiens

<400> SEQUENCE: 33

Met Ser Glu Thr Pro Ala Gln Cys Ser Ile Lys Gln Glu Arg Ile Ser
1               5                   10                  15

Tyr Thr Pro Pro Glu Ser Pro Val Pro Ser Tyr Ala Ser Ser Thr Pro
            20                  25                  30

Leu His Val Pro Val Pro Arg Ala Leu Arg Met Glu Glu Asp Ser Ile
        35                  40                  45

Arg Leu Pro Ala His Leu Arg Leu Gln Pro Ile Tyr Trp Ser Arg Asp
    50                  55                  60

Asp Val Ala Gln Trp Leu Lys Trp Ala Glu Asn Glu Phe Ser Leu Arg
65                  70                  75                  80

Pro Ile Asp Ser Asn Thr Phe Glu Met Asn Gly Lys Ala Leu Leu Leu
                85                  90                  95

Leu Thr Lys Glu Asp Phe Arg Tyr Arg Ser Pro His Ser Gly Asp Val
            100                 105                 110

Leu Tyr Glu Leu Leu Gln His Ile Leu Lys Gln Arg Lys Pro Arg Ile
        115                 120                 125

Leu Phe Ser Pro Phe Phe His Pro Gly Asn Ser Ile His Thr Gln Pro
    130                 135                 140

Glu Val Ile Leu His Gln Asn His Glu Glu Asp Asn Cys Val Gln Arg
145                 150                 155                 160

Thr Pro Arg Pro Ser Val Asp Asn Val His His Asn Pro Pro Thr Ile
                165                 170                 175

Glu Leu Leu His Arg Ser Arg Ser Pro Ile Thr Thr Asn His Arg Pro
            180                 185                 190

Ser Pro Asp Pro Glu Gln Arg Pro Leu Arg Ser Pro Leu Asp Asn Met
        195                 200                 205

Ile Arg Arg Leu Ser Pro Ala Glu Arg Ala Gln Gly Pro Arg Pro His
    210                 215                 220

Gln Glu Asn Asn His Gln Glu Ser Tyr Pro Leu Ser Val Ser Pro Met
225                 230                 235                 240

Glu Asn Asn His Cys Pro Ala Ser Ser Glu Ser His Pro Lys Pro Ser
                245                 250                 255

Ser Pro Arg Gln Glu Ser Thr Arg Val Ile Gln Leu Met Pro Ser Pro
            260                 265                 270

Ile Met His Pro Leu Ile Leu Asn Pro Arg His Ser Val Asp Phe Lys
        275                 280                 285

Gln Ser Arg Leu Ser Glu Asp Gly Leu His Arg Glu Gly Lys Pro Ile
    290                 295                 300

Asn Leu Ser His Arg Glu Asp Leu Ala Tyr Met Asn His Ile Met Val
305                 310                 315                 320

Ser Val Ser Pro Pro Glu Glu His Ala Met Pro Ile Gly Arg Ile Ala
                325                 330                 335

Asp Cys Arg Leu Leu Trp Asp Tyr Val Tyr Gln Leu Leu Ser Asp Ser
            340                 345                 350

Arg Tyr Glu Asn Phe Ile Arg Trp Glu Asp Lys Glu Ser Lys Ile Phe
        355                 360                 365

Arg Ile Val Asp Pro Asn Gly Leu Ala Arg Leu Trp Gly Asn His Lys
    370                 375                 380
```

```
Asn Arg Thr Asn Met Thr Tyr Glu Lys Met Ser Arg Ala Leu Arg His
385                 390                 395                 400

Tyr Tyr Lys Leu Asn Ile Ile Arg Lys Glu Pro Gly Gln Arg Leu Leu
                405                 410                 415

Phe Arg Phe Met Lys Thr Pro Asp Glu Ile Met Ser Gly Arg Thr Asp
            420                 425                 430

Arg Leu Glu His Leu Glu Ser Gln Glu Leu Asp Glu Gln Ile Tyr Gln
        435                 440                 445

Glu Asp Glu Cys
    450
```

<210> SEQ ID NO 34
<211> LENGTH: 573
<212> TYPE: PRT
<213> ORGANISM: Artificial Sequence
<220> FEATURE:
<223> OTHER INFORMATION: An artificially synthesized polypeptide
      sequence

<400> SEQUENCE: 34

```
Met Ser Glu Thr Pro Ala Gln Cys Ser Ile Lys Gln Glu Arg Ile Ser
1               5                   10                  15

Tyr Thr Pro Pro Glu Ser Pro Val Pro Ser Tyr Ala Ser Ser Thr Pro
                20                  25                  30

Leu His Val Pro Val Pro Arg Ala Leu Arg Met Glu Glu Asp Ser Ile
            35                  40                  45

Arg Leu Pro Ala His Leu Arg Leu Gln Pro Ile Tyr Trp Ser Arg Asp
50                  55                  60

Asp Val Ala Gln Trp Leu Lys Trp Ala Glu Asn Glu Phe Ser Leu Arg
65                  70                  75                  80

Pro Ile Asp Ser Asn Thr Phe Glu Met Asn Gly Lys Ala Leu Leu Leu
                85                  90                  95

Leu Thr Lys Glu Asp Phe Arg Tyr Arg Ser Pro His Ser Gly Asp Val
            100                 105                 110

Leu Tyr Glu Leu Leu Gln His Ile Leu Lys Gln Arg Lys Pro Arg Ile
        115                 120                 125

Leu Phe Ser Pro Phe Phe His Pro Gly Asn Ser Ile His Thr Gln Pro
130                 135                 140

Glu Val Ile Leu His Gln Asn His Glu Glu Asp Asn Cys Val Gln Arg
145                 150                 155                 160

Thr Pro Arg Pro Ser Val Asp Asn Val His His Asn Pro Pro Thr Ile
                165                 170                 175

Glu Leu Leu His Arg Val Ser Ala Glu Ser Ser Ser Ser Met Asn Ser
            180                 185                 190

Asn Thr Pro Leu Val Arg Ile Thr Thr Arg Leu Ser Ser Thr Ala Asp
        195                 200                 205

Thr Pro Met Leu Ala Gly Val Ser Glu Tyr Glu Leu Pro Glu Asp Pro
210                 215                 220

Lys Trp Glu Phe Pro Arg Asp Lys Leu Thr Leu Gly Lys Pro Leu Gly
225                 230                 235                 240

Glu Gly Cys Phe Gly Gln Val Val Met Ala Glu Ala Val Gly Ile Asp
                245                 250                 255

Lys Asp Lys Pro Lys Glu Ala Val Thr Val Ala Val Lys Met Leu Lys
            260                 265                 270

Asp Asp Ala Thr Glu Lys Asp Leu Ser Asp Leu Val Ser Glu Met Glu
        275                 280                 285
```

```
Met Met Lys Met Ile Gly Lys His Lys Asn Ile Ile Asn Leu Leu Gly
    290                 295                 300

Ala Cys Thr Gln Asp Gly Pro Leu Tyr Val Ile Val Glu Tyr Ala Ser
305                 310                 315                 320

Lys Gly Asn Leu Arg Glu Tyr Leu Arg Ala Arg Arg Pro Pro Gly Met
                325                 330                 335

Glu Tyr Ser Tyr Asp Ile Asn Arg Val Pro Glu Glu Gln Met Thr Phe
            340                 345                 350

Lys Asp Leu Val Ser Cys Thr Tyr Gln Leu Ala Arg Gly Met Glu Tyr
        355                 360                 365

Leu Ala Ser Gln Lys Cys Ile His Arg Asp Leu Ala Ala Arg Asn Val
    370                 375                 380

Leu Val Thr Glu Asn Asn Val Met Lys Ile Ala Asp Phe Gly Leu Ala
385                 390                 395                 400

Arg Asp Ile Asn Asn Ile Asp Tyr Tyr Lys Lys Thr Thr Asn Gly Arg
                405                 410                 415

Leu Pro Val Lys Trp Met Ala Pro Glu Ala Leu Phe Asp Arg Val Tyr
            420                 425                 430

Thr His Gln Ser Asp Val Trp Ser Phe Gly Val Leu Met Trp Glu Ile
        435                 440                 445

Phe Thr Leu Gly Gly Ser Pro Tyr Pro Gly Ile Pro Val Glu Glu Leu
    450                 455                 460

Phe Lys Leu Leu Lys Glu Gly His Arg Met Asp Lys Pro Ala Asn Cys
465                 470                 475                 480

Thr Asn Glu Leu Tyr Met Met Met Arg Asp Cys Trp His Ala Val Pro
                485                 490                 495

Ser Gln Arg Pro Thr Phe Lys Gln Leu Val Glu Asp Leu Asp Arg Ile
            500                 505                 510

Leu Thr Leu Thr Thr Asn Glu Glu Tyr Leu Asp Leu Ser Gln Pro Leu
        515                 520                 525

Glu Gln Tyr Ser Pro Ser Tyr Pro Asp Thr Arg Ser Ser Cys Ser Ser
    530                 535                 540

Gly Asp Asp Ser Val Phe Ser Pro Asp Pro Met Pro Tyr Glu Pro Cys
545                 550                 555                 560

Leu Pro Gln Tyr Pro His Ile Asn Gly Ser Val Lys Thr
                565                 570

<210> SEQ ID NO 35
<211> LENGTH: 573
<212> TYPE: PRT
<213> ORGANISM: Artificial Sequence
<220> FEATURE:
<223> OTHER INFORMATION: An artificially synthesized polypeptide
      sequence

<400> SEQUENCE: 35

Met Ser Glu Thr Pro Ala Gln Cys Ser Ile Lys Gln Glu Arg Ile Ser
1               5                   10                  15

Tyr Thr Pro Pro Glu Ser Pro Val Pro Ser Tyr Ala Ser Ser Thr Pro
            20                  25                  30

Leu His Val Pro Val Pro Arg Ala Leu Arg Met Glu Glu Asp Ser Ile
        35                  40                  45

Arg Leu Pro Ala His Leu Arg Leu Gln Pro Ile Tyr Trp Ser Arg Asp
    50                  55                  60

Asp Val Ala Gln Trp Leu Lys Trp Ala Glu Asn Glu Phe Ser Leu Arg
```

-continued

```
             65                  70                  75                  80
Pro Ile Asp Ser Asn Thr Phe Glu Met Asn Gly Lys Ala Leu Leu Leu
                     85                  90                  95

Leu Thr Lys Glu Asp Phe Arg Tyr Arg Ser Pro His Ser Gly Asp Val
                    100                 105                 110

Leu Tyr Glu Leu Leu Gln His Ile Leu Lys Gln Arg Lys Pro Arg Ile
                    115                 120                 125

Leu Phe Ser Pro Phe His Pro Gly Asn Ser Ile His Thr Gln Pro
    130                 135                 140

Glu Val Ile Leu His Gln Asn His Glu Glu Asp Asn Cys Val Gln Arg
145                 150                 155                 160

Thr Pro Arg Pro Ser Val Asp Asn Val His His Asn Pro Pro Thr Ile
                    165                 170                 175

Glu Leu Leu His Arg Val Ser Ala Glu Ser Ser Ser Met Asn Ser
                180                 185                 190

Asn Thr Pro Leu Val Arg Ile Thr Thr Arg Leu Ser Ser Thr Ala Asp
                195                 200                 205

Thr Pro Met Leu Ala Gly Val Ser Glu Tyr Glu Leu Pro Glu Asp Pro
    210                 215                 220

Lys Trp Glu Phe Pro Arg Asp Lys Leu Thr Leu Gly Lys Pro Leu Gly
225                 230                 235                 240

Glu Gly Cys Phe Gly Gln Val Val Met Ala Glu Ala Val Gly Ile Asp
                    245                 250                 255

Lys Asp Lys Pro Lys Glu Ala Val Thr Val Ala Val Lys Met Leu Lys
                260                 265                 270

Asp Asp Ala Thr Glu Lys Asp Leu Ser Asp Leu Val Ser Glu Met Glu
            275                 280                 285

Met Met Lys Met Ile Gly Lys His Lys Asn Ile Ile Asn Leu Leu Gly
            290                 295                 300

Ala Cys Thr Gln Asp Gly Pro Leu Tyr Val Ile Phe Glu Tyr Ala Ser
305                 310                 315                 320

Lys Gly Asn Leu Arg Glu Tyr Leu Arg Ala Arg Arg Pro Pro Gly Met
                    325                 330                 335

Glu Tyr Ser Tyr Asp Ile Asn Arg Val Pro Glu Glu Gln Met Thr Phe
                340                 345                 350

Lys Asp Leu Val Ser Cys Thr Tyr Gln Leu Ala Arg Gly Met Glu Tyr
                355                 360                 365

Leu Ala Ser Gln Lys Cys Ile His Arg Asp Leu Ala Ala Arg Asn Val
    370                 375                 380

Leu Val Thr Glu Asn Asn Val Met Lys Ile Ala Asp Phe Gly Leu Ala
385                 390                 395                 400

Arg Asp Ile Asn Asn Ile Asp Tyr Tyr Lys Lys Thr Thr Asn Gly Arg
                    405                 410                 415

Leu Pro Val Lys Trp Met Ala Pro Glu Ala Leu Phe Asp Arg Val Tyr
                420                 425                 430

Thr His Gln Ser Asp Val Trp Ser Phe Gly Val Leu Met Trp Glu Ile
            435                 440                 445

Phe Thr Leu Gly Gly Ser Pro Tyr Pro Gly Ile Pro Val Glu Glu Leu
    450                 455                 460

Phe Lys Leu Leu Lys Glu Gly His Arg Met Asp Lys Pro Ala Asn Cys
465                 470                 475                 480

Thr Asn Glu Leu Tyr Met Met Met Arg Asp Cys Trp His Ala Val Pro
                    485                 490                 495
```

```
Ser Gln Arg Pro Thr Phe Lys Gln Leu Val Glu Asp Leu Asp Arg Ile
            500                 505                 510
Leu Thr Leu Thr Thr Asn Glu Glu Tyr Leu Asp Leu Ser Gln Pro Leu
        515                 520                 525
Glu Gln Tyr Ser Pro Ser Tyr Pro Asp Thr Arg Ser Ser Cys Ser Ser
    530                 535                 540
Gly Asp Asp Ser Val Phe Ser Pro Asp Pro Met Pro Tyr Glu Pro Cys
545                 550                 555                 560
Leu Pro Gln Tyr Pro His Ile Asn Gly Ser Val Lys Thr
                565                 570

<210> SEQ ID NO 36
<211> LENGTH: 573
<212> TYPE: PRT
<213> ORGANISM: Artificial Sequence
<220> FEATURE:
<223> OTHER INFORMATION: An artificially synthesized polypeptide
      sequence

<400> SEQUENCE: 36

Met Ser Glu Thr Pro Ala Gln Cys Ser Ile Lys Gln Glu Arg Ile Ser
1               5                   10                  15
Tyr Thr Pro Pro Glu Ser Pro Val Pro Ser Tyr Ala Ser Ser Thr Pro
            20                  25                  30
Leu His Val Pro Val Pro Arg Ala Leu Arg Met Glu Glu Asp Ser Ile
        35                  40                  45
Arg Leu Pro Ala His Leu Arg Leu Gln Pro Ile Tyr Trp Ser Arg Asp
    50                  55                  60
Asp Val Ala Gln Trp Leu Lys Trp Ala Glu Asn Glu Phe Ser Leu Arg
65                  70                  75                  80
Pro Ile Asp Ser Asn Thr Phe Glu Met Asn Gly Lys Ala Leu Leu Leu
                85                  90                  95
Leu Thr Lys Glu Asp Phe Arg Tyr Arg Ser Pro His Ser Gly Asp Val
            100                 105                 110
Leu Tyr Glu Leu Leu Gln His Ile Leu Lys Gln Arg Lys Pro Arg Ile
        115                 120                 125
Leu Phe Ser Pro Phe Phe His Pro Gly Asn Ser Ile His Thr Gln Pro
    130                 135                 140
Glu Val Ile Leu His Gln Asn His Glu Glu Asp Asn Cys Val Gln Arg
145                 150                 155                 160
Thr Pro Arg Pro Ser Val Asp Asn Val His His Asn Pro Pro Thr Ile
                165                 170                 175
Glu Leu Leu His Arg Val Ser Ala Glu Ser Ser Ser Ser Met Asn Ser
            180                 185                 190
Asn Thr Pro Leu Val Arg Ile Thr Thr Arg Leu Ser Ser Thr Ala Asp
        195                 200                 205
Thr Pro Met Leu Ala Gly Val Ser Glu Tyr Glu Leu Pro Glu Asp Pro
    210                 215                 220
Lys Trp Glu Phe Pro Arg Asp Lys Leu Thr Leu Gly Lys Pro Leu Gly
225                 230                 235                 240
Glu Gly Cys Phe Gly Gln Val Val Met Ala Glu Ala Val Gly Ile Asp
                245                 250                 255
Lys Asp Lys Pro Lys Glu Ala Val Thr Val Ala Val Lys Met Leu Lys
            260                 265                 270
Asp Asp Ala Thr Glu Lys Asp Leu Ser Asp Leu Val Ser Glu Met Glu
```

```
                275                 280                 285
Met Met Lys Met Ile Gly Lys His Lys Asn Ile Ile Asn Leu Leu Gly
    290                 295                 300

Ala Cys Thr Gln Asp Gly Pro Leu Tyr Leu Ile Val Glu Tyr Ala Ser
305                 310                 315                 320

Lys Gly Asn Leu Arg Glu Tyr Leu Arg Ala Arg Arg Pro Pro Gly Met
                325                 330                 335

Glu Tyr Ser Tyr Asp Ile Asn Arg Val Pro Glu Glu Gln Met Thr Phe
            340                 345                 350

Lys Asp Leu Val Ser Cys Thr Tyr Gln Leu Ala Arg Gly Met Glu Tyr
                355                 360                 365

Leu Ala Ser Gln Lys Cys Ile His Arg Asp Leu Ala Ala Arg Asn Val
        370                 375                 380

Leu Val Thr Glu Asn Asn Val Met Lys Ile Ala Asp Phe Gly Leu Ala
385                 390                 395                 400

Arg Asp Ile Asn Asn Ile Asp Tyr Tyr Lys Lys Thr Thr Asn Gly Arg
                405                 410                 415

Leu Pro Val Lys Trp Met Ala Pro Glu Ala Leu Phe Asp Arg Val Tyr
                420                 425                 430

Thr His Gln Ser Asp Val Trp Ser Phe Gly Val Leu Met Trp Glu Ile
        435                 440                 445

Phe Thr Leu Gly Gly Ser Pro Tyr Pro Gly Ile Pro Val Glu Glu Leu
    450                 455                 460

Phe Lys Leu Leu Lys Glu Gly His Arg Met Asp Lys Pro Ala Asn Cys
465                 470                 475                 480

Thr Asn Glu Leu Tyr Met Met Met Arg Asp Cys Trp His Ala Val Pro
                485                 490                 495

Ser Gln Arg Pro Thr Phe Lys Gln Leu Val Glu Asp Leu Asp Arg Ile
                500                 505                 510

Leu Thr Leu Thr Thr Asn Glu Glu Tyr Leu Asp Leu Ser Gln Pro Leu
        515                 520                 525

Glu Gln Tyr Ser Pro Ser Tyr Pro Asp Thr Arg Ser Ser Cys Ser Ser
    530                 535                 540

Gly Asp Asp Ser Val Phe Ser Pro Asp Pro Met Pro Tyr Glu Pro Cys
545                 550                 555                 560

Leu Pro Gln Tyr Pro His Ile Asn Gly Ser Val Lys Thr
                565                 570

<210> SEQ ID NO 37
<211> LENGTH: 769
<212> TYPE: PRT
<213> ORGANISM: Homo sapiens

<400> SEQUENCE: 37

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
        50                  55                  60

Lys Asp Ala Ala Val Ile Ser Trp Thr Lys Asp Gly Val His Leu Gly
65                  70                  75                  80
```

```
Pro Asn Asn Arg Thr Val Leu Ile Gly Glu Tyr Leu Gln Ile Lys Gly
                85                  90                  95
Ala Thr Pro Arg Asp Ser Gly Leu Tyr Ala Cys Thr Ala Ser Arg Thr
            100                 105                 110
Val Asp Ser Glu Thr Trp Tyr Phe Met Val Asn Val Thr Asp Ala Ile
        115                 120                 125
Ser Ser Gly Asp Asp Glu Asp Thr Asp Gly Ala Glu Asp Phe Val
130                 135                 140
Ser Glu Asn Ser Asn Asn Lys Arg Ala Pro Tyr Trp Thr Asn Thr Glu
145                 150                 155                 160
Lys Met Glu Lys Arg Leu His Ala Val Pro Ala Ala Asn Thr Val Lys
                165                 170                 175
Phe Arg Cys Pro Ala Gly Gly Asn Pro Met Pro Thr Met Arg Trp Leu
            180                 185                 190
Lys Asn Gly Lys Glu Phe Lys Gln Glu His Arg Ile Gly Gly Tyr Lys
        195                 200                 205
Val Arg Asn Gln His Trp Ser Leu Ile Met Glu Ser Val Val Pro Ser
    210                 215                 220
Asp Lys Gly Asn Tyr Thr Cys Val Val Glu Asn Glu Tyr Gly Ser Ile
225                 230                 235                 240
Asn His Thr Tyr His Leu Asp Val Val Glu Arg Ser Pro His Arg Pro
                245                 250                 255
Ile Leu Gln Ala Gly Leu Pro Ala Asn Ala Ser Thr Val Val Gly Gly
            260                 265                 270
Asp Val Glu Phe Val Cys Lys Val Tyr Ser Asp Ala Gln Pro His Ile
        275                 280                 285
Gln Trp Ile Lys His Val Glu Lys Asn Gly Ser Lys Tyr Gly Pro Asp
    290                 295                 300
Gly Leu Pro Tyr Leu Lys Val Leu Lys His Ser Gly Ile Asn Ser Ser
305                 310                 315                 320
Asn Ala Glu Val Leu Ala Leu Phe Asn Val Thr Glu Ala Asp Ala Gly
                325                 330                 335
Glu Tyr Ile Cys Lys Val Ser Asn Tyr Ile Gly Gln Ala Asn Gln Ser
            340                 345                 350
Ala Trp Leu Thr Val Leu Pro Lys Gln Gln Ala Pro Gly Arg Glu Lys
        355                 360                 365
Glu Ile Thr Ala Ser Pro Asp Tyr Leu Glu Ile Ala Ile Tyr Cys Ile
    370                 375                 380
Gly Val Phe Leu Ile Ala Cys Met Val Val Thr Val Ile Leu Cys Arg
385                 390                 395                 400
Met Lys Asn Thr Thr Lys Lys Pro Asp Phe Ser Ser Gln Pro Ala Val
                405                 410                 415
His Lys Leu Thr Lys Arg Ile Pro Leu Arg Arg Gln Val Thr Val Ser
            420                 425                 430
Ala Glu Ser Ser Ser Ser Met Asn Ser Asn Thr Pro Leu Val Arg Ile
        435                 440                 445
Thr Thr Arg Leu Ser Ser Thr Ala Asp Thr Pro Met Leu Ala Gly Val
    450                 455                 460
Ser Glu Tyr Glu Leu Pro Glu Asp Pro Lys Trp Glu Phe Pro Arg Asp
465                 470                 475                 480
Lys Leu Thr Leu Gly Lys Pro Leu Gly Glu Gly Cys Phe Gly Gln Val
                485                 490                 495
Val Met Ala Glu Ala Val Gly Ile Asp Lys Asp Lys Pro Lys Glu Ala
```

```
                        500                 505                 510
Val Thr Val Ala Val Lys Met Leu Lys Asp Asp Ala Thr Glu Lys Asp
            515                 520                 525

Leu Ser Asp Leu Val Ser Glu Met Glu Met Lys Met Ile Gly Lys
        530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
            580                 585                 590

Arg Val Pro Glu Glu Gln Met Thr Phe Lys Asp Leu Val Ser Cys Thr
        595                 600                 605

Tyr Gln Leu Ala Arg Gly Met Glu Tyr Leu Ala Ser Gln Lys Cys Ile
    610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
        675                 680                 685

Ser Phe Gly Val Leu Met Trp Glu Ile Phe Thr Leu Gly Gly Ser Pro
    690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765

Ile

<210> SEQ ID NO 38
<211> LENGTH: 709
<212> TYPE: PRT
<213> ORGANISM: Homo sapiens

<400> SEQUENCE: 38

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
```

```
              100                 105                 110
Val Asp Ser Glu Thr Trp Tyr Phe Met Val Asn Val Thr Asp Ala Ile
            115                 120                 125

Ser Ser Gly Asp Asp Glu Asp Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
            195                 200                 205

Val Arg Asn Gln His Trp Ser Leu Ile Met Glu Ser Val Val Pro Ser
            210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Ala Pro Gly Arg Glu Lys Glu
                245                 250                 255

Ile Thr Ala Ser Pro Asp Tyr Leu Glu Ile Ala Ile Tyr Cys Ile Gly
            260                 265                 270

Val Phe Leu Ile Ala Cys Met Val Val Thr Val Ile Leu Cys Arg Met
            275                 280                 285

Lys Asn Thr Thr Lys Lys Pro Asp Phe Ser Ser Gln Pro Ala Val His
            290                 295                 300

Lys Leu Thr Lys Arg Ile Pro Leu Arg Arg Gln Val Thr Val Ser Ala
305                 310                 315                 320

Glu Ser Ser Ser Ser Met Asn Ser Asn Thr Pro Leu Val Arg Ile Thr
                325                 330                 335

Thr Arg Leu Ser Ser Thr Ala Asp Thr Pro Met Leu Ala Gly Val Ser
            340                 345                 350

Glu Tyr Glu Leu Pro Glu Asp Pro Lys Trp Glu Phe Pro Arg Asp Lys
            355                 360                 365

Leu Thr Leu Gly Lys Pro Leu Gly Glu Gly Cys Phe Gly Gln Val Val
            370                 375                 380

Met Ala Glu Ala Val Gly Ile Asp Lys Asp Lys Pro Lys Glu Ala Val
385                 390                 395                 400

Thr Val Ala Val Lys Met Leu Lys Asp Asp Ala Thr Glu Lys Asp Leu
                405                 410                 415

Ser Asp Leu Val Ser Glu Met Glu Met Met Lys Met Ile Gly Lys His
            420                 425                 430

Lys Asn Ile Ile Asn Leu Leu Gly Ala Cys Thr Gln Asp Gly Pro Leu
            435                 440                 445

Tyr Val Ile Val Glu Tyr Ala Ser Lys Gly Asn Leu Arg Glu Tyr Leu
            450                 455                 460

Arg Ala Arg Arg Pro Pro Gly Met Glu Tyr Ser Tyr Asp Ile Asn Arg
465                 470                 475                 480

Val Pro Glu Glu Gln Met Thr Phe Lys Asp Leu Val Ser Cys Thr Tyr
                485                 490                 495

Gln Leu Ala Arg Gly Met Glu Tyr Leu Ala Ser Gln Lys Cys Ile His
            500                 505                 510

Arg Asp Leu Ala Ala Arg Asn Val Leu Val Thr Glu Asn Asn Val Met
            515                 520                 525
```

Lys Ile Ala Asp Phe Gly Leu Ala Arg Asp Ile Asn Asn Ile Asp Tyr
    530                 535                 540

Tyr Lys Lys Thr Thr Asn Gly Arg Leu Pro Val Lys Trp Met Ala Pro
545                 550                 555                 560

Glu Ala Leu Phe Asp Arg Val Tyr Thr His Gln Ser Asp Val Trp Ser
                565                 570                 575

Phe Gly Val Leu Met Trp Glu Ile Phe Thr Leu Gly Gly Ser Pro Tyr
                580                 585                 590

Pro Gly Ile Pro Val Glu Glu Leu Phe Lys Leu Leu Lys Glu Gly His
            595                 600                 605

Arg Met Asp Lys Pro Ala Asn Cys Thr Asn Glu Leu Tyr Met Met Met
610                 615                 620

Arg Asp Cys Trp His Ala Val Pro Ser Gln Arg Pro Thr Phe Lys Gln
625                 630                 635                 640

Leu Val Glu Asp Leu Asp Arg Ile Leu Thr Leu Thr Thr Asn Glu Glu
                645                 650                 655

Tyr Leu Asp Leu Ser Gln Pro Leu Glu Gln Tyr Ser Pro Ser Tyr Pro
                660                 665                 670

Asp Thr Arg Ser Ser Cys Ser Ser Gly Asp Asp Ser Val Phe Ser Pro
            675                 680                 685

Asp Pro Met Pro Tyr Glu Pro Cys Leu Pro Gln Tyr Pro His Ile Asn
690                 695                 700

Gly Ser Val Lys Thr
705

<210> SEQ ID NO 39
<211> LENGTH: 707
<212> TYPE: PRT
<213> ORGANISM: Homo sapiens

<400> SEQUENCE: 39

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Asp Ala Ile Ser Ser Gly Asp Asp Glu Asp Asp Thr
            35                  40                  45

Asp Gly Ala Glu Asp Phe Val Ser Glu Asn Ser Asn Asn Lys Arg Ala
    50                  55                  60

Pro Tyr Trp Thr Asn Thr Glu Lys Met Glu Lys Arg Leu His Ala Val
65                  70                  75                  80

Pro Ala Ala Asn Thr Val Lys Phe Arg Cys Pro Ala Gly Gly Asn Pro
                85                  90                  95

Met Pro Thr Met Arg Trp Leu Lys Asn Gly Lys Glu Phe Lys Gln Glu
                100                 105                 110

His Arg Ile Gly Gly Tyr Lys Val Arg Asn Gln His Trp Ser Leu Ile
            115                 120                 125

Met Glu Ser Val Val Pro Ser Asp Lys Gly Asn Tyr Thr Cys Val Val
130                 135                 140

Glu Asn Glu Tyr Gly Ser Ile Asn His Thr Tyr His Leu Asp Val Val
145                 150                 155                 160

Glu Arg Ser Pro His Arg Pro Ile Leu Gln Ala Gly Leu Pro Ala Asn
                165                 170                 175

Ala Ser Thr Val Val Gly Gly Asp Val Glu Phe Val Cys Lys Val Tyr

```
            180                 185                 190
Ser Asp Ala Gln Pro His Ile Gln Trp Ile Lys His Val Glu Lys Asn
            195                 200                 205
Gly Ser Lys Tyr Gly Pro Asp Gly Leu Pro Tyr Leu Lys Val Leu Lys
            210                 215                 220
Ala Ala Gly Val Asn Thr Thr Asp Lys Glu Ile Glu Val Leu Tyr Ile
225                 230                 235                 240
Arg Asn Val Thr Phe Glu Asp Ala Gly Glu Tyr Thr Cys Leu Ala Gly
                245                 250                 255
Asn Ser Ile Gly Ile Ser Phe His Ser Ala Trp Leu Thr Val Leu Pro
            260                 265                 270
Ala Pro Gly Arg Glu Lys Glu Ile Thr Ala Ser Pro Asp Tyr Leu Glu
            275                 280                 285
Ile Ala Ile Tyr Cys Ile Gly Val Phe Leu Ile Ala Cys Met Val Val
            290                 295                 300
Thr Val Ile Leu Cys Arg Met Lys Asn Thr Thr Lys Lys Pro Asp Phe
305                 310                 315                 320
Ser Ser Gln Pro Ala Val His Lys Leu Thr Lys Arg Ile Pro Leu Arg
                325                 330                 335
Arg Gln Val Thr Val Ser Ala Glu Ser Ser Ser Ser Met Asn Ser Asn
                340                 345                 350
Thr Pro Leu Val Arg Ile Thr Thr Arg Leu Ser Ser Thr Ala Asp Thr
            355                 360                 365
Pro Met Leu Ala Gly Val Ser Glu Tyr Glu Leu Pro Glu Asp Pro Lys
            370                 375                 380
Trp Glu Phe Pro Arg Asp Lys Leu Thr Leu Gly Lys Pro Leu Gly Glu
385                 390                 395                 400
Gly Cys Phe Gly Gln Val Val Met Ala Glu Ala Val Gly Ile Asp Lys
                405                 410                 415
Asp Lys Pro Lys Glu Ala Val Thr Val Ala Val Lys Met Leu Lys Asp
            420                 425                 430
Asp Ala Thr Glu Lys Asp Leu Ser Asp Leu Val Ser Glu Met Glu Met
            435                 440                 445
Met Lys Met Ile Gly Lys His Lys Asn Ile Ile Asn Leu Leu Gly Ala
            450                 455                 460
Cys Thr Gln Asp Gly Pro Leu Tyr Val Ile Val Glu Tyr Ala Ser Lys
465                 470                 475                 480
Gly Asn Leu Arg Glu Tyr Leu Arg Ala Arg Arg Pro Pro Gly Met Glu
                485                 490                 495
Tyr Ser Tyr Asp Ile Asn Arg Val Pro Glu Glu Gln Met Thr Phe Lys
                500                 505                 510
Asp Leu Val Ser Cys Thr Tyr Gln Leu Ala Arg Gly Met Glu Tyr Leu
            515                 520                 525
Ala Ser Gln Lys Cys Ile His Arg Asp Leu Ala Ala Arg Asn Val Leu
            530                 535                 540
Val Thr Glu Asn Asn Val Met Lys Ile Ala Asp Phe Gly Leu Ala Arg
545                 550                 555                 560
Asp Ile Asn Asn Ile Asp Tyr Tyr Lys Lys Thr Thr Asn Gly Arg Leu
                565                 570                 575
Pro Val Lys Trp Met Ala Pro Glu Ala Leu Phe Asp Arg Val Tyr Thr
            580                 585                 590
His Gln Ser Asp Val Trp Ser Phe Gly Val Leu Met Trp Glu Ile Phe
            595                 600                 605
```

```
Thr Leu Gly Gly Ser Pro Tyr Pro Gly Ile Pro Val Glu Glu Leu Phe
    610                 615                 620

Lys Leu Leu Lys Glu Gly His Arg Met Asp Lys Pro Ala Asn Cys Thr
625                 630                 635                 640

Asn Glu Leu Tyr Met Met Met Arg Asp Cys Trp His Ala Val Pro Ser
                645                 650                 655

Gln Arg Pro Thr Phe Lys Gln Leu Val Glu Asp Leu Asp Arg Ile Leu
                660                 665                 670

Thr Leu Thr Thr Asn Glu Glu Lys Lys Val Ser Gly Ala Val Asp
            675                 680                 685

Cys His Lys Pro Pro Cys Asn Pro Ser His Leu Pro Cys Val Leu Ala
690                 695                 700

Val Asp Gln
705
```

<210> SEQ ID NO 40
<211> LENGTH: 706
<212> TYPE: PRT
<213> ORGANISM: Homo sapiens

<400> SEQUENCE: 40

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Gly Ala Pro Tyr Trp Thr Asn Thr Glu Lys Met Glu
            35                  40                  45

Lys Arg Leu His Ala Val Pro Ala Ala Asn Thr Val Lys Phe Arg Cys
50                  55                  60

Pro Ala Gly Gly Asn Pro Met Pro Thr Met Arg Trp Leu Lys Asn Gly
65                  70                  75                  80

Lys Glu Phe Lys Gln Glu His Arg Ile Gly Gly Tyr Lys Val Arg Asn
                85                  90                  95

Gln His Trp Ser Leu Ile Met Glu Ser Val Val Pro Ser Asp Lys Gly
                100                 105                 110

Asn Tyr Thr Cys Val Val Glu Asn Glu Tyr Gly Ser Ile Asn His Thr
            115                 120                 125

Tyr His Leu Asp Val Val Glu Arg Ser Pro His Arg Pro Ile Leu Gln
        130                 135                 140

Ala Gly Leu Pro Ala Asn Ala Ser Thr Val Val Gly Gly Asp Val Glu
145                 150                 155                 160

Phe Val Cys Lys Val Tyr Ser Asp Ala Gln Pro His Ile Gln Trp Ile
                165                 170                 175

Lys His Val Glu Lys Asn Gly Ser Lys Tyr Gly Pro Asp Gly Leu Pro
                180                 185                 190

Tyr Leu Lys Val Leu Lys Ala Ala Gly Val Asn Thr Thr Asp Lys Glu
            195                 200                 205

Ile Glu Val Leu Tyr Ile Arg Asn Val Thr Phe Glu Asp Ala Gly Glu
        210                 215                 220

Tyr Thr Cys Leu Ala Gly Asn Ser Ile Gly Ile Ser Phe His Ser Ala
225                 230                 235                 240

Trp Leu Thr Val Leu Pro Ala Pro Gly Arg Glu Lys Glu Ile Thr Ala
                245                 250                 255

Ser Pro Asp Tyr Leu Glu Ile Ala Ile Tyr Cys Ile Gly Val Phe Leu
```

-continued

```
              260                 265                 270
Ile Ala Cys Met Val Thr Val Ile Leu Cys Arg Met Lys Asn Thr
            275                 280                 285

Thr Lys Lys Pro Asp Phe Ser Ser Gln Pro Ala Val His Lys Leu Thr
            290                 295                 300

Lys Arg Ile Pro Leu Arg Arg Gln Val Thr Val Ser Ala Glu Ser Ser
305                 310                 315                 320

Ser Ser Met Asn Ser Asn Thr Pro Leu Val Arg Ile Thr Thr Arg Leu
                325                 330                 335

Ser Ser Thr Ala Asp Thr Pro Met Leu Ala Gly Val Ser Glu Tyr Glu
                340                 345                 350

Leu Pro Glu Asp Pro Lys Trp Glu Phe Pro Arg Asp Lys Leu Thr Leu
            355                 360                 365

Gly Lys Pro Leu Gly Glu Gly Cys Phe Gly Gln Val Val Met Ala Glu
            370                 375                 380

Ala Val Gly Ile Asp Lys Asp Lys Pro Lys Glu Ala Val Thr Val Ala
385                 390                 395                 400

Val Lys Met Leu Lys Asp Asp Ala Thr Glu Lys Asp Leu Ser Asp Leu
                405                 410                 415

Val Ser Glu Met Glu Met Met Lys Met Ile Gly Lys His Lys Asn Ile
                420                 425                 430

Ile Asn Leu Leu Gly Ala Cys Thr Gln Asp Gly Pro Leu Tyr Val Ile
            435                 440                 445

Val Glu Tyr Ala Ser Lys Gly Asn Leu Arg Glu Tyr Leu Arg Ala Arg
            450                 455                 460

Arg Pro Pro Gly Met Glu Tyr Ser Tyr Asp Ile Asn Arg Val Pro Glu
465                 470                 475                 480

Glu Gln Met Thr Phe Lys Asp Leu Val Ser Cys Thr Tyr Gln Leu Ala
                485                 490                 495

Arg Gly Met Glu Tyr Leu Ala Ser Gln Lys Cys Ile His Arg Asp Leu
                500                 505                 510

Ala Ala Arg Asn Val Leu Val Thr Glu Asn Asn Val Met Lys Ile Ala
            515                 520                 525

Asp Phe Gly Leu Ala Arg Asp Ile Asn Asn Ile Asp Tyr Tyr Lys Lys
            530                 535                 540

Thr Thr Asn Gly Arg Leu Pro Val Lys Trp Met Ala Pro Glu Ala Leu
545                 550                 555                 560

Phe Asp Arg Val Tyr Thr His Gln Ser Asp Val Trp Ser Phe Gly Val
                565                 570                 575

Leu Met Trp Glu Ile Phe Thr Leu Gly Gly Ser Pro Tyr Pro Gly Ile
                580                 585                 590

Pro Val Glu Glu Leu Phe Lys Leu Leu Lys Glu Gly His Arg Met Asp
            595                 600                 605

Lys Pro Ala Asn Cys Thr Asn Glu Leu Tyr Met Met Met Arg Asp Cys
            610                 615                 620

Trp His Ala Val Pro Ser Gln Arg Pro Thr Phe Lys Gln Leu Val Glu
625                 630                 635                 640

Asp Leu Asp Arg Ile Leu Thr Leu Thr Thr Asn Glu Glu Tyr Leu Asp
                645                 650                 655

Leu Ser Gln Pro Leu Glu Gln Tyr Ser Pro Ser Tyr Pro Asp Thr Arg
                660                 665                 670

Ser Ser Cys Ser Ser Gly Asp Asp Ser Val Phe Ser Pro Asp Pro Met
            675                 680                 685
```

-continued

Pro Tyr Glu Pro Cys Leu Pro Gln Tyr Pro His Ile Asn Gly Ser Val
690                 695                 700

Lys Thr
705

<210> SEQ ID NO 41
<211> LENGTH: 705
<212> TYPE: PRT
<213> ORGANISM: Homo sapiens

<400> SEQUENCE: 41

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Val Ser Ala Glu Ser Ser Ser
305                 310                 315                 320

Ser Met Asn Ser Asn Thr Pro Leu Val Arg Ile Thr Thr Arg Leu Ser
                325                 330                 335

Ser Thr Ala Asp Thr Pro Met Leu Ala Gly Val Ser Glu Tyr Glu Leu

```
            340             345             350
Pro Glu Asp Pro Lys Trp Glu Phe Pro Arg Asp Lys Leu Thr Leu Gly
            355                     360                 365

Lys Pro Leu Gly Glu Gly Cys Phe Gly Gln Val Val Met Ala Glu Ala
        370                     375                 380

Val Gly Ile Asp Lys Asp Lys Pro Lys Glu Ala Val Thr Val Ala Val
385                     390                     395                 400

Lys Met Leu Lys Asp Asp Ala Thr Glu Lys Asp Leu Ser Asp Leu Val
                405                     410                 415

Ser Glu Met Glu Met Met Lys Met Ile Gly Lys His Lys Asn Ile Ile
            420                     425                 430

Asn Leu Leu Gly Ala Cys Thr Gln Asp Gly Pro Leu Tyr Val Ile Val
            435                     440                 445

Glu Tyr Ala Ser Lys Gly Asn Leu Arg Glu Tyr Leu Arg Ala Arg Arg
        450                     455                 460

Pro Pro Gly Met Glu Tyr Ser Tyr Asp Ile Asn Arg Val Pro Glu Glu
465                     470                     475                 480

Gln Met Thr Phe Lys Asp Leu Val Ser Cys Thr Tyr Gln Leu Ala Arg
                485                     490                 495

Gly Met Glu Tyr Leu Ala Ser Gln Lys Cys Ile His Arg Asp Leu Ala
            500                     505                 510

Ala Arg Asn Val Leu Val Thr Glu Asn Asn Val Met Lys Ile Ala Asp
            515                     520                 525

Phe Gly Leu Ala Arg Asp Ile Asn Asn Ile Asp Tyr Tyr Lys Lys Thr
        530                     535                 540

Thr Asn Gly Arg Leu Pro Val Lys Trp Met Ala Pro Glu Ala Leu Phe
545                     550                     555                 560

Asp Arg Val Tyr Thr His Gln Ser Asp Val Trp Ser Phe Gly Val Leu
                565                     570                 575

Met Trp Glu Ile Phe Thr Leu Gly Gly Ser Pro Tyr Pro Gly Ile Pro
            580                     585                 590

Val Glu Glu Leu Phe Lys Leu Leu Lys Glu Gly His Arg Met Asp Lys
            595                     600                 605

Pro Ala Asn Cys Thr Asn Glu Leu Tyr Met Met Met Arg Asp Cys Trp
    610                     615                     620

His Ala Val Pro Ser Gln Arg Pro Thr Phe Lys Gln Leu Val Glu Asp
625                     630                     635                 640

Leu Asp Arg Ile Leu Thr Leu Thr Thr Asn Glu Glu Tyr Leu Asp Leu
                645                     650                 655

Ser Gln Pro Leu Glu Gln Tyr Ser Pro Ser Tyr Pro Asp Thr Arg Ser
            660                     665                 670

Ser Cys Ser Ser Gly Asp Asp Ser Val Phe Ser Pro Asp Pro Met Pro
            675                     680                 685

Tyr Glu Pro Cys Leu Pro Gln Tyr Pro His Ile Asn Gly Ser Val Lys
    690                     695                     700

Thr
705

<210> SEQ ID NO 42
<211> LENGTH: 704
<212> TYPE: PRT
<213> ORGANISM: Homo sapiens

<400> SEQUENCE: 42
```

-continued

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Gly Ala Pro Tyr Trp Thr Asn Thr Glu Lys Met Glu
        35                  40                  45

Lys Arg Leu His Ala Val Pro Ala Ala Asn Thr Val Lys Phe Arg Cys
    50                  55                  60

Pro Ala Gly Gly Asn Pro Met Pro Thr Met Arg Trp Leu Lys Asn Gly
65                  70                  75                  80

Lys Glu Phe Lys Gln Glu His Arg Ile Gly Gly Tyr Lys Val Arg Asn
                85                  90                  95

Gln His Trp Ser Leu Ile Met Glu Ser Val Val Pro Ser Asp Lys Gly
            100                 105                 110

Asn Tyr Thr Cys Val Val Glu Asn Glu Tyr Gly Ser Ile Asn His Thr
        115                 120                 125

Tyr His Leu Asp Val Val Glu Arg Ser Pro His Arg Pro Ile Leu Gln
    130                 135                 140

Ala Gly Leu Pro Ala Asn Ala Ser Thr Val Val Gly Gly Asp Val Glu
145                 150                 155                 160

Phe Val Cys Lys Val Tyr Ser Asp Ala Gln Pro His Ile Gln Trp Ile
                165                 170                 175

Lys His Val Glu Lys Asn Gly Ser Lys Tyr Gly Pro Asp Gly Leu Pro
            180                 185                 190

Tyr Leu Lys Val Leu Lys Ala Ala Gly Val Asn Thr Thr Asp Lys Glu
        195                 200                 205

Ile Glu Val Leu Tyr Ile Arg Asn Val Thr Phe Glu Asp Ala Gly Glu
    210                 215                 220

Tyr Thr Cys Leu Ala Gly Asn Ser Ile Gly Ile Ser Phe His Ser Ala
225                 230                 235                 240

Trp Leu Thr Val Leu Pro Ala Pro Gly Arg Glu Lys Glu Ile Thr Ala
                245                 250                 255

Ser Pro Asp Tyr Leu Glu Ile Ala Ile Tyr Cys Ile Gly Val Phe Leu
            260                 265                 270

Ile Ala Cys Met Val Val Thr Val Ile Leu Cys Arg Met Lys Asn Thr
        275                 280                 285

Thr Lys Lys Pro Asp Phe Ser Ser Gln Pro Ala Val His Lys Leu Thr
    290                 295                 300

Lys Arg Ile Pro Leu Arg Arg Gln Val Ser Ala Glu Ser Ser Ser Ser
305                 310                 315                 320

Met Asn Ser Asn Thr Pro Leu Val Arg Ile Thr Thr Arg Leu Ser Ser
                325                 330                 335

Thr Ala Asp Thr Pro Met Leu Ala Gly Val Ser Glu Tyr Glu Leu Pro
            340                 345                 350

Glu Asp Pro Lys Trp Glu Phe Pro Arg Asp Lys Leu Thr Leu Gly Lys
        355                 360                 365

Pro Leu Gly Glu Gly Cys Phe Gly Gln Val Val Met Ala Glu Ala Val
    370                 375                 380

Gly Ile Asp Lys Asp Lys Pro Lys Glu Ala Val Thr Val Ala Val Lys
385                 390                 395                 400

Met Leu Lys Asp Asp Ala Thr Glu Lys Asp Leu Ser Asp Leu Val Ser
                405                 410                 415

Glu Met Glu Met Met Lys Met Ile Gly Lys His Lys Asn Ile Ile Asn
```

```
            420              425              430
Leu Leu Gly Ala Cys Thr Gln Asp Gly Pro Leu Tyr Val Ile Val Glu
            435              440              445
Tyr Ala Ser Lys Gly Asn Leu Arg Glu Tyr Leu Arg Ala Arg Arg Pro
450              455              460
Pro Gly Met Glu Tyr Ser Tyr Asp Ile Asn Arg Val Pro Glu Glu Gln
465              470              475              480
Met Thr Phe Lys Asp Leu Val Ser Cys Thr Tyr Gln Leu Ala Arg Gly
            485              490              495
Met Glu Tyr Leu Ala Ser Gln Lys Cys Ile His Arg Asp Leu Ala Ala
            500              505              510
Arg Asn Val Leu Val Thr Glu Asn Asn Val Met Lys Ile Ala Asp Phe
            515              520              525
Gly Leu Ala Arg Asp Ile Asn Asn Ile Asp Tyr Tyr Lys Lys Thr Thr
            530              535              540
Asn Gly Arg Leu Pro Val Lys Trp Met Ala Pro Glu Ala Leu Phe Asp
545              550              555              560
Arg Val Tyr Thr His Gln Ser Asp Val Trp Ser Phe Gly Val Leu Met
            565              570              575
Trp Glu Ile Phe Thr Leu Gly Gly Ser Pro Tyr Pro Gly Ile Pro Val
            580              585              590
Glu Glu Leu Phe Lys Leu Leu Lys Glu Gly His Arg Met Asp Lys Pro
            595              600              605
Ala Asn Cys Thr Asn Glu Leu Tyr Met Met Met Arg Asp Cys Trp His
            610              615              620
Ala Val Pro Ser Gln Arg Pro Thr Phe Lys Gln Leu Val Glu Asp Leu
625              630              635              640
Asp Arg Ile Leu Thr Leu Thr Thr Asn Glu Glu Tyr Leu Asp Leu Ser
            645              650              655
Gln Pro Leu Glu Gln Tyr Ser Pro Ser Tyr Pro Asp Thr Arg Ser Ser
            660              665              670
Cys Ser Ser Gly Asp Asp Ser Val Phe Ser Pro Asp Pro Met Pro Tyr
            675              680              685
Glu Pro Cys Leu Pro Gln Tyr Pro His Ile Asn Gly Ser Val Lys Thr
            690              695              700

<210> SEQ ID NO 43
<211> LENGTH: 680
<212> TYPE: PRT
<213> ORGANISM: Homo sapiens

<400> SEQUENCE: 43

Met Val Ser Trp Gly Arg Phe Ile Cys Leu Val Val Thr Met Ala
1               5               10              15
Thr Leu Ser Leu Ala Arg Pro Ser Phe Ser Leu Val Glu Asp Thr Thr
            20              25              30
Leu Glu Pro Glu Asp Ala Ile Ser Ser Gly Asp Asp Glu Asp Thr
            35              40              45
Asp Gly Ala Glu Asp Phe Val Ser Glu Asn Ser Asn Asn Lys Arg Ala
50              55              60
Pro Tyr Trp Thr Asn Thr Glu Lys Met Glu Lys Arg Leu His Ala Val
65              70              75              80
Pro Ala Ala Asn Thr Val Lys Phe Arg Cys Pro Ala Gly Gly Asn Pro
            85              90              95
```

```
Met Pro Thr Met Arg Trp Leu Lys Asn Gly Lys Glu Phe Lys Gln Glu
            100                 105                 110

His Arg Ile Gly Gly Tyr Lys Val Arg Asn Gln His Trp Ser Leu Ile
        115                 120                 125

Met Glu Ser Val Val Pro Ser Asp Lys Gly Asn Tyr Thr Cys Val Val
    130                 135                 140

Glu Asn Glu Tyr Gly Ser Ile Asn His Thr Tyr His Leu Asp Val Val
145                 150                 155                 160

Glu Arg Ser Pro His Arg Pro Ile Leu Gln Ala Gly Leu Pro Ala Asn
                165                 170                 175

Ala Ser Thr Val Val Gly Gly Asp Val Glu Phe Val Cys Lys Val Tyr
            180                 185                 190

Ser Asp Ala Gln Pro His Ile Gln Trp Ile Lys His Val Glu Lys Asn
        195                 200                 205

Gly Ser Lys Tyr Gly Pro Asp Gly Leu Pro Tyr Leu Lys Val Leu Lys
    210                 215                 220

His Ser Gly Ile Asn Ser Ser Asn Ala Glu Val Leu Ala Leu Phe Asn
225                 230                 235                 240

Val Thr Glu Ala Asp Ala Gly Glu Tyr Ile Cys Lys Val Ser Asn Tyr
                245                 250                 255

Ile Gly Gln Ala Asn Gln Ser Ala Trp Leu Thr Val Leu Pro Lys Gln
            260                 265                 270

Gln Ala Pro Gly Arg Glu Lys Glu Ile Thr Ala Ser Pro Asp Tyr Leu
        275                 280                 285

Glu Ile Ala Ile Tyr Cys Ile Gly Val Phe Leu Ile Ala Cys Met Val
    290                 295                 300

Val Thr Val Ile Leu Cys Arg Met Lys Asn Thr Thr Lys Lys Pro Asp
305                 310                 315                 320

Phe Ser Ser Gln Pro Ala Val His Lys Leu Thr Lys Arg Ile Pro Leu
                325                 330                 335

Arg Arg Gln Val Thr Val Ser Ala Glu Ser Ser Ser Ser Met Asn Ser
            340                 345                 350

Asn Thr Pro Leu Val Arg Ile Thr Thr Arg Leu Ser Ser Thr Ala Asp
        355                 360                 365

Thr Pro Met Leu Ala Gly Val Ser Glu Tyr Glu Leu Pro Glu Asp Pro
    370                 375                 380

Lys Trp Glu Phe Pro Arg Asp Lys Leu Thr Leu Gly Lys Pro Leu Gly
385                 390                 395                 400

Glu Gly Cys Phe Gly Gln Val Val Met Ala Glu Ala Val Gly Ile Asp
                405                 410                 415

Lys Asp Lys Pro Lys Glu Ala Val Thr Val Ala Val Lys Met Leu Lys
            420                 425                 430

Asp Asp Ala Thr Glu Lys Asp Leu Ser Asp Leu Val Ser Glu Met Glu
        435                 440                 445

Met Met Lys Met Ile Gly Lys His Lys Asn Ile Ile Asn Leu Leu Gly
    450                 455                 460

Ala Cys Thr Gln Asp Gly Pro Leu Tyr Val Ile Val Glu Tyr Ala Ser
465                 470                 475                 480

Lys Gly Asn Leu Arg Glu Tyr Leu Arg Ala Arg Arg Pro Pro Gly Met
                485                 490                 495

Glu Tyr Ser Tyr Asp Ile Asn Arg Val Pro Glu Glu Gln Met Thr Phe
            500                 505                 510

Lys Asp Leu Val Ser Cys Thr Tyr Gln Leu Ala Arg Gly Met Glu Tyr
```

```
            515                 520                 525
Leu Ala Ser Gln Lys Cys Ile His Arg Asp Leu Ala Ala Arg Asn Val
    530                 535                 540

Leu Val Thr Glu Asn Asn Val Met Lys Ile Ala Asp Phe Gly Leu Ala
545                 550                 555                 560

Arg Asp Ile Asn Asn Ile Asp Tyr Tyr Lys Thr Thr Asn Gly Arg
                565                 570                 575

Leu Pro Val Lys Trp Met Ala Pro Glu Ala Leu Phe Asp Arg Val Tyr
                580                 585                 590

Thr His Gln Ser Asp Val Trp Ser Phe Gly Val Leu Met Trp Glu Ile
            595                 600                 605

Phe Thr Leu Gly Gly Ser Pro Tyr Pro Gly Ile Pro Val Glu Glu Leu
        610                 615                 620

Phe Lys Leu Leu Lys Glu Gly His Arg Met Asp Lys Pro Ala Asn Cys
625                 630                 635                 640

Thr Asn Glu Leu Tyr Met Met Met Arg Asp Cys Trp His Ala Val Pro
                645                 650                 655

Ser Gln Arg Pro Thr Phe Lys Gln Leu Val Glu Asp Leu Asp Arg Ile
                660                 665                 670

Leu Thr Leu Thr Thr Asn Glu Ile
            675                 680

<210> SEQ ID NO 44
<211> LENGTH: 732
<212> TYPE: PRT
<213> ORGANISM: Homo sapiens

<400> SEQUENCE: 44

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Asp Ala Ile Ser Ser Gly Asp Asp Glu Asp Asp Thr
        35                  40                  45

Asp Gly Ala Glu Asp Phe Val Ser Glu Asn Ser Asn Asn Lys Arg Ala
50                  55                  60

Pro Tyr Trp Thr Asn Thr Glu Lys Met Glu Lys Arg Leu His Ala Val
65                  70                  75                  80

Pro Ala Ala Asn Thr Val Lys Phe Arg Cys Pro Ala Gly Gly Asn Pro
                85                  90                  95

Met Pro Thr Met Arg Trp Leu Lys Asn Gly Lys Glu Phe Lys Gln Glu
            100                 105                 110

His Arg Ile Gly Gly Tyr Lys Val Arg Asn Gln His Trp Ser Leu Ile
        115                 120                 125

Met Glu Ser Val Val Pro Ser Asp Lys Gly Asn Tyr Thr Cys Val Val
    130                 135                 140

Glu Asn Glu Tyr Gly Ser Ile Asn His Thr Tyr His Leu Asp Val Val
145                 150                 155                 160

Glu Arg Ser Pro His Arg Pro Ile Leu Gln Ala Gly Leu Pro Ala Asn
                165                 170                 175

Ala Ser Thr Val Val Gly Gly Asp Val Glu Phe Val Cys Lys Val Tyr
            180                 185                 190

Ser Asp Ala Gln Pro His Ile Gln Trp Ile Lys His Val Glu Lys Asn
        195                 200                 205
```

```
Gly Ser Lys Tyr Gly Pro Asp Gly Leu Pro Tyr Leu Lys Val Leu Lys
    210                 215                 220

Ala Ala Gly Val Asn Thr Thr Asp Lys Glu Ile Glu Val Leu Tyr Ile
225                 230                 235                 240

Arg Asn Val Thr Phe Glu Asp Ala Gly Glu Tyr Thr Cys Leu Ala Gly
                245                 250                 255

Asn Ser Ile Gly Ile Ser Phe His Ser Ala Trp Leu Thr Val Leu Pro
            260                 265                 270

Ala Pro Gly Arg Glu Lys Glu Ile Thr Ala Ser Pro Asp Tyr Leu Glu
                275                 280                 285

Ile Ala Ile Tyr Cys Ile Gly Val Phe Leu Ile Ala Cys Met Val Val
    290                 295                 300

Thr Val Ile Leu Cys Arg Met Lys Asn Thr Thr Lys Lys Pro Asp Phe
305                 310                 315                 320

Ser Ser Gln Pro Ala Val His Lys Leu Thr Lys Arg Ile Pro Leu Arg
                325                 330                 335

Arg Gln Val Thr Val Ser Ala Glu Ser Ser Ser Ser Met Asn Ser Asn
            340                 345                 350

Thr Pro Leu Val Arg Ile Thr Thr Arg Leu Ser Ser Thr Ala Asp Thr
    355                 360                 365

Pro Met Leu Ala Gly Val Ser Glu Tyr Glu Leu Pro Glu Asp Pro Lys
370                 375                 380

Trp Glu Phe Pro Arg Asp Lys Leu Thr Leu Gly Lys Pro Leu Gly Glu
385                 390                 395                 400

Gly Cys Phe Gly Gln Val Val Met Ala Glu Ala Val Gly Ile Asp Lys
                405                 410                 415

Asp Lys Pro Lys Glu Ala Val Thr Val Ala Val Lys Met Leu Lys Asp
            420                 425                 430

Asp Ala Thr Glu Lys Asp Leu Ser Asp Leu Val Ser Glu Met Glu Met
                435                 440                 445

Met Lys Met Ile Gly Lys His Lys Asn Ile Ile Asn Leu Leu Gly Ala
    450                 455                 460

Cys Thr Gln Asp Gly Pro Leu Tyr Val Ile Val Glu Tyr Ala Ser Lys
465                 470                 475                 480

Gly Asn Leu Arg Glu Tyr Leu Arg Ala Arg Arg Pro Pro Gly Met Glu
                485                 490                 495

Tyr Ser Tyr Asp Ile Asn Arg Val Pro Glu Glu Gln Met Thr Phe Lys
            500                 505                 510

Asp Leu Val Ser Cys Thr Tyr Gln Leu Ala Arg Gly Met Glu Tyr Leu
                515                 520                 525

Ala Ser Gln Lys Cys Ile His Arg Asp Leu Ala Ala Arg Asn Val Leu
    530                 535                 540

Val Thr Glu Asn Asn Val Met Lys Ile Ala Asp Phe Gly Leu Ala Arg
545                 550                 555                 560

Asp Ile Asn Asn Ile Asp Tyr Tyr Lys Lys Thr Thr Asn Gly Arg Leu
                565                 570                 575

Pro Val Lys Trp Met Ala Pro Glu Ala Leu Phe Asp Arg Val Tyr Thr
            580                 585                 590

His Gln Ser Asp Val Trp Ser Phe Gly Val Leu Met Trp Glu Ile Phe
                595                 600                 605

Thr Leu Gly Gly Ser Pro Tyr Pro Gly Ile Pro Val Glu Glu Leu Phe
    610                 615                 620

Lys Leu Leu Lys Glu Gly His Arg Met Asp Lys Pro Ala Asn Cys Thr
```

```
                   625                 630                 635                 640
Asn Glu Leu Tyr Met Met Met Arg Asp Cys Trp His Ala Val Pro Ser
                    645                 650                 655

Gln Arg Pro Thr Phe Lys Gln Leu Val Glu Asp Leu Asp Arg Ile Leu
                    660                 665                 670

Thr Leu Thr Thr Asn Glu Glu Tyr Leu Asp Leu Ser Gln Pro Leu Glu
                    675                 680                 685

Gln Tyr Ser Pro Ser Tyr Pro Asp Thr Arg Ser Ser Cys Ser Ser Gly
                    690                 695                 700

Asp Asp Ser Val Phe Ser Pro Asp Pro Met Pro Tyr Glu Pro Cys Leu
705                 710                 715                 720

Pro Gln Tyr Pro His Ile Asn Gly Ser Val Lys Thr
                    725                 730

<210> SEQ ID NO 45
<211> LENGTH: 820
<212> TYPE: PRT
<213> ORGANISM: Homo sapiens

<400> SEQUENCE: 45

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
        50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270
```

```
Val Glu Phe Met Cys Lys Val Tyr Ser Asp Pro Gln Pro His Ile Gln
            275                 280                 285

Trp Leu Lys His Ile Glu Val Asn Gly Ser Lys Ile Gly Pro Asp Asn
        290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
        355                 360                 365

Met Thr Ser Pro Leu Tyr Leu Glu Ile Ile Ile Tyr Cys Thr Gly Ala
    370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
                405                 410                 415

Leu Ala Lys Ser Ile Pro Leu Arg Arg Gln Val Ser Ala Asp Ser Ser
            420                 425                 430

Ala Ser Met Asn Ser Gly Val Leu Leu Val Arg Pro Ser Arg Leu Ser
        435                 440                 445

Ser Ser Gly Thr Pro Met Leu Ala Gly Val Ser Glu Tyr Glu Leu Pro
    450                 455                 460

Glu Asp Pro Arg Trp Glu Leu Pro Arg Asp Arg Leu Val Leu Gly Lys
465                 470                 475                 480

Pro Leu Gly Glu Gly Cys Phe Gly Gln Val Val Leu Ala Glu Ala Ile
                485                 490                 495

Gly Leu Asp Lys Asp Lys Pro Asn Arg Val Thr Lys Val Ala Val Lys
            500                 505                 510

Met Leu Lys Ser Asp Ala Thr Glu Lys Asp Leu Ser Asp Leu Ile Ser
        515                 520                 525

Glu Met Glu Met Met Lys Met Ile Gly Lys His Lys Asn Ile Ile Asn
    530                 535                 540

Leu Leu Gly Ala Cys Thr Gln Asp Gly Pro Leu Tyr Val Ile Val Glu
545                 550                 555                 560

Tyr Ala Ser Lys Gly Asn Leu Arg Glu Tyr Leu Gln Ala Arg Arg Pro
                565                 570                 575

Pro Gly Leu Glu Tyr Cys Tyr Asn Pro Ser His Asn Pro Glu Glu Gln
            580                 585                 590

Leu Ser Ser Lys Asp Leu Val Ser Cys Ala Tyr Gln Val Ala Arg Gly
        595                 600                 605

Met Glu Tyr Leu Ala Ser Lys Lys Cys Ile His Arg Asp Leu Ala Ala
    610                 615                 620

Arg Asn Val Leu Val Thr Glu Asp Asn Val Met Lys Ile Ala Asp Phe
625                 630                 635                 640

Gly Leu Ala Arg Asp Ile His His Ile Asp Tyr Tyr Lys Lys Thr Thr
                645                 650                 655

Asn Gly Arg Leu Pro Val Lys Trp Met Ala Pro Glu Ala Leu Phe Asp
            660                 665                 670

Arg Ile Tyr Thr His Gln Ser Asp Val Trp Ser Phe Gly Val Leu Leu
        675                 680                 685

Trp Glu Ile Phe Thr Leu Gly Gly Ser Pro Tyr Pro Gly Val Pro Val
```

```
                        690                 695                 700
Glu Glu Leu Phe Lys Leu Leu Lys Glu Gly His Arg Met Asp Lys Pro
705                 710                 715                 720

Ser Asn Cys Thr Asn Glu Leu Tyr Met Met Met Arg Asp Cys Trp His
                725                 730                 735

Ala Val Pro Ser Gln Arg Pro Thr Phe Lys Gln Leu Val Glu Asp Leu
                740                 745                 750

Asp Arg Ile Val Ala Leu Thr Ser Asn Gln Glu Tyr Leu Asp Leu Ser
                755                 760                 765

Met Pro Leu Asp Gln Tyr Ser Pro Ser Phe Pro Asp Thr Arg Ser Ser
770                 775                 780

Thr Cys Ser Ser Gly Glu Asp Ser Val Phe Ser His Glu Pro Leu Pro
785                 790                 795                 800

Glu Glu Pro Cys Leu Pro Arg His Pro Ala Gln Leu Ala Asn Gly Gly
                805                 810                 815

Leu Lys Arg Arg
                820

<210> SEQ ID NO 46
<211> LENGTH: 812
<212> TYPE: PRT
<213> ORGANISM: Homo sapiens

<400> SEQUENCE: 46

Met Ala Ala Val Thr Arg Asp Phe Gly Glu Met Leu Leu His Ser Gly
1               5                   10                  15

Arg Val Leu Pro Ala Glu Ala Gln Pro Trp Gly Ala Pro Val Glu Val
                20                  25                  30

Glu Ser Phe Leu Val His Pro Gly Asp Leu Leu Gln Leu Arg Cys Arg
                35                  40                  45

Leu Arg Asp Asp Val Gln Ser Ile Asn Trp Leu Arg Asp Gly Val Gln
            50                  55                  60

Leu Ala Glu Ser Asn Arg Thr Arg Ile Thr Gly Glu Glu Val Glu Val
65                  70                  75                  80

Gln Asp Ser Val Pro Ala Asp Ser Gly Leu Tyr Ala Cys Val Thr Ser
                85                  90                  95

Ser Pro Ser Gly Ser Asp Thr Thr Tyr Phe Ser Val Asn Val Ser Asp
                100                 105                 110

Ala Leu Pro Ser Ser Glu Asp Asp Asp Asp Asp Asp Ser Ser Ser
                115                 120                 125

Glu Glu Lys Glu Thr Asp Asn Thr Lys Pro Asn Arg Met Pro Val Ala
                130                 135                 140

Pro Tyr Trp Thr Ser Pro Glu Lys Met Glu Lys Lys Leu His Ala Val
145                 150                 155                 160

Pro Ala Ala Lys Thr Val Lys Phe Lys Cys Pro Ser Ser Gly Thr Pro
                165                 170                 175

Asn Pro Thr Leu Arg Trp Leu Lys Asn Gly Lys Glu Phe Lys Pro Asp
                180                 185                 190

His Arg Ile Gly Gly Tyr Lys Val Arg Tyr Ala Thr Trp Ser Ile Ile
                195                 200                 205

Met Asp Ser Val Val Pro Ser Asp Lys Gly Asn Tyr Thr Cys Ile Val
            210                 215                 220

Glu Asn Glu Tyr Gly Ser Ile Asn His Thr Tyr Gln Leu Asp Val Val
225                 230                 235                 240
```

```
Glu Arg Ser Pro His Arg Pro Ile Leu Gln Ala Gly Leu Pro Ala Asn
                245                 250                 255
Lys Thr Val Ala Leu Gly Ser Asn Val Glu Phe Met Cys Lys Val Tyr
            260                 265                 270
Ser Asp Pro Gln Pro His Ile Gln Trp Leu Lys His Ile Glu Val Asn
            275                 280                 285
Gly Ser Lys Ile Gly Pro Asp Asn Leu Pro Tyr Val Gln Ile Leu Lys
        290                 295                 300
Thr Ala Gly Val Asn Thr Thr Asp Lys Glu Met Glu Val Leu His Leu
305                 310                 315                 320
Arg Asn Val Ser Phe Glu Asp Ala Gly Glu Tyr Thr Cys Leu Ala Gly
                325                 330                 335
Asn Ser Ile Gly Leu Ser His His Ser Ala Trp Leu Thr Val Leu Glu
            340                 345                 350
Ala Leu Glu Glu Arg Pro Ala Val Met Thr Ser Pro Leu Tyr Leu Glu
            355                 360                 365
Ile Ile Ile Tyr Cys Thr Gly Ala Phe Leu Ile Ser Cys Met Val Gly
        370                 375                 380
Ser Val Ile Val Tyr Lys Met Lys Ser Gly Thr Lys Lys Ser Asp Phe
385                 390                 395                 400
His Ser Gln Met Ala Val His Lys Leu Ala Lys Ser Ile Pro Leu Arg
                405                 410                 415
Arg Gln Val Ser Ala Asp Ser Ser Ala Ser Met Asn Ser Gly Val Leu
            420                 425                 430
Leu Val Arg Pro Ser Arg Leu Ser Ser Ser Gly Thr Pro Met Leu Ala
            435                 440                 445
Gly Val Ser Glu Tyr Glu Leu Pro Glu Asp Pro Arg Trp Glu Leu Pro
        450                 455                 460
Arg Asp Arg Leu Val Leu Gly Lys Pro Leu Gly Glu Gly Cys Phe Gly
465                 470                 475                 480
Gln Val Val Leu Ala Glu Ala Ile Gly Leu Asp Lys Asp Lys Pro Asn
                485                 490                 495
Arg Val Thr Lys Val Ala Val Lys Met Leu Lys Ser Asp Ala Thr Glu
            500                 505                 510
Lys Asp Leu Ser Asp Leu Ile Ser Glu Met Glu Met Met Lys Met Ile
            515                 520                 525
Gly Lys His Lys Asn Ile Ile Asn Leu Leu Gly Ala Cys Thr Gln Asp
        530                 535                 540
Gly Pro Leu Tyr Val Ile Val Glu Tyr Ala Ser Lys Gly Asn Leu Arg
545                 550                 555                 560
Glu Tyr Leu Gln Ala Arg Arg Pro Pro Gly Leu Glu Tyr Cys Tyr Asn
                565                 570                 575
Pro Ser His Asn Pro Glu Glu Gln Leu Ser Ser Lys Asp Leu Val Ser
            580                 585                 590
Cys Ala Tyr Gln Val Ala Arg Gly Met Glu Tyr Leu Ala Ser Lys Lys
            595                 600                 605
Cys Ile His Arg Asp Leu Ala Ala Arg Asn Val Leu Val Thr Glu Asp
        610                 615                 620
Asn Val Met Lys Ile Ala Asp Phe Gly Leu Ala Arg Asp Ile His His
625                 630                 635                 640
Ile Asp Tyr Tyr Lys Lys Thr Thr Asn Gly Arg Leu Pro Val Lys Trp
                645                 650                 655
Met Ala Pro Glu Ala Leu Phe Asp Arg Ile Tyr Thr His Gln Ser Asp
```

```
                    660                 665                 670
Val Trp Ser Phe Gly Val Leu Leu Trp Glu Ile Phe Thr Leu Gly Gly
                675                 680                 685

Ser Pro Tyr Pro Gly Val Pro Val Glu Glu Leu Phe Lys Leu Leu Lys
            690                 695                 700

Glu Gly His Arg Met Asp Lys Pro Ser Asn Cys Thr Asn Glu Leu Tyr
705                 710                 715                 720

Met Met Met Arg Asp Cys Trp His Ala Val Pro Ser Gln Arg Pro Thr
                725                 730                 735

Phe Lys Gln Leu Val Glu Asp Leu Asp Arg Ile Val Ala Leu Thr Ser
            740                 745                 750

Asn Gln Glu Tyr Leu Asp Leu Ser Met Pro Leu Asp Gln Tyr Ser Pro
        755                 760                 765

Ser Phe Pro Asp Thr Arg Ser Ser Thr Cys Ser Ser Gly Glu Asp Ser
    770                 775                 780

Val Phe Ser His Glu Pro Leu Pro Glu Glu Pro Cys Leu Pro Arg His
785                 790                 795                 800

Pro Ala Gln Leu Ala Asn Gly Gly Leu Lys Arg Arg
                805                 810

<210> SEQ ID NO 47
<211> LENGTH: 820
<212> TYPE: PRT
<213> ORGANISM: Homo sapiens

<400> SEQUENCE: 47

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
    210                 215                 220
```

```
Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
            245                 250                 255

Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
            275                 280                 285

Lys His Ile Glu Val Asn Gly Ser Lys Ile Gly Pro Asp Asn Leu Pro
290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
            325                 330                 335

Tyr Thr Cys Leu Ala Gly Asn Ser Ile Gly Leu Ser His His Ser Ala
            340                 345                 350

Trp Leu Thr Val Leu Glu Ala Leu Glu Glu Arg Pro Ala Val Met Thr
            355                 360                 365

Ser Pro Leu Tyr Leu Glu Ile Ile Ile Tyr Cys Thr Gly Ala Phe Leu
370                 375                 380

Ile Ser Cys Met Val Gly Ser Val Ile Val Tyr Lys Met Lys Ser Gly
385                 390                 395                 400

Thr Lys Lys Ser Asp Phe His Ser Gln Met Ala Val His Lys Leu Ala
            405                 410                 415

Lys Ser Ile Pro Leu Arg Arg Gln Val Thr Val Ser Ala Asp Ser Ser
            420                 425                 430

Ala Ser Met Asn Ser Gly Val Leu Leu Val Arg Pro Ser Arg Leu Ser
            435                 440                 445

Ser Ser Gly Thr Pro Met Leu Ala Gly Val Ser Glu Tyr Glu Leu Pro
450                 455                 460

Glu Asp Pro Arg Trp Glu Leu Pro Arg Asp Arg Leu Val Leu Gly Lys
465                 470                 475                 480

Pro Leu Gly Glu Gly Cys Phe Gly Gln Val Val Leu Ala Glu Ala Ile
            485                 490                 495

Gly Leu Asp Lys Asp Lys Pro Asn Arg Val Thr Lys Val Ala Val Lys
            500                 505                 510

Met Leu Lys Ser Asp Ala Thr Glu Lys Asp Leu Ser Asp Leu Ile Ser
            515                 520                 525

Glu Met Glu Met Met Lys Met Ile Gly Lys His Lys Asn Ile Ile Asn
530                 535                 540

Leu Leu Gly Ala Cys Thr Gln Asp Gly Pro Leu Tyr Val Ile Val Glu
545                 550                 555                 560

Tyr Ala Ser Lys Gly Asn Leu Arg Glu Tyr Leu Gln Ala Arg Arg Pro
            565                 570                 575

Pro Gly Leu Glu Tyr Cys Tyr Asn Pro Ser His Asn Pro Glu Glu Gln
            580                 585                 590

Leu Ser Ser Lys Asp Leu Val Ser Cys Ala Tyr Gln Val Ala Arg Gly
            595                 600                 605

Met Glu Tyr Leu Ala Ser Lys Lys Cys Ile His Arg Asp Leu Ala Ala
            610                 615                 620

Arg Asn Val Leu Val Thr Glu Asp Asn Val Met Lys Ile Ala Asp Phe
625                 630                 635                 640

Gly Leu Ala Arg Asp Ile His His Ile Asp Tyr Tyr Lys Lys Thr Thr
```

```
                    645                 650                 655
Asn Gly Arg Leu Pro Val Lys Trp Met Ala Pro Glu Ala Leu Phe Asp
            660                 665                 670

Arg Ile Tyr Thr His Gln Ser Asp Val Trp Ser Phe Gly Val Leu Leu
            675                 680                 685

Trp Glu Ile Phe Thr Leu Gly Gly Ser Pro Tyr Pro Gly Val Pro Val
            690                 695                 700

Glu Glu Leu Phe Lys Leu Leu Lys Glu Gly His Arg Met Asp Lys Pro
705                 710                 715                 720

Ser Asn Cys Thr Asn Glu Leu Tyr Met Met Met Arg Asp Cys Trp His
                725                 730                 735

Ala Val Pro Ser Gln Arg Pro Thr Phe Lys Gln Leu Val Glu Asp Leu
            740                 745                 750

Asp Arg Ile Val Ala Leu Thr Ser Asn Gln Glu Tyr Leu Asp Leu Ser
            755                 760                 765

Met Pro Leu Asp Gln Tyr Ser Pro Ser Phe Pro Asp Thr Arg Ser Ser
770                 775                 780

Thr Cys Ser Ser Gly Glu Asp Ser Val Phe Ser His Glu Pro Leu Pro
785                 790                 795                 800

Glu Glu Pro Cys Leu Pro Arg His Pro Ala Gln Leu Ala Asn Gly Gly
                805                 810                 815

Leu Lys Arg Arg
            820

<210> SEQ ID NO 48
<211> LENGTH: 733
<212> TYPE: PRT
<213> ORGANISM: Homo sapiens

<400> SEQUENCE: 48

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Asp Ala
            20                  25                  30

Leu Pro Ser Ser Glu Asp Asp Asp Asp Asp Asp Ser Ser Ser Glu
            35                  40                  45

Glu Lys Glu Thr Asp Asn Thr Lys Pro Asn Arg Met Pro Val Ala Pro
        50                  55                  60

Tyr Trp Thr Ser Pro Glu Lys Met Glu Lys Lys Leu His Ala Val Pro
65                  70                  75                  80

Ala Ala Lys Thr Val Lys Phe Lys Cys Pro Ser Ser Gly Thr Pro Asn
                85                  90                  95

Pro Thr Leu Arg Trp Leu Lys Asn Gly Lys Glu Phe Lys Pro Asp His
            100                 105                 110

Arg Ile Gly Gly Tyr Lys Val Arg Tyr Ala Thr Trp Ser Ile Ile Met
            115                 120                 125

Asp Ser Val Val Pro Ser Asp Lys Gly Asn Tyr Thr Cys Ile Val Glu
        130                 135                 140

Asn Glu Tyr Gly Ser Ile Asn His Thr Tyr Gln Leu Asp Val Val Glu
145                 150                 155                 160

Arg Ser Pro His Arg Pro Ile Leu Gln Ala Gly Leu Pro Ala Asn Lys
                165                 170                 175

Thr Val Ala Leu Gly Ser Asn Val Glu Phe Met Cys Lys Val Tyr Ser
            180                 185                 190
```

```
Asp Pro Gln Pro His Ile Gln Trp Leu Lys His Ile Glu Val Asn Gly
            195                 200                 205

Ser Lys Ile Gly Pro Asp Asn Leu Pro Tyr Val Gln Ile Leu Lys Thr
        210                 215                 220

Ala Gly Val Asn Thr Thr Asp Lys Glu Met Glu Val Leu His Leu Arg
225                 230                 235                 240

Asn Val Ser Phe Glu Asp Ala Gly Glu Tyr Thr Cys Leu Ala Gly Asn
                245                 250                 255

Ser Ile Gly Leu Ser His His Ser Ala Trp Leu Thr Val Leu Glu Ala
            260                 265                 270

Leu Glu Glu Arg Pro Ala Val Met Thr Ser Pro Leu Tyr Leu Glu Ile
        275                 280                 285

Ile Ile Tyr Cys Thr Gly Ala Phe Leu Ile Ser Cys Met Val Gly Ser
290                 295                 300

Val Ile Val Tyr Lys Met Lys Ser Gly Thr Lys Lys Ser Asp Phe His
305                 310                 315                 320

Ser Gln Met Ala Val His Lys Leu Ala Lys Ser Ile Pro Leu Arg Arg
                325                 330                 335

Gln Val Thr Val Ser Ala Asp Ser Ser Ala Ser Met Asn Ser Gly Val
            340                 345                 350

Leu Leu Val Arg Pro Ser Arg Leu Ser Ser Ser Gly Thr Pro Met Leu
        355                 360                 365

Ala Gly Val Ser Glu Tyr Glu Leu Pro Glu Asp Pro Arg Trp Glu Leu
    370                 375                 380

Pro Arg Asp Arg Leu Val Leu Gly Lys Pro Leu Gly Glu Gly Cys Phe
385                 390                 395                 400

Gly Gln Val Val Leu Ala Glu Ala Ile Gly Leu Asp Lys Asp Lys Pro
                405                 410                 415

Asn Arg Val Thr Lys Val Ala Val Lys Met Leu Lys Ser Asp Ala Thr
            420                 425                 430

Glu Lys Asp Leu Ser Asp Leu Ile Ser Glu Met Glu Met Met Lys Met
        435                 440                 445

Ile Gly Lys His Lys Asn Ile Ile Asn Leu Leu Gly Ala Cys Thr Gln
450                 455                 460

Asp Gly Pro Leu Tyr Val Ile Val Glu Tyr Ala Ser Lys Gly Asn Leu
465                 470                 475                 480

Arg Glu Tyr Leu Gln Ala Arg Arg Pro Pro Gly Leu Glu Tyr Cys Tyr
                485                 490                 495

Asn Pro Ser His Asn Pro Glu Glu Gln Leu Ser Ser Lys Asp Leu Val
            500                 505                 510

Ser Cys Ala Tyr Gln Val Ala Arg Gly Met Glu Tyr Leu Ala Ser Lys
        515                 520                 525

Lys Cys Ile His Arg Asp Leu Ala Ala Arg Asn Val Leu Val Thr Glu
530                 535                 540

Asp Asn Val Met Lys Ile Ala Asp Phe Gly Leu Ala Arg Asp Ile His
545                 550                 555                 560

His Ile Asp Tyr Tyr Lys Lys Thr Thr Asn Gly Arg Leu Pro Val Lys
                565                 570                 575

Trp Met Ala Pro Glu Ala Leu Phe Asp Arg Ile Tyr Thr His Gln Ser
            580                 585                 590

Asp Val Trp Ser Phe Gly Val Leu Leu Trp Glu Ile Phe Thr Leu Gly
        595                 600                 605

Gly Ser Pro Tyr Pro Gly Val Pro Val Glu Glu Leu Phe Lys Leu Leu
```

610                 615                 620
Lys Glu Gly His Arg Met Asp Lys Pro Ser Asn Cys Thr Asn Glu Leu
625                 630                 635                 640

Tyr Met Met Arg Asp Cys Trp His Ala Val Pro Ser Gln Arg Pro
            645                 650                 655

Thr Phe Lys Gln Leu Val Glu Asp Leu Asp Arg Ile Val Ala Leu Thr
                660                 665                 670

Ser Asn Gln Glu Tyr Leu Asp Leu Ser Met Pro Leu Asp Gln Tyr Ser
            675                 680                 685

Pro Ser Phe Pro Asp Thr Arg Ser Ser Thr Cys Ser Ser Gly Glu Asp
        690                 695                 700

Ser Val Phe Ser His Glu Pro Leu Pro Glu Glu Pro Cys Leu Pro Arg
705                 710                 715                 720

His Pro Ala Gln Leu Ala Asn Gly Gly Leu Lys Arg Arg
                725                 730

<210> SEQ ID NO 49
<211> LENGTH: 731
<212> TYPE: PRT
<213> ORGANISM: Homo sapiens

<400> SEQUENCE: 49

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Asp Ala
                20                  25                  30

Leu Pro Ser Ser Glu Asp Asp Asp Asp Asp Asp Ser Ser Ser Glu Glu
            35                  40                  45

Lys Glu Thr Asp Asn Thr Lys Pro Asn Pro Val Ala Pro Tyr Trp
50                  55                  60

Thr Ser Pro Glu Lys Met Glu Lys Lys Leu His Ala Val Pro Ala Ala
65                  70                  75                  80

Lys Thr Val Lys Phe Lys Cys Pro Ser Ser Gly Thr Pro Asn Pro Thr
                85                  90                  95

Leu Arg Trp Leu Lys Asn Gly Lys Glu Phe Lys Pro Asp His Arg Ile
            100                 105                 110

Gly Gly Tyr Lys Val Arg Tyr Ala Thr Trp Ser Ile Ile Met Asp Ser
        115                 120                 125

Val Val Pro Ser Asp Lys Gly Asn Tyr Thr Cys Ile Val Glu Asn Glu
130                 135                 140

Tyr Gly Ser Ile Asn His Thr Tyr Gln Leu Asp Val Val Glu Arg Ser
145                 150                 155                 160

Pro His Arg Pro Ile Leu Gln Ala Gly Leu Pro Ala Asn Lys Thr Val
                165                 170                 175

Ala Leu Gly Ser Asn Val Glu Phe Met Cys Lys Val Tyr Ser Asp Pro
            180                 185                 190

Gln Pro His Ile Gln Trp Leu Lys His Ile Glu Val Asn Gly Ser Lys
        195                 200                 205

Ile Gly Pro Asp Asn Leu Pro Tyr Val Gln Ile Leu Lys Thr Ala Gly
210                 215                 220

Val Asn Thr Thr Asp Lys Glu Met Glu Val Leu His Leu Arg Asn Val
225                 230                 235                 240

Ser Phe Glu Asp Ala Gly Glu Tyr Thr Cys Leu Ala Gly Asn Ser Ile
                245                 250                 255

-continued

Gly Leu Ser His His Ser Ala Trp Leu Thr Val Leu Glu Ala Leu Glu
        260                 265                 270

Glu Arg Pro Ala Val Met Thr Ser Pro Leu Tyr Leu Glu Ile Ile Ile
    275                 280                 285

Tyr Cys Thr Gly Ala Phe Leu Ile Ser Cys Met Val Gly Ser Val Ile
    290                 295                 300

Val Tyr Lys Met Lys Ser Gly Thr Lys Lys Ser Asp Phe His Ser Gln
305                 310                 315                 320

Met Ala Val His Lys Leu Ala Lys Ser Ile Pro Leu Arg Arg Gln Val
                325                 330                 335

Thr Val Ser Ala Asp Ser Ser Ala Ser Met Asn Ser Gly Val Leu Leu
            340                 345                 350

Val Arg Pro Ser Arg Leu Ser Ser Ser Gly Thr Pro Met Leu Ala Gly
        355                 360                 365

Val Ser Glu Tyr Glu Leu Pro Glu Asp Pro Arg Trp Glu Leu Pro Arg
    370                 375                 380

Asp Arg Leu Val Leu Gly Lys Pro Leu Gly Glu Gly Cys Phe Gly Gln
385                 390                 395                 400

Val Val Leu Ala Glu Ala Ile Gly Leu Asp Lys Asp Lys Pro Asn Arg
                405                 410                 415

Val Thr Lys Val Ala Val Lys Met Leu Lys Ser Asp Ala Thr Glu Lys
            420                 425                 430

Asp Leu Ser Asp Leu Ile Ser Glu Met Glu Met Met Lys Met Ile Gly
        435                 440                 445

Lys His Lys Asn Ile Ile Asn Leu Leu Gly Ala Cys Thr Gln Asp Gly
450                 455                 460

Pro Leu Tyr Val Ile Val Glu Tyr Ala Ser Lys Gly Asn Leu Arg Glu
465                 470                 475                 480

Tyr Leu Gln Ala Arg Arg Pro Pro Gly Leu Glu Tyr Cys Tyr Asn Pro
                485                 490                 495

Ser His Asn Pro Glu Glu Gln Leu Ser Ser Lys Asp Leu Val Ser Cys
            500                 505                 510

Ala Tyr Gln Val Ala Arg Gly Met Glu Tyr Leu Ala Ser Lys Lys Cys
        515                 520                 525

Ile His Arg Asp Leu Ala Ala Arg Asn Val Leu Val Thr Glu Asp Asn
    530                 535                 540

Val Met Lys Ile Ala Asp Phe Gly Leu Ala Arg Asp Ile His His Ile
545                 550                 555                 560

Asp Tyr Tyr Lys Lys Thr Thr Asn Gly Arg Leu Pro Val Lys Trp Met
                565                 570                 575

Ala Pro Glu Ala Leu Phe Asp Arg Ile Tyr Thr His Gln Ser Asp Val
            580                 585                 590

Trp Ser Phe Gly Val Leu Leu Trp Glu Ile Phe Thr Leu Gly Gly Ser
        595                 600                 605

Pro Tyr Pro Gly Val Pro Val Glu Glu Leu Phe Lys Leu Leu Lys Glu
    610                 615                 620

Gly His Arg Met Asp Lys Pro Ser Asn Cys Thr Asn Glu Leu Tyr Met
625                 630                 635                 640

Met Met Arg Asp Cys Trp His Ala Val Pro Ser Gln Arg Pro Thr Phe
                645                 650                 655

Lys Gln Leu Val Glu Asp Leu Asp Arg Ile Val Ala Leu Thr Ser Asn
            660                 665                 670

Gln Glu Tyr Leu Asp Leu Ser Met Pro Leu Asp Gln Tyr Ser Pro Ser

```
                    675                 680                 685
Phe Pro Asp Thr Arg Ser Ser Thr Cys Ser Ser Gly Glu Asp Ser Val
    690                 695                 700
Phe Ser His Glu Pro Leu Pro Glu Glu Pro Cys Leu Pro Arg His Pro
705                 710                 715                 720
Ala Gln Leu Ala Asn Gly Gly Leu Lys Arg Arg
                    725                 730

<210> SEQ ID NO 50
<211> LENGTH: 822
<212> TYPE: PRT
<213> ORGANISM: Homo sapiens

<400> SEQUENCE: 50

Met Trp Ser Trp Lys Cys Leu Leu Phe Trp Ala Val Leu Val Thr Ala
1               5                   10                  15
Thr Leu Cys Thr Ala Arg Pro Ser Pro Thr Leu Pro Glu Gln Ala Gln
                20                  25                  30
Pro Trp Gly Ala Pro Val Glu Val Glu Ser Phe Leu Val His Pro Gly
            35                  40                  45
Asp Leu Leu Gln Leu Arg Cys Arg Leu Arg Asp Asp Val Gln Ser Ile
        50                  55                  60
Asn Trp Leu Arg Asp Gly Val Gln Leu Ala Glu Ser Asn Arg Thr Arg
65                  70                  75                  80
Ile Thr Gly Glu Glu Val Glu Val Gln Asp Ser Val Pro Ala Asp Ser
                85                  90                  95
Gly Leu Tyr Ala Cys Val Thr Ser Ser Pro Ser Gly Ser Asp Thr Thr
            100                 105                 110
Tyr Phe Ser Val Asn Val Ser Asp Ala Leu Pro Ser Ser Glu Asp Asp
        115                 120                 125
Asp Asp Asp Asp Asp Ser Ser Ser Glu Glu Lys Glu Thr Asp Asn Thr
    130                 135                 140
Lys Pro Asn Arg Met Pro Val Ala Pro Tyr Trp Thr Ser Pro Glu Lys
145                 150                 155                 160
Met Glu Lys Lys Leu His Ala Val Pro Ala Ala Lys Thr Val Lys Phe
                165                 170                 175
Lys Cys Pro Ser Ser Gly Thr Pro Asn Pro Thr Leu Arg Trp Leu Lys
            180                 185                 190
Asn Gly Lys Glu Phe Lys Pro Asp His Arg Ile Gly Gly Tyr Lys Val
        195                 200                 205
Arg Tyr Ala Thr Trp Ser Ile Ile Met Asp Ser Val Val Pro Ser Asp
    210                 215                 220
Lys Gly Asn Tyr Thr Cys Ile Val Glu Asn Glu Tyr Gly Ser Ile Asn
225                 230                 235                 240
His Thr Tyr Gln Leu Asp Val Val Glu Arg Ser Pro His Arg Pro Ile
                245                 250                 255
Leu Gln Ala Gly Leu Pro Ala Asn Lys Thr Val Ala Leu Gly Ser Asn
            260                 265                 270
Val Glu Phe Met Cys Lys Val Tyr Ser Asp Pro Gln Pro His Ile Gln
        275                 280                 285
Trp Leu Lys His Ile Glu Val Asn Gly Ser Lys Ile Gly Pro Asp Asn
    290                 295                 300
Leu Pro Tyr Val Gln Ile Leu Lys Thr Ala Gly Val Asn Thr Thr Asp
305                 310                 315                 320
```

-continued

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
        355                 360                 365

Met Thr Ser Pro Leu Tyr Leu Glu Ile Ile Ile Tyr Cys Thr Gly Ala
    370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
                405                 410                 415

Leu Ala Lys Ser Ile Pro Leu Arg Arg Gln Val Thr Val Ser Ala Asp
            420                 425                 430

Ser Ser Ala Ser Met Asn Ser Gly Val Leu Leu Val Arg Pro Ser Arg
        435                 440                 445

Leu Ser Ser Gly Thr Pro Met Leu Ala Gly Val Ser Glu Tyr Glu
    450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
                485                 490                 495

Ala Ile Gly Leu Asp Lys Asp Lys Pro Asn Arg Val Thr Lys Val Ala
            500                 505                 510

Val Lys Met Leu Lys Ser Asp Ala Thr Glu Lys Asp Leu Ser Asp Leu
        515                 520                 525

Ile Ser Glu Met Glu Met Met Lys Met Ile Gly Lys His Lys Asn Ile
    530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
                565                 570                 575

Arg Pro Pro Gly Leu Glu Tyr Cys Tyr Asn Pro Ser His Asn Pro Glu
            580                 585                 590

Glu Gln Leu Ser Ser Lys Asp Leu Val Ser Cys Ala Tyr Gln Val Ala
        595                 600                 605

Arg Gly Met Glu Tyr Leu Ala Ser Lys Lys Cys Ile His Arg Asp Leu
    610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
                645                 650                 655

Thr Thr Asn Gly Arg Leu Pro Val Lys Trp Met Ala Pro Glu Ala Leu
            660                 665                 670

Phe Asp Arg Ile Tyr Thr His Gln Ser Asp Val Trp Ser Phe Gly Val
        675                 680                 685

Leu Leu Trp Glu Ile Phe Thr Leu Gly Gly Ser Pro Tyr Pro Gly Val
    690                 695                 700

Pro Val Glu Glu Leu Phe Lys Leu Leu Lys Glu Gly His Arg Met Asp
705                 710                 715                 720

Lys Pro Ser Asn Cys Thr Asn Glu Leu Tyr Met Met Met Arg Asp Cys
                725                 730                 735

Trp His Ala Val Pro Ser Gln Arg Pro Thr Phe Lys Gln Leu Val Glu

```
                    740                 745                 750
Asp Leu Asp Arg Ile Val Ala Leu Thr Ser Asn Gln Glu Tyr Leu Asp
            755                 760                 765

Leu Ser Met Pro Leu Asp Gln Tyr Ser Pro Ser Phe Pro Asp Thr Arg
        770                 775                 780

Ser Ser Thr Cys Ser Ser Gly Glu Asp Ser Val Phe Ser His Glu Pro
785                 790                 795                 800

Leu Pro Glu Glu Pro Cys Leu Pro Arg His Pro Ala Gln Leu Ala Asn
                805                 810                 815

Gly Gly Leu Lys Arg Arg
                820

<210> SEQ ID NO 51
<211> LENGTH: 808
<212> TYPE: PRT
<213> ORGANISM: Homo sapiens

<400> SEQUENCE: 51

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285
```

-continued

```
Lys His Val Glu Val Asn Gly Ser Lys Val Gly Pro Asp Gly Thr Pro
    290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp
                340                 345                 350

Leu Ser Val His Gly Pro Arg Ala Glu Glu Leu Val Glu Ala
                355                 360                 365

Asp Glu Ala Gly Ser Val Tyr Ala Gly Ile Leu Ser Tyr Gly Val Gly
    370                 375                 380

Phe Phe Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
                405                 410                 415

Ser Arg Phe Pro Leu Lys Arg Gln Val Ser Leu Glu Ser Asn Ala Ser
                420                 425                 430

Met Ser Ser Asn Thr Pro Leu Val Arg Ile Ala Arg Leu Ser Ser Gly
    435                 440                 445

Glu Gly Pro Thr Leu Ala Asn Val Ser Glu Leu Glu Leu Pro Ala Asp
    450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
                500                 505                 510

Lys Asp Asp Ala Thr Asp Lys Asp Leu Ser Asp Leu Val Ser Glu Met
    515                 520                 525

Glu Met Met Lys Met Ile Gly Lys His Lys Asn Ile Ile Asn Leu Leu
    530                 535                 540

Gly Ala Cys Thr Gln Gly Gly Pro Leu Tyr Val Leu Val Glu Tyr Ala
545                 550                 555                 560

Ala Lys Gly Asn Leu Arg Glu Phe Leu Arg Ala Arg Arg Pro Pro Gly
                565                 570                 575

Leu Asp Tyr Ser Phe Asp Thr Cys Lys Pro Pro Glu Glu Gln Leu Thr
                580                 585                 590

Phe Lys Asp Leu Val Ser Cys Ala Tyr Gln Val Ala Arg Gly Met Glu
                595                 600                 605

Tyr Leu Ala Ser Gln Lys Cys Ile His Arg Asp Leu Ala Ala Arg Asn
    610                 615                 620

Val Leu Val Thr Glu Asp Asn Val Met Lys Ile Ala Asp Phe Gly Leu
625                 630                 635                 640

Ala Arg Asp Val His Asn Leu Asp Tyr Tyr Lys Lys Thr Thr Asn Gly
                645                 650                 655

Arg Leu Pro Val Lys Trp Met Ala Pro Glu Ala Leu Phe Asp Arg Val
                660                 665                 670

Tyr Thr His Gln Ser Asp Val Trp Ser Phe Gly Val Leu Leu Trp Glu
                675                 680                 685

Ile Phe Thr Leu Gly Gly Ser Pro Tyr Pro Gly Ile Pro Val Glu Glu
    690                 695                 700

Leu Phe Lys Leu Leu Lys Glu Gly His Arg Met Asp Lys Pro Ala Asn
```

```
                    705                 710                 715                 720
Cys Thr His Asp Leu Tyr Met Ile Met Arg Glu Cys Trp His Ala Ala
                725                 730                 735
Pro Ser Gln Arg Pro Thr Phe Lys Gln Leu Val Glu Asp Leu Asp Arg
                740                 745                 750
Val Leu Thr Val Thr Ser Thr Asp Glu Tyr Leu Asp Leu Ser Ala Pro
                755                 760                 765
Phe Glu Gln Tyr Ser Pro Gly Gly Gln Asp Thr Pro Ser Ser Ser Ser
                770                 775                 780
Ser Gly Asp Asp Ser Val Phe Ala His Asp Leu Leu Pro Pro Ala Pro
785                 790                 795                 800
Pro Ser Ser Gly Gly Ser Arg Thr
                805

<210> SEQ ID NO 52
<211> LENGTH: 694
<212> TYPE: PRT
<213> ORGANISM: Homo sapiens

<400> SEQUENCE: 52

Met Gly Ala Pro Ala Cys Ala Leu Ala Leu Cys Val Ala Val Ala Ile
1               5                   10                  15
Val Ala Gly Ala Ser Ser Glu Ser Leu Gly Thr Glu Gln Arg Val Val
                20                  25                  30
Gly Arg Ala Ala Glu Val Pro Gly Pro Glu Pro Gly Gln Gln Glu Gln
                35                  40                  45
Leu Val Phe Gly Ser Gly Asp Ala Val Glu Leu Ser Cys Pro Pro Pro
            50                  55                  60
Gly Gly Gly Pro Met Gly Pro Thr Val Trp Val Lys Asp Gly Thr Gly
65              70                  75                  80
Leu Val Pro Ser Glu Arg Val Leu Val Gly Pro Gln Arg Leu Gln Val
                85                  90                  95
Leu Asn Ala Ser His Glu Asp Ser Gly Ala Tyr Ser Cys Arg Gln Arg
                100                 105                 110
Leu Thr Gln Arg Val Leu Cys His Phe Ser Val Arg Val Thr Asp Ala
                115                 120                 125
Pro Ser Ser Gly Asp Asp Glu Asp Gly Glu Asp Glu Ala Glu Asp Thr
            130                 135                 140
Gly Val Asp Thr Gly Ala Pro Tyr Trp Thr Arg Pro Glu Arg Met Asp
145                 150                 155                 160
Lys Lys Leu Leu Ala Val Pro Ala Ala Asn Thr Val Arg Phe Arg Cys
                165                 170                 175
Pro Ala Ala Gly Asn Pro Thr Pro Ser Ile Ser Trp Leu Lys Asn Gly
                180                 185                 190
Arg Glu Phe Arg Gly Glu His Arg Ile Gly Gly Ile Lys Leu Arg His
                195                 200                 205
Gln Gln Trp Ser Leu Val Met Glu Ser Val Val Pro Ser Asp Arg Gly
            210                 215                 220
Asn Tyr Thr Cys Val Val Glu Asn Lys Phe Gly Ser Ile Arg Gln Thr
225                 230                 235                 240
Tyr Thr Leu Asp Val Leu Glu Arg Ser Pro His Arg Pro Ile Leu Gln
                245                 250                 255
Ala Gly Leu Pro Ala Asn Gln Thr Ala Val Leu Gly Ser Asp Val Glu
                260                 265                 270
```

```
Phe His Cys Lys Val Tyr Ser Asp Ala Gln Pro His Ile Gln Trp Leu
            275                 280                 285
Lys His Val Glu Val Asn Gly Ser Lys Val Gly Pro Asp Gly Thr Pro
        290                 295                 300
Tyr Val Thr Val Leu Lys Val Ser Leu Glu Ser Asn Ala Ser Met Ser
305                 310                 315                 320
Ser Asn Thr Pro Leu Val Arg Ile Ala Arg Leu Ser Ser Gly Glu Gly
                325                 330                 335
Pro Thr Leu Ala Asn Val Ser Glu Glu Leu Pro Ala Asp Pro Lys
            340                 345                 350
Trp Glu Leu Ser Arg Ala Arg Leu Thr Leu Gly Lys Pro Leu Gly Glu
        355                 360                 365
Gly Cys Phe Gly Gln Val Val Met Ala Glu Ala Ile Gly Ile Asp Lys
    370                 375                 380
Asp Arg Ala Ala Lys Pro Val Thr Val Ala Val Lys Met Leu Lys Asp
385                 390                 395                 400
Asp Ala Thr Asp Lys Asp Leu Ser Asp Leu Val Ser Glu Met Glu Met
            405                 410                 415
Met Lys Met Ile Gly Lys His Lys Asn Ile Ile Asn Leu Leu Gly Ala
        420                 425                 430
Cys Thr Gln Gly Gly Pro Leu Tyr Val Leu Val Glu Tyr Ala Ala Lys
    435                 440                 445
Gly Asn Leu Arg Glu Phe Leu Arg Ala Arg Arg Pro Pro Gly Leu Asp
    450                 455                 460
Tyr Ser Phe Asp Thr Cys Lys Pro Pro Glu Glu Gln Leu Thr Phe Lys
465                 470                 475                 480
Asp Leu Val Ser Cys Ala Tyr Gln Val Ala Arg Gly Met Glu Tyr Leu
            485                 490                 495
Ala Ser Gln Lys Cys Ile His Arg Asp Leu Ala Ala Arg Asn Val Leu
        500                 505                 510
Val Thr Glu Asp Asn Val Met Lys Ile Ala Asp Phe Gly Leu Ala Arg
    515                 520                 525
Asp Val His Asn Leu Asp Tyr Tyr Lys Lys Thr Thr Asn Gly Arg Leu
    530                 535                 540
Pro Val Lys Trp Met Ala Pro Glu Ala Leu Phe Asp Arg Val Tyr Thr
545                 550                 555                 560
His Gln Ser Asp Val Trp Ser Phe Gly Val Leu Leu Trp Glu Ile Phe
            565                 570                 575
Thr Leu Gly Gly Ser Pro Tyr Pro Gly Ile Pro Val Glu Glu Leu Phe
        580                 585                 590
Lys Leu Leu Lys Glu Gly His Arg Met Asp Lys Pro Ala Asn Cys Thr
    595                 600                 605
His Asp Leu Tyr Met Ile Met Arg Glu Cys Trp His Ala Ala Pro Ser
    610                 615                 620
Gln Arg Pro Thr Phe Lys Gln Leu Val Glu Asp Leu Asp Arg Val Leu
625                 630                 635                 640
Thr Val Thr Ser Thr Asp Glu Tyr Leu Asp Leu Ser Ala Pro Phe Glu
            645                 650                 655
Gln Tyr Ser Pro Gly Gly Gln Asp Thr Pro Ser Ser Ser Ser Ser Gly
        660                 665                 670
Asp Asp Ser Val Phe Ala His Asp Leu Leu Pro Pro Ala Pro Pro Ser
    675                 680                 685
Ser Gly Gly Ser Arg Thr
```

690

```
<210> SEQ ID NO 53
<211> LENGTH: 10
<212> TYPE: PRT
<213> ORGANISM: Homo sapiens

<400> SEQUENCE: 53

Gly Pro Leu Tyr Val Ile Val Glu Tyr Ala
1               5                   10

<210> SEQ ID NO 54
<211> LENGTH: 10
<212> TYPE: PRT
<213> ORGANISM: Homo sapiens

<400> SEQUENCE: 54

Gly Pro Leu Tyr Val Leu Val Glu Tyr Ala
1               5                   10
```

FGFR GATEKEEPER MUTANT GENE AND DRUG TARGETING SAME

CROSS-REFERENCE TO RELATED APPLICATIONS

This application is the National Stage of International Application Serial No. PCT/JP2014/084521, filed on Dec. 26, 2014, which claims the benefit of Japanese Application Serial No. 2013-273053, filed on Dec. 27, 2013.

TECHNICAL FIELD

The present invention relates to mutant polypeptides comprising novel gatekeeper mutations; polynucleotides encoding the polypeptides; vectors comprising the polynucleotides; cells comprising the vectors; antibodies and fragments thereof that specifically bind to the polypeptides; oligonucleotide primers or oligonucleotide probes that hybridize to the polynucleotides; oligonucleotides that inhibit the expression of the polypeptides; pharmaceutical compositions comprising the antibodies or oligonucleotides; methods and kits for detecting the polynucleotides or mutant polypeptides; methods for testing whether a subject is resistant to an FGFR inhibitor based on the presence or absence of the polynucleotides or mutant polypeptides; methods for selecting cancer patients for whom an FGFR inhibitor is applicable; pharmaceutical compositions for treating cancer wherein compounds having FGFR inhibitory activity or pharmaceutically acceptable salts thereof are used for administration to patients expressing the mutant polypeptides or carrying the polynucleotides; methods for treating or preventing cancer that comprise the step of administering an effective amount of compounds having FGFR inhibitory activity or pharmaceutically acceptable salts thereof to patients expressing the mutant polypeptides or carrying the polynucleotides; use of compounds having FGFR inhibitory activity or pharmaceutically-acceptable salts thereof in the production of pharmaceutical compositions for cancer treatment for administration to patients expressing the mutant polypeptides or carrying the polynucleotides; compounds having FGFR inhibitory activity or pharmaceutically acceptable salts thereof for use in treating or preventing patients expressing the mutant polypeptides or carrying the polynucleotides; as well as methods for identifying FGFR inhibitors, and such.

BACKGROUND ART

Cancer can develop in any organ or tissue, and is highly refractory and lethal. It goes without saying that cancer is a highly cumbersome disease. Recent statistical data show that one out of every two people is diagnosed with cancer during his/her lifetime, and one out of four men and one out of six women die of cancer. Thus, cancer remains an extremely serious disease.

Fibroblast growth factor receptors (FGFRs) are kinases belonging to the receptor tyrosine kinase family. FGFR1, FGFR2, FGFR3, and FGFR4 constitute the FGFR family. The ligand is fibroblast growth factor (FGF), and 22 types of structurally similar proteins form the family.

Signals transmitted via FGFR are conveyed to the MAPK pathway or PI3K/AKT pathway. It has been reported that in cancer, signal transduction is involved in cell growth, angiogenesis, cell migration, invasion, metastasis, etc.; and FGFR is activated as a result of overexpression, gene hyper-amplification, mutation, or translocation (Non-patent Document 1). For example, it is known that for FGFR3, genetic translocation is observed in multiple myeloma (Non-patent Document 2); gene mutation is observed in bladder cancer (Non-patent Document 3); and overexpression is observed in ovarian cancer, non-small cell lung carcinoma, and hepatocellular carcinoma.

The findings described above suggest a connection between FGFR and cancer. Thus, attempts have been made to develop compounds with FGFR-inhibitory activity as anticancer agents (Non-patent Documents 4 and 5).

Currently, various molecule-targeting drugs specific to various types of kinases are commercially available. However, certain amino acid mutations in EGFR tyrosine kinase which is a target molecule of gefitinib, erlotinib, and such, have become the main cause for acquisition of resistance to gefitinib, erlotinib, and such. Such mutations are called gatekeeper (GK) mutations, and there have been reports on GK mutations in FGFR2 as well (Non-Patent Document 6).

PRIOR ART DOCUMENTS

Non-Patent Documents

[Non-patent Document 1] Cytokine & Growth Factor Reviews, 2005, 16: 139-149
[Non-patent Document 2] Blood, 2003, 101: 4569-4575
[Non-patent Document 3] Nature Genetics, 1999 Sep. 23(1): 18-20
[Non-patent Document 4] Cancer Research, 2012, 72: 2045-2056
[Non-patent Document 5] J. Med. Chem., 2011, 54: 7066-7083
[Non-patent Document 6] Neoplasia (2013), 15(8), 975-988

SUMMARY OF THE INVENTION

Problems to be Solved by the Invention

The present inventors identified novel gatekeeper mutations in the FGFR gene, and also discovered that specific FGFR inhibitors have an inhibitory activity on FGFR carrying those mutations, which activity is equivalent that on FGFR not carrying the mutations.

In other words, an objective of the present invention is to provide novel antitumor agents that have high anticancer effects even for cancers with an FGFR that has acquired resistance to other FGFR inhibitors as a result of acquiring the above-mentioned mutations.

Means for Solving the Problems

To solve the above-mentioned problems, the present inventors conducted dedicated research on mutant genes that may cause gatekeeper mutations of various FGFRs, by performing crystal structure analyses on FGFRs. As a result, the inventors identified novel GK mutations (for example, the V564F mutation in SEQ ID NO: 1) and mutations corresponding to the above-mentioned GK mutations (for example, the V562L mutation in SEQ ID NO: 1) and found that FGFRs carrying these mutations demonstrated resistance to known FGFR inhibitors such as AZD4547, and at the same time, they demonstrated sensitivity to Compound A, and thus completed the present invention.

That is, the present invention specifically relates to: an FGFR mutant polypeptide comprising a novel gate keeper mutation; a polynucleotide encoding the mutant polypeptide; a vector comprising the polynucleotide; a cell comprising the vector; an antibody and a fragment thereof that specifically bind to the mutant polypeptide; oligonucleotide primers or oligonucleotide probe(s) that hybridize to the polynucleotide; an oligonucleotide that inhibits the expression of the mutant polypeptide; a method and a kit for detecting the mutant polypeptide or the polynucleotide; a pharmaceutical composition for cancer treatment characterized in being used by administering it to a patient expressing the mutant polypeptide; a method for treating or preventing cancer by administering the pharmaceutical composition to a patient expressing the mutant polypeptide; a method for selecting a patient to which the pharmaceutical composition is applicable; and a pharmaceutical composition and such for use in cancer treatment in a patient expressing the mutant polypeptide.

Basic characteristics and various embodiments of the present invention are listed below:

[1] A pharmaceutical composition for cancer treatment comprising as an active ingredient the compound represented by Formula (I) below or a pharmaceutically acceptable salt thereof, wherein the pharmaceutical composition for cancer treatment is characterized in being used by administering it to a patient expressing an FGFR mutant polypeptide comprising a substitution of valine to phenylalanine at the $7^{th}$ amino acid from the N terminus and/or a substitution of valine to leucine at the $5^{th}$ amino acid from the N terminus in the partial amino acid sequence described in SEQ ID NO: 53 or 54 in an FGFR polypeptide, or having a polynucleotide encoding said mutant polypeptide:

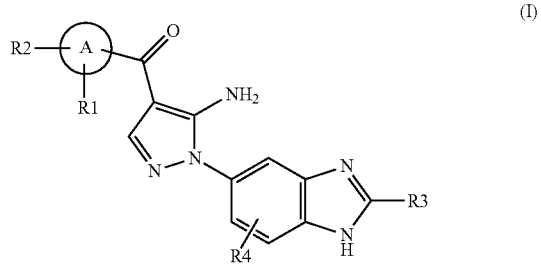

wherein $R_1$, $R_2$, $R_3$, and $R_4$ each independently represents the group listed below:

$R_1$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$;

$R_2$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$; or $R_1$ and $R_2$, together with an atom linked thereto, form 3- to 10-membered heterocyclyl or 5- to 10-membered heteroaryl, wherein the heterocyclyl or heteroaryl is optionally substituted by halogen;

$R_3$ represents methyl;

$R_4$ represents hydrogen;

A is indole;

$R_5$ represents $C_{1-5}$ alkyl, $C_{3-7}$ cycloalkyl, $C_{3-7}$ cycloalkyl $C_{1-3}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{1-3}$ alkoxy $C_{1-4}$ alkoxy $C_{1-4}$ alkyl, $C_{1-4}$ aminoalkyl, $C_{1-4}$ alkylamino $C_{1-4}$ alkyl, di($C_{1-4}$ alkyl)amino $C_{1-4}$ alkyl, $C_{6-10}$ aryl, $C_{6-10}$ aryl $C_{1-3}$ alkyl, or 3- to 10-membered heterocyclyl $C_{1-3}$ alkyl, 3- to 10-membered heterocyclyl, 5- to 10-membered heteroaryl, 5- to 10-membered heteroaryl $C_{1-3}$ alkyl, $C_{1-6}$ monohydroxy alkyl, $C_{1-6}$ dihydroxy alkyl, or $C_{1-6}$ trihydroxy alkyl which is optionally substituted by one or more groups independently selected from group Q;

$R_6$ and $R_7$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl $C_{1-3}$ alkyl, 3- to 10-membered heterocyclyl $C_{1-3}$ alkyl, 5- to 10-membered heteroaryl $C_{1-3}$ alkyl, $C_{1-6}$ monohydroxy alkyl, $C_{1-6}$ dihydroxy alkyl, $C_{1-6}$ trihydroxy alkyl, 3- to 10-membered heterocyclyl, $C_{1-4}$ aminoalkyl, $C_{1-4}$ alkylamino $C_{1-4}$ alkyl, di($C_{1-4}$ alkyl)amino $C_{1-4}$ alkyl, or cyano($C_{1-3}$ alkyl); or alternatively $R_6$ and $R_7$, together with a nitrogen atom linked thereto, form 3- to 10-membered heterocyclyl or 5- to 10-membered heteroaryl;

n represents 1 to 3;

$R_8$ and $R_9$, which can be the same or different, each represents hydrogen, $C_{1-4}$ alkyl, or halogen; or alternatively $R_8$ and $R_9$, together with a carbon atom linked thereto, form a cycloaliphatic ring;

$Z_1$ represents hydrogen, $NR_{10}R_{11}$, —OH, or 3- to 10-membered heterocyclyl or 5- to 10-membered heteroaryl which is optionally substituted by one or more groups independently selected from group Q;

$R_{10}$ and $R_{11}$, which can be the same or different, each represents $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, cyano($C_{1-3}$ alkyl), or $C_{1-3}$ alkylsulfonyl $C_{1-4}$ alkyl; or alternatively $R_{10}$ and $R_{11}$, together with a nitrogen atom linked thereto, form 3- to 10-membered heterocyclyl or 5- to 10-membered heteroaryl;

$R_{12}$ and $R_{13}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, 3- to 10-membered cycloaliphatic ring, 5- to 10-membered heteroaryl, or 3- to 10-membered heterocyclyl; or alternatively $R_{12}$ and $R_{13}$, together with a nitrogen atom linked thereto, form 3- to 10-membered heterocyclyl or 5- to 10-membered heteroaryl which is optionally substituted by one or more groups independently selected from group Q;

$R_{14}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{15}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{16}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{17}$ represents hydrogen or $C_{1-4}$ alkyl;

$R_{18}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{19}$ represents hydrogen, $C_{1-4}$ alkyl, $C_{3-7}$ cycloalkyl, $C_{1-4}$ haloalkyl, $C_{6-10}$ aryl, or 5- to 10-membered heteroaryl or 3- to 10-membered heterocyclyl which is optionally substituted by one or more groups independently selected from group Q;

$R_{20}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{21}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{22}$ represents hydrogen, $C_{1-4}$ alkyl, or $C_{1-4}$ haloalkyl;

$R_{23}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{24}$ represents hydrogen, $C_{1-4}$ alkyl, or $C_{1-4}$ haloalkyl;

$R_{25}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{26}$ and $R_{27}$, which can be the same or different, each represents hydrogen, $C_{1-4}$ alkyl, $C_{1-6}$ alkenyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively $R_{26}$ and $R_{27}$, together with a nitrogen atom linked thereto, form 3- to 10-membered heterocyclyl or 5- to 10-membered heteroaryl;

$R_{28}$ and $R_{29}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively $R_{28}$ and $R_{29}$, together with a nitrogen atom linked thereto, form 3- to 10-membered heterocyclyl or 5- to 10-membered heteroaryl;

$R_{30}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{31}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{32}$ represents $C_{1-4}$ alkyl or $C_{6-10}$ aryl;

<Group P>
halogen, $C_{1-4}$ alkyl, $C_{1-4}$ haloalkyl, —OH, $C_{1-3}$ alkoxy, $C_{1-3}$ haloalkoxy, 3- to 10-membered heterocyclylamino, —$SO_2R_{16}$, —CN, —$NO_2$, and 3- to 10-membered heterocyclyl;

<Group Q>
halogen, $C_{1-4}$ alkyl, $C_{1-4}$ haloalkyl, —OH, $C_{1-3}$ alkoxy, $C_{1-6}$ monohydroxy alkyl, $C_{1-6}$ dihydroxy alkyl, $C_{1-6}$ trihydroxy alkyl, 3- to 10-membered heterocyclyl amine, —$SO_2R_{16}$, —CN, —$NO_2$, $C_{3-7}$ cycloalkyl, —$COR_{19}$, and 3- to 10-membered heterocyclyl which is optionally substituted by $C_{1-4}$ alkyl;

[2] the pharmaceutical composition of [1], comprising as an active ingredient the compound represented by the formula below or a pharmaceutically acceptable salt thereof:

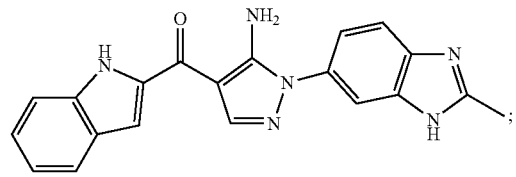 [SMILES: Cc1nc2ccc(-n3ncc(C(=O)c4cc5ccccc5[nH]4)c3N)cc2[nH]1]

[3] an FGFR mutant polypeptide comprising a substitution of valine to phenylalanine at the $7^{th}$ amino acid from the N terminus and/or a substitution of valine to leucine at the $5^{th}$ amino acid from the N terminus in the partial amino acid sequence described in SEQ ID NO: 53 or 54 in an FGFR polypeptide;

[4] a polynucleotide encoding the mutant polypeptide of [3];

[5] a vector comprising the polynucleotide of [4];

[6] a recombinant cell comprising the vector of [5];

[7] an antibody, or antigen-binding fragment thereof, that specifically binds to the mutant polypeptide of [3];

[8] a pair of oligonucleotide primers or an oligonucleotide probe(s) comprising an oligonucleotide(s) specifically hybridizing to a polynucleotide encoding the mutant polypeptide of [3] for detecting or amplifying the polynucleotide;

[9] an oligonucleotide that binds to an mRNA polynucleotide encoding the mutant polypeptide of [3] and has an activity to inhibit translation of the mRNA polynucleotide into protein;

[10] the oligonucleotide of [9], which is an siRNA that cleaves the mRNA polynucleotide;

[11] a method for detecting an FGFR mutant polypeptide, which comprises the step of detecting the mutant polypeptide in a sample isolated from a subject by using an antibody, or antigen-binding fragment thereof, that specifically binds to the mutant polypeptide of [3];

[12] a method for detecting a polynucleotide encoding an FGFR mutant polypeptide, which comprises the step of detecting a polynucleotide encoding the mutant polypeptide in a sample isolated from a subject by using a pair of oligonucleotide primers or an oligonucleotide probe(s) comprising an oligonucleotide(s) specifically hybridizing to a polynucleotide encoding the mutant polypeptide of [3] for detecting or amplifying the polynucleotide;

[13] a kit for detecting a polynucleotide encoding an FGFR mutant polypeptide, which comprises a pair of oligonucleotide primers or an oligonucleotide probe(s) comprising an oligonucleotide(s) specifically hybridizing to a polynucleotide encoding the mutant polypeptide of [3] for detecting or amplifying the polynucleotide;

[14] a kit for detecting an FGFR mutant polypeptide, which comprises an antibody or antigen-binding fragment thereof that specifically binds to the mutant polypeptide of [3];

[15] a method for treating cancer, which comprises determining the presence or absence of the mutant polypeptide of [3] or a polynucleotide encoding the mutant polypeptide in a sample isolated from a subject and administering the pharmaceutical composition of [1] or [2] to the subject when the mutant polypeptide or the polynucleotide is detected;

[16] the method of [15], wherein the cancer is bladder cancer, brain tumor, head and neck squamous cell carcinoma, lung cancer, lung adenocarcinoma, lung squamous cell carcinoma, skin melanoma, endometrial cancer, breast cancer, prostate cancer, colon cancer, esophageal cancer, gastric cancer, bile duct cancer, biliary tract cancer, or liver cancer;

[17] a method for selecting a patient to which the pharmaceutical composition of [1] or [2] is applicable, which comprises the steps of:
  (a) determining the presence or absence of the mutant polypeptide of [3] in a sample isolated from a subject; and
  (b) selecting a subject confirmed to have the mutant polypeptide as a patient to which the pharmaceutical composition is applicable;

[18] a method for selecting a patient to which the pharmaceutical composition of [1] or [2] is applicable, which comprises the steps of:
  (a) determining the presence or absence of a polynucleotide encoding the mutant polypeptide of [3] in a sample isolated from a subject; and
  (b) selecting a subject confirmed to have a polynucleotide encoding the mutant polypeptide as a patient to which the pharmaceutical composition is applicable;

[19] the method of [18], wherein the cancer is bladder cancer, brain tumor, head and neck squamous cell carcinoma, lung cancer, lung adenocarcinoma, lung squamous cell carcinoma, skin melanoma, endometrial cancer, breast cancer, prostate cancer, colon cancer, esophageal cancer, gastric cancer, bile duct cancer, biliary tract cancer, or liver cancer;

[20] the compound defined in [1] or [2] or a pharmaceutically acceptable salt thereof for use in cancer treatment in a patient who expresses the mutant polypeptide of [3] or has a polynucleotide encoding the mutant polypeptide;

[21] the compound of [20] or a pharmaceutically acceptable salt thereof, wherein the cancer is bladder cancer, brain tumor, head and neck squamous cell cancer, lung cancer, lung adenocarcinoma, lung squamous cell carcinoma, skin melanoma, endometrial cancer, breast cancer, prostate cancer, colon cancer, esophageal cancer, gastric cancer, bile duct cancer, biliary tract cancer, or liver cancer;

[22] a pharmaceutical composition for cancer treatment comprising as an active ingredient the compound represented by the formula below or a pharmaceutically acceptable salt thereof, wherein the cancer expresses an FGFR mutant polypeptide comprising a substitution of valine to phenylalanine at the $7^{th}$ amino acid from the N terminus and/or a substitution of valine to leucine at the $5^{th}$ amino acid from the N terminus in the partial amino acid sequence described in SEQ ID NO: 53 or 54 in an FGFR polypeptide:

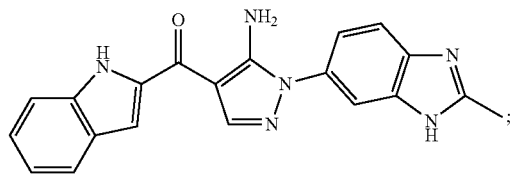 [SMILES: Cc1nc2ccc(-n3ncc(C(=O)c4cc5ccccc5[nH]4)c3N)cc2[nH]1]

[23] a pharmaceutical composition for cancer treatment comprising as an active ingredient a substance that inhibits the function or expression of an FGFR mutant polypeptide comprising a substitution of valine to phenylalanine at the $7^{th}$ amino acid from the N terminus and/or a substitution of valine to leucine at the $5^{th}$ amino acid from the N terminus in the partial amino acid sequence described in SEQ ID NO: 53 or 54 in an FGFR polypeptide;

[24] use of the compound defined in the aforementioned [1] or [2] or a pharmaceutically acceptable salt thereof in the manufacture of a pharmaceutical composition for treating or preventing cancer which is to be administered to a patient expressing the mutant polypeptide of [3] or has a polynucleotide encoding the mutant polypeptide;

[25] a method for detecting resistance to an FGFR inhibitor selected from the group consisting of PD173074, AZD4547, BGJ398, and AZD2171, which comprises the steps of:
  (a) determining the presence or absence of the mutant polypeptide of [3] or a polynucleotide encoding the mutant polypeptide in a sample isolated from a subject; and
  (b) determining that the subject confirmed to have the mutant polypeptide or the polynucleotide has resistance to the FGFR inhibitor;

[26] the antibody or antigen-binding fragment thereof of [7], or the oligonucleotide primers or oligonucleotide probe(s) of [8] for use in detecting resistance to an FGFR inhibitor selected from the group consisting of PD173074, AZD4547, BGJ398, and AZD2171;

[27] use of the antibody or antigen-binding fragment thereof of [7], or the oligonucleotide primers or oligonucleotide probe(s) of [8] for detecting resistance to an FGFR inhibitor selected from the group consisting of PD173074, AZD4547, BGJ398, and AZD2171;

[28] a method for predicting the response of a cancer patient to treatment by an FGFR inhibitor selected from the group consisting of PD173074, AZD4547, BGJ398, and AZD2171, which comprises the steps of:
  (a) determining the presence or absence of the mutant polypeptide of [3] or a polynucleotide encoding the mutant polypeptide in a sample isolated from the patient; and
  (b) determining that the patient confirmed to have the mutant polypeptide or the polynucleotide has low sensitivity to the FGFR inhibitor;

[29] the antibody or antigen-binding fragment thereof of [7], or the oligonucleotide primers or oligonucleotide probe(s) of [8] for use in predicting the response of a cancer patient to treatment by an FGFR inhibitor selected from the group consisting of PD173074, AZD4547, BGJ398, and AZD2171;

[30] use of the antibody or antigen-binding fragment thereof of [7], or the oligonucleotide primers or oligonucleotide probe(s) of [8] for predicting the response of a cancer patient to treatment by an FGFR inhibitor selected from the group consisting of PD173074, AZD4547, BGJ398, and AZD2171;

[31] a kit for predicting an effect of an FGFR inhibitor in cancer treatment, which comprises the antibody or antigen-binding fragment thereof of [7], or the oligonucleotide primers or oligonucleotide probe(s) of [8]; and

[32] The kit of [31], wherein the FGFR inhibitor is selected from the group consisting of PD173074, AZD4547, BGJ398, and AZD2171.

Effects of the Invention

The present invention can provide novel antitumor agents that have high anticancer effects on cancers with an FGFR which has acquired resistance to other FGFR inhibitors.

MODE FOR CARRYING OUT THE INVENTION

Figure 1:
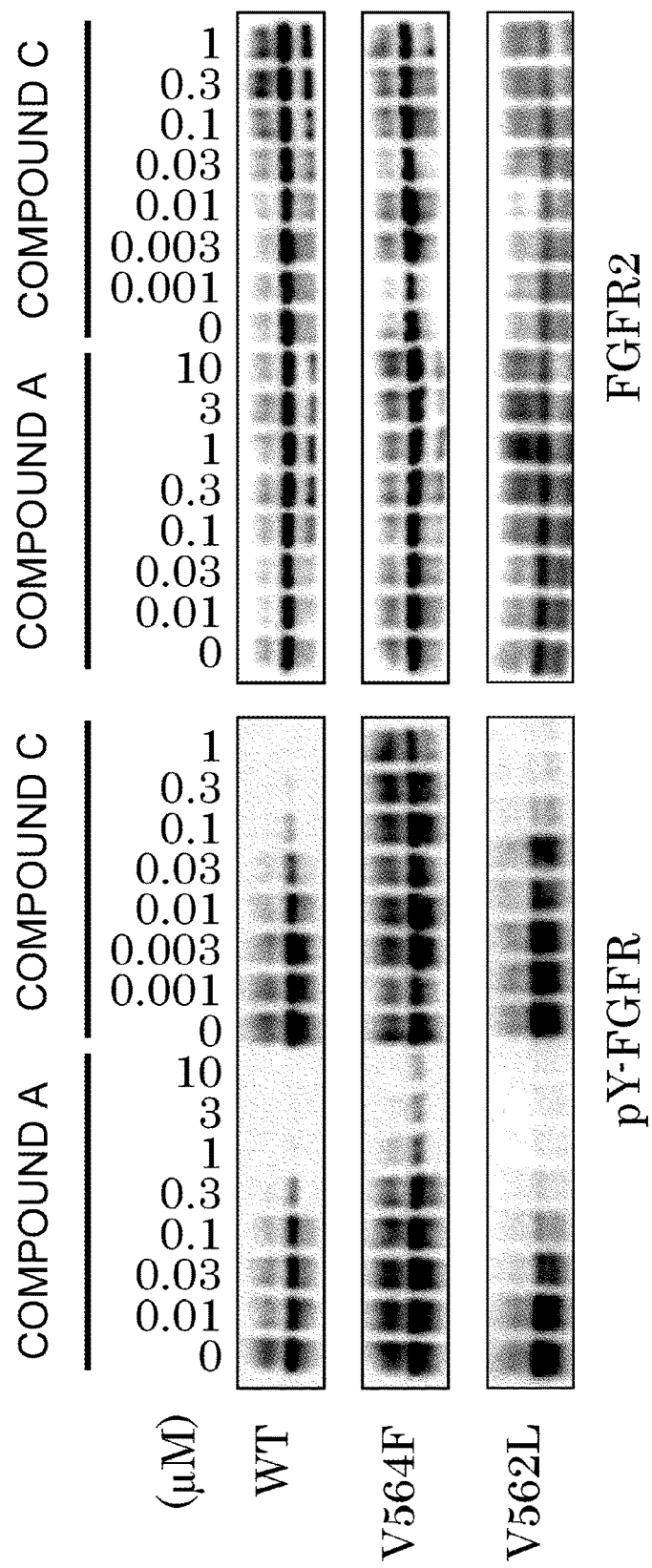
FIG. 1 shows the effects of Compounds A and C on tyrosine phosphorylation of FGFR in cells made to express the wild-type FGFR2, the FGFR2 V564F mutant, or the FGFR2 V562L mutant.

The present invention is an invention illustratively described in the above-mentioned [1] to [31] and provides: an FGFR mutant polypeptide comprising a novel gate keeper mutation; a polynucleotide encoding the mutant polypeptide; a vector comprising the polynucleotide; a cell comprising the vector; an antibody and a fragment thereof that specifically bind to the mutant polypeptide; oligonucleotide primers or oligonucleotide probe(s) that hybridize to the polynucleotide; an oligonucleotide that inhibits the expression of the mutant polypeptide; a method and a kit for detecting the mutant polypeptide or the polynucleotide; a pharmaceutical composition for cancer treatment characterized in being used by administering it to a patient expressing the mutant polypeptide; a method for treating or preventing cancer by administering the pharmaceutical composition to a patient expressing the mutant polypeptide; a method for selecting a patient to which the pharmaceutical composition is applicable; a compound having FGFR inhibitory activity or a pharmaceutically-acceptable salt thereof for use in treating or preventing cancer in a patient expressing the mutant polypeptide; use of a compound having FGFR inhibitory activity or a pharmaceutically acceptable salt thereof in the manufacture of a pharmaceutical composition for treating or preventing cancer for administration to a patient expressing the mutant polypeptide; a method for detecting resistance to an FGFR inhibitor; a method for predicting response of a cancer patient to treatment using an FGFR inhibitor; and such.

In the present invention, "FGFR" refers to any FGFR belonging to the FGFR family comprising FGFR1, FGFR2, FGFR3, and FGFR4, which are fibroblast growth factor receptors (FGFRs) belonging to the receptor tyrosine kinase family (Cytokine & Growth Factor Reviews, 2005, 16: 139-149). FGFRs of the present invention may be of any origin, and are preferably FGFRs derived from mammals (humans, mice, rats, guinea pigs, rabbits, sheep, monkeys, goats, donkeys, bovines, horses, pigs, etc.), more preferably human FGFRs, and still more preferably human FGFR2, human FGFR1, FGFR3, each of them are known to have many isoforms.

In the present invention, "human FGFR2" is a wild-type human FGFR2 polypeptide consisting of the amino acid sequence of SEQ ID NO: 1, 2, 37, 38, 39, 40, 41, 42, 43, or 44 (GenBank Accession No: NP_000132.3, NP_075259.4, NP_001138385.1, NP_001138386.1, NP_001138387.1, NP_001138388.1, NP_001138389.1, NP_001138390.1, NP_001138391.1, or NP_075418.1, respectively), or a mutant polypeptide with one or more (preferably one to ten, and particularly preferably one to five) amino acids being substituted, deleted, or inserted in the wild-type polypeptide.

In the present invention, "human FGFR1" is a wild-type human FGFR1 polypeptide consisting of the amino acid sequence of SEQ ID NO: 21, 45, 46, 47, 48, 49, or 50 (GenBank Accession No: NP_001167538.1, NP_001167534.1, NP_001167535.1, NP_001167536.1, NP_001167537.1, NP_075594.1, or NT 075598.2, respectively), or a mutant polypeptide with one or more (preferably one to ten, and particularly preferably one to five) amino acids being substituted, deleted, or inserted in the wild-type polypeptide.

In the present invention, "human FGFR3" is a wild-type human FGFR3 polypeptide consisting of the amino acid sequence of SEQ ID NO: 22, 51, or 52 (GenBank Accession No: NP_000133.1, NP_001156685.1, or NP_075254.1, respectively), or a mutant polypeptide with one or more (preferably one to ten, and particularly preferably one to five) amino acids being substituted, deleted, or inserted in the wild-type polypeptide. The mutant polypeptides also include polypeptides having 70% or greater homology, preferably polypeptides having 80% or greater homology, more preferably polypeptides having 90% or greater homology, and even more preferably polypeptides having 95% or greater homology to the amino acid sequence of the wild-type polypeptide.

Amino acid sequence (or nucleotide sequence) identity can be determined using the BLAST algorithm by Karlin and Altschul (Proc. Natl. Acad. Sci. USA (1993) 90, 5873-7). Programs such as BLASTN and BLASTX were developed based on this algorithm (Altschul et al., J. Mol. Biol. (1990) 215, 403-10). To analyze nucleotide sequences according to BLASTN based on BLAST, the parameters are set to, for example, score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (one can refer to the information on the website of the National Center for Biotechnology Information (NCBI), Basic Local Alignment Search Tool (BLAST)).

In the present invention, "mutant polypeptide" refers to an FGFR mutant polypeptide containing a substitution of valine to phenylalanine at the 7$^{th}$ amino acid from the N terminus and/or a substitution of valine to leucine at the 5$^{th}$ amino acid from the N terminus in the partial amino acid sequence described in SEQ ID NO: 53 or 54 in the FGFR polypeptide, and it may be also called as a polypeptide containing a mutation of the present invention.

The mutant polypeptide of the present invention is not limited to a FGFR mutant polypeptide consisting of an amino acid sequence in which an above-mentioned mutations are introduced into the amino acid sequence of the wild-type FGFR polypeptide consisting of the above-mentioned full-length amino acid sequence, as long as it is an FGFR mutant polypeptide carrying at least one of the two mutations described above. In addition, the mutant polypeptide includes peptide fragments thereof that contain the mutations, and fused polypeptides formed by fusing such FGFR mutant polypeptides or peptide fragments with other peptides, and the mutant polypeptide may also have one or more (preferably one to ten, and particularly preferably one to five) amino acid substitutions, deletions, additions, or insertions at positions other than the positions of the above-mentioned mutations.

"Other peptide" which constitute the fusion polypeptides with the FGFR mutant polypeptides or peptide fragments thereof include the TEL (also called ETV6; see Cancer Research, 2001, 61: 8371-8374 and Blood, 2005, 105(5): 2115-2123) polypeptide (a wild-type polypeptide consisting of the amino acid sequence of SEQ ID NO: 33 or mutant polypeptides with one or more amino acids being substituted, deleted, added, or inserted in the wild-type polypeptide, or peptide fragments thereof), the BAIA2P2L1 polypeptide (a wild-type polypeptide consisting of the amino acid sequence of SEQ ID NO: 31 or mutant polypeptides with one or more amino acids being substituted, deleted, added, or inserted in the wild-type polypeptide, or peptide fragments thereof), and the TACC3 polypeptide (a wild-type polypeptide consisting of the amino acid sequence of SEQ ID NO: 32 or mutant polypeptides with one or more amino acids being substituted, deleted, added, or inserted in the wild-type polypeptide, or peptide fragments thereof). A number of other FGFR fusion polypeptides are also known (see, Cancer Discovery 2013; 3: 636-647), and FGFR fusion polypeptides produced by introducing the mutations of the present invention to these fusion polypeptides are also included in the mutant polypeptides of the present invention.

Preferably, mutant polypeptides of the present invention refers to the FGFR mutant polypeptides selected from (1) to (20) shown below, peptide fragments of (1) to (20) containing those mutations, or fusion polypeptides formed by fusing the FGFR mutant polypeptides of (1) to (20) or peptide fragments thereof with other peptides:

(1) an FGFR2 mutant polypeptide containing at least the V564F and/or V562L mutations in the amino acid sequence of the above-mentioned wild-type FGFR2 polypeptide (SEQ ID NO: 1);

(2) an FGFR2 mutant polypeptide containing at least the V565F and/or V563L mutations in the amino acid sequence of the above-mentioned wild-type FGFR2 polypeptide (SEQ ID NO: 2);

(3) an FGFR2 mutant polypeptide containing at least the V565F and/or V563L mutations in the amino acid sequence of the above-mentioned wild-type FGFR2 polypeptide (SEQ ID NO: 37);

(4) an FGFR2 mutant polypeptide containing at least the V452F and/or V450L mutations in the amino acid sequence of the above-mentioned wild-type FGFR2 polypeptide (SEQ ID NO: 38);

(5) an FGFR2 mutant polypeptide containing at least the V475F and/or V473L mutations in the amino acid sequence of the above-mentioned wild-type FGFR2 polypeptide (SEQ ID NO: 39);

(6) an FGFR2 mutant polypeptide containing at least the V449F and/or V447L mutations in the amino acid sequence of the above-mentioned wild-type FGFR2 polypeptide (SEQ ID NO: 40);

(7) an FGFR2 mutant polypeptide containing at least the V448F and/or V446L mutations in the amino acid sequence of the above-mentioned wild-type FGFR2 polypeptide (SEQ ID NO: 41);

(8) an FGFR2 mutant polypeptide containing at least the V447F and/or V445L mutations in the amino acid sequence of the above-mentioned wild-type FGFR2 polypeptide (SEQ ID NO: 42);

(9) an FGFR2 mutant polypeptide containing at least the V476F and/or V474L mutations in the amino acid sequence of the above-mentioned wild-type FGFR2 polypeptide (SEQ ID NO: 43);

(10) an FGFR2 mutant polypeptide containing at least the V475F and/or V473L mutations in the amino acid sequence of the above-mentioned wild-type FGFR2 polypeptide (SEQ ID NO: 44);

(11) an FGFR1 mutant polypeptide containing at least the V559F and/or V557L mutations in the amino acid sequence of the above-mentioned wild-type FGFR1 polypeptide (SEQ ID NO: 21);

(12) an FGFR1 mutant polypeptide containing at least the V559F and/or V557L mutations in the amino acid sequence of the above-mentioned wild-type FGFR1 polypeptide (SEQ ID NO: 45);

(13) an FGFR1 mutant polypeptide containing at least the V551F and/or V549L mutations in the amino acid sequence of the above-mentioned wild-type FGFR1 polypeptide (SEQ ID NO: 46);

(14) an FGFR1 mutant polypeptide containing at least the V559F and/or V557L mutations in the amino acid sequence of the above-mentioned wild-type FGFR1 polypeptide (SEQ ID NO: 47);

(15) an FGFR1 mutant polypeptide containing at least the V472F and/or V470L mutations in the amino acid sequence of the above-mentioned wild-type FGFR1 polypeptide (SEQ ID NO: 48);

(16) an FGFR1 mutant polypeptide containing at least the V470F and/or V468L mutations in the amino acid sequence of the above-mentioned wild-type FGFR1 polypeptide (SEQ ID NO: 49);

(17) an FGFR1 mutant polypeptide containing at least the V561F and/or V559L mutations in the amino acid sequence of the above-mentioned wild-type FGFR1 polypeptide (SEQ ID NO: 50);

(18) an FGFR3 mutant polypeptide containing at least the V555F and/or V553L mutations in the amino acid sequence of the above-mentioned wild-type FGFR3 polypeptide (SEQ ID NO: 22);

(19) an FGFR3 mutant polypeptide containing at least the V557F and/or V555L mutations in the amino acid sequence of the above-mentioned wild-type FGFR3 polypeptide (SEQ ID NO: 51); or

(20) an FGFR3 mutant polypeptide containing at least the V443F and/or V441L mutations in the amino acid sequence of the above-mentioned wild-type FGFR3 polypeptide (SEQ ID NO: 52).

Particularly preferably, the FGFR mutant polypeptides of the present invention are, for example, an FGFR2 mutant polypeptide comprising the amino acid sequence of SEQ ID NO: 9, 10, 29, or 30; an FGFR1 mutant polypeptide comprising the amino acid sequence of SEQ ID NO: 25 or 26; and an FGFR3 mutant polypeptide comprising the amino acid sequence of SEQ ID NO: 27 or 28; as well as a TEL-fused FGFR2 mutant polypeptide comprising the amino acid sequence of SEQ ID NO: 35 or 36.

Preferably, the FGFR mutant polypeptides of the present invention retain biological activities (for example, tyrosine phosphorylation activity on the intracellular domain of FGFR, cell proliferation activity, angiogenic activity, cell migration activity, cell infiltration activity, and cell transfer activity, preferably cell proliferation activity) that are the same in degree or stronger than those of the wild-type FGFR polypeptide. Whether the FGFR mutant polypeptide of the present invention has such biological activities can be determined by assay methods known to those skilled in the art (for example, by methods described in the following Examples).

Polynucleotides of the present invention include polynucleotides encoding an FGFR mutant polypeptide of the present invention described above, which include any polynucleotide that can encode an FGFR mutant polypeptide of the present invention. The polynucleotides include genomic DNAs and cDNAs. Genomic DNAs include exons and introns. Furthermore, the cDNAs may include nucleic acid sequences derived from a portion of an intron sequence that encodes amino acid sequence.

The polynucleotides also include degenerate polynucleotides constituted with any codon as long as the codon encodes the same amino acids.

The polynucleotides of the present invention also include polynucleotides encoding mutant polypeptides derived from mammals. In a preferred embodiment, the polynucleotides of the present invention include polynucleotides encoding mutant polypeptides derived from humans.

The polynucleotides of the present invention may be obtained by any methods. The polynucleotides of the present invention include, for example, all complementary DNAs (cDNAs) prepared from mRNAs, DNAs prepared from genomic DNA, DNAs obtained by chemical synthesis, DNAs obtained by PCR amplification using RNA or DNA as template, and DNAs constructed by appropriately combining these methods.

Polynucleotides encoding mutant polypeptides of the present invention can be obtained using routine methods by cloning cDNA from mRNA encoding a mutant polypeptide of the present invention or isolating genomic DNA and subjecting it to splicing treatment, or by chemical synthesis.

For example, in a method that clones cDNA from mRNA encoding a mutant polypeptide of the present invention, first, mRNA encoding a mutant polypeptide of the present invention is prepared from arbitrary tissues or cells expressing and producing the mutant polypeptide of the present invention according to routine methods. This may be achieved, for example, by preparing total RNA using a method such as the guanidine-thiocyanate method, hot phenol method, or AGPC method, and treating the total RNA with affinity chromatography using oligo(dT) cellulose, poly U-Sepharose, or the like.

Then, cDNA strand synthesis is carried out using the prepared mRNA as template by a known method that uses, for example, reverse transcriptase (Mol. Cell. Biol., Vol. 2, p. 161, 1982; Mol. Cell. Biol., Vol. 3, p. 280, 1983; Gene, Vol. 25, p. 263, 1983). The cDNA is converted to double-stranded cDNA, and inserted into a plasmid vector, phage vector, cosmid vector, or such. To prepare a cDNA library, the resulting vector is transformed into *E. coli*, or transfected into *E. coli* after in vitro packaging.

The present invention also relates to vectors (recombinant vectors) carrying the above-described polynucleotide encoding a mutant polypeptide of the present invention.

The vectors of the present invention are not particularly limited as long as they can replicate and maintain or self-propagate in various prokaryotic and/or eukaryotic cells as a host. The vectors of the present invention include plasmid vectors and phage vectors.

Cloning vectors include, for example, pUC19, λgt10, and λgt11. When isolating host cells capable of expressing a mutant polypeptide of the present invention, preferably the vector is one that has a promoter which enables expression of the polynucleotide of the present invention.

Recombinant vectors of the present invention can be prepared using routine methods simply by ligating a polynucleotide encoding a mutant polypeptide of the present invention to a recombinant vector available in the art (plasmid DNA and bacteriophage DNA).

Recombinant vectors for use in the present invention include, for example, *E. coli*-derived plasmids (pBR322, pBR325, pUC12, pUC13, pUC19, etc.), yeast-derived plasmids (pSH19, pSH15, etc.), and *Bacillus subtilis*-derived plasmids (pUB110, pTP5, pC194, etc.).

Examples of phages are bacteriophages such as λ phage, and animal or insect viruses (pVL1393, Invitrogen) such as retrovirus, vaccinia virus, nuclear polyhedrosis virus, and lentivirus.

Expression vectors are useful for the purpose of producing a mutant polypeptide of the present invention by expressing a polynucleotide encoding the mutant polypeptide of the present invention. Expression vectors are not particular limited as long as they have the function of producing mutant polypeptides of the present invention by expressing polynucleotides encoding the polypeptides in various prokaryotic and/or eukaryotic cells as a host.

Such expression vectors include, for example, pMAL C2, pEF-BOS (Nucleic Acid Research, Vol. 18, 1990, p. 5322) and pME18S (Jikken Igaku Bessatsu (Experimental Medicine: SUPPLEMENT), "Idenshi Kougaku Handbook (Handbook of Genetic Engineering)" (1992)).

Alternatively, mutant polypeptides of the present invention may be produced as fusion proteins with other proteins. For example, when preparing as a fusion protein with glutathione S-transferase (GST), cDNA encoding a mutant polypeptide of the present invention can be subcloned into, for example, plasmid pGEX4T1 (Pharmacia). *E. coli* DH5α is transformed with the resulting plasmid, and the transformants are cultured to prepare the fusion protein.

Alternatively, fusion polypeptides of the present invention may be produced as fusions with influenza hemagglutinin (HA), immunoglobulin constant region, β-galactosidase, maltose-binding protein (MBP), or such. Furthermore, fusion polypeptides of the present invention may be produced as fusions with known peptides, for example, FLAG (Hopp, T. P. et al., BioTechnology (1988) 6, 1204-1210), 6× His consisting of 6 histidine (His) residues, 10× His, influenza hemagglutinin (HA), fragments of human c-myc, fragments of VSV-GP, fragments of p18HIV, T7-tag, HSV-tag, E-tag, fragments of SV40T antigen, lck tag, fragments of α-tubulin, B-tag, fragments of Protein C, Stag, StrepTag, and HaloTag.

When using bacteria, in particular *E coli*, as a host cell, vectors of the present invention preferably contain at least a promoter-operator region, a start codon, a polynucleotide encoding a mutant polypeptide of the present invention, a stop codon, a terminator region, and a replicon.

When yeast, animal cells, or insect cells are used as a host, expression vectors preferably contain a promoter, a start codon, a polynucleotide encoding a mutant polypeptide of the present invention, and a stop codon.

The vectors may also contain DNA encoding a signal peptide, an enhancer sequence, 5' and 3' untranslated regions of the gene encoding a protein of the present invention, splice junctions, polyadenylation sites, a selection marker region, a replicon, and such.

Furthermore, if necessary, the vectors may contain marker genes (genes for gene amplification, drug resistance genes, etc.) that enable selection of transformed hosts or hosts with gene amplification.

Marker genes include, for example, the dihydrofolate reductase (DHFR) gene, thymidine kinase gene, neomycin resistance gene, glutamate synthase gene, adenosine deaminase gene, ornithine decarboxylase gene, hygromycin-B-phosphotransferase gene, and aspartate transcarbamylase gene.

A promoter-operator region for expressing the mutant polypeptide of the present invention in bacteria comprises a promoter, an operator, and a Shine-Dalgarno (SD) sequence (for example, AAGG).

For example, when the host is the genus *Escherichia*, it comprises, for example, the Trp promoter, lac promoter, recA promoter, λPL promoter, lpp promoter, tac promoter, or such.

Examples of a promoter for expressing the mutant polypeptide of the present invention in yeast are the PH05 promoter, PGK promoter, GAP promoter, ADH promoter, and such.

When the host is *Bacillus*, examples are the SL01 promoter, SP02 promoter, penP promoter, and such.

When the host is a eukaryotic cell such as a mammalian cell, examples are an SV40-derived promoter, retrovirus promoter, heat shock promoter, and such; and SV40 and retrovirus are preferred. Nevertheless, the promoter is not limited to the above examples. In addition, use of an enhancer is effective for expression.

A preferable initiation codon is, for example, a methionine codon (ATG). A commonly used termination codon (for example, TAG, TAA, TGA) is exemplified as a termination codon. Commonly used natural or synthetic terminators are used as a terminator region.

A replicon refers to a DNA capable of replicating the whole DNA sequence in host cells, and includes a natural plasmid, an artificially modified plasmid (DNA fragment prepared from a natural plasmid), a synthetic plasmid, and such. Examples of preferable plasmids for *E. coli* are pBR322 or its artificial derivatives (DNA fragment obtained by treating pBR322 with appropriate restriction enzymes), for yeast are yeast 2μ plasmid or yeast chromosomal DNA, and pRSVneo ATCC 37198, and for mammalian cells are plasmid pSV2dhfr ATCC 37145, plasmid pdBPV-MMTneo ATCC 37224, plasmid pSV2neo ATCC 37149, and such.

An enhancer sequence, polyadenylation site, and splicing junction that are usually used in the art, such as those derived from SV40 can also be used.

The expression vector of the present invention can be prepared by continuously and circularly linking at least the above-mentioned promoter, initiation codon, polynucleotide encoding the mutant polypeptide of the present invention, termination codon, and terminator region, to an appropriate replicon. If desired, appropriate DNA fragments (for example, linkers, restriction sites, and such), can be used by a common method such as restriction enzyme digestion or ligation using T4 DNA ligase.

The present invention also relates to recombinant cells transformed with the above-mentioned vectors of the present invention, and recombinant cells of the present invention can be prepared by introducing the expression vector mentioned above into host cells.

Host cells used in the present invention are not particularly limited as long as they are compatible with an expression vector mentioned above and can be transformed. Examples thereof include various cells such as wild-type cells or artificially established recombinant cells commonly used in the technical field of the present invention (for example, bacteria (the genera *Escherichia* and *Bacillus*), yeast (the genus *Saccharomyces*, the genus *Pichia*, and such), animal cells, or insect cells).

*E. coli* or animal cells are preferred. Specific examples are *E. coli* (DH5α, TB1, HB101, and such), mouse-derived cells (COP, L, C127, Sp2/0, NS-1, NIH3T3, and such), rat-derived cells (PC12, PC12h), hamster-derived cells (BHK, CHO, and such), monkey-derived cells (COS1, COS3, COST, CV1, Velo, and such), and human-derived cells (Hela, diploid fibroblast-derived cells, myeloma cells, and HepG2, and such).

An expression vector can be introduced (transformed (transfected)) into host cells according to routine methods. [when the host is *E. coli, Bacillus subtilis*, or such]: Proc. Natl. Acad. Sci. USA, Vol. 69, p. 2110 (1972); Mol. Gen. Genet., Vol. 168, p. 111 (1979); J. Mol. Biol., Vol. 56, p. 209 (1971);
[when the host is *Saccharomyces cerevisiae*]: Proc. Natl. Acad. Sci. USA, Vol. 75, p. 1927 (1978); J. Bacteriol., Vol. 153, p. 163 (1983);
[when the host is an animal cell]: Virology, Vol. 52, p. 456 (1973);
[when the host is an insect cell]: Mol. Cell. Biol., Vol. 3, pp. 2156-2165 (1983).

Mutant polypeptides of the present invention can be produced by culturing transformed recombinant cells (hereinafter, the term also refers to inclusion bodies) comprising an expression vector prepared as described above in nutritive media according to routine methods.

Mutant polypeptides of the present invention can be produced by culturing the above-described recombinant cells, in particular animal cells, and allowing them to secrete into culture supernatants.

The resulting culture is filtered or centrifuged to obtain a culture filtrate (supernatant). Mutant polypeptides of the present invention are purified and isolated from the culture filtrate by routine methods commonly used to purify and isolate natural or synthetic proteins. Examples of an isolation and purification method are methods that utilize solubility such as the salting out and solvent precipitation methods; methods that utilize difference in molecular weight such as dialysis, ultrafiltration, gel filtration, and sodium dodecyl sulfate-polyacrylamide gel electrophoresis; methods that utilize charge such as ion exchange chromatography and hydroxylapatite chromatography; method that utilize specific affinity such as affinity column chromatography; methods that utilize difference in hydrophobicity such as reverse phase high performance liquid chromatography; and methods that utilize difference in the isoelectric point such as isoelectric focusing.

Meanwhile, when a mutant polypeptide of the present invention is in the periplasm or cytoplasm of cultured recombinant cells (such as *E. coli*), the cells are collected by routine methods such as filtration and centrifugation of the culture, and then suspended in an appropriate buffer. After the cell wall and/or cell membrane of the cells are disrupted using methods such as sonication, lysozyme, and cryolysis, a membrane fraction containing the protein of the present invention is obtained using methods such as centrifugation and filtration. The membrane fraction is solubilized with a detergent such as Triton-X100 to obtain the crude solution. Then, the protein of the present invention can be isolated and purified from the crude solution using routine methods such as those exemplified above.

The present invention also relates to arbitrary oligonucleotides that hybridize to polynucleotides (cDNAs and genomic DNAs) encoding the above-described mutant polypeptides of the present invention.

Oligonucleotides of the present invention have nucleotide sequences that are complementary to arbitrary partial nucleotide sequences of the cDNAs and genomic DNAs, and which are useful as a pair of oligonucleotide primers consisting of sense and antisense primers in polymerase chain reaction (PCR). The whole nucleotide sequence of a polynucleotide encoding a mutant polypeptide of the present invention or an arbitrary portion of the nucleotide sequence can be amplified by PCR using the pair of oligonucleotide primers.

Oligonucleotide primers of the present invention include oligonucleotides of any length that are complementary to the nucleotide sequence of a polynucleotide of the present invention. The oligonucleotide primers of the present invention preferably include those having a sequence of at least 12 consecutive nucleotides, more preferably 12 to 50 nucleotides, and still more preferably 12 to 20 nucleotides.

Oligonucleotides of the present invention are also useful as a probe when handling DNA or RNA hybridization. When used as a probe, the DNAs include a partial nucleotide sequence of 15 or more consecutive nucleotides, preferably a partial nucleotide sequence of 50 or more consecutive nucleotides, more preferably a partial nucleotide sequence of 100 or more consecutive nucleotides, even more preferably a partial nucleotide sequence of 200 or more consecutive nucleotides, and still more preferably a partial nucleotide sequence of 300 or more consecutive nucleotides, which hybridize to a polynucleotide of the present invention.

The present invention also relates to oligonucleotides that bind to mRNA polynucleotides encoding mutant polypeptides of the present invention and have an activity of inhibiting translation of the mRNAs into proteins. It is particularly preferable that the oligonucleotides include siRNAs that cleave the mRNAs by binding to the mRNA polynucleotides encoding mutant polypeptides of the present invention.

The oligonucleotides refer to those which bind to mRNAs encoding mutant polypeptides of the present invention and thereby inhibit their expression and include, for example, antisense oligonucleotides, ribozymes, and short interfering RNAs (siRNA). They bind to the mRNAs and then inhibit their translation into proteins.

An antisense oligonucleotide refers to an oligonucleotide that specifically hybridizes to genomic DNA and/or mRNA, and inhibits their protein expression by inhibiting the transcription and/or translation.

The binding to a target polynucleotide (mRNA, etc.) may be a result of common base pair complementarity. Alternatively, when an antisense oligonucleotide binds to, for example, a DNA duplex, the binding may be a result of specific interaction at the major grooves in double helix. Target sites for an antisense oligonucleotide include the 5' end of an mRNA, for example, 5' untranslated sequences up to or including the AUG start codon, and 3' untranslated sequences of an mRNA, as well as coding region sequences.

When using as an antisense oligonucleotide of the present invention, antisense oligonucleotides include partial nucleotide sequences of 5 to 100 consecutive nucleotides, preferably partial nucleotide sequences of 5 to 70 consecutive nucleotides, more preferably partial nucleotide sequences of 5 to 50 consecutive nucleotides, and still more preferably partial nucleotide sequences of 5 to 30 consecutive nucleotides.

Furthermore, antisense oligonucleotides of the present invention can be partially modified by chemical modification to prolong their half-life in blood (to stabilize them) or increase their intracellular membrane permeability when administered to patients, or to enhance their resistance to degradation or absorption in the digestive organs in oral administration. Such chemical modification includes, for example, chemical modification of a phosphate bond, ribose, nucleobase, sugar moiety in oligonucleotides, and 3' and/or 5' ends of oligonucleotides.

The modification of phosphate bonds includes, for example, conversion of one or more of the bonds to phosphodiester bonds (D-oligo), phosphorothioate bonds, phosphorodithioate bonds (S-oligo), methyl phosphonate (MP-oligo), phosphoroamidate bonds, non-phosphate bonds and methyl phosphonothioate bonds, and combinations thereof. The modification of ribose includes, for example, conversion to 2'-fluororibose or 2'-O-methylribose. The modification of nucleotide base includes, for example, conversion to 5-propynyluracil or 2-aminoadenine.

Ribozyme refers to oligonucleotides having a catalytic activity of cleaving mRNA. In general, ribozymes have endonuclease, ligase, or polymerase activity. Ribozymes include various types of trans-acting ribozymes, for example, hammerhead ribozymes and hairpin ribozymes.

siRNA refers to double-stranded oligonucleotides capable of carrying out RNA interference (for example, Bass, 2001, Nature, 411, 428-429; Elbashir et al., 2001, Nature, 411, 494-498).

siRNA cleaves mRNA in a sequence-specific manner, and as a result inhibits translation of the mRNA into protein. siRNA includes double-stranded RNAs that are 20 to 25 base pairs long and comprise a sequence complementary to the target polynucleotide sequence. siRNAs of the present invention also include oligonucleotides comprising chemically modified nucleotides and non-nucleotides.

The present invention also relates to antibodies which bind to the above-described mutant polypeptide of the present invention, and antigen-binding fragments thereof.

Antibodies of the present invention are not limited by their origin, form, function, etc. Antibodies of the present invention may be any antibodies, monoclonal or polyclonal antibodies. However, preferred antibodies of the present invention are monoclonal antibodies. Antibodies of the present invention may be those derived from any animal, such as human antibodies, mouse antibodies, and rat antibodies. Antibodies of the present invention may also be recombinant antibodies such as chimeric antibodies and humanized antibodies. Preferred antibodies of the present invention include chimeric antibodies, human antibodies, and humanized antibodies.

The humanized antibodies of the present invention can be prepared by methods known to those skilled in the art. The variable region of an antibody is typically composed of three complementarity-determining regions (CDRs) sandwiched by four frames (FRs). The CDRs practically determine the binding specificity of an antibody. The amino acid sequences of CDRs are highly diverse. On the other hand, amino acid sequences that constitute FRs often exhibit high homology among antibodies having different binding specificities.

Therefore, it is said that in general the binding specificity of an antibody can be transplanted to a different antibody by grafting the CDRs.

Humanized antibodies are also referred to as reshaped human antibodies, and they are prepared by transferring the CDRs of an antibody derived from a non-human mammal such as a mouse, to the complementarity determining regions of a human antibody. General genetic recombination techniques for their preparation are also known (see European Patent Application Publication No. 125023 and WO 96/02576).

Specifically, for example, when the CDRs are derived from a mouse antibody, a DNA sequence is designed such that the CDRs of the mouse antibody are linked with the framework regions (FRs) of a human antibody, and it is synthesized by PCR using, as primers, several oligonucleotides that have portions overlapping the ends of both CDRs and FRs (see the method described in WO 98/13388). The resulting DNA is then ligated to a DNA encoding a human antibody constant region, inserted into an expression vector, and introduced into a host to produce the antibody (see European Patent Application Publication No. EP 239400 and International Patent Application Publication No. WO 96/02576).

Human antibody framework regions to be linked with CDRs are selected so that the complementarity determining regions form a favorable antigen-binding site. If needed, amino acids of the framework region in an antibody variable region may be substituted, deleted, added, and/or inserted so that the complementarity determining regions of the reshaped human antibody form a proper antigen-binding site. For example, mutations can be introduced into the amino acid sequence of the FR by applying the PCR method used to graft mouse CDRs to human FRs. Specifically, mutations can be introduced into a portion of the nucleotide sequences of primers that anneal to the FRs. The mutations are introduced into FRs synthesized using such primers. Mutant FR sequences having desired properties can be selected by assessing and determining the antigen-binding activity of amino acid-substituted mutant antibodies by the method described above and (Sato, K. et al., Cancer Res. (1993) 53, 851-856).

In general, constant regions from human antibodies are used for those of humanized antibodies.

There are no particular limitations to the human antibody constant regions to be used in the present invention; and for example, when using a heavy-chain constant region, it may be a human IgG1 constant region, human IgG2 constant region, human IgG3 constant region, human IgG4 constant region, or human IgM, IgA, IgE, or IgD constant region. Alternatively, when using a light-chain constant region, it may be a human κ chain constant region or human 2 chain constant region. Furthermore, constant regions derived from a human antibody may have a naturally-occurring sequence or may be a constant region having a sequence with modification (substitution, deletion, addition, and/or insertion) of one or more amino acids in the naturally-occurring sequence.

Moreover, after a humanized antibody is prepared, amino acids in the variable region (for example, CDR and FR) and constant region of the humanized antibody may be deleted, added, inserted, and/or substituted with other amino acids. The humanized antibodies of the present invention also include such humanized antibodies with amino acid substitutions and such.

The origin of the CDRs of a humanized antibody is not particularly limited, and may be any animal. For example, it is possible to use sequences of mouse antibodies, rat antibodies, rabbit antibodies, camel antibodies, and such. CDR sequences of mouse antibodies are preferred.

When administered to humans for therapeutic purposes, humanized antibodies are useful because their immunogenicity in the human body is reduced.

Chimeric antibodies comprise, for example, heavy and light chain constant regions of a human antibody, and heavy and light chain variable regions of an antibody of a non-human mammal, such as mouse. Chimeric antibodies can be prepared using known methods. For example, antibodies can be produced by cloning an antibody gene from hybridomas, inserting it into an appropriate vector, and introducing the construct into hosts (see, for example, Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, cDNAs of the antibody variable regions (V regions) are synthesized from the hybridoma mRNAs using reverse transcriptase. Once DNAs encoding the V regions of an antibody of interest are obtained, they are linked with DNAs encoding the constant regions (C regions) of a desired human antibody. The resulting constructs are inserted into expression vectors. Alternatively, DNAs encoding the antibody V regions may be inserted into an expression vector comprising DNAs encoding the C regions of a human antibody. The DNAs are inserted into an expression vector so that they are expressed under the regulation of expression regulatory regions, for example, enhancers and promoters. In the next step, host cells can be transformed with the expression vector to allow expression of chimeric antibodies.

Human antibodies can be obtained using methods known to those skilled in the art. For example, desired human antibodies with antigen-binding activity can be obtained by sensitizing human lymphocytes with an antigen of interest or cells expressing an antigen of interest in vitro; and fusing the sensitized lymphocytes with human myeloma cells such as U266 (see Japanese Patent Application Kokoku Publication No. (JP-B) H01-59878 (examined, approved Japanese patent application published for opposition)). Alternatively, the desired human antibody can also be obtained by immunizing a transgenic animal having an entire repertoire of human antibody genes with a desired antigen (see International Patent Application Publication Nos. WO 93/12227, WO 92/03918, WO 94/02602, WO 94/25585, WO 96/34096, and WO 96/33735).

Alternatively, B cells expressing antibodies that have antigen-binding activity are isolated from a pool of human lymphocytes by flow cytometry, cell array, or such. The antibody genes from selected B cells can be analyzed, and DNA sequences of the human antibodies that bind to the antigen can be determined (Jin, A. et al., Nature Medicine (2009) 15, 1088-92; Scheid, J. F. et al., Nature (2009) 458, 636-640; Wrammert, J. et al., Nature (2008) 453, 667-672; Tiller, T. et al., Journal of Immunological Methods (2008) 329, 112-124). When DNA sequences of the antigen-binding antibodies are revealed, human antibodies can be prepared by constructing appropriate expression vectors carrying the sequences. Such methods are known, and WO 92/01047, WO 92/20791, WO 93/06213, WO 93/11236, WO 93/19172, WO 95/01438, and WO 95/15388 can be used as references.

Furthermore, techniques for obtaining human antibodies by panning with a human antibody phage library are known. For example, the variable region of a human antibody is expressed as a single chain antibody (scFv) on the phage surface using a phage display method, and phages that bind to the antigen can be selected. By analyzing the genes of selected phages, DNA sequences encoding the variable regions of human antibodies that bind to the antigen can be determined. If the DNA sequences of scFvs that bind to the antigen are identified, appropriate expression vectors comprising these sequences can be constructed to obtain human antibodies. Such methods are well known. Reference can be made to WO 92/01047, WO 92/20791, WO 93/06213, WO 93/11236, WO 93/19172, WO 95/01438, WO 95/15388, and such.

The antibodies of the present invention include not only divalent antibodies as represented by IgG, but also monovalent antibodies, multivalent antibodies as represented by IgM. In addition, the antibodies of the present invention also include bispecific antibodies capable of binding to different antigens.

Antibodies of the present invention include not only whole antibody molecules but also any antigen-binding fragments such as low-molecular-weight antibodies.

Antibodies of the present invention also include modified antibodies that are linked to cytotoxic substances. Antibodies of the present invention also include those with altered sugar chains.

Low-molecular-weight antibodies (minibodies) included in antigen-binding fragments of the present invention are antibodies comprising an antibody fragment that lacks part of a whole antibody (for example, whole IgG, etc.). The minibodies are not particularly limited, as long as they have the activity to bind to a mutant polypeptide of the present invention.

Minibodies of the present invention are not particularly limited, as long as they comprise a portion of a whole antibody. It is however preferable that the minibodies comprise an antigen-binding domain. In general, the antigen-binding domain is antibody CDR, and is preferably six CDRs of an antibody. Thus, the preferred antigen-binding domains include, for example, six CDRs of an antibody and antibody variable regions (heavy chain and/or light chain variable regions).

The minibodies of the present invention preferably have a smaller molecular weight than whole antibodies. However, the minibodies may form multimers, for example, dimers, trimers, or tetramers, and thus their molecular weights can be greater than those of whole antibodies.

Other specific examples of the antigen-binding molecule fragments include, for example, Fab, Fab', F(ab')2, and Fv. Meanwhile, specific examples of low-molecular-weight antibodies include, for example, Fab, Fab', F(ab')2, Fv, scFv (single chain Fv), diabodies, and sc(Fv)2 (single chain (Fv)2). Multimers (for example, dimers, trimers, tetramers, and polymers) of these antibodies are also included in the low-molecular-weight antibodies of the present invention.

Antigen-binding fragments can be obtained, for example, by treating antibodies with enzymes to produce antibody fragments. Enzymes known to generate antibody fragments include, for example, papain, pepsin, and plasmin. Alternatively, a gene encoding such an antibody fragment can be constructed, introduced into an expression vector, and expressed in appropriate host cells (see, for example, Co, M. S. et al., J. Immunol. (1994) 152, 2968-2976; Better, M. & Horwitz, A. H. Methods in Enzymology (1989) 178, 476-496; Plueckthun, A. & Skerra, A. Methods in Enzymology (1989) 178, 476-496; Lamoyi, E., Methods in Enzymology (1989) 121, 652-663; Rousseaux, J. et al., Methods in Enzymology (1989) 121, 663-669; Bird, R. E. et al., TIBTECH (1991) 9, 132-137).

Digestive enzymes cleave at a specific site in an antibody fragment, yielding antibody fragments of specific structures shown below. Genetic engineering techniques can be applied to such enzymatically-obtained antibody fragments to delete an arbitrary portion of the antibody.

Antibody fragments obtained by using the above-described digestive enzymes are as follows:
Papain digestion: F(ab)2 or Fab
Pepsin digestion: F(ab')2 or Fab'
Plasmin digestion: Facb The minibodies of the present invention include antibody fragments lacking an arbitrary region, as long as they have the activity to bind to a mutant polypeptide of the present invention.

"Diabody" refers to a bivalent antibody fragment constructed by gene fusion (Holliger P et al., Proc. Natl. Acad. Sci. USA 90: 6444-6448 (1993); EP 404,097; WO 93/11161, etc.). Diabodies are dimers composed of two polypeptide chains. In each of the polypeptide chains forming a dimer, a VL and a VH are usually linked by a linker in the same chain. In general, the linker in a diabody is short enough such that the VL and VH cannot bind to each other. Specifically, the number of amino acid residues constituting the linker is, for example, about five residues. Thus, the VL and VH encoded on the same polypeptide cannot form a single-chain variable region fragment, and will form a dimer with another single-chain variable region fragment. As a result, the diabody has two antigen binding sites.

scFv antibodies are single-chain polypeptides produced by linking a heavy chain variable region ([VH]) to a light chain variable region ([VL]) via a linker or such (Huston, J. S. et al., Proc. Natl. Acad. Sci. U.S.A. (1988) 85, 5879-5883; Plickthun "The Pharmacology of Monoclonal Antibodies" Vol. 113, eds., Resenburg and Moore, Springer Verlag, New York, pp. 269-315, (1994)). The H-chain V region and L-chain V region of scFv may be derived from any antibody described herein. The peptide linker for linking the V regions is not particularly limited. For example, an arbitrary single-chain peptide containing about three to 25 residues can be used as a linker. Specifically, it is possible to use the peptide linkers or such described below.

The V regions of both chains can be linked, for example, by PCR as described above. To link the V regions by PCR, first, a DNA from the DNAs below that encodes a complete or desired partial amino acid sequence is used as a template:
DNA sequence encoding an H chain or H-chain V region of an antibody, and
DNA sequence encoding an L chain or L-chain V region of an antibody.

DNAs encoding the H-chain and L-chain V regions are amplified by PCR using a pair of primers having sequences corresponding to sequences at both ends of the DNA to be amplified. Then, a DNA encoding the peptide linker portion is prepared. The peptide linker-encoding DNA can also be synthesized by PCR. Here, nucleotide sequences that can be ligated to the amplification products of V regions synthesized separately are added to the 5' end of the primers to be used. Then, PCR is carried out using each DNA of the [H chain V region DNA]-[peptide linker DNA]-[L chain V region DNA], and assembly PCR primers.

The assembly PCR primers are composed of a combination of a primer that anneals to the 5' end of the [H chain V region DNA] and a primer that anneals to the 3' end of the [L chain V region DNA]. In other words, the assembly PCR primers are a set of primers that can be used to amplify DNA encoding the full-length sequence of an scFv to be synthesized. Meanwhile, nucleotide sequences that can be ligated to the V-region DNAs have been added to the [peptide linker DNA]. Thus, these DNAs are linked together, and then the whole scFv is ultimately generated as an amplification product by the assembly PCR primers. Once the scFv-encoding DNAs are generated, expression vectors carrying these DNAs and recombinant cells transformed with these expression vectors can be obtained by conventional methods. Furthermore, the scFv can be obtained by culturing the resulting recombinant cells to express the scFv-encoding DNAs.

The order of the heavy chain and light chain variable regions to be linked together is not particularly limited, and they may be arranged in any order. Examples of the arrangement are listed below.

[VH] linker [VL]
[VL] linker [VH]

sc(Fv)2 is a single-chain low-molecular-weight antibody produced by linking two VHs and two VLs using linkers and such (Hudson et al., J Immunol. Methods 1999; 231: 177-189). For example, sc(Fv)2 can be produced by linking scFvs via a linker.

Antibodies in which two VHs and two VLs are arranged in the order of VH, VL, VH, and VL ([VH] linker [VL] linker [VH] linker [VL]) from the N terminus of the single-chain polypeptide are preferred. However, the order of the two VHs and two VLs is not limited to the above arrangement, and they may be arranged in any order. Examples of the arrangement are listed below:

[VL] linker [VH] linker [VH] linker [VL]
[VH] linker [VL] linker [VL] linker [VH]
[VH] linker [VH] linker [VL] linker [VL]
[VL] linker [VL] linker [VH] linker [VH]
[VL] linker [VH] linker [NIL] linker [VH]

The amino acid sequence of the heavy chain variable region or light chain variable region in a low-molecular-weight antibody may contain a substitution, deletion, addition, and/or insertion. Furthermore, the heavy chain variable region and light chain variable region may also lack some portions or be added with other polypeptides, as long as they have antigen binding ability when linked together. Alternatively, the variable regions may be chimerized or humanized.

In the present invention, linkers which bind the variable regions of the antibody include arbitrary peptide linkers that can be introduced using genetic engineering, or synthetic linkers such as those disclosed in Protein Engineering, 9(3), 299-305, 1996.

The preferred linkers in the present invention are peptide linkers. The length of the peptide linkers is not particularly limited, and those skilled in the art can appropriately select the length depending on the purpose. A typical length is one to 100 amino acids, preferably 3 to 50 amino acids, more preferably 5 to 30 amino acids, and particularly preferably 12 to 18 amino acids (for example, 15 amino acids).

Amino acid sequences of such peptide linkers include, for example:

```
Ser;

Gly-Ser;

Gly-Gly-Ser;

Ser-Gly-Gly;

(SEQ ID NO: 13)
Gly-Gly-Gly-Ser;
```

```
                                           (SEQ ID NO: 14)
Ser-Gly-Gly-Gly;

(SEQ ID NO: 15)
Gly-Gly-Gly-Gly-Ser;

(SEQ ID NO: 16)
Ser-Gly-Gly-Gly-Gly;

(SEQ ID NO: 17)
Gly-Gly-Gly-Gly-Gly-Ser;

(SEQ ID NO: 18)
Ser-Gly-Gly-Gly-Gly-Gly;

(SEQ ID NO: 19)
Gly-Gly-Gly-Gly-Gly-Gly-Ser;

(SEQ ID NO: 20)
Ser-Gly-Gly-Gly-Gly-Gly-Gly;

(Gly-Gly-Gly-Gly-Ser (SEQ ID NO: 15))n;
and (Ser-Gly-Gly-Gly-Gly (SEQ ID NO: 16))n,
``` where n is an integer of 1 or larger.

The amino acid sequence of a peptide linker can be appropriately selected by those skilled in the art according to the purpose. For example, the above-mentioned "n", which determines the length of the peptide linker, is usually 1 to 5, preferably 1 to 3, and more preferably 1 or 2.

Synthetic linkers (chemical crosslinking agents) include crosslinking agents that are routinely used to crosslink peptides, for example, N-hydroxy succinimide (NHS), disuccinimidyl suberate (DSS), bis(sulfosuccinimidyl) suberate (BS3), dithiobis(succinimidyl propionate) (DSP), dithiobis(sulfosuccinimidyl propionate) (DTSSP), ethylene glycol bis(succinimidyl succinate) (EGS), ethylene glycol bis(sulfosuccinimidyl succinate) (sulfo-EGS), disuccinimidyl tartrate (DST), disulfosuccinimidyl tartrate (sulfo-DST), bis[2-(succinimidoxycarbonyloxy)ethyl] sulfone (BSOCOES), and bis[2-(sulfosuccinimidoxycarbonyloxy)ethyl] sulfone (sulfo-BSOCOES). These crosslinking agents are commercially available.

When four antibody variable regions are linked, three linkers are usually required. Such multiple linkers may be the same or different.

The antibodies of the present invention include antibodies in which one or more amino acid residues have been added to the amino acid sequence of an antibody of the present invention. Further, fusion proteins which result from a fusion between one of the above antibodies and a second peptide or protein is included in the present invention. The fusion proteins can be prepared by ligating a polynucleotide encoding an antibody of the present invention with a polynucleotide encoding a second peptide or polypeptide in frame, inserting this into an expression vector, and expressing the fusion construct in a host. Some techniques known to those skilled in the an are available for this purpose. The partner peptide or polypeptide to be fused with an antibody of the present invention may be a known peptide, for example, FLAG (Hopp, T. P. et al., BioTechnology 6, 1204-1210 (1988)), 6× His consisting of six His (histidine) residues, 10× His, influenza hemagglutinin (HA), human c-myc fragment, VSV-GP fragment, p18HIV fragment, T7-tag, HSV-tag, E-tag, SV40 T antigen fragment, lck tag, α-tubulin fragment, B-tag, Protein C fragment, Stag, StrepTag, HaloTag. Other partner polypeptides to be fused with the antibodies of the present invention include, for example, GST (glutathione-S-transferase), HA (influenza hemagglutinin), immunoglobulin constant region, β-galactosidase, and MBP (maltose-binding protein). A polynucleotide encoding one of these commercially available peptides or polypeptides can be fused with a polynucleotide encoding an antibody of the present invention. The fusion polypeptide can be prepared by expressing the fusion construct.

Furthermore, the antibodies of the present invention may be conjugated antibodies which are linked to any of various molecules including polymeric substances such as polyethylene glycol (PEG) and hyaluronic acid, radioactive substances, fluorescent substances, luminescent substances, enzymes, and toxins. Such conjugated antibodies can be obtained by chemically modifying the obtained antibodies. Methods for modifying antibodies have been established in this field (for example, U.S. Pat. Nos. 5,057,313 and 5,156,840). The "antibodies" of the present invention also include such conjugated antibodies.

Furthermore, the antibodies used in the present invention may be bispecific antibodies. The bispecific antibody refers to an antibody that has variable regions recognizing different epitopes in the same antibody molecule. In the present invention, the bispecific antibodies may recognize different epitopes on the mutant polypeptide molecule of the present invention, or recognize the mutant polypeptide of the present invention with one antigen-binding site and a different substance with the other antigen-binding site.

Methods for producing bispecific antibodies are known. Bispecific antibodies can be prepared, for example, by linking two antibodies that recognize different antigens. Antibodies to be linked together may be half molecules each of which contains an H chain and an L chain, or quarter molecules that consist of only one H chain. Alternatively, hybridomas producing different monoclonal antibodies can be fused to produce a bispecific antibody-producing fused cell. Furthermore, bispecific antibodies can be produced by genetic engineering techniques.

The antibodies of the present invention may differ in amino acid sequence, molecular weight, isoelectric point, presence/absence of sugar chains, and conformation depending on the cell or host producing the antibody or the purification method as described below. However, a resulting antibody is included in the present invention, as long as it is functionally equivalent to an antibody of the present invention. For example, when an antibody of the present invention is expressed in prokaryotic cells, for example E. coli, a methionine residue is added to the N terminus of the original antibody amino acid sequence. Such antibodies are included in the present invention.

Antibodies of the present invention may be antibodies with altered sugar chains. Methods for modifying antibody sugar chains are known to those skilled in the art, and include, for example, methods for improving ADCC by modifying antibody glycosylation, methods for adjusting ADCC by the presence or absence of fucose in antibody sugar chains, methods for preparing antibodies having sugar chains that do not contain α-1,6 core fucose by producing antibodies in YB2/0 cells, and methods for adding sugar chains having bisecting GlcNAc (WO 99/54342; WO 00/61739; WO 02/31140; WO 02/79255, etc.).

Antibodies of the present invention can be produced by known methods using as an immunogen a mutant polypeptide of the present invention (derived from mammals such as humans and mice) or a fragment thereof. Specifically, non-human mammals are immunized by a known immunization method, using as a sensitizing antigen a desired antigen or cells expressing a desired antigen. Immune cells prepared from the immunized animals are fused with known parental cells by a general cell fusion method. The resulting monoclonal antibody-producing cells (hybridomas) are sorted by general screening methods, and monoclonal antibodies are prepared by culturing the cells.

Non-human mammals to be immunized include, for example, animals such as mice, rats, rabbits, sheep, monkeys, goats, donkeys, cows, horses, and pigs. The antigen can be prepared using a polynucleotide encoding the mutant polypeptide of the present invention according to known methods, for example, by methods using baculovirus (for example, WO 98/46777) or such.

Hybridomas can be prepared, for example, according to the method of Milstein et al. (Kohler, G. and Milstein, C., Methods Enzymol. (1981) 73: 3-46) or such. When the immunogenicity of an antigen is low, immunization may be performed after linking the antigen with a macromolecule having immunogenicity, such as albumin.

In an embodiment, antibodies that bind to the mutant polypeptides of the present invention include monoclonal antibodies that bind to the mutant polypeptides of the present invention. Immunogens for preparing monoclonal antibodies having binding activity to a mutant polypeptide of the present invention are not particularly limited, as long as antibodies having binding activity to the mutant polypeptide of the present invention can be prepared.

Meanwhile, the activity of an antibody to bind to a mutant polypeptide of the present invention can be assayed by methods known to those skilled in the art.

Meanwhile, monoclonal antibodies can also be obtained by DNA immunization. DNA immunization is a method in which a vector DNA constructed such that an antigen protein-encoding gene can be expressed in an animal to be immunized is administered to the animal, and the immunogen is expressed within the body of the animal to provide immunostimulation. As compared to common immunization methods based on the administration of protein antigens, DNA immunization is expected to be advantageous in that:

it enables immunostimulation while retaining the structure of a membrane protein; and the immunogen does not need to be purified.

In order to obtain monoclonal antibodies by DNA immunization, first, a polynucleotide encoding a mutant polypeptide of the present invention is administered to an animal to be immunized. The polynucleotide encoding a mutant polypeptide of the present invention can be synthesized according to an above-described method by known techniques such as PCR. The resulting DNA (polynucleotide) is inserted into an appropriate expression vector and then administered to an animal to be immunized. The expression vector includes any vectors described above (for example, commercially available expression vectors such as pcDNA3.1). Vectors can be administered to a living body by commonly used methods. For example, DNA immunization can be performed, for example, by using a gene gun to inject gold particles immobilized with an expression vector into cells. A preferred method for obtaining monoclonal antibodies is to perform booster immunization with cells expressing the mutant polypeptide of the present invention after DNA immunization.

Once the mammal is immunized as described above and the serum level of a desired antibody is confirmed to be increased, immune cells are collected from the mammal and subjected to cell fusion. Preferred immune cells are spleen cells in particular.

Mammalian myeloma cells are used for fusion with the above immune cells. It is preferred that myeloma cells have appropriate selection markers for screening. The selection marker refers to a phenotype that allows (or does not allow) survival under particular culture conditions. Known selection markers include hypoxanthine-guanine-phosphoribosyltransferase deficiency (hereinafter abbreviated as "HGPRT deficiency") and thymidine kinase deficiency (hereinafter abbreviated as "TK deficiency"). HGPRT- or TK-deficient cells exhibit hypoxanthine-aminopterin-thymidine sensitivity (hereinafter abbreviated as "HAT sensitivity"). In HAT selection medium, HAT-sensitive cells cannot synthesize DNA and thus will die. However, when fused with normal cells, they can continue to synthesize DNA via the salvage pathway of the normal cells and thus can grow even in HAT selection medium.

HGPRT- or TK-deficient cells can be selected using a medium containing 6-thioguanine, 8-azaguanine (hereinafter abbreviated as "8AG"), or 5'-bromodeoxyuridine. While normal cells are killed due to incorporation of these pyrimidine analogs into DNA, cells lacking these enzymes can survive in the selection medium because they cannot incorporate these pyrimidine analogs. Another selection marker called G418 resistance confers resistance to 2-deoxystreptamine antibiotics (gentamicin analogs) due to the neomycin resistance gene. Various myeloma cells suitable for cell fusion are known.

Cell fusion between immune cells and myeloma cells can be essentially carried out according to known methods, for example, the method by Kohler and Milstein et al. (Kohler. G. and Milstein, C., Methods Enzymol. (1981) 73, 3-46).

More specifically, cell fusion can be carried out, for example, in a common culture medium in the presence of a cell fusion-promoting agent. The fusion-promoting agent includes, for example, polyethylene glycol (PEG) and Sendai virus (HVJ). If required, an auxiliary agent such as dimethyl sulfoxide may also be added to improve fusion efficiency.

The immune cells and myeloma cells may be used at an arbitrarily determined ratio. For example, the ratio of immune cells to myeloma cells is preferably from 1 to 10. Culture media to be used for cell fusion include, for example, media that are suitable for the cell growth of myeloma cell line, such as RPMI1640 and MEM, and other common culture media used for this type of cell culture. In addition, the culture media may also be supplemented with serum supplement such as fetal calf serum (FCS).

Predetermined amounts of immune cells and myeloma cells are mixed well in the culture medium, and then mixed with a PEG solution pre-heated to about 37° C. to produce fused cells (hybridomas). In the cell fusion method, for example, PEG with mean molecular weight of about 1,000-6,000 can be added to the cells typically at a concentration of 30% to 60% (w/v). Then, successive addition of the appropriate culture medium listed above and removal of supernatant by centrifugation are repeated to eliminate the cell fusion agent and such, which are unfavorable to the growth of hybridomas.

The resulting hybridomas can be screened using a selection medium according to the selection marker possessed by myeloma cells used in the cell fusion. For example, HGPRT- or TK-deficient cells can be screened by culturing them in a HAT medium (a medium containing hypoxanthine, aminopterin, and thymidine). Specifically, when HAT-sensitive myeloma cells are used in cell fusion, cells successfully fused with normal cells can be selectively grown in the HAT medium. The cell culture using the above HAT medium is continued for a sufficient period of time to allow all cells except the desired hybridomas (non-fused cells) to die.

Specifically, in general, the desired hybridomas can be selected by culturing the cells for several days to several weeks. Then, screening and single cloning of hybridomas that produce an antibody of interest can be carried out by performing ordinary limiting dilution methods.

Screening and single cloning of an antibody of interest can be suitably carried out by known screening methods based on antigen-antibody reaction. For example, an antigen is bound to a carrier such as beads made of polystyrene or such and commercially available 96-well microtiter plates, and then reacted with the culture supernatant of hybridoma. Next, the carrier is washed and then reacted with an enzyme-labeled secondary antibody or such. When the culture supernatant contains an antibody of interest reactive to the sensitizing antigen, the secondary antibody binds to the carrier via this antibody. Finally, the secondary antibody bound to the carrier is detected to determine whether the culture supernatant contains the antibody of interest. Hybridomas producing a desired antibody capable of binding to the antigen can be cloned by the limiting dilution method or such.

In addition to the above-described method for preparing hybridomas through immunization of a nonhuman animal with an antigen, antibodies of interest can also be obtained by sensitizing human lymphocytes with an antigen. Specifically, first, human lymphocytes are sensitized with the mutant polypeptide of the present invention in vitro. Then, the sensitized lymphocytes are fused with an appropriate fusion partner. For example, human-derived myeloma cells with the ability to divide permanently can be used as the fusion partner (see JP-B (Kokoku) H01-59878). Antibodies obtained by this method are human antibodies having an activity of binding to the mutant polypeptide of the present invention.

The nucleotide sequence encoding an antibody that binds to the mutant polypeptide of the present invention obtained by the above-described method or such, and its amino acid sequence can be obtained by methods known to those skilled in the art.

Based on the obtained sequence of the antibody that binds to the mutant polypeptide of the present invention, the antibody that binds to the mutant polypeptide of the present invention can be prepared by genetic recombination techniques known to those skilled in the art. Specifically, a polynucleotide encoding an antibody can be constructed based on the sequence of the antibody that recognizes the mutant polypeptides of the present invention, inserted into an expression vector, and then expressed in appropriate host cells (see for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

The vectors include M13 vectors, pUC vectors, pBR322, pBluescript, and pCR-Script. Alternatively, when aiming to subclone and excise cDNA, the vectors include, for example, pGEM-T, pDIRECT, and pT7, in addition to the vectors described above. Expression vectors are particularly useful when using vectors for producing the antibodies of the present invention. For example, when aiming for expression in $E.$ $coli$ such as JM109, DH5α, HB101, and XL1-Blue, the expression vectors not only have the above-described characteristics that allow vector amplification in $E.$ $coli$, but must also carry a promoter that allows efficient expression in $E.$ $coli$, for example, lacZ promoter (Ward et al., Nature (1989) 341, 544-546; FASEB J. (1992) 6, 2422-2427), araB promoter (Better et al., Science (1988) 240, 1041-1043), T7 promoter or such. Such vectors include pGEX-5X-1 (Pharmacia), "QIAexpress system" (Qiagen), pEGFP, or pET (in this case, the host is preferably BL21 that expresses T7 RNA polymerase) in addition to the vectors described above.

The vectors may contain signal sequences for antibody secretion. As a signal sequence for antibody secretion, a pelB signal sequence (Lei, S. P. et al J. Bacteriol. (1987) 169, 4379) may be used when a protein is secreted into the *E. coli* periplasm. The vector can be introduced into host cells by calcium chloride or electroporation methods, for example.

In addition to vectors for *E. coli*, the vectors for producing the antibodies of the present invention include mammalian expression vectors (for example, pcDNA3 (Invitrogen), pEF-BOS (Nucleic Acids. Res. 1990, 18(17), p5322), pEF, and pCDM8), insect cell-derived expression vectors (for example, the "Bac-to-BAC baculovirus expression system" (Gibco-BRL) and pBacPAK8), plant-derived expression vectors (for example, pMH1 and pMH2), animal virus-derived expression vectors (for example, pHSV, pMV, and pAdexLcw), retroviral expression vectors (for example, pZIPneo), yeast expression vectors (for example, "*Pichia* Expression Kit" (Invitrogen), pNV 11, and SP-Q01), and *Bacillus subtilis* expression vectors (for example, pPL608 and pKTH50), for example.

When aiming for expression in animal cells such as CHO, COS, and NIH3T3 cells, the vectors must have a promoter essential for expression in cells, for example, SV40 promoter (Mulligan et al., Nature (1979) 277, 108), MMLV-LTR promoter, EF1α promoter (Mizushima et al., Nucleic Acids Res. (1990) 18, 5322), and CMV promoter, and more preferably they have a gene for selecting transformed cells (for example, a drug resistance gene that allows evaluation using an agent (neomycin, G418, or such)). Vectors with such characteristics include pMAM, pDR2, pBK-RSV, pBK-CMV, pOPRSV, and pOP13, for example.

In addition, the following method can be used for stable gene expression and gene amplification in cells: CHO cells deficient in a nucleic acid synthesis pathway are introduced with a vector (for example, pSV2-dhfr ("Molecular Cloning $2^{nd}$ edition", Cold Spring Harbor Laboratory Press, 1989)) that carries a DHFR gene which compensates for the deficiency, and the vector is amplified using methotrexate (MTX). Alternatively, the following method can be used for transient gene expression: COS cells with a gene expressing SV40 T antigen on their chromosome are transformed with a vector (pcD and such) with an SV40 replication origin. Replication origins derived from polyoma virus, adenovirus, bovine papilloma virus (BPV), and such can also be used. To amplify gene copy number in host cells, the expression vectors may further carry selection markers such as aminoglycoside transferase (APH) gene, thymidine kinase (TK) gene, *E. coli* xanthine-guanine phosphoribosyltransferase (Ecogpt) gene, and dihydrofolate reductase (dhfr) gene.

The antibodies of the present invention obtained by the methods described above can be isolated from inside host cells or from outside the cells (the medium, or such), and purified to homogeneity. The antibodies can be isolated and purified by methods routinely used for isolating and purifying antibodies, and the type of method is not limited. For example, the antibodies can be isolated and purified by appropriately selecting and combining column chromatography, filtration, ultrafiltration, salting out, solvent precipitation, solvent extraction, distillation, immunoprecipitation, SDS-polyacrylamide gel electrophoresis, isoelectrofocusing, dialysis, recrystallization, and such.

The chromatographies include, for example, affinity chromatography, ion exchange chromatography, hydrophobic chromatography, gel filtration, reverse phase chromatography, and adsorption chromatography (Strategies for Protein Purification and Characterization: A Laboratory Course Manual. Ed Daniel R. Marshak et al., Cold Spring Harbor Laboratory Press, 1996). The chromatographic methods described above can be conducted using liquid chromatography, for example, HPLC and FPLC. Columns that can be used for affinity chromatography include protein A columns and protein G columns. Columns using protein A include, for example, Hyper D, POROS, and Sepharose FF (GE Amersham Biosciences). The present invention includes antibodies that are highly purified using these purification methods.

The binding activity to the mutant polypeptide of the present invention of the obtained antibodies can be determined by methods known to those skilled in the art. Methods for determining the antigen-binding activity of an antibody include, for example, ELISA (enzyme-linked immunosorbent assay), EIA (enzyme immunoassay), RL4 (radioimmunoassay), and fluorescent antibody method. For example, when enzyme immunoassay is used, antibody-containing samples, such as purified antibodies and culture supernatants of antibody-producing cells, are added to antigen-coated plates. A secondary antibody labeled with an enzyme, such as alkaline phosphatase, is added and the plates are incubated. After washing, an enzyme substrate, such as p-nitrophenyl phosphate, is added, and the absorbance is measured to evaluate the antigen-binding activity.

In the present invention, "cancer" generally refers to malignant neoplasm which may be metastatic or non-metastatic. For instance, non-limiting examples of cancer that develops from epithelial tissues such as gastrointestinal tract and skin include brain tumor, skin cancer, head and neck cancer, esophageal cancer, lung cancer, gastric cancer, duodenal cancer, breast cancer, prostate cancer, cervical cancer, cancer of uterine body, pancreatic cancer, liver cancer, colorectal cancer, colon cancer, bladder cancer, and ovarian cancer. Meanwhile, non-limiting examples of sarcoma that develops from non-epithelial tissues (stroma) such as muscles include osteosarcoma, chondrosarcoma, rhabdomyosarcoma, leiomyosarcoma, liposarcoma, and angiosarcoma. Furthermore, non-limiting examples of hematological cancer derived from hematopoietic organs include malignant lymphoma including Hodgkin's lymphoma and non-Hodgkin's lymphoma, leukemia including acute myelocytic leukemia, chronic myelocytic leukemia, acute lymphatic leukemia, and chronic lymphatic leukemia, and multiple myeloma.

In the present invention, cancer includes any newly developed pathological tissue tumor (neoplasm). In the present invention, neoplasm leads to tumor formation which is characterized by partial neovascularization. Neoplasm can be benign, for example, angioma, glioma, and teratoma, or malignant, for example, cancer, sarcoma, glial tumor, astrocytoma, neuroblastoma, and retinoblastoma.

In the present invention, preferred examples of cancer include bladder cancer, brain tumor, head and neck squamous cell carcinoma, lung cancer, lung adenocarcinoma, lung squamous cell carcinoma, skin melanoma, endometrial cancer, breast cancer, prostate cancer, colon cancer, esophageal cancer, gastric cancer, bile duct cancer, biliary tract cancer, and liver cancer.

In the present invention, "cancer tissue" refers to a tissue containing at least one cancer cell. For example, as cancer tissues contain cancer cells and blood vessels, cancer tissue refers to all cell types that contribute to the formation of tumor mass containing cancer cells and endothelial cells. Herein, tumor mass refers to foci of tumor tissue. The term "tumor" is generally used to refer to benign or malignant neoplasm.

The present invention relates to pharmaceutical compositions comprising an above-described antibody or antigen-binding fragment thereof, oligonucleotides, or a compound of the present invention.

In the present invention, the pharmaceutical composition generally refers to a pharmaceutical agent for treating, preventing, or examining/diagnosing diseases.

The pharmaceutical compositions of the present invention can be formulated by methods known to those skilled in the art. For example, they can be used parenterally, in an injectable form of sterile solutions or suspensions including water or other pharmaceutically acceptable liquid. For example, such compositions may be formulated by mixing in a unit dose form required by the generally approved pharmaceutical manufacturing practice, by appropriately combining with pharmacologically acceptable carriers or media, specifically sterile water, physiological saline, vegetable oil, emulsifier, suspension, surfactant, stabilizer, flavoring agent, excipient, vehicle, preservative, binder, or such. The amount of active ingredient in such formulations is adjusted so that an appropriate amount can be obtained within a specified range.

Sterile compositions for injection can be formulated according to general formulation practice using vehicles such as distilled water for injection. Aqueous solutions for injection include, for example, physiological saline, and isotonic solutions containing glucose or other adjuvants (e.g., D-sorbitol, D-mannose, D-mannitol, and sodium chloride). These can be used in combination with appropriate solubilizers, for example, alcohol (ethanol, etc.), polyalcohol (propylene glycol, polyethylene glycol, etc.), and non-ionic detergents (Polysorbate 80™, HCO-50, etc.).

Oils include sesame oil and soybean oils. Benzyl benzoate and/or benzyl alcohol can be used in combination as solubilizers. It is also possible to combine buffers (for example, phosphate buffer and sodium acetate buffer), soothing agents (for example, procaine hydrochloride), stabilizers (for example, benzyl alcohol and phenol), and/or antioxidants. Appropriate ampules are filled with the prepared injections.

The pharmaceutical compositions of the present invention are preferably administered parenterally. For example, compositions are administered in an injectable form, or in a form for transnasal administration, transpulmonary administration, or transdermal administration. For example, they can be administered systemically or locally by intravenous injection, intramuscular injection, intraperitoneal injection, subcutaneous injection, or such.

Administration methods can be appropriately selected in consideration of the patient's age and symptoms. The dose of a pharmaceutical composition containing an antigen-binding molecule may be, for example, 0.0001 mg to 1,000 mg/kg for each administration. Alternatively, the dose may be, for example, 0.001 to 100,000 mg per patient. However, the present invention is not limited by the numeric values described above. The dosage and administration method vary according to the patient's weight, age, symptoms, and such. Those skilled in the art can set an appropriate dosage and administration method in consideration of the factors described above.

Amino acids in the amino acid sequences described herein may be modified after translation (for example, modification of N-terminal glutamine into pyroglutamic acid by pyroglutamylation is well known to those skilled in the art). As a matter of course, such posttranslationally modified amino acids are also included in the amino acid sequences of the present invention.

The present invention also relates to methods for detecting an above-described mutant polypeptide of the present invention or a polynucleotide encoding the mutant polypeptide in samples from subjects (including cancer patients and healthy persons).

The presence or absence of a mutant polypeptide of the present invention in a sample from a subject can be tested and determined, for example, using antigen-antibody reaction which is performed by contacting an above-described antibody or antigen-binding fragment thereof that binds to a mutant polypeptide of the present invention with a sample (tumor tissue, normal tissue, and various body fluid specimens containing cancer or normal cells (blood, serum, urine, saliva, ascites, pleural effusion, etc.)) collected from a subject (cancer patient, person who may be affected with cancer, person with the risk of getting cancer, or healthy person; however, it is not limited to human).

The antigen (i.e., a mutant polypeptide of the present invention) in an antigen-antibody reaction can be detected, for example, by using conventional immunoassay.

In the present invention, immunoassay refers to a method for detecting a mutant polypeptide of the present invention in a sample (tumor tissue, normal tissue, and various body fluid specimens containing cancer or normal cells (blood, serum, urine, saliva, ascites, pleural effusion, etc.)) based on the reaction mechanism between an antigen (i.e., a mutant polypeptide of the present invention) and an antibody that binds to the antigen or antigen-binding fragment thereof. Any immunoassay is included in the present invention as long as it is a method that can detect the fusion polypeptides of the present invention.

For immunoassay in the present invention, for example, the principles of various methods such as those described in "Kouso Men-eki Sokutei Hou (Enzyme immunoassay)" (3rd Ed., eds., Eiji Ishikawa et al., Igakushoin, 1987) can be applied. Specifically, these various methods can be carried out using one or more antibodies that bind to an antigen of interest to capture (trap) the antigen to be detected in a sample.

Applicable principles preferably include, for example, single antibody solid phase methods, double antibody liquid phase methods, double antibody solid phase methods, sandwich methods, and one-pot methods such as described in JP-B (Kokoku) H02-39747. Meanwhile, assays based on antigen-antibody reaction also include enzyme multiplied immunoassay technique (EMIT), enzyme channeling immunoassay, enzyme modulator mediated enzyme immunoassay (EMMIA), enzyme inhibitor immunoassay, immunoenzymometric assay, enzyme enhanced immunoassay, and proximal linkage immunoassay.

In the present invention, it is possible to select and use any appropriate immunoassay principle such as those described above depending on the objective of the test.

The immunoassays of the present invention also include sandwich methods using a biotin- or enzyme-labeled antibody, and multi-well microtiter plates having a number of wells including 96-well microplate, as well as one-pot methods using beads and antibodies labeled with biotin or enzyme such as peroxidase.

As described above, antibodies that bind to a mutant polypeptide of the present invention or antigen-binding fragments thereof, which are used in immunoassays of the present invention, may be labeled with a labeling substance that can provide a detectable signal by itself or upon reaction with other substances.

Such labeling substances include, for example, enzymes, fluorescent substances, chemiluminescent substances, biotin, avidin, and radioisotopes. More specifically, the substances include enzymes such as peroxidase (e.g., horseradish peroxidase), alkaline phosphatase, β-D-galactosidase, glucose oxidase, glucose-6-phosphate dehydrogenase, alcohol dehydrogenase, malate dehydrogenase, penicillinase, catalase, apoglucoseoxidase, urease, luciferase, and acetylcholinesterase; fluorescent substances such as fluorescein isothiocyanate, phycobiliprotein, rare earth metal chelates, dansyl chloride, and tetramethylrhodamine isothiocyanate; radioisotopes such as $^3$H, $^{14}$C, $^{125}$I, and $^{131}$I; biotin; avidin; and chemiluminescent substances.

Such radioisotopes and fluorescent substances can provide a detectable signal by themselves.

Meanwhile, enzymes, chemiluminescent substances, biotin, and avidin cannot provide any detectable signal by themselves, but provide a detectable signal when reacting with one or more different substances.

For example, when an enzyme is used, at least a substrate is necessary. Various substrates are used according to the type of enzymatic activity assay method (colorimetric assay, fluorescent assay, bioluminescence assay, chemiluminescent assay, etc.). For example, hydrogen peroxide is used as a substrate for peroxidase. Meanwhile, biotin is generally reacted with at least avidin or enzyme-modified avidin, but substrates are not limited thereto. If needed, it is also possible to use various chromogenic substances according to the substrates.

The presence or absence of a polynucleotide encoding a mutant polypeptide of the present invention in a sample from a subject can be tested and determined, for example, according to routine methods using various oligonucleotides (a pair of oligonucleotide primers, oligonucleotide probes, etc.) of the present invention described above, and mRNA, cDNA prepared using mRNA as a template, genomic DNA, or such in a sample (tumor tissue, normal tissue, and various body fluid specimens containing cancer or normal cells (blood, serum, urine, saliva, ascites, pleural effusion, etc.)) collected from a subject (cancer patient, person who may be affected with cancer, person with the risk of getting cancer, or healthy person; however, it is not limited to human) by using various gene analysis methods. Such gene analysis methods include, for example, Northern blotting, polymerase chain reaction (PCR), Southern blotting, ligase chain reaction (LCR), strand displacement amplification (SDA), nucleic acid sequence-based amplification (NASBA), isothermal and chimeric primer-initiated amplification of nucleic acids (ICAN), loop-mediated isothermal amplification (LAMP), TMA method (Gen-Probe's TMA system), microarray, and next-generation sequencing method.

These assays utilize hybridization of oligonucleotides of the present invention to a polynucleotide encoding a mutant polypeptide of the present invention derived from a sample. Desired stringent conditions for such hybridization include, for example, the conditions of 6 M urea, 0.4% SDS, 0.5× SSC, and 37° C.; and hybridization conditions of equivalent stringency. Depending on the objective, it is possible to use more stringent conditions, for example, 6 M urea, 0.4% SDS, and 0.1×SSC, and 42° C.

The present invention also relates to kits for detecting an above-described mutant polypeptide of the present invention or a polynucleotide encoding the mutant polypeptide in samples from subjects described above (including cancer patients and healthy persons).

Specifically, detection kits of the present invention may contain an above-described antibody or antigen-binding fragment thereof that binds to a mutant polypeptide of the present invention (including antibodies or antigen-binding fragments thereof labeled with above-described various labeling substances). Depending on the objective of each immunoassay described above, the kits may also contain various detection reagents (enzymes, substrates, etc.) and instruction manuals.

Specifically, detection kits of the present invention may contain various oligonucleotides of the present invention described above (a pair of oligonucleotide primers, oligonucleotide probes, etc.) that hybridize to mRNA derived from a polynucleotide encoding an above-described mutant polypeptide of the present invention, cDNA prepared using the mRNA as template, or genomic DNA. According to the objective of each gene analysis, the kits may also contain various reagents (enzymes, other oligonucleotides, nucleic acid, reaction buffer, etc.) and instruction manuals.

The present invention also relates to methods of testing for the presence or absence of resistance to various FGFR inhibitors, prediction of response of a subject to treatment with FGFR inhibitors, or prediction of the effects of FGFR inhibitors in cancer treatment, based on the presence or absence of mutant polypeptides of the present invention or polynucleotides encoding those mutant polypeptides in samples isolated from the subjects.

Specifically, methods of the present invention are, for example, methods of testing and determining the presence or absence of mutant polypeptides of the present invention in samples (tumor tissues, normal tissues, or various body fluids (such as blood, serum, urine, and saliva) that contain cancer cells or normal cells) collected from subjects (cancer patients, those who may have cancer, those at risk of having cancer, or healthy persons, without being limited to humans) by using the above-described methods and kits for detecting the mutant polypeptides of the present invention, and thereby testing for the presence or absence of resistance to various FGFR inhibitors, prediction of response of the subjects to treatment with FGFR inhibitors, or prediction of effects of FGFR inhibitors in cancer treatment, based on the criteria that the presence of the mutant polypeptide indicates the presence of resistance to various FGFR inhibitors.

Furthermore, methods of the present invention are, for example, methods of testing and determining the presence or absence of polynucleotides encoding the mutant polypeptides of the present invention in samples (tumor tissues, normal tissues, or various body fluids (such as blood, serum, urine, and saliva) that contain cancer cells or normal cells) collected from subjects (cancer patients, those who may have cancer, those at risk of having cancer, or healthy persons, without being limited to humans) by using the above-described methods and kits for detecting polynucleotides encoding the mutant polypeptides of the present invention, and thereby testing for the presence or absence of resistance to various FGFR inhibitors, prediction of response of the subjects to treatment with FGFR inhibitors, or prediction of effects of FGFR inhibitors in cancer treatment, based on the criteria that the presence of the mutant polypeptide indicates the presence of resistance to various FGFR inhibitors.

The present invention also relates to methods for selecting a patient to whom an anticancer agent (as described below) containing a compound having FGFR inhibitory activity is applicable, based on the presence or absence of mutant polypeptides of the present invention or polynucleotides encoding the mutant polypeptides in samples isolated from subjects.

Specifically, methods of the present invention are, for example, methods of testing and determining the presence or absence of mutant polypeptides of the present invention in samples (tumor tissues, normal tissues, or various body fluids (such as blood, serum, urine, and saliva) that contain cancer cells or normal cells) collected from subjects (cancer patients or those who may have cancer, without being limited to humans) by using the above-described methods and kits for detecting mutant polypeptides of the present invention, and when the mutant polypeptides are detected, selecting the subject as a patient to whom an anticancer agent (or a pharmaceutical composition for cancer treatment, as described below) containing a compound having FGFR inhibitory activity is applicable. Here, the compound of formula (I) is preferred as the compound having FGFR inhibitory activity. Furthermore, methods of the present invention are, for example, methods of testing and determining the presence or absence of polynucleotides encoding the mutant polypeptides of the present invention in samples (tumor tissues, normal tissues, or various body fluids (such as blood, serum, urine, and saliva) that contain cancer cells or normal cells) collected from subjects (cancer patients or those who may have cancer, without being limited to humans) by using the above-described methods and kits for detecting polynucleotides encoding the mutant polypeptides of the present invention, and when the polynucleotides encoding the mutant polypeptides are detected, selecting the subject as a patient to whom an anticancer agent (as described below) containing a compound having FGFR inhibitory activity is applicable. Here, the compound of formula (I) is preferred as the compound having FGFR inhibitory activity.

In the present invention, "FGFR inhibitor" and "compound having FGFR inhibitory activity" are used interchangeably, and refer to a compound having the activity of inhibiting the activity of the above-mentioned FGFR, specifically, one or more arbitrary FGFRs belonging to the FGFR family comprising FGFR1, FGFR2, FGFR3, and FGFR4, which are fibroblast growth factor receptors (FGFRs) belonging to the receptor tyrosine kinase family. Preferably, they refer to a compound having the activity of inhibiting human FGFR activity, and more preferably a compound having the activity of inhibiting the activity of human FGFR3 comprising the amino acid sequence of SEQ ID NO: 1 or 2 (cDNA sequences, SEQ ID NOs: 3 and 4, respectively/GenBank Accession Nos. NM_000141.4 and NM_022970.3, respectively).

Any FGFR inhibitors are included in the FGFR inhibitors of the present invention as long as the compounds have the activity of inhibiting FGFR activity.

Specifically, the FGFR inhibitors of the present invention include any compounds, antibodies, nucleic acid pharmaceuticals (siRNA, antisense nucleic acids, ribozymes, and such) having an action mechanism of:
(1) inhibiting the FGFR kinase activity;
(2) inhibiting dimerization between FGFR, TACC3, and BAIAP2L1;
(3) inhibiting FGFR-mediated signaling (MAPK pathway and PI3K/AKT pathway) (for example, MEK inhibitors, RAF inhibitors, ERK inhibitors, PI3K inhibitors, mTOR inhibitors, AKT inhibitors, PDK inhibitors, S6K inhibitors, etc.); or
(4) inhibiting FGFR expression (for example, siRNA, HSP90 inhibitors, etc.).

Antibodies having the activity of inhibiting FGFR activity, which are included as FGFR inhibitors of the present invention, comprise antibodies identified by the following code names: RG7444, FP-1039, AV370, and PRO-001.

Low-molecular-weight compounds having the activity of inhibiting FGFR activity, which are included as FGFR inhibitors of the present invention, include, for example:
(1) compounds disclosed in the following Patent Document and Non-patent Documents: Cancer Research, 2012, 72: 2045-2056; J. Med. Chem., 2011, 54: 7066-7083; International Publication WO 2011/016528;
(2) compounds identified by the following generic names or code names: AZD-4547 (compound C in Table 1 described below), BGJ-398 (compound D in Table 1 described below), LY-2874455, cediranib (AZD2171; compound E in Table 1 described below), PD173074 (compound B in Table 1 described below), regorafenib, ponatinib, orantinib, nintedanib, masitinib, lenvatinib, dovitinib (TKI258), brivanib, volasertib, golvatinib, ENMD-2076, E-3810, XL-999, XL-228, ARQ087, Tivozanib, motesanib, and regorafenib; and
(3) compounds exemplified below; however, FGFR inhibitors are not limited thereto:

[Compound 1]

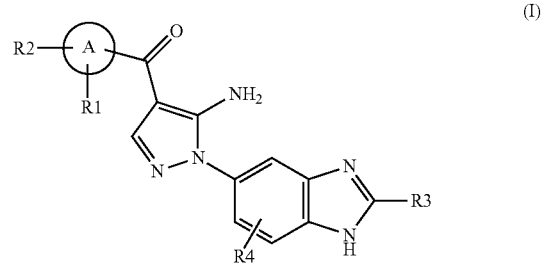

(I)

wherein $R_1$, $R_2$, $R_3$, and $R_4$ each independently represents the group listed below:

$R_1$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, $-OR_5$, $-NR_6R_7$, $-(CR_8R_9)_nZ_1$, $-C(O)NR_{12}R_{13}$, $-SR_{14}$, $-SOR_{15}$, $-SO_2R_{16}$, $-NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, $-COR_{19}$, $-COOR_{20}$, $-OC(O)R_{21}$, $-NR_{22}C(O)R_{23}$, $-NR_{24}C(S)R_{25}$, $-C(S)NR_{26}R_{27}$, $-SO_2NR_{28}R_{29}$, $-OSO_2R_{30}$, $-SO_3R_{31}$, or $-Si(R_{32})_3$;

$R_2$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, $-OR_5$, $-NR_6R_7$, $-(CR_8R_9)_nZ_1$, $-C(O)NR_{12}R_{13}$, $-SR_{14}$, $-SOR_{15}$, $-SO_2R_{16}$, $-NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, —COR$_{19}$, —COOR$_{20}$, —OC(O)R$_{21}$, —NR$_{22}$C(O)R$_{23}$, —NR$_{24}$C(S)R$_{25}$, —C(S)NR$_{26}$R$_{27}$, —SO$_2$NR$_{28}$R$_{29}$, —OSO$_2$R$_{30}$, —SO$_3$R$_{31}$, or —Si(R$_{32}$)$_3$; or R$_1$ and R$_2$, together with an atom linked thereto, form 3- to 10-membered heterocyclyl or 5- to 10-membered heteroaryl, wherein the heterocyclyl or heteroaryl is optionally substituted by halogen;

R$_3$ represents methyl;

R$_4$ represents hydrogen;

A is indole;

R$_5$ represents C$_{1-5}$ alkyl, C$_{3-7}$ cycloalkyl, C$_{3-7}$ cycloalkyl C$_{1-3}$ alkyl, C$_{2-6}$ alkenyl, C$_{2-6}$ alkynyl, C$_{1-4}$ haloalkyl, C$_{1-3}$ alkoxy C$_{1-4}$ alkyl, C$_{1-3}$ alkoxy C$_{1-4}$ alkoxy C$_{1-4}$ alkyl, C$_{1-4}$ aminoalkyl, C$_{1-4}$ alkylamino C$_{1-4}$ alkyl, di(C$_{1-4}$ alkyl)amino C$_{1-4}$ alkyl, C$_{6-10}$ aryl, C$_{6-10}$ aryl C$_{1-3}$ alkyl, or 3- to 10-membered heterocyclyl C$_{1-3}$ alkyl, 3- to 10-membered heterocyclyl, 5- to 10-membered heteroaryl, 5- to 10-membered heteroaryl C$_{1-3}$ alkyl, C$_{1-6}$ monohydroxy alkyl, C$_{1-6}$ dihydroxy alkyl, or C$_{1-6}$ trihydroxy alkyl which is optionally substituted by one or more groups independently selected from group Q;

R$_6$ and R$_7$, which can be the same or different, each represents hydrogen, C$_{1-4}$ alkyl, C$_{2-6}$ alkenyl, C$_{2-6}$ alkynyl, C$_{1-4}$ haloalkyl, C$_{1-3}$ alkoxy C$_{1-4}$ alkyl, C$_{6-10}$ aryl C$_{1-3}$ alkyl, 3- to 10-membered heterocyclyl C$_{1-3}$ alkyl, 5- to 10-membered heteroaryl C$_{1-3}$ alkyl, C$_{1-6}$ monohydroxy alkyl, C$_{1-6}$ dihydroxy alkyl, C$_{1-6}$ trihydroxy alkyl, 3- to 10-membered heterocyclyl, C$_{1-4}$ aminoalkyl, C$_{1-4}$ alkylamino C$_{1-4}$ alkyl, di(C$_{1-4}$ alkyl)amino C$_{1-4}$ alkyl, or cyano(C$_{1-3}$ alkyl); or alternatively R$_6$ and R$_7$, together with a nitrogen atom linked thereto, form 3- to 10-membered heterocyclyl or 5- to 10-membered heteroaryl;

n represents 1 to 3;

R$_8$ and R$_9$, which can be the same or different, each represents hydrogen, C$_{1-4}$ alkyl, or halogen; or alternatively R$_8$ and R$_9$, together with a carbon atom linked thereto, form a cycloaliphatic ring;

Z$_1$ represents hydrogen, NR$_{10}$R$_{11}$, —OH, or 3- to 10-membered heterocyclyl or 5- to 10-membered heteroaryl which is optionally substituted by one or more groups independently selected from group Q;

R$_{10}$ and R$_{11}$, which can be the same or different, each represents C$_{1-4}$ alkyl, C$_{2-6}$ alkenyl, C$_{2-6}$ alkynyl, C$_{1-4}$ haloalkyl, C$_{1-3}$ alkoxy C$_{1-4}$ alkyl, cyano(C$_{1-3}$ alkyl), or C$_{1-3}$ alkylsulfonyl C$_{1-4}$ alkyl; or alternatively R$_{10}$ and R$_{11}$, together with a nitrogen atom linked thereto, form 3- to 10-membered heterocyclyl or 5- to 10-membered heteroaryl;

R$_{12}$ and R$_{13}$, which can be the same or different, each represents hydrogen, C$_{1-4}$ alkyl, C$_{2-6}$ alkenyl, C$_{2-6}$ alkynyl, C$_{1-4}$ haloalkyl, C$_{1-3}$ alkoxy C$_{1-4}$ alkyl, C$_{6-10}$ aryl, 5- to 10-membered heteroaryl, 3- to 10-membered heterocyclyl, C$_{6-10}$ aryl C$_{1-4}$ alkyl, 3- to 10-membered heterocyclyl C$_{1-3}$ alkyl, 5- to 10-membered heteroaryl C$_{1-3}$ alkyl, cyano(C$_{1-3}$ alkyl), C$_{1-3}$ alkylsulfonyl C$_{1-4}$ alkyl, 3- to 10-membered cycloaliphatic ring, 5- to 10-membered heteroaryl, or 3- to 10-membered heterocyclyl; or alternatively R$_{12}$ and R$_{13}$, together with a nitrogen atom linked thereto, form 3- to 10-membered heterocyclyl or 5- to 10-membered heteroaryl which is optionally substituted by one or more groups independently selected from group Q;

R$_{14}$ represents C$_{1-4}$ alkyl, C$_{2-6}$ alkenyl, C$_{2-6}$ alkynyl, C$_{1-4}$ haloalkyl, C$_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

R$_{15}$ represents C$_{1-4}$ alkyl, C$_{2-6}$ alkenyl, C$_{2-6}$ alkynyl, C$_{1-4}$ haloalkyl, C$_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

R$_{16}$ represents C$_{1-4}$ alkyl, C$_{2-6}$ alkenyl, C$_{2-6}$ alkynyl, C$_{1-4}$ haloalkyl, C$_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

R$_{17}$ represents hydrogen or C$_{1-4}$ alkyl;

R$_{18}$ represents C$_{1-4}$ alkyl, C$_{2-6}$ alkenyl, C$_{2-6}$ alkynyl, C$_{1-4}$ haloalkyl, C$_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

R$_{19}$ represents hydrogen, C$_{1-4}$ alkyl, C$_{3-7}$ cycloalkyl, C$_{1-4}$ haloalkyl, C$_{6-10}$ aryl, or 5- to 10-membered heteroaryl or 3- to 10-membered heterocyclyl which is optionally substituted by one or more groups independently selected from group Q;

R$_{20}$ represents C$_{1-4}$ alkyl, C$_{3-7}$ cycloalkyl, C$_{1-4}$ haloalkyl, C$_{6-10}$ aryl, 5- to 10-membered heteroaryl, or 3- to 10-membered heterocyclyl;

R$_{21}$ represents C$_{1-4}$ alkyl, C$_{3-7}$ cycloalkyl, C$_{1-4}$ haloalkyl, C$_{6-10}$ aryl, 5- to 10-membered heteroaryl, or 3- to 10-membered heterocyclyl;

R$_{22}$ represents hydrogen, C$_{1-4}$ alkyl, or C$_{1-4}$ haloalkyl;

R$_{23}$ represents hydrogen, C$_{1-4}$ alkyl, C$_{3-7}$ cycloalkyl, C$_{1-4}$ haloalkyl, C$_{6-10}$ aryl, 5- to 10-membered heteroaryl, or 3- to 10-membered heterocyclyl;

R$_{24}$ represents hydrogen, C$_{1-4}$ alkyl, or C$_{1-4}$ haloalkyl;

R$_{25}$ represents C$_{1-4}$ alkyl, C$_{3-7}$ cycloalkyl, C$_{1-4}$ haloalkyl, C$_{6-10}$ aryl, 5- to 10-membered heteroaryl, or 3- to 10-membered heterocyclyl;

R$_{26}$ and R$_{27}$, which can be the same or different, each represents hydrogen, C$_{1-4}$ alkyl, C$_{2-6}$ alkenyl, C$_{2-6}$ alkynyl, C$_{1-4}$ haloalkyl, C$_{1-3}$ alkoxyl C$_{1-4}$ alkyl, C$_{6-10}$ aryl, 5- to 10-membered heteroaryl, 3- to 10-membered heterocyclyl, C$_{6-10}$ aryl C$_{1-4}$ alkyl, 3- to 10-membered heterocyclyl C$_{1-3}$ alkyl, 5- to 10-membered heteroaryl C$_{1-3}$ alkyl, cyano(C$_{1-3}$ alkyl), C$_{1-3}$ alkylsulfonyl C$_{1-4}$ alkyl, or 3- to 10-membered cycloaliphatic ring; or alternatively R$_{26}$ and R$_{27}$, together with a nitrogen atom linked thereto, form 3- to 10-membered heterocyclyl or 5- to 10-membered heteroaryl;

R$_{28}$ and R$_{29}$, which can be the same or different, each represents hydrogen, C$_{1-4}$ alkyl, C$_{2-6}$ alkenyl, C$_{2-6}$ alkynyl, C$_{1-4}$ haloalkyl, C$_{1-3}$ alkoxyl C$_{1-4}$ alkyl, C$_{6-10}$ aryl, 5- to 10-membered heteroaryl, 3- to 10-membered heterocyclyl, C$_{6-10}$ aryl C$_{1-4}$ alkyl, 3- to 10-membered heterocyclyl C$_{1-3}$ alkyl, 5- to 10-membered heteroaryl C$_{1-3}$ alkyl, cyano(C$_{1-3}$ alkyl), C$_{1-3}$ alkylsulfonyl C$_{1-4}$ alkyl, or 3- to 10-membered cycloaliphatic ring; or alternatively R$_{28}$ and R$_{29}$, together with a nitrogen atom linked thereto, form 3- to 10-membered heterocyclyl or 5- to 10-membered heteroaryl;

R$_{30}$ represents C$_{1-4}$ alkyl, C$_{3-7}$ cycloalkyl, C$_{1-4}$ haloalkyl, C$_{6-10}$ aryl, 5- to 10-membered heteroaryl, or 3- to 10-membered heterocyclyl;

R$_{31}$ represents C$_{1-4}$ alkyl, C$_{3-7}$ cycloalkyl, C$_{1-4}$ haloalkyl, C$_{6-10}$ aryl, 5- to 10-membered heteroaryl, or 3- to 10-membered heterocyclyl;

R$_{32}$ represents C$_{1-4}$ alkyl or C$_{6-10}$ aryl;

<Group P>
halogen, $C_{1-4}$ alkyl, $C_{1-4}$ haloalkyl, —OH, $C_{1-3}$ alkoxy, $C_{1-3}$ haloalkoxy, 3- to 10-membered heterocyclylamino, —SO$_2$R$_{16}$, —CN, —NO$_2$, and 3- to 10-membered heterocyclyl;

<Group Q>
halogen, $C_{1-4}$ alkyl, $C_{1-4}$ haloalkyl, —OH, $C_{1-3}$ alkoxy, $C_{1-6}$ monohydroxy alkyl, $C_{1-6}$ dihydroxy alkyl, $C_{1-6}$ trihydroxy alkyl, 3- to 10-membered heterocyclyl amine, —SO$_2$R$_{16}$, —CN, —NO$_2$, $C_{3-7}$ cycloalkyl, —COR$_{19}$, and 3- to 10-membered heterocyclyl which is optionally substituted by $C_{1-4}$ alkyl.

[Compound 2]

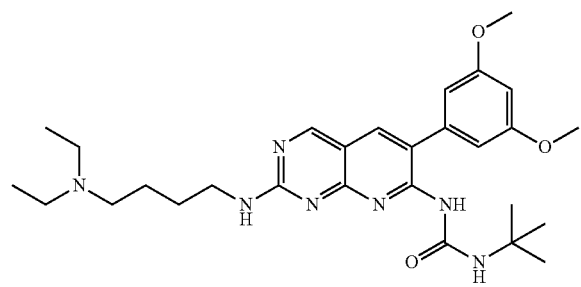 [SMILES: CCN(CC)CCCCNc1ncc2cc(-c3cc(OC)cc(OC)c3)c(NC(=O)NC(C)(C)C)nc2n1]

[Compound 3]

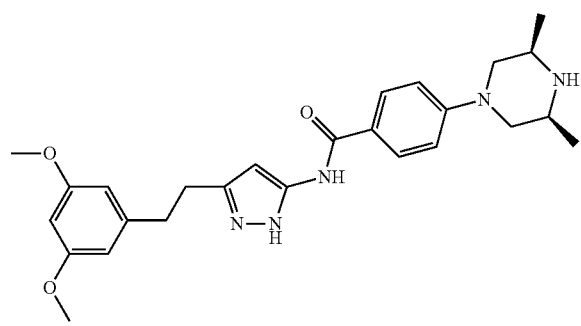

[Compound 4]

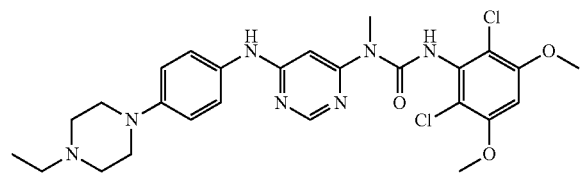 [SMILES: CCN1CCN(c2ccc(Nc3cc(N(C)C(=O)Nc4c(Cl)c(OC)cc(OC)c4Cl)ncn3)cc2)CC1]

[Compound 5]

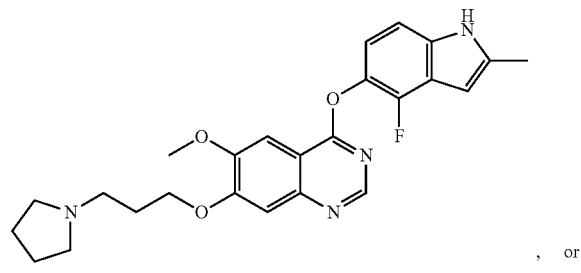

, or

[Compound 6]

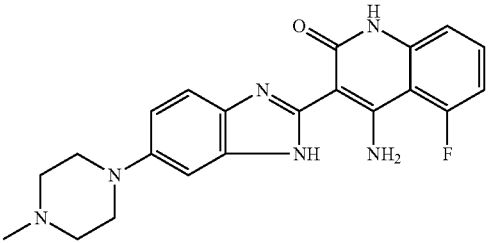

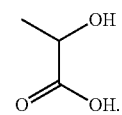

Herein, the "alkyl" refers to a monovalent group derived from an aliphatic hydrocarbon by removing an arbitrary hydrogen atom. It contains no heteroatom or unsaturated carbon-carbon bond in the backbone, and has a subset of hydrocarbyl or hydrocarbon group structures which contain hydrogen and carbon atoms. The alkyl group includes linear and branched structures. Preferred alkyl groups include alkyl groups with one to six carbon atoms ($C_{1-6}$; hereinafter, "$C_{p-q}$" means that the number of carbon atoms is p to q), $C_{1-5}$ alkyl groups, $C_{1-4}$ alkyl groups, and $C_{1-3}$ alkyl groups.

Specifically, the alkyl includes, for example, methyl group, ethyl group, n-propyl group, isopropyl group, n-butyl group, isobutyl group, s-butyl group, t-butyl group, pentyl group, isopentyl group, 2,3-dimethylpropyl group, 3,3-dimethylbutyl group, and hexyl group.

Herein, "alkenyl" refers to a monovalent hydrocarbon group having at least one double bond (two adjacent SP2 carbon atoms), and includes those of linear and branched forms. Depending on the configuration of the double bond and substituents (if any), the geometry of the double bond can be of entgegen (E) or zusammen (Z), or cis or trans configuration. Preferred alkenyl groups include $C_{2-6}$ alkenyl groups.

Specifically, the alkenyl includes, for example, vinyl group, allyl group, 1-propenyl group, 2-propenyl group, 1-butenyl group, 2-butenyl group (including cis and trans), 3-butenyl group, pentenyl group, and hexenyl group.

Herein, "alkynyl" refers to a monovalent hydrocarbon group having at least one triple bond (two adjacent SP carbon atoms), and includes those of linear and branched forms. Preferred alkynyl groups include $C_{2-6}$ alkynyl groups.

Specifically, the alkynyl includes, for example, ethynyl group, 1-propynyl group, propargyl group, 3-butynyl group, pentynyl group, and hexynyl group.

The alkenyl and alkynyl may each have one, two or more double bonds or triple bonds.

Herein, "cycloalkyl" refers to a saturated or partially saturated cyclic monovalent aliphatic hydrocarbon group, and includes monocyclic groups, bicyclo rings, and spiro rings. Preferred cycloalkyl includes $C_{3-7}$ cycloalkyl groups. Specifically, the cycloalkyl group includes, for example, cyclopropyl group, cyclobutyl group, cyclopentyl group, cyclohexyl group, and cycloheptyl group.

Herein, "cycloalkylalkyl" refers to a group in which an arbitrary hydrogen atom of an "alkyl" defined above is substituted with a "cycloalkyl" defined above. Preferred cycloalkylalkyl groups include $C_{3-7}$ cycloalkyl$C_{1-3}$ alkyl, and specifically include, for example, cyclopropylmethyl group and cyclopropylethyl group.

Herein, "hetero atom" refers to a nitrogen atom (N), oxygen atom (O), or sulfur atom (S).

Herein, "halogen" refers to a fluorine atom, chlorine atom, bromine atom, or iodine atom.

Herein, "haloalkyl" refers to a group in which preferably one to nine, more preferably one to five identical or different "halogen atoms" defined above are linked to an "alkyl" defined above.

Specifically, the haloalkyl includes, for example, chloromethyl group, dichloromethyl group, trichloromethyl group, fluoromethyl group, difluoromethyl group, perfluoroalkyl group (such as trifluoromethyl group and —$CF_2CF_3$), and 2,2,2-trifluoroethyl group.

Herein, "alkoxy" refers to an oxy group linked with an "alkyl" defined above. Preferred alkoxy includes $C_{1-4}$ alkoxy groups and $C_{1-3}$ alkoxy groups. Specifically, alkoxy includes, for example, methoxy group, ethoxy group, 1-propoxy group, 2-propoxy group, n-butoxy group, i-butoxy group, sec-butoxy group, and tert-butoxy group.

Herein, "haloalkoxy" refers to a group in which preferably one to nine, more preferably one to five identical or different halogen atoms defined above are linked to an "alkoxy" defined above.

Specifically, the haloalkoxy includes, for example, chloromethoxy group, trichloromethoxy group, and trifluoromethoxy group.

Herein, "aryl" refers to a monovalent aromatic hydrocarbon ring. The aryl preferably includes $C_{6-10}$ aryl. Specifically, the aryl includes, for example, phenyl group and naphthyl groups (for example, 1-naphthyl group and 2-naphthyl group).

Herein, "alicyclic ring" refers to a monovalent non-aromatic hydrocarbon ring. The alicyclic ring may have unsaturated bonds within its ring, and may be a multicyclic group having two or more rings. The carbon atoms constituting the ring may be oxidized to form a carbonyl. The number of atoms constituting an alicyclic ring preferably ranges from three to ten (3- to 10-membered aliphatic ring). The alicyclic ring includes, for example, cycloalkyl rings, cycloalkenyl rings, and cycloalkynyl rings.

Herein, "heteroaryl" refers to a monovalent aromatic heterocyclic group in which the ring-constituting atoms include preferably one to five hetero atoms. The heteroaryl may be partially saturated, and may be a monocyclic or condensed ring (for example, a bicyclic heteroaryl condensed with a benzene ring or monocyclic heteroaryl ring). The number of ring-constituting atoms preferably ranges from five to ten (5- to 10-membered heteroaryl).

Specifically, the heteroaryl includes, for example, furyl group, thienyl group, pyrrolyl group, imidazolyl group, pyrazolyl group, thiazolyl group, isothiazolyl group, oxazolyl group, isooxazolyl group, oxadiazolyl group, thiadiazolyl group, triazolyl group, tetrazolyl group, pyridyl group, pyrimidyl group, pyridazinyl group, pyrazinyl group, triazinyl group, benzofuranyl group, benzothienyl group, benzothiadiazolyl group, benzothiazolyl group, benzoxazolyl group, benzoxadiazolyl group, benzoimidazolyl group, indolyl group, isoindolyl group, azaindolyl group, indazolyl group, quinolyl group, isoquinolyl group, cinnolinyl group, quinazolinyl group, quinoxalinyl group, benzodioxolyl group, indolydinyl group, and imidazopyridyl group.

Herein, "heterocyclyl" refers to a non-aromatic monovalent heterocyclic group in which the ring-constituting atoms include preferably one to five hetero atoms. The heterocyclyl may contain double or triple bonds in its ring. The carbon atoms may be oxidized to form carbonyl. The ring may be a monocyclic or condensed ring. The number of the ring-constituting atoms preferably ranges from three to ten (3- to 10-membered heterocyclyl).

Specifically, the heterocyclyl includes, for example, oxetanyl group, dihydrofuryl group, tetrahydrofuryl group, dihydropyranyl group, tetrahydropyranyl group, tetrahydropyridyl group, morpholinyl group, thiomorpholinyl group, pyrrolidinyl group, piperidinyl group, piperazinyl group, pyrazolidinyl group, imidazolinyl group, imidazolidinyl group, oxazolidinyl group, isooxazolidinyl group, thiazolidinyl group, isothiazolidinyl group, thiadiazolidinyl group, azetidinyl group, oxazolidone group, benzodioxanyl group, benzoxazolyl group, dioxolanyl group, and dioxanyl group.

Herein, "arylalkyl" refers to a group in which an arbitrary hydrogen atom in an "alkyl" defined above is substituted with an "aryl" defined above. The arylalkyl preferably includes $C_{6-10}$ aryl $C_{1-4}$ alkyl and $C_{6-10}$ aryl $C_{1-3}$ alkyl. Specifically, the arylalkyl includes, for example, benzyl group, phenethyl group, and naphthylmethyl group.

Herein, "heteroarylalkyl" refers to a group in which an arbitrary hydrogen atom in an alkyl defined above is substituted with a "heteroaryl" defined above. The heteroarylalkyl preferably includes 5- to 10-membered heteroaryl $C_{1-3}$ alkyl. Specifically, the heteroarylalkyl includes, for example, pyrrolylmethyl group, imidazolylmethyl group, thienylmethyl group, pyridylmethyl group, pyrimidylmethyl group, quinolylmethyl group, and pyridylethyl group.

Herein, "heterocyclylalkyl" refers to a group in which an arbitrary hydrogen atom in an "alkyl" defined above is substituted with a "heterocyclyl" defined above. The heterocyclylalkyl preferably includes 3- to 10-membered heterocyclyl $C_{1-3}$ alkyl. Specifically, the heterocyclylalkyl includes, for example, morpholinylmethyl group, morpholinylethyl group, thiomorpholinylmethyl group, pyrrolidinylmethyl group, piperidinylmethyl group, piperazinylmethyl group, piperazinylethyl group, and oxetanylmethyl group.

Herein, "monohydroxyalkyl" refers to a group in which an arbitrary hydrogen atom in an "alkyl" defined above is substituted with a hydroxyl group. The monohydroxyalkyl preferably includes $C_{1-6}$ monohydroxyalkyl and $C_{1-6}$ monohydroxyalkyl. Specifically, the monohydroxyalkyl includes, for example, hydroxy methyl group, 1-hydroxyethyl group, and 2-hydroxyethyl group.

Herein, "dihydroxyalkyl" refers to a group in which two arbitrary hydrogen atoms in an "alkyl" defined above are substituted with two hydroxyl groups. The dihydroxyalkyl preferably includes $C_{1-6}$ dihydroxyalkyl and $C_{2-6}$ dihydroxyalkyl. Specifically, the dihydroxyalkyl includes, for example, 1,2-dihydroxyethyl group, 1,2-dihydroxypropyl group, and 1,3-dihydroxypropyl group.

Herein, "trihydroxyalkyl" refers to a group in which three arbitrary hydrogen atoms in an "alkyl" defined above are substituted with three hydroxyl groups. The trihydroxyalkyl preferably includes $C_{1-6}$ trihydroxyalkyl and $C_{2-6}$ trihydroxyalkyl.

Herein, "alkoxyalkyl" refers to a group in which an arbitrary hydrogen atom in an "alkyl" defined above is substituted with an "alkoxy" defined above. The alkoxyalkyl preferably includes $C_{1-3}$ alkoxy $C_{1-4}$ alkyl and $C_{1-3}$ alkoxy $C_{2-4}$ alkyl. Specifically, the alkoxyalkyl includes, for example, methoxyethyl.

Herein, "alkoxyalkoxyalkyl" refers to a group in which an arbitrary hydrogen atom in the terminal alkyl of an "alkoxyalkyl" defined above is substituted with an "alkoxy" defined above. The alkoxyalkoxyalkyl preferably includes $C_{1-3}$ alkoxy $C_{1-4}$ alkoxy $C_{1-4}$ alkyl and $C_{1-3}$ alkoxy $C_{2-4}$ alkoxy $C_{2-4}$ alkyl.

Herein, "aminoalkyl" refers to a group in which an arbitrary hydrogen atom in an "alkyl" defined above is substituted with an amino group. The aminoalkyl group preferably includes $C_{1-4}$ aminoalkyl and $C_{2-4}$ aminoalkyl.

Herein, "alkylamino" refers to an amino group linked with an "alkyl" defined above. The alkylamino preferably includes $C_{1-4}$ alkylamino.

Herein, "dialkylamino" refers to an amino group linked with two "alkyls" defined above. The two alkyl groups may be same or different. The dialkylamino preferably includes di($C_{1-4}$ alkyl)amino.

Herein, "alkylaminoalkyl" refers to a group in which an arbitrary hydrogen atom in an "alkyl" defined above is substituted with an "alkylamino" defined above. The alkylaminoalkyl preferably includes $C_{1-4}$ alkylamino $C_{1-4}$ alkyl and $C_{1-4}$ alkylamino $C_{2-4}$ alkyl.

Herein, "dialkylaminoalkyl" refers to a group in which an arbitrary hydrogen atom in an "alkyl" defined above is substituted with a "dialkylamino" defined above. The dialkylaminoalkyl preferably includes di($C_{1-4}$ alkyl)amino $C_{1-4}$ alkyl and di($C_{1-4}$ alkyl)amino $C_{2-4}$ alkyl.

Herein, "heterocyclylamino" refers to an amino group linked with a "heterocyclyl" defined above. The heterocyclylamino preferably includes 3- to 10-membered heterocyclylamino.

Herein, "cyanoalkyl" refers to a group in which an arbitrary hydrogen atom in an "alkyl" defined above is substituted with a cyano group. The cyanoalkyl preferably includes cyano($C_{1-3}$ alkyl).

Herein, "alkylsulfonyl" refers to a sulfonyl group linked with an "alkyl" defined above (i.e. alkyl-$SO_2$—). The alkylsulfonyl preferably includes $C_{1-3}$ alkylsulfonyl. Specifically, the alkylsulfonyl includes methylsulfonyl, ethylsulfonyl, n-propylsulfonyl, and i-propylsulfonyl.

Herein, "alkylsulfonylalkyl" refers to a group in which an arbitrary hydrogen atom in an "alkyl" defined above is substituted with an "alkylsulfonyl" defined above. The alkylsulfonylalkyl preferably includes $C_{1-3}$ alkylsulfonyl $C_{1-4}$ alkyl and $C_{1-3}$ alkylsulfonyl $C_{2-4}$ alkyl.

Preferably, the compounds represented by formula (I) shown above are as follows:

$R_1$ shown above preferably represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$NR_{17}SO_2R_{18}$, COOH, $C_{6-10}$ aryl which is optionally substituted with one or more groups independently selected from group P, 5- to 10-membered heteroaryl or 3- to 10-membered heterocyclyl each of which is optionally substituted with one or more groups independently selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$.

$R_1$ shown above more preferably represents hydrogen, hydroxy, halogen, cyano, $C_{1-4}$ haloalkyl, $C_{1-6}$ alkyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SO_2R_{16}$, —$NR_{17}SO_2R_{18}$, COOH, $C_{6-10}$ aryl which is optionally substituted with one or more groups independently selected from group P, or 5- to 10-membered heteroaryl or 3- to 10-membered heterocyclyl each of which is optionally substituted with one or more groups independently selected from group Q. Specifically, the above 5- to 10-membered heteroaryl is particularly preferably an imidazolyl group, thienyl group, pyridyl group, pyridazinyl group, or pyrazolyl group. The above 3- to 10-membered heterocyclyl is particularly preferably a morpholinyl group, tetrahydropyridyl group, or piperidinyl group.

$R_2$ shown above preferably represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted with one or more groups independently selected from group P, 5- to 10-membered heteroaryl or 3- to 10-membered heterocyclyl each of which is optionally substituted with one or more groups independently selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$.

$R_2$ shown above more preferably represents hydrogen, halogen, $C_{1-4}$ haloalkyl, $C_{1-6}$ alkyl, —$OR_5$, $C_{6-10}$ aryl which is optionally substituted with one or more groups independently selected from group P, or 5- to 10-membered heteroaryl which is optionally substituted with one or more groups independently selected from group Q. Specifically, this 5- to 10-membered heteroaryl is particularly preferably a pyridyl group.

$R_1$ and $R_2$ shown above can preferably be taken together with the atoms to which they are attached to form 3- to 10-membered heterocyclyl or 5- to 10-membered heteroaryl. The heterocyclyl or heteroaryl may have a halogen atom as a substituent. Specifically, the 3- to 10-membered heterocyclyl formed together with the atoms to which $R_1$ and $R_2$ are attached, is particularly preferably a dioxolanyl group or dioxanyl group.

$R_3$ shown above preferably represents hydrogen, $C_{1-5}$ alkyl, $C_{6-10}$ aryl $C_{1-6}$ alkyl, or $C_{1-4}$ haloalkyl, more preferably hydrogen, $C_{1-4}$ alkyl, $C_{6-10}$ aryl $C_{1-4}$ alkyl, or $C_{1-3}$perfluoroalkyl, and particularly preferably $C_1$ alkyl.

$R_4$ shown above preferably represents hydrogen, halogen, $C_{1-3}$ alkyl, $C_{1-4}$ haloalkyl, hydroxy, cyano, nitro, $C_{1-4}$ alkoxy, —$(CH_2)_nZ_1$, —$NR_6R_7$, —$OR_5$, —$C(O)NR_{12}R_{13}$, —$SR_{14}$, —$SOR_{15}$, —$SO_2R_{16}$, $NR_{17}SO_2R_{13}$, COOH, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$—$SO_3R_{31}$, or —$Si(R_{32})_3$.

$R_4$ shown above more preferably represents hydrogen, halogen, $C_{1-3}$ alkyl, $C_{1-3}$ perfluoroalkyl, cyano, methanesulfonyl, hydroxyl, alkoxy, or amino, and particularly preferably hydrogen or halogen.

Ring A mentioned above is preferably a 5- to 10-membered heteroaryl ring or $C_{6-10}$ aryl ring, more preferably benzene, indole, azaindole, benzofuran, benzothiophene, benzothiazole, quinoline, or pyrrole, and particularly preferably indole or pyrrole.

$R_5$ shown above preferably represents $C_{1-5}$ alkyl, $C_{3-7}$ cycloalkyl, $C_{3-7}$ cycloalkyl $C_{1-3}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{1-3}$ alkoxy $C_{1-4}$ alkoxy $C_{1-4}$ alkyl, $C_{1-4}$ amino alkyl, $C_{1-4}$ alkylamino $C_{1-4}$ alkyl, di($C_{1-4}$ alkyl)amino $C_{1-4}$ alkyl, $C_{6-10}$ aryl, $C_{6-10}$ aryl $C_{1-3}$ alkyl, or 3- to 10-membered heterocyclyl $C_{1-3}$ alkyl, 3- to 10-membered heterocyclyl, 5- to 10-membered heteroaryl, or 5- to 10-membered heteroaryl $C_{1-3}$ alkyl, each of which is optionally substituted with one or more groups independently selected from group Q, $C_{1-6}$ monohydroxyalkyl, $C_{1-6}$ dihydroxyalkyl, or $C_{1-6}$ trihydroxyalkyl.

$R_5$ shown above more preferably represents $C_{1-5}$ alkyl, $C_{3-7}$ cycloalkyl $C_{1-3}$ alkyl, $C_{1-4}$ haloalkyl, $C_{1-3}$ alkoxy $C_{1-4}$ alkyl, $C_{6-10}$ aryl, $C_{6-10}$ aryl $C_{1-3}$ alkyl, or 3- to 10-membered heterocyclyl $C_{1-3}$ alkyl or 3- to 10-membered heterocyclyl each of which is optionally substituted with one or more groups independently selected from group Q. Specifically, the above 3- to 10-membered heterocyclylalkyl is particularly preferably a piperazinylethyl group, oxetanylmethyl group, or morpholinylethyl group. The above 3- to 10-membered heterocyclyl is particularly preferably an oxetanyl group or tetrahydropyranyl group.

$R_6$ and $R_7$ shown above may be the same or different, and each preferably represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{2-4}$ alkyl, $C_{6-10}$ aryl $C_{1-3}$ alkyl, 3- to 10-membered heterocyclyl $C_{1-3}$ alkyl, 5- to 10-membered heteroaryl $C_{1-3}$ alkyl, $C_{1-6}$ monohydroxyalkyl, $C_{1-6}$ dihydroxyalkyl, $C_{1-6}$ trihydroxyalkyl, 3- to 10-membered heterocyclyl, $C_{1-4}$ aminoalkyl, $C_{1-4}$ alkylamino $C_{1-4}$ alkyl, di($C_{1-4}$ alkyl)amino $C_{1-4}$ alkyl, or cyano ($C_{1-3}$ alkyl).

$R_6$ and $R_7$ shown above more preferably each independently represent hydrogen, $C_{1-3}$ alkoxy $C_{1-4}$ alkyl, 3- to 10-membered heterocyclyl $C_{1-3}$ alkyl, 5- to 10-membered heteroaryl $C_{1-3}$ alkyl, or $C_{1-6}$ dihydroxyalkyl. Specifically, the 3- to 10-membered heterocyclylalkyl is particularly preferably a morpholinylethyl group, and the 5- to 10-membered heteroarylalkyl is particularly preferably a pyridylethyl group.

Alternatively, $R_6$ and $R_7$ shown above can preferably be taken together with the nitrogen atoms to which they are attached to form 3- to 10-membered heterocyclyl or 5- to 10-membered heteroaryl.

"n" shown above represents an integer from 1 to 3. Preferably, n is 1.

$R_8$ and $R_9$ shown above preferably may be the same or different, and each represents hydrogen, $C_{1-4}$ alkyl, or halogen, and more preferably hydrogen.

Alternatively, $R_8$ and $R_9$ shown above can preferably be taken together with the carbon atoms to which they are attached to form an alicyclic ring.

$Z_1$ shown above preferably represents hydrogen, $NR_{10}R_{11}$, —OH, or 3- to 10-membered heterocyclyl or 5- to 10-membered heteroaryl each of which is optionally substituted with one or more groups independently selected from group Q, more preferably $NR_{10}R_{11}$ or —OH, or 3- to 10-membered heterocyclyl which is optionally substituted with one or more groups independently selected from group Q. Specifically, the above 3- to 10-membered heterocyclyl is particularly preferably a pyrrolidinyl group, piperazinyl group, piperidinyl group, or morpholinyl group.

$R_{10}$ and $R_{11}$ shown above preferably may be the same or different, and each preferably represents $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, cyano($C_{1-3}$ alkyl), or $C_{1-3}$ alkylsulfonyl $C_{1-4}$ alkyl, more preferably $C_{1-4}$ alkyl, $C_{2-6}$ alkynyl, or $C_{1-3}$ alkoxy $C_{2-4}$ alkyl.

Alternatively, $R_{10}$ and $R_{11}$ shown above can preferably be taken together with the nitrogen atoms to which they are attached to form 3- to 10-membered heterocyclyl or 5- to 10-membered heteroaryl.

$R_{12}$ and $R_{13}$ shown above preferably may be the same or different, and each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered alicyclic ring, more preferably hydrogen, $C_{1-4}$ alkyl, or $C_{1-4}$ haloalkyl.

Alternatively, $R_{12}$ and $R_{13}$ shown above preferably can be taken together with the nitrogen atoms to which they are attached to form 3- to 10-membered heterocyclyl or 5- to 10-membered heteroaryl each of which is optionally substituted with one or more groups independently selected from group Q, and particularly preferably 3- to 10-membered heterocyclylalkyl. Specifically, piperazinyl group, morpholinyl group, pyrrolidinyl group, and piperidinyl group are more preferred.

$R_{14}$ shown above preferably represents $C_{1-4}$ alkyl, $C_{2-6}$ alkenyl, $C_{2-6}$ alkynyl, $C_{1-4}$ haloalkyl, $C_{6-10}$ aryl which is optionally substituted with one or more groups independently selected from group P, or 5- to 10-membered heteroaryl or 3- to 10-membered heterocyclyl each of which is optionally substituted with one or more groups independently selected from group Q, and more preferably represents $C_{1-4}$ alkyl or $C_{1-4}$ haloalkyl.

$R_{15}$ shown above preferably represents $C_{1-4}$ alkyl, $C_{2-6}$ alkenyl, $C_{2-6}$ alkynyl, $C_{1-4}$ haloalkyl, $C_{6-10}$ aryl which is optionally substituted with one or more groups independently selected from group P, or 5- to 10-membered heteroaryl or 3- to 10-membered heterocyclyl each of which is optionally substituted with one or more groups independently selected from group Q.

$R_{16}$ shown above preferably represents $C_{1-4}$ alkyl, $C_{2-6}$ alkenyl, $C_{2-6}$ alkynyl, $C_{1-4}$ haloalkyl, $C_{6-10}$ aryl which is optionally substituted with one or more groups independently selected from group P, or 5- to 10-membered heteroaryl or 3- to 10-membered heterocyclyl each of which is optionally substituted with one or more groups independently selected from group Q, and more preferably represents $C_{1-4}$ alkyl.

$R_{17}$ shown above preferably represents hydrogen or $C_{1-4}$ alkyl, and more preferably hydrogen.

$R_{18}$ shown above preferably represents $C_{1-4}$ alkyl, $C_{2-6}$ alkenyl, $C_{2-6}$ alkynyl, $C_{1-4}$ haloalkyl, $C_{6-10}$ aryl which is optionally substituted with one or more groups independently selected from group P, or 5- to 10-membered heteroaryl or 3- to 10-membered heterocyclyl each of which is optionally substituted with one or more groups independently selected from group Q, and more preferably represents $C_{1-4}$ alkyl.

$R_{19}$ shown above preferably represents hydrogen, $C_{1-4}$ alkyl, $C_{3-7}$ cycloalkyl, $C_{1-4}$ haloalkyl, $C_{6-10}$ aryl, or 5- to 10-membered heteroaryl or 3- to 10-membered heterocyclyl each of which is optionally substituted with one or more groups independently selected from group Q, and more preferably represents hydrogen, or 5- to 10-membered heteroaryl or 3- to 10-membered heterocyclyl each of which is optionally substituted with one or more groups independently selected from group Q. Specifically, this 3- to 10-membered heterocyclyl is more preferably a piperazinyl group, morpholinyl group, pyrrolidinyl group, or piperidinyl group.

$R_{20}$ shown above preferably represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl.

$R_{21}$ shown above preferably represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl.

$R_{22}$ shown above preferably represents hydrogen, $C_{1-4}$ alkyl, or $C_{1-4}$ haloalkyl.

$R_{23}$ shown above preferably represents hydrogen, $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl.

$R_{24}$ shown above preferably represents hydrogen, $C_{1-4}$ alkyl, or $C_{1-4}$ haloalkyl.

$R_{25}$ shown above preferably represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl.

R$_{26}$ and R$_{27}$ shown above preferably may be the same or different, and each represents hydrogen, C$_{1-4}$ alkyl, C$_{2-6}$ alkenyl, C$_{2-6}$ alkynyl, C$_{1-4}$ haloalkyl, C$_{1-3}$ alkoxy C$_{1-4}$ alkyl, C$_{6-10}$ aryl, 5- to 10-membered heteroaryl, 3- to 10-membered heterocyclyl, C$_{6-10}$ aryl C$_{1-4}$ alkyl, 3- to 10-membered heterocyclyl C$_{1-3}$ alkyl, 5- to 10-membered heteroaryl C$_{1-3}$ alkyl, cyano(C$_{1-3}$ alkyl), C$_{1-3}$ alkylsulfonyl C$_{1-4}$ alkyl, or 3- to 10-membered alicyclic ring.

Alternatively, R$_{26}$ and R$_{27}$ shown above can preferably be taken together with the nitrogen atoms to which they are attached to form 3- to 10-membered heterocyclyl or 5- to 10-membered heteroaryl.

R$_{28}$ and R$_{29}$ shown above preferably may be the same or different, and each represents hydrogen, C$_{1-4}$ alkyl, C$_{2-6}$ alkenyl, C$_{2-6}$ alkynyl, C$_{1-4}$ haloalkyl, C$_{1-3}$ alkoxy C$_{1-4}$ alkyl, C$_{6-10}$ aryl, 5- to 10-membered heteroaryl, 3- to 10-membered heterocyclyl, C$_{6-10}$ aryl C$_{1-4}$ alkyl, 3- to 10-membered heterocyclyl C$_{1-3}$ alkyl, 5- to 10-membered heteroaryl C$_{1-3}$ alkyl, cyano(C$_{1-3}$ alkyl), C$_{1-3}$ alkylsulfonyl C$_{1-4}$ alkyl, or 3- to 10-membered alicyclic ring.

Alternatively, R$_{28}$ and R$_{29}$ shown above preferably can be taken together with the nitrogen atoms to which they are attached to form 3- to 10-membered heterocyclyl or 5- to 10-membered heteroaryl.

R$_{30}$ shown above preferably represents C$_{1-4}$ alkyl, C$_{3-7}$ cycloalkyl, C$_{1-4}$ haloalkyl, C$_{6-10}$ aryl, 5- to 10-membered heteroaryl, or 3- to 10-membered heterocyclyl.

R$_{31}$ shown above preferably represents C$_{1-4}$ alkyl, C$_{3-7}$ cycloalkyl, C$_{1-4}$ haloalkyl, C$_{6-10}$ aryl, 5- to 10-membered heteroaryl, or 3- to 10-membered heterocyclyl.

R$_{32}$ shown above preferably represents C$_{1-4}$ alkyl, or C$_{6-10}$ aryl.

Preferred substituents included in group P defined above are halogen, C$_{1-4}$ alkyl, C$_{1-4}$ haloalkyl, —OH, C$_{1-3}$ alkoxy, C$_{1-3}$ haloalkoxy, 3- to 10-membered heterocyclylamino, —SO$_2$R, —CN, —NO$_2$, and 3- to 10-membered heterocyclyl; and more preferably halogen, C$_{1-4}$ haloalkyl, C$_{1-3}$ alkoxy, C$_{1-3}$ haloalkoxy, and 3- to 10-membered heterocyclyl. Specifically, this 3- to 10-membered heterocyclyl is particularly preferably a morpholinyl group.

Preferred substituents included in group Q defined above are halogen, C$_{1-4}$ alkyl, C$_{1-4}$ haloalkyl, —OH, C$_{1-3}$ alkoxy, C$_{1-6}$ monohydroxyalkyl, C$_{1-6}$ dihydroxyalkyl, C$_{1-6}$ trihydroxyalkyl, 3- to 10-membered heterocyclylamino, —SO$_2$R, —CN, —NO$_2$, C$_{3-7}$ cycloalkyl, and —COR$_{19}$, and 3- to 10-membered heterocyclyl which is optionally substituted with C$_{1-4}$ alkyl; and more preferably halogen, C$_{1-4}$ alkyl, C$_{1-4}$ haloalkyl, —OH, C$_{1-3}$ alkoxy, C$_{1-6}$ monohydroxyalkyl, —SO$_2$R$_{16}$, C$_{3-7}$ cycloalkyl, —COR$_{19}$, and 3- to 10-membered heterocyclyl which is optionally substituted with C$_{1-4}$ alkyl. Specifically, this 3- to 10-membered heterocyclyl is more preferably a piperazinyl group, piperidinyl group, or morpholinyl group.

Specific examples of the compounds include:
(1) [5-amino-1-(2-methyl-1H-benzimidazol-5-yl)-1H-pyrazol-4-yl]-(1H-indol-2-yl)-methanone;
(2) [5-amino-1-(2-methyl-1H-benzimidazol-5-yl)-1H-pyrazol-4-yl]-(6-pyrrolidin-1-ylmethyl-1H-indol-2-yl)-methanone;
(3) [5-amino-1-(2-methyl-1H-benzimidazol-5-yl)-1H-pyrazol-4-yl]-[6-(4-hydroxy-piperidin-1-ylmethyl)-1H-indol-2-yl]-methanone;
(4) [5-amino-1-(2-methyl-1H-benzimidazol-5-yl)-1H-pyrazol-4-yl]-(1H-pyrrolo[3,2-c]pyridin-2-yl)-methanone;
(5) [5-amino-1-(2-methyl-1H-benzimidazol-5-yl)-1H-pyrazol-4-yl]-(6-piperazin-1-ylmethyl-1H-indol-2-yl)-methanone;
(6) [5-amino-1-(2-methyl-1H-benzimidazol-5-yl)-1H-pyrazol-4-yl]-[6-(2-morpholin-4-yl-ethoxy)-1H-indol-2-yl]-methanone;
(7) [5-amino-1-(2-methyl-1H-benzimidazol-5-yl)-1H-pyrazol-4-yl]-[6-(tetrahydro-pyran-4-yloxy)-1H-indol-2-yl]-methanone;
(8) [5-amino-1-(2-methyl-1H-benzimidazol-5-yl)-1H-pyrazol-4-yl]-[4-chloro-1H-indol-2-yl]-methanone;
(9) [5-amino-1-(2-methyl-1H-benzimidazol-5-yl)-1H-pyrazol-4-yl]-(5-bromo-1H-indol-2-yl)-methanone;
(10) [5-amino-1-(2-methyl-1H-benzimidazol-5-yl)-1H-pyrazol-4-yl]-(4-iodo-1H-indol-2-yl)-methanone;
(11) 2-[5-amino-1-(2-methyl-1H-benzimidazol-5-yl)-1H-pyrazole-4-carbonyl]-1H-indole-5-carbonitrile;
(12) [5-amino-1-(2-methyl-1H-benzimidazol-5-yl)-1H-pyrazol-4-yl]-[6-bromo-5-fluoro-1H-indol-2-yl]-methanone;
(13) [5-amino-1-(2-methyl-1H-benzimidazol-5-yl)-1H-pyrazol-4-yl]-(5-ethynyl-1H-indol-2-yl)-methanone;
(14) [5-amino-1-(2-methyl-1H-benzimidazol-5-yl)-1H-pyrazol-4-yl]-[6-(2-fluoro-phenyl)-1H-indol-2-yl]-methanone;
(15) [5-amino-1-(2-methyl-1H-benzimidazol-5-yl)-1H-pyrazol-4-yl]-[6-(3-fluoro-phenyl)-1H-indol-2-yl]-methanone;
(16) [5-amino-1-(2-methyl-1H-benzimidazol-5-yl)-1H-pyrazol-4-yl]-[6-(4-fluoro-phenyl)-1H-indol-2-yl]-methanone;
(17) [5-amino-1-(2-methyl-1H-benzimidazol-5-yl)-1H-pyrazol-4-yl]-[6-(2-chloro-phenyl)-1H-indol-2-yl]-methanone;
(18) [5-amino-1-(2-methyl-1H-benzimidazol-5-yl)-1H-pyrazol-4-yl]-[6-(3-chloro-phenyl)-1H-indol-2-yl]-methanone;
(19) [5-amino-1-(2-methyl-1H-benzimidazol-5-yl)-1H-pyrazol-4-yl]-[6-(4-chloro-phenyl)-1H-indol-2-yl]-methanone;
(20) [5-amino-1-(2-methyl-1H-benzimidazol-5-yl)-1H-pyrazol-4-yl]-[6-(2-trifluoromethyl-phenyl)-1H-indol-2-yl]-methanone;
(21) [5-amino-1-(2-methyl-1H-benzimidazol-5-yl)-1H-pyrazol-4-yl]-[6-(3-trifluoromethyl-phenyl)-1H-indol-2-yl]-methanone;
(22) [5-amino-1-(2-methyl-1H-benzimidazol-5-yl)-1H-pyrazol-4-yl]-[6-(4-trifluoromethyl-phenyl)-1H-indol-2-yl]-methanone;
(23) [5-amino-1-(2-methyl-1H-benzimidazol-5-yl)-1H-pyrazol-4-yl]-(4-bromo-1H-indol-2-yl)-methanone;
(24) [5-amino-1-(2-methyl-1H-benzimidazol-5-yl)-1H-pyrazol-4-yl]-[6-(3-fluoro-pyridin-2-yl)-1H-indol-2-yl]-methanone;
(25) [5-amino-1-(2-methyl-1H-benzimidazol-5-yl)-1H-pyrazol-4-yl]-(6-methyl-1H-indol-2-yl)-methanone;
(26) [5-amino-1-(2-methyl-1H-benzimidazol-5-yl)-1H-pyrazol-4-yl]-[5-(4,4-difluoro-piperidine-1-carbonyl)-1H-indol-2-yl]-methanone;
(27) [5-amino-1-(2-methyl-1H-benzimidazol-5-yl)-1H-pyrazol-4-yl]-[5-(3,3-difluoro-piperidine-1-carbonyl)-1H-indol-2-yl]-methanone;
(28) 2-[5-amino-1-(2-methyl-1H-benzimidazol-5-yl)-1H-pyrazole-4-carbonyl]-1H-indole-5-carboxylic acid (2,2,2-trifluoro-ethyl)-amide;
(29) [5-amino-1-(2-methyl-1H-benzimidazol-5-yl)-1H-pyrazol-4-yl]-[6-(5-trifluoromethyl-pyridin-2-yl)-1H-indol-2-yl]-methanone;

(30) [5-amino-1-(2-methyl-1H-benzimidazol-5-yl)-1H-pyrazol-4-yl]-[6-(6-trifluoromethyl-pyridin-2-yl)-1H-indol-2-yl]-methanone;
(31) [5-amino-1-(2-methyl-1H-benzimidazol-5-yl)-1H-pyrazol-4-yl]-[6-(5-chloro-pyridin-2-yl)-1H-indol-2-yl]-methanone;
(32) [5-amino-1-(2-methyl-1H-benzimidazol-5-yl)-1H-pyrazol-4-yl]-[6-(4-methyl-pyridin-2-yl)-1H-indol-2-yl]methanone;
(33) [5-amino-1-(2-methyl-1H-benzimidazol-5-yl)-1H-pyrazol-4-yl]-[6-(3-chloro-4-fluoro-phenyl)-1H-indol-2-yl]-methanone;
(34) [5-amino-1-(2-methyl-1H-benzimidazol-5-yl)-1H-pyrazol-4-yl]-[6-(3-trifluoromethyl-pyridin-2-yl)-1H-indol-2-yl]-methanone;
(35) [5-amino-1-(2-methyl-1H-benzimidazol-5-yl)-1H-pyrazol-4-yl]-[6-(4-trifluoromethyl-pyridin-2-yl)-1H-indol-2-yl]methanone;
(36) [5-amino-1-(6-fluoro-2-methyl-1H-benzimidazol-5-yl)-1H-pyrazol-4-yl]-(1H-indol-2-yl)-methanone;
(37) 2-[5-amino-1-(2-methyl-1H-benzimidazol-5-yl)-1H-pyrazole-4-carbonyl]-1H-indole-6-carboxylic acid;
(38) [5-amino-1-(2-methyl-1H-benzimidazol-5-yl)-1H-pyrazol-4-yl]-(6-hydroxymethyl-1H-indol-2-yl)-methanone;
(39) [5-amino-1-(2-methyl-1H-benzimidazol-5-yl)-1H-pyrazol-4-yl]-{6-[2-(4-methyl-piperazin-1-yl)-ethoxy]-1H-indol-2-yl}-methanone;
(40) [5-amino-1-(2-methyl-1H-benzimidazol-5-yl)-1H-pyrazol-4-yl]-[6-(3-methyl-oxetan-3-ylmethoxy)-1H-indol-2-yl]-methanone;
(41) [5-amino-1-(2-methyl-1H-benzimidazol-5-yl)-1H-pyrazol-4-yl]-[6-(3-fluoro-piperidin-1-ylmethyl)-1H-indol-2-yl]-methanone;
(42) [5-amino-1-(2-methyl-1H-benzimidazol-5-yl)-1H-pyrazol-4-yl]-(6-{[bis(2-methoxy-ethyl)-amino]-methyl}-1H-indol-2-yl)-methanone;
(43) [5-amino-1-(2-methyl-1H-benzimidazol-5-yl)-1H-pyrazol-4-yl]-{6-[(methyl-prop-2-ynyl-amino)-methyl]-1H-indol-2-yl}-methanone;
(44) [5-amino-1-(2-methyl-1H-benzimidazol-5-yl)-1H-pyrazol-4-yl]-[6-(3,3-difluoro-pyrrolidin-1-ylmethyl)-1H-indol-2-yl]-methanone;
(45) [5-amino-1-(2-methyl-1H-benzimidazol-5-yl)-1H-pyrazol-4-yl]-[6-(2,5-dimethyl-pyrrolidin-1-ylmethyl)-1H-indol-2-yl]-methanone;
(46) [5-amino-1-(2-methyl-1H-benzimidazol-5-yl)-1H-pyrazol-4-yl]-[6-(3,3-difluoro-piperidin-1-ylmethyl)-1H-indol-2-yl]-methanone;
(47) [5-amino-1-(2-methyl-1H-benzimidazol-5-yl)-1H-pyrazol-4-yl]-[6-((S)-3-methyl-morpholin-4-ylmethyl)-1H-indol-2-yl]-methanone;
(48) [5-amino-1-(2-methyl-1H-benzimidazol-5-yl)-1H-pyrazol-4-yl]-(6-bromo-1H-indol-2-yl)-methanone;
(49) [5-amino-1-(2-methyl-1H-benzimidazol-5-yl)-1H-pyrazol-4-yl]-(5-iodo-1H-indol-2-yl)-methanone;
(50) [5-amino-1-(2-methyl-1H-benzimidazol-5-yl)-1H-pyrazol-4-yl]-(1H-pyrrolo[3,2-b]pyridin-2-yl)-methanone;
(51) [5-amino-1-(2-methyl-1H-benzimidazol-5-yl)-1H-pyrazol-4-yl]-(5-bromo-6-trifluoromethyl-1H-indol-2-yl)-methanone;
(52) [5-amino-1-(2-methyl-1H-benzimidazol-5-yl)-1H-pyrazol-4-yl]-(6-iodo-1H-indol-2-yl)-methanone;
(53) [5-amino-1-(2-methyl-1H-benzimidazol-5-yl)-1H-pyrazol-4-yl]-(4-methyl-1H-indol-2-yl)-methanone;
(54) [5-amino-1-(2-methyl-1H-benzimidazol-5-yl)-1H-pyrazol-4-yl]-(4-isopropyl-1H-indol-2-yl)-methanone;
(55) [5-amino-1-(2-methyl-1H-benzimidazol-5-yl)-1H-pyrazol-4-yl]-[5-(2-fluoro-phenyl)-1H-indol-2-yl]-methanone;
(56) [5-amino-1-(2-methyl-1H-benzimidazol-5-yl)-1H-pyrazol-4-yl]-(5-benzyl-1H-indol-2-yl)-methanone;
(57) [5-amino-1-(2-methyl-1H-benzimidazol-5-yl)-1H-pyrazol-4-yl]-[5-(2-trifluoromethyl-phenyl)-1H-indol-2-yl]-methanone;
(58) [5-amino-1-(2-methyl-1H-benzimidazol-5-yl)-1H-pyrazol-4-yl]-[5-(3-fluorophenyl)-1H-indol-2-yl]-methanone;
(59) [5-amino-1-(2-methyl-1H-benzimidazol-5-yl)-1H-pyrazol-4-yl]-[5-(3-trifluoromethyl-phenyl)-1H-indol-2-yl]-methanone;
(60) [5-amino-1-(2-methyl-1H-benzimidazol-5-yl)-1H-pyrazol-4-yl]-(4-ethynyl-1H-indol-2-yl)-methanone;
(61) [5-amino-1-(2-methyl-1H-benzimidazol-5-yl)-1H-pyrazol-4-yl]-(5H-[1,3]dioxolo[4,5-f]indol-6-yl)-methanone;
(62) [5-amino-1-(7-fluoro-2-methyl-1H-benzimidazol-5-yl)-1H-pyrazol-4-yl]-(1H-indol-2-yl)-methanone;
(63) [5-amino-1-(2-methyl-1H-benzimidazol-5-yl)-1H-pyrazol-4-yl]-[5-(4-trifluoromethyl-phenyl)-1H-indol-2-yl]-methanone;
(64) [5-amino-1-(2-methyl-1H-benzimidazol-5-yl)-1H-pyrazol-4-yl]-(5-butoxy-1H-indol-2-yl)-methanone;
(65) [5-amino-1-(2-methyl-1H-benzimidazol-5-yl)-1H-pyrazol-4-yl]-[5-(1-methyl-piperidin-4-yl)-1H-indol-2-yl]methanone;
(66) N-{2-[5-amino-1-(2-methyl-1H-benzimidazol-5-yl)-1H-pyrazole-4-carbonyl]-1H-indol-6-yl}-methanesulfonamide;
(67) [5-amino-1-(2-methyl-1H-benzimidazol-5-yl)-1H-pyrazol-4-yl]-[6-(6-morpholin-4-yl-pyridin-3-yl)-1H-indol-2-yl]-methanone;
(68) [5-amino-1-(2-methyl-1H-benzimidazol-5-yl)-1H-pyrazol-4-yl]-(6-butyl-1H-indol-2-yl)-methanone;
(69) [5-amino-1-(2-methyl-1H-benzimidazol-5-yl)-1H-pyrazol-4-yl]-[6-(1-methyl-1H-pyrazol-4-yl)-1H-indol-2-yl]-methanone;
(70) [5-amino-1-(2-methyl-1H-benzimidazol-5-yl)-1H-pyrazol-4-yl]-[6-(5-methoxy-pyridin-3-yl)-1H-indol-2-yl]-methanone;
(71) [5-amino-1-(2-methyl-1H-benzimidazol-5-yl)-1H-pyrazol-4-yl]-[6-(2-methoxy-pyridin-3-yl)-1H-indol-2-yl]-methanone;
(72) [5-amino-1-(2-methyl-1H-benzimidazol-5-yl)-1H-pyrazol-4-yl]-(6-cyclopropyl-1H-indol-2-yl)-methanone;
(73) [5-amino-1-(2-methyl-1H-benzimidazol-5-yl)-1H-pyrazol-4-yl]-[6-(2-methoxy-phenyl)-1H-indol-2-yl]-methanone;
(74) [5-amino-1-(2-methyl-1H-benzimidazol-5-yl)-1H-pyrazol-4-yl]-(6-phenyl-1H-indol-2-yl)-methanone;
(75) [5-amino-1-(2-methyl-1H-benzimidazol-5-yl)-1H-pyrazol-4-yl]-[6-(5-methanesulfonyl-pyridin-3-yl)-1H-indol-2-yl]-methanone;
(76) [5-amino-1-(2-methyl-1H-benzimidazol-5-yl)-1H-pyrazol-4-yl]-(6-isopropyl-1H-indol-2-yl)-methanone;
(77) [5-amino-1-(2-methyl-1H-benzimidazol-5-yl)-1H-pyrazol-4-yl]-(6-pyridin-2-yl-1H-indol-2-yl)-methanone;
(78) [5-amino-1-(2-methyl-1H-benzimidazol-5-yl)-1H-pyrazol-4-yl]-(5-cyclopropyl-1H-indol-2-yl)-methanone;
(79) [5-amino-1-(2-methyl-1H-benzimidazol-5-yl)-1H-pyrazol-4-yl]-(6-pyridazin-3-yl-1H-indol-2-yl)-methanone;

(80) [5-amino-1-(2-methyl-1H-benzimidazol-5-yl)-1H-pyrazol-4-yl]-(5-isopropoxy-1H-indol-2-yl)-methanone;
(81) [5-amino-1-(2-methyl-1H-benzimidazol-5-yl)-1H-pyrazol-4-yl]-[5-(2-methoxy-ethoxy)-1H-indol-2-yl]-methanone;
(82) [5-amino-1-(2-methyl-1H-benzimidazol-5-yl)-1H-pyrazol-4-yl]-(5-cyclopropylmethoxy-1H-indol-2-yl)-methanone;
(83) [5-amino-1-(2-methyl-1H-benzimidazol-5-yl)-1H-pyrazol-4-yl]-(2,2-difluoro-5H-[1,3]dioxolo[4,5-f]indol-6-yl)-methanone;
(84) [5-amino-1-(2-methyl-1H-benzimidazol-5-yl)-1H-pyrazol-4-yl]-[6-(3-chloro-pyridin-2-yl)-1H-indol-2-yl]-methanone;
(85) [5-amino-1-(2-methyl-1H-benzimidazol-5-yl)-1H-pyrazol-4-yl]-[6-(5-fluoro-pyridin-2-yl)-1H-indol-2-yl]-methanone;
(86) [5-amino-1-(2-methyl-1H-benzimidazol-5-yl)-1H-pyrazol-4-yl]-[6-(6-morpholin-4-yl-pyridazin-3-yl)-1H-indol-2-yl]-methanone;
(87) [5-amino-1-(2-methyl-1H-benzimidazol-5-yl)-1H-pyrazol-4-yl]-(5-chloro-6-cyclopropylmethoxy-1H-indol-2-yl)-methanone;
(88) [5-amino-1-(2-methyl-1H-benzimidazol-5-yl)-1H-pyrazol-4-yl]-[6-(2,4-difluoro-phenyl)-1H-indol-2-yl]-methanone;
(89) [5-amino-1-(2-methyl-1H-benzimidazol-5-yl)-1H-pyrazol-4-yl]-(6-pyridazin-4-yl-1H-indol-2-yl)-methanone;
(90) [5-amino-1-(2-methyl-1H-benzimidazol-5-yl)-1H-pyrazol-4-yl]-(3-fluoro-1H-indol-2-yl)-methanone;
(91) [5-amino-1-(2-methyl-1H-benzimidazol-5-yl)-1H-pyrazol-4-yl]-[5-(1-isopropyl-piperidin-4-yl)-6-trifluoromethyl-1H-indol-2-yl]-methanone;
(92) 2-[5-amino-1-(2-methyl-1H-benzimidazol-5-yl)-1H-pyrazole-4-carbonyl]-1H-indole-6-carbonitrile;
(93) [5-amino-1-(2-methyl-1H-benzimidazol-5-yl)-1H-pyrazol-4-yl]-[5-(1,2,3,6-tetrahydro-pyridin-4-yl)-1H-indol-2-yl]-methanone,
(94) [5-amino-1-(2-methyl-1H-benzimidazol-5-yl)-1H-pyrazol-4-yl]-(5-piperidin-4-yl-1H-indol-2-yl)-methanone;
(95) [5-amino-1-(2-methyl-1H-benzimidazol-5-yl)-1H-pyrazol-4-yl]-[5-((R)-3-fluoro-pyrrolidin-1-ylmethyl)-1H-indol-2-yl]-methanone;
(96) [5-amino-1-(2-methyl-1H-benzimidazol-5-yl)-1H-pyrazol-4-yl]-(6-fluoro-5-piperidin-4-yl-1H-indol-2-yl)-methanone;
(97) [5-amino-1-(2-methyl-1H-benzimidazol-5-yl)-1H-pyrazol-4-yl]-[6-fluoro-5-(1-methyl-piperidin-4-yl)-1H-indol-2-yl]-methanone;
(98) [5-amino-1-(2-methyl-1H-benzimidazol-5-yl)-1H-pyrazol-4-yl]-[5-(1-isopropyl-piperidin-4-yl)-1H-indol-2-yl]-methanone;
(99) [5-amino-1-(2-methyl-1H-benzimidazol-5-yl)-1H-pyrazol-4-yl]-[6-fluoro-5-(1-isopropyl-piperidin-4-yl)-1H-indol-2-yl]-methanone;
(100) [5-amino-1-(2-methyl-1H-benzimidazol-5-yl)-1H-pyrazol-4-yl]-(6-pyridin-3-yl-1H-indol-2-yl)-methanone;
(101) [5-amino-1-(2-methyl-1H-benzimidazol-5-yl)-1H-pyrazol-4-yl]-[5-(6-morpholin-4-yl-pyridin-3-yl)-1H-indol-2-yl]-methanone;
(102) [5-amino-1-(2-methyl-1H-benzimidazol-5-yl)-1H-pyrazol-4-yl]-(5-pyridin-3-yl-1H-indol-2-yl)-methanone;
(103) [5-amino-1-(2-methyl-1H-benzimidazol-5-yl)-1H-pyrazol-4-yl]-[5-(6-piperazin-1-yl-pyridin-3-yl)-1H-indol-2-yl]-methanone;
(104) [5-amino-1-(2-methyl-1H-benzimidazol-5-yl)-1H-pyrazol-4-yl]-[5-(6-hydroxy-pyridin-3-yl)-1H-indol-2-yl]-methanone;
(105) [5-amino-1-(2-methyl-1H-benzimidazol-5-yl)-1H-pyrazol-4-yl]-[6-fluoro-5-(4-methyl-piperazin-1-ylmethyl)-1H-indol-2-yl]-methanone;
(106) [5-amino-1-(2-methyl-1H-benzimidazol-5-yl)-1H-pyrazol-4-yl]-(6-fluoro-5-pyrrolidin-1-ylmethyl-1H-indol-2-yl)-methanone;
(107) [5-amino-1-(2-methyl-1H-benzimidazol-5-yl)-1H-pyrazol-4-yl]-[6-(1-methyl-piperidin-4-yl)-1H-indol-2-yl]-methanone;
(108) [5-amino-1-(2-methyl-1H-benzimidazol-5-yl)-1H-pyrazol-4-yl]-[6-(4-morpholin-4-yl-phenyl)-1H-indol-2-yl]-methanone;
(109) [5-amino-1-(2-methyl-1H-benzimidazol-5-yl)-1H-pyrazol-4-yl]-[6-(3,4,5,6-tetrahydro-2H-[1,2']b]pyridin-5'-yl)-1H-indol-2-yl]-methanone;
(110) [5-amino-1-(2-methyl-1H-benzimidazol-5-yl)-1H-pyrazol-4-yl]-[6-(6-piperazin-1-yl-pyridin-3-yl)-1H-indol-2-yl]-methanone;
(111) [5-amino-1-(2-methyl-1H-benzimidazol-5-yl)-1H-pyrazol-4-yl]-[5-(6-methoxy-pyridin-3-yl)-1H-indol-2-yl]-methanone;
(112) [5-amino-1-(2-methyl-1H-benzimidazol-5-yl)-1H-pyrazol-4-yl]-[5-((S)-3-methyl-morpholin-4-ylmethyl)-1H-indol-2-yl]-methanone;
(113) [5-amino-1-(2-methyl-1H-benzimidazol-5-yl)-1H-pyrazol-4-yl]-[6-((R)-3-fluoro-pyrrolidin-1-ylmethyl)-1H-indol-2-yl]-methanone;
(114) [5-amino-1-(2-methyl-1H-benzimidazol-5-yl)-1H-pyrazol-4-yl]-[5-(2,5-dimethyl-pyrrolidin-1-ylmethyl)-1H-indol-2-yl]-methanone;
(115) [5-amino-1-(2-methyl-1H-benzimidazol-5-yl)-1H-pyrazol-4-yl]-[5-(3-fluoro-piperidin-1-ylmethyl)-1H-indol-2-yl]-methanone;
(116) [5-amino-1-(2-methyl-1H-benzimidazol-5-yl)-1H-pyrazol-4-yl]-[5-(3,3-difluoro-piperidin-1-ylmethyl)-1H-indol-2-yl]-methanone;
(117) [5-amino-1-(2-methyl-1H-benzimidazol-5-yl)-1H-pyrazol-4-yl]-{6-[2-(4-methyl-piperazin-1-yl)pyridin-4-yl]-1H-indol-2-yl}-methanone;
(118) [5-amino-1-(2-methyl-1H-benzimidazol-5-yl)-1H-pyrazol-4-yl]-(6-pyridin-4-yl-1H-indol-2-yl)-methanone;
(119) [5-amino-1-(2-methyl-1H-benzimidazol-5-yl)-1H-pyrazol-4-yl]-[5-(4-fluoropiperidin-1-ylmethyl)-1H-indol-2-yl]-methanone;
(120) [5-amino-1-(2-methyl-1H-benzimidazol-5-yl)-1H-pyrazol-4-yl]-[5-(4,4-difluoro-piperidin-1-ylmethyl)-1H-indol-2-yl]-methanone;
(121) [5-amino-1-(2-difluoromethyl-1H-benzimidazol-5-yl)-1H-pyrazol-4-yl]-[5-(1-methyl-piperidin-4-yl)-1H-indol-2-yl]-methanone;
(122) [5-amino-1-(2-difluoromethyl-1H-benzimidazol-5-yl)-1H-pyrazol-4-yl]-(1H-indol-2-yl)-methanone;
(123) [5-amino-1-(2-methyl-1H-benzimidazol-5-yl)-1H-pyrazol-4-yl]-[5-(3,3-difluoro-pyrrolidin-1-ylmethyl)-1H-indol-2-yl]-methanone;
(124) [5-amino-1-(2-methyl-1H-benzimidazol-5-yl)-1H-pyrazol-4-yl]-[5-(1-cyclopentyl-piperidin-4-yl)-1H-indol-2-yl]-methanone;
(125) [5-amino-1-(2-methyl-1H-benzimidazol-5-yl)-1H-pyrazol-4-yl]-[5-(1-cyclohexyl-piperidin-4-yl)-1H-indol-2-yl]-methanone;
(126) [5-amino-1-(2-methyl-1H-benzimidazol-5-yl)-1H-pyrazol-4-yl]-(4-bromo-1H-pyrrol-2-yl)-methanone;

(127) [5-amino-1-(2-methyl-1H-benzimidazol-5-yl)-1H-pyrazol-4-yl]-(1H-pyrrol-2-yl)-methanone;
(128) [5-amino-1-(2-methyl-1H-benzimidazol-5-yl)-1H-pyrazol-4-yl]-(4-phenyl-1H-pyrrol-2-yl)-methanone;
(129) [5-amino-1-(2-methyl-1H-benzimidazol-5-yl)-1H-pyrazol-4-yl]-[4-(3-chloro-phenyl)-1H-pyrrol-2-yl]-methanone;
(130) [5-amino-1-(2-methyl-1H-benzimidazol-5-yl)-1H-pyrazol-4-yl]-[4-(4-fluoro-phenyl)-1H-pyrrol-2-yl]-methanone;
(131) [5-amino-1-(2-methyl-1H-benzimidazol-5-yl)-1H-pyrazol-4-yl]-[4-(3-fluoro-phenyl)-1H-pyrrol-2-yl]-methanone;
(132) [5-amino-1-(2-methyl-1H-benzimidazol-5-yl)-1H-pyrazol-4-yl]-(6-morpholin-4-ylmethyl-1H-indol-2-yl)-methanone;
(133) [5-amino-1-(2-methyl-1H-benzimidazol-5-yl)-1H-pyrazol-4-yl]-[4-(2-morpholin-4-yl-ethylamino)-1H-indol-2-yl]-methanone;
(134) [5-amino-1-(2-methyl-1H-benzimidazol-5-yl)-1H-pyrazol-4-yl]-[5-(4-methyl-piperazine-1-carbonyl)-1H-indol-2-yl]-methanone;
(135) [5-amino-1-(2-methyl-1H-benzimidazol-5-yl)-1H-pyrazol-4-yl]-[6-(2-morpholin-4-yl-ethylamino)-1H-indol-2-yl]-methanone;
(136) [5-amino-1-(2-methyl-1H-benzimidazol-5-yl)-1H-pyrazol-4-yl]-[5-(piperazine-1-carbonyl)-1H-indol-2-yl]-methanone;
(137) [5-amino-1-(2-methyl-1H-benzimidazol-5-yl)-1H-pyrazol-4-yl]-[4-(2-methoxy-ethylamino)-1H-indol-2-yl]-methanone;
(138) [5-amino-1-(2-methyl-1H-benzimidazol-5-yl)-1H-pyrazol-4-yl]-[4-(2-hydroxy-1-hydroxymethyl-ethylamino)-1H-indol-2-yl]-methanone;
(139) [5-amino-1-(2-methyl-1H-benzimidazol-5-yl)-1H-pyrazol-4-yl]-[4-(2-pyridin-4-yl-ethylamino)-1H-indol-2-yl]-methanone;
(140) [5-amino-1-(2-methyl-1H-benzimidazol-5-yl)-1H-pyrazol-4-yl]-[6-(2-methoxy-ethylamino)-1H-indol-2-yl]-methanone;
(141) [5-amino-1-(2-methyl-1H-benzimidazol-5-yl)-1H-pyrazol-4-yl]-(6-morpholin-4-yl-1H-indol-2-yl)-methanone;
(142) [5-amino-1-(2-methyl-1H-benzimidazol-5-yl)-1H-pyrazol-4-yl]-(4-morpholin-4-yl-1H-indol-2-yl)-methanone;
(143) [5-amino-1-(2-methyl-1H-benzimidazol-5-yl)-1H-pyrazol-4-yl]-(4-morpholin-4-ylmethyl-1H-indol-2-yl)-methanone;
(144) [5-amino-1-(2-methyl-1H-benzimidazol-5-yl)-1H-pyrazol-4-yl]-(5-morpholin-4-ylmethyl-1H-indol-2-yl)-methanone;
(145) [5-amino-1-(2-methyl-1H-benzimidazol-5-yl)-1H-pyrazol-4-yl]-[5-(morpholine-4-carbonyl)-1H-indol-2-yl]-methanone;
(146) [5-amino-1-(2-isopropyl-1H-benzimidazol-5-yl)-1H-pyrazol-4-yl]-(1H-indol-2-yl)-methanone;
(147) [5-amino-1-(2-propyl-1H-benzimidazol-5-yl)-1H-pyrazol-4-yl]-(1H-indol-2-yl)-methanone;
(148) [5-amino-1-(1H-benzimidazol-5-yl)-1H-pyrazol-4-yl]-(1H-indol-2-yl)-methanone;
(149) [5-amino-1-(2-trifluoromethyl-1H-benzimidazol-5-yl)-1H-pyrazol-4-yl]-(1H-indol-2-yl)-methanone;
(150) [5-amino-1-(2-ethyl-1H-benzimidazol-5-yl)-1H-pyrazol-4-yl]-(1H-indol-2-yl)-methanone;
(151) [5-amino-1-(2-benzyl-1H-benzimidazol-5-yl)-1H-pyrazol-4-yl]-(1H-indol-2-yl)methanone;
(152) 1-(4-{2-[5-amino-1-(2-methyl-1H-benzimidazol-5-yl)-1H-pyrazole-4-carbonyl]-1H-indol-5-ylmethyl}-piperazin-1-yl)-ethanone;
(153) [5-amino-1-(2-methyl-1H-benzimidazol-5-yl)-1H-pyrazol-4-yl]-[5-(4-methanesulfonyl-piperazin-1-ylmethyl)-1H-indol-2-yl]-methanone;
(154) [5-amino-1-(2-methyl-1H-benzimidazol-5-yl)-1H-pyrazol-4-yl]-(5-piperazin-1-ylmethyl-1H-indol-2-yl)-methanone;
(155) 1-(4-{2-[5-amino-1-(2-methyl-1H-benzimidazol-5-yl)-1H-pyrazole-4-carbonyl]-1H-indol-6-ylmethyl}-piperazin-1-yl)-ethanone;
(156) [5-amino-1-(2-methyl-1H-benzimidazol-5-yl)-1H-pyrazol-4-yl]-[6-(4-methyl-piperazin-1-ylmethyl)-1H-indol-2-yl]-methanone;
(157) [5-amino-1-(2-methyl-1H-benzimidazol-5-yl)-1H-pyrazol-4-yl]-[5-(4-methyl-piperazin-1-ylmethyl)-1H-indol-2-yl]-methanone;
(158) [5-amino-1-(2-methyl-1H-benzimidazol-5-yl)-1H-pyrazol-4-yl]-[4-(5-pyrrolidin-1-ylmethyl-1H-indol-2-yl)-methanone;
(159) [5-amino-1-(2-methyl-1H-benzimidazol-5-yl)-1H-pyrazol-4-yl]-(4-fluoro-1H-indol-2-yl)-methanone;
(160) [5-amino-1-(2-methyl-1H-benzimidazol-5-yl)-1H-pyrazol-4-yl]-(5-fluoro-1H-indol-2-yl)-methanone;
(161) [5-amino-1-(2-methyl-1H-benzimidazol-5-yl)-1H-pyrazol-4-yl]-(6-fluoro-1H-indol-2-yl)-methanone;
(162) [5-amino-1-(2-methyl-1H-benzimidazol-5-yl)-1H-pyrazol-4-yl]-(1H-pyrrolo[2,3-b]pyridin-2-yl)-methanone;
(163) [5-amino-1-(2-methyl-1H-benzimidazol-5-yl)-1H-pyrazol-4-yl]-(5-fluoro-6-morpholin-4-ylmethyl-1H-indol-2-yl)-methanone;
(164) 2-[5-amino-1-(2-methyl-1H-benzimidazol-5-yl)-1H-pyrazole-4-carbonyl]-1H-indole-5-carboxylic acid;
(165) [5-amino-1-(2-methyl-1H-benzimidazol-5-yl)-1H-pyrazol-4-yl]-(5-methoxy-1H-indol-2-yl)-methanone;
(166) [5-amino-1-(2-methyl-1H-benzimidazol-5-yl)-1H-pyrazol-4-yl]-(4,6-dimethoxy-1H-indol-2-yl)-methanone;
(167) [5-amino-1-(2-methyl-1H-benzimidazol-5-yl)-1H-pyrazol-4-yl]-(4-methoxy-1H-indol-2-yl)-methanone;
(168) [5-amino-1-(2-methyl-1H-benzimidazol-5-yl)-1H-pyrazol-4-yl]-(6-methoxy-1H-indol-2-yl)-methanone;
(169) [5-amino-1-(2-methyl-1H-benzimidazol-5-yl)-1H-pyrazol-4-yl]-(4,6-dimethyl-1H-indol-2-yl)-methanone;
(170) [5-amino-1-(2-methyl-1H-benzimidazol-5-yl)-1H-pyrazol-4-yl]-(5-tert-butyl-1H-indol-2-yl)-methanone;
(171) [5-amino-1-(2-methyl-1H-benzimidazol-5-yl)-1H-pyrazol-4-yl]-(5-isopropyl-1H-indol-2-yl)-methanone;
(172) [5-amino-1-(2-methyl-1H-benzimidazol-5-yl)-1H-pyrazol-4-yl]-(5-benzyloxy-1H-indol-2-yl)-methanone;
(173) [5-amino-1-(2-methyl-1H-benzimidazol-5-yl)-1H-pyrazol-4-yl]-(4-benzyloxy-1H-indol-2-yl)-methanone;
(174) [5-amino-1-(2-methyl-1H-benzimidazol-5-yl)-1H-pyrazol-4-yl]-(5,6-dimethoxy-1H-indol-2-yl)-methanone;
(175) [5-amino-1-(2-methyl-1H-benzimidazol-5-yl)-1H-pyrazol-4-yl]-(6-tert-butyl-1H-indol-2-yl)-methanone;
(176) [5-amino-1-(2-methyl-1H-benzimidazol-5-yl)-1H-pyrazol-4-yl]-(5-fluoro-4-trifluoromethyl-1H-indol-2-yl)-methanone;
(177) [5-amino-1-(2-methyl-1H-benzimidazol-5-yl)-1H-pyrazol-4-yl]-(5-phenoxy-1H-indol-2-yl)-methanone;
(178) [5-amino-1-(2-methyl-1H-benzimidazol-5-yl)-1H-pyrazol-4-yl]-(6-methylsulfanyl-1H-indol-2-yl)-methanone;

(179) [5-amino-1-(2-methyl-1H-benzimidazol-5-yl)-1H-pyrazol-4-yl]-(4-tert-butyl-1H-indol-2-yl)-methanone;
(180) [5-amino-1-(2-methyl-1H-benzimidazol-5-yl)-1H-pyrazol-4-yl]-(5-methyl-1H-indol-2-yl)-methanone;
(181) [5-amino-1-(2-methyl-1H-benzimidazol-5-yl)-1H-pyrazol-4-yl]-(5-ethyl-1H-indol-2-yl)-methanone;
(182) [5-amino-1-(2-methyl-1H-benzimidazol-5-yl)-1H-pyrazol-4-yl]-(5-fluoro-6-trifluoromethyl-1H-indol-2-yl)-methanone;
(183) [5-amino-1-(2-methyl-1H-benzimidazol-5-yl)-1H-pyrazol-4-yl]-(6-fluoro-5-methoxy-1H-indol-2-yl)-methanone;
(184) [5-amino-1-(2-methyl-1H-benzimidazol-5-yl)-1H-pyrazol-4-yl]-(6-chloro-5-methoxy-1H-indol-2-yl)-methanone;
(185) [5-amino-1-(2-methyl-1H-benzimidazol-5-yl)-1H-pyrazol-4-yl]-(5-chloro-6-methoxy-1H-indol-2-yl)-methanone;
(186) [5-amino-1-(2-methyl-1H-benzimidazol-5-yl)-1H-pyrazol-4-yl]-(6-isopropoxy-1H-indol-2-yl)-methanone;
(187) [5-amino-1-(2-methyl-1H-benzimidazol-5-yl)-1H-pyrazol-4-yl]-(6-benzyloxy-1H-indol-2-yl)-methanone;
(188) [5-amino-1-(2-methyl-1H-benzimidazol-5-yl)-1H-pyrazol-4-yl]-(4-isopropoxy-1H-indol-2-yl)-methanone;
(189) [5-amino-1-(2-methyl-1H-benzimidazol-5-yl)-1H-pyrazol-4-yl]-(2,3-dihydro-6H-[1,4]dioxino[2,3-f]indol-7-yl)-methanone;
(190) [5-amino-1-(2-methyl-1H-benzimidazol-5-yl)-1H-pyrazol-4-yl]-(4,6-di-tert-butyl-1H-indol-2-yl)-methanone;
(191) 2-[5-amino-1-(2-methyl-1H-benzimidazol-5-yl)-1H-pyrazole-4-carbonyl]-1H-indole-4-carbonitrile;
(192) [5-amino-1-(2-methyl-1H-benzimidazol-5-yl)-1H-pyrazol-4-yl]-(5-imidazol-1-yl-1H-indol-2-yl)-methanone;
(193) [5-amino-1-(2-methyl-1H-benzimidazol-5-yl)-1H-pyrazol-4-yl]-(5-trifluoromethylsulfanyl-1H-indol-2-yl)-methanone;
(194) [5-amino-1-(2-methyl-1H-benzimidazol-5-yl)-1H-pyrazol-4-yl]-(5-methylsulfanyl-1H-indol-2-yl)-methanone;
(195) [5-amino-1-(2-methyl-1H-benzimidazol-5-yl)-1H-pyrazol-4-yl]-(5-methanesulfonyl-1H-indol-2-yl)-methanone;
(196) [5-amino-1-(2-methyl-1H-benzimidazol-5-yl)-1H-pyrazol-4-yl]-[6-(4,4-difluoro-piperidin-1-ylmethyl)-1H-indol-2-yl]-methanone;
(197) [5-amino-1-(2-methyl-1H-benzimidazol-5-yl)-1H-pyrazol-4-yl]-[6-(4-fluoro-piperidin-1-ylmethyl)-1H-indol-2-yl]-methanone;
(198) [5-amino-1-(2-methyl-1H-benzimidazol-5-yl)-1H-pyrazol-4-yl]-[6-(oxetan-3-yloxy)-1H-indol-2-yl]methanone;
(199) [5-amino-1-(2-methyl-1H-benzimidazol-5-yl)-1H-pyrazol-4-yl]-(6-hydroxy-1H-indol-2-yl)-methanone;
(200) [5-amino-1-(2-methyl-1H-benzimidazol-5-yl)-1H-pyrazol-4-yl]-(6-methanesulfonyl-1H-indol-2-yl)-methanone;
(201) [5-amino-1-(2-methyl-1H-benzimidazol-5-yl)-1H-pyrazol-4-yl]-(4,5-dibromo-1H-pyrrol-2-yl)-methanone;
(202) [5-amino-1-(2-methyl-1H-benzimidazol-5-yl)-1H-pyrazol-4-yl]-(4,5-diphenyl-1H-pyrrol-2-yl)-methanone; and
(203) [5-amino-1-(2-methyl-1H-benzimidazol-5-yl)-1H-pyrazol-4-yl]-(4,5-dipyridin-3-yl-1H-pyrrol-2-yl)-methanone.
(204) [5-amino-1-(2-methyl-3H-benzimidazol-5-yl)-1H-pyrazol-4-yl]-(6-chloro-1H-indol-2-yl)-methanone;
(205) [5-amino-1-(2-methyl-1H-benzimidazol-5-yl)-1H-pyrazol-4-yl]-(5-chloro-1H-indol-2-yl)-methanone;
(206) [5-amino-1-(2-methyl-1H-benzimidazol-5-yl)-1H-pyrazol-4-yl]-(1H-indol-3-yl)-methanone;
(207) [5-amino-1-(2-methyl-1H-benzimidazol-5-yl)-1H-pyrazol-4-yl]-(1H-indol-6-yl)-methanone;
(208) [5-amino-1-(2-methyl-1H-benzimidazol-5-yl)-1H-pyrazol-4-yl]-(5-bromo-6-fluoro-1H-indol-2-yl)-methanone;
(209) [5-amino-1-(2-ethyl-1H-benzimidazol-5-yl)-1H-pyrazol-4-yl]-(5-bromo-6-fluoro-1H-indol-2-yl)-methanone;
(210) [5-amino-1-(2-methyl-1H-benzimidazol-5-yl)-1H-pyrazol-4-yl]-(5-trifluoromethyl-1H-indol-2-yl)-methanone;
(211) [5-amino-1-(2-methyl-1H-benzimidazol-5-yl)-1H-pyrazol-4-yl]-(5-trifluoromethoxy-1H-indol-2-yl)-methanone;
(212) [5-amino-1-(2-methyl-1H-benzimidazol-5-yl)-1H-pyrazol-4-yl]-(4,6-dichloro-1H-indol-2-yl)-methanone;
(213) [5-amino-1-(2-methyl-1H-benzimidazol-5-yl)-1H-pyrazol-4-yl]-(6-bromo-4-fluoro-1H-indol-2-yl)-methanone;
(214) [5-amino-1-(2-methyl-1H-benzimidazol-5-yl)-1H-pyrazol-4-0]-(6-trifluoromethoxy-1H-indol-2-yl)-methanone;
(215) [5-amino-1-(2-ethyl-1H-benzimidazol-5-yl)-1H-pyrazol-4-yl]-(5-trifluoromethoxy-1H-indol-2-yl)-methanone;
(216) [5-amino-1-(2-ethyl-1H-benzimidazol-5-yl)-1H-pyrazol-4-yl]-(5-trifluoromethyl-1H-indol-2-yl)-methanone;
(217) [5-amino-1-(2-methyl-1H-benzimidazol-5-yl)-1H-pyrazol-4-yl]-(5,6-dichloro-1H-indol-2-yl)-methanone;
(218) [5-amino-1-(2-ethyl-1H-benzimidazol-5-yl)-1H-pyrazol-4-yl]-(6-bromo-5-fluoro-1H-indol-2-yl)-methanone;
(219) [5-amino-1-(2-methyl-1H-benzimidazol-5-yl)-1H-pyrazol-4-yl]-(4,5-dichloro-1H-indol-2-yl)-methanone;
(220) [5-amino-1-(2-methyl-1H-benzimidazol-5-yl)-1H-pyrazol-4-yl]-(4,6-difluoro-1H-indol-2-yl)-methanone;
(221) [5-amino-1-(2-methyl-1H-benzimidazol-5-yl)-1H-pyrazol-4-yl]-[6-(3-chloro-pyridin-4-yl)-1H-indol-2-yl]-methanone;
(222) [5-amino-1-(2-methyl-1H-benzimidazol-5-yl)-1H-pyrazol-4-yl]-[6-(6-methyl-pyridin-3-yl)-1H-indol-2-yl]-methanone;
(223) [5-amino-1-(2-methyl-1H-benzimidazol-5-yl)-1H-pyrazol-4-yl]-[6-(5-fluoro-pyridin-3-yl)-1H-indol-2-yl]-methanone;
(224) [5-amino-1-(2-methyl-1H-benzimidazol-5-yl)-1H-pyrazol-4-yl]-[6-(2-trifluoromethyl-pyridin-3-yl)-1H-indol-2-yl]-methanone;
(225) [5-amino-1-(2-methyl-1H-benzimidazol-5-yl)-1H-pyrazol-4-yl]-[6-(5-chloro-2-methoxy-pyridin-3-yl)-1H-indol-2-yl]-methanone;
(226) [5-amino-1-(2-methyl-1H-benzimidazol-5-yl)-1H-pyrazol-4-yl]-[6-(5-chloro-pyridin-3-yl)-1H-indol-2-yl]-methanone;
(227) [5-amino-1-(2-methyl-1H-benzimidazol-5-yl)-1H-pyrazol-4-yl]-(6-thiophen-3-yl-1H-indol-2-yl)-methanone;
(228) [5-amino-1-(2-methyl-1H-benzimidazol-5-yl)-1H-pyrazol-4-yl]-[6-(4-chloropyridin-3-yl)-1H-indol-2-yl]-methanone;
(229) [5-amino-1-(2-methyl-1H-benzimidazol-5-yl)-1H-pyrazol-4-yl]-(6-thiophen-2-yl-1H-indol-2-yl)-methanone;

(230) [5-amino-1-(2-methyl-1H-benzimidazol-5-yl)-1H-pyrazol-4-yl]-[6-(3-fluoro-pyridin-4-yl)-1H-indol-2-yl]-methanone;
(231) [5-amino-1-(2-methyl-1H-benzimidazol-5-yl)-1H-pyrazol-4-yl]-[6-(2-trifluoromethyl-pyridin-4-yl)-1H-indol-2-yl]-methanone;
(232) [5-amino-1-(2-methyl-1H-benzimidazol-5-yl)-1H-pyrazol-4-yl]-[5-(3,3-difluoro-pyrrolidine-1-carbonyl)-1H-indol-2-yl]-methanone;
(233) [5-amino-1-(2-methyl-1H-benzimidazol-5-yl)-1H-pyrazol-4-yl]-[5-(2,6-dimethyl-morpholine-4-carbonyl)-1H-indol-2-yl]-methanone;
(234) [5-amino-1-(2-methyl-1H-benzimidazol-5-yl)-1H-pyrazol-4-yl]-[5-([1,4'] bipiperidinyl-1'-carbonyl)-1H-indol-2-yl]-methanone;
(235) [5-amino-1-(2-methyl-1H-benzimidazol-5-yl)-1H-pyrazol-4-yl]-{5-[4-(2,2,2-trifluoroethyl)-piperazine-1-carbonyl]-1H-indol-2-yl}-methanone;
(236) [5-amino-1-(2-methyl-1H-benzimidazol-5-yl)-1H-pyrazol-4-yl]-{5-[4-(2-hydroxy-ethyl)-piperazine-1-carbonyl]-1H-indol-2-yl}-methanone;
(237) [5-amino-1-(2-methyl-1H-benzimidazol-5-yl)-1H-pyrazol-4-yl]-[5-(3,3,4,4-tetrafluoro-pyrrolidine-1-carbonyl)-1H-indol-2-yl]-methanone;
(238) [5-amino-1-(2-methyl-1H-benzimidazol-5-yl)-1H-pyrazol-4-yl]-[5-((R)-3-fluoro-pyrrolidine-1-carbonyl)-1H-indol-2-yl]-methanone;
(239) [5-amino-1-(2-methyl-1H-benzimidazol-5-yl)-1H-pyrazol-4-yl]-[5-((S)-3-fluoro-pyrrolidine-1-carbonyl)-1H-indol-2-yl]-methanone;
(240) [5-amino-1-(2-methyl-1H-benzimidazol-5-yl)-1H-pyrazol-4-yl]-[4-(4-methoxy-phenyl)-1H-pyrrol-2-yl]-methanone;
(241) [5-amino-1-(2-methyl-1H-benzimidazol-5-yl)-1H-pyrazol-4-yl]-[4-(3-methoxy-phenyl)-1H-pyrrol-2-yl]-methanone;
(242) [5-amino-1-(2-methyl-1H-benzimidazol-5-yl)-1H-pyrazol-4-yl]-[4,5-bis-(3-fluoro-phenyl)-1H-pyrrol-2-yl]-methanone;
(243) [5-amino-1-(2-methyl-1H-benzimidazol-5-yl)-1H-pyrazol-4-yl]-[4,5-bis-(4-methoxy-phenyl)-1H-pyrrol-2-yl]-methanone;
(244) [5-amino-1-(2-methyl-1H-benzimidazol-5-yl)-1H-pyrazol-4-yl]-[4-(2,4-difluoro-phenyl)-1H-pyrrol-2-yl]-methanone;
(245) [5-amino-1-(2-methyl-1H-benzimidazol-5-yl)-1H-pyrazol-4-yl]-[4-(4-trifluoromethoxy-phenyl)-1H-pyrrol-2-yl]-methanone;
(246) [5-amino-1-(2-methyl-1H-benzimidazol-5-yl)-1H-pyrazol-4-yl]-[4,5-bis-(3-methoxy-phenyl)-1H-pyrrol-2-yl]-methanone;
(247) [5-amino-1-(2-methyl-1H-benzimidazol-5-yl)-1H-pyrazol-4-yl]-benzofuran-2-yl-methanone;
(248) [5-amino-1-(2-methyl-1H-benzimidazol-5-yl)-1H-pyrazol-4-yl]-benzo[b] thiophen-2-yl-methanone;
(249) [5-amino-1-(2-methyl-1H-benzimidazol-5-yl)-1H-pyrazol-4-yl]-benzothiazol-2-yl-methanone;
(250) [5-amino-1-(2-methyl-1H-benzimidazol-5-yl)-1H-pyrazol-4-yl]-(4-fluoro-phenyl)-methanone;
(251) [5-amino-1-(2-methyl-1H-benzimidazol-5-yl)-1H-pyrazol-4-yl]-(3-chloro-phenyl)-methanone;
(252) [5-amino-1-(2-methyl-1H-benzimidazol-5-yl)-1H-pyrazol-4-yl]-quinolin-3-yl-methanone;
(253) [5-amino-1-(2-methyl-1H-benzimidazol-5-yl)-1H-pyrazol-4-yl]-quinolin-7-yl-methanone; and
(254) [5-amino-1-(2-methyl-1H-benzimidazol-5-yl)-1H-pyrazol-4-yl]-quinolin-6-yl-methanone.

More specific examples include compounds in which A is indole, $R_3$ is methyl, and $R_4$ is hydrogen in formula (I) described above, and compounds shown in Table 1 can be included as examples.

TABLE 1

| CODE | STRUCTURAL FORMULA/CHEMICAL NAME |
|---|---|
| A |  |
| B | COMPOUND REPRESENTED BY [COMPOUND 2] |
| C |  |
| | COMPOUND REPRESENTED BY [COMPOUND 3] |

TABLE 1-continued

| CODE | STRUCTURAL FORMULA/CHEMICAL NAME |
|---|---|
| D | 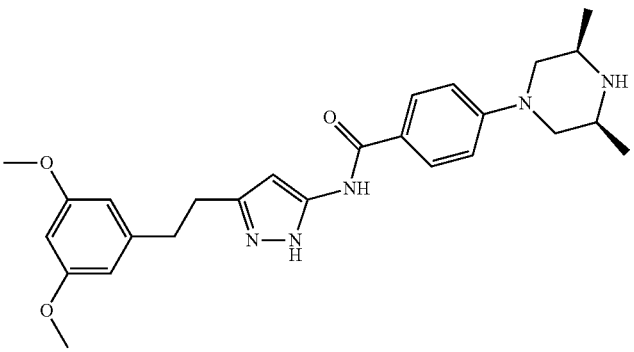<br>COMPOUND REPRESENTED BY [COMPOUND 4] |
| E | 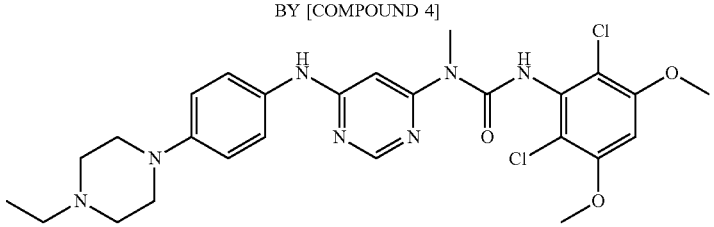<br>COMPOUND REPRESENTED BY [COMPOUND 5]<br>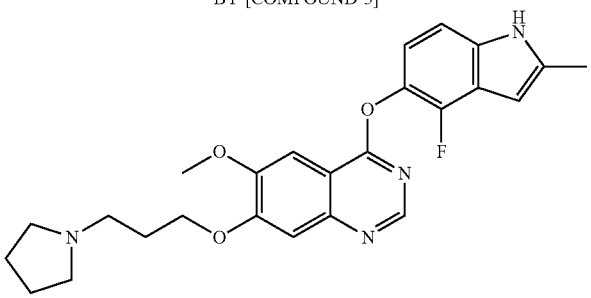 |

The above-mentioned compounds can be produced according to the production method described in International Publication WO 2011/016528.

In the present invention, compounds having FGFR inhibitory activity as describe above include not only free forms but also pharmaceutically acceptable salts thereof.

Such "salts" include, for example, inorganic acid salts, organic salts, inorganic base salts, organic base salts, and acidic or basic amino acid salts.

Preferred inorganic acid salts include, for example, hydrochloride, hydrobromide, sulfate, nitrate, and phosphate. Preferred organic salts include, for example, acetate, succinate, fumarate, maleate, tartrate, citrate, lactate, malate, stearate, benzoate, methanesulfonate, and p-toluenesulfonate. A particularly preferred salt in the present invention is malate.

Preferred inorganic base salts include, for example, alkali metal salts such as sodium salts and potassium salts; alkali earth metal salts such as calcium salts and magnesium salts; aluminum salts; and ammonium salts. Preferred organic base salts include, for example, diethylamine salts, diethanolamine salts, meglumine salts, and N,N-dibenzylethylenediamine salts.

Preferred acidic amino acid salts include, for example, aspartate and glutamate. Preferred basic amino acid salts include, for example, arginine salts, lysine salts, and ornithine salts.

In the present invention, compounds having FGFR inhibitory activity also include hydrates thereof. Furthermore, in the present invention, compounds having FGFR inhibitory activity may absorb some type of solvents to form solvates. Such solvates are also included.

In addition, compounds having FGFR inhibitory activity in the present invention include all possible structural isomers (geometric isomers, optical isomers, stereoisomers, tautomers, etc.), and mixtures of isomers.

Compounds having FGFR inhibitory activity in the present invention also include any crystalline polymorphism thereof.

In the present invention, compounds having FGFR inhibitory activity also include prodrugs thereof. "Prodrug" refers to derivatives of the compounds of the present invention which have a chemically or metabolically degradable group, and upon administration to the living body, revert to the original compounds and exhibit the original drug efficacy. The prodrugs include non-covalent complexes and salts.

In the present invention, compounds having FGFR inhibitory activity include those in which one or more atoms within the molecule have been replaced with isotopes. Herein, "isotope" refers to an atom which has the same atomic number (proton number) but different mass number (sum of protons and neutrons). The target atoms to be replaced with an isotope in the compounds of the present invention include, for example, hydrogen atom, carbon atom, nitrogen atom, oxygen atom, phosphorus atom, sulfur atom, fluorine atom, and chlorine atom. Their isotopes include $^2$H, $^3$H, $^{13}$C, $^{14}$C, $^{15}$N, $^{17}$O, $^{18}$O, $^{31}$P, $^{32}$P, $^{35}$S, $^{18}$F, and $^{36}$Cl. In particular, radioisotopes such as $^3$H and $^{14}$C, which emit radiation and decay, are useful in in vivo tissue distribution studies or such of pharmaceuticals or compounds. Stable isotopes do not decay, and thus their quantity rarely changes; and since there is no emission of radiation, stable isotopes can be used safely. The compounds of the present invention can be converted into isotope-substituted compounds according to routine methods by replacing reagents used in synthesis with reagents containing corresponding isotopes.

Herein, "anticancer agent" or "pharmaceutical composition for treating cancer" which comprises an FGFR inhibitor are used interchangeably, and refers to a cancer therapeutic composition that comprises an above-described compound having FGFR inhibitory activity and pharmaceutically acceptable carriers.

The compounds having FGFR inhibitory activity of the present invention can be formulated into tablets, powders, fine granules, granules, coated tablets, capsules, syrups, troches, inhalants, suppositories, injections, ointments, eye ointments, eye drops, nasal drops, ear drops, cataplasms, lotions, and such by routine methods. For the formulation, conventional excipients, binders, lubricants, colorants, flavoring agents, and if needed, stabilizers, emulsifiers, absorbefacients, surfactants, pH adjusting agents, preservatives, antioxidants, and such can be used. The compounds of the present invention are formulated using routine methods, by combining ingredients that are generally used as materials for pharmaceutical preparations.

For example, to produce oral formulations, the compounds of the present invention or pharmacologically acceptable salts thereof are combined with excipients, and if needed, binders, disintegrating agents, lubricants, coloring agents, flavoring agents, and the like; and then formulated into powders, fine granules, granules, tablets, coated tablets, capsules, and such by routine methods.

The ingredients include, for example, animal and vegetable oils such as soybean oils, beef tallow, and synthetic glycerides; hydrocarbons such as liquid paraffin, squalane, and solid paraffin; ester oils such as octyldodecyl myristate and isopropyl myristate; higher alcohols such as cetostearyl alcohol and behenyl alcohol; silicon resins; silicon oils; surfactants such as polyoxyethylene fatty acid esters, sorbitan fatty acid esters, glycerin fatty acid esters, polyoxyethylene sorbitan fatty acid esters, polyoxyethylene hydrogenated castor oils, and polyoxyethylene/polyoxypropylene block copolymers; water-soluble polymers such as hydroxyethyl cellulose, polyacrylic acids, carboxyvinyl polymers, polyethylene glycol, polyvinylpyrrolidone, and methyl cellulose; lower alcohols such as ethanol and isopropanol; polyalcohols such as glycerin, propylene glycol, dipropylene glycol, and sorbitol; saccharides such as glucose and sucrose; inorganic powders such as silicic anhydride, magnesium aluminum silicate, and aluminum silicate; and purified water.

Excipients include, for example, lactose, cornstarch, sucrose, glucose, mannitol, sorbit, crystalline cellulose, and silicon dioxide.

Binders include, for example, polyvinyl alcohol, polyvinyl ether, methyl cellulose, ethyl cellulose, Arabic gum, tragacanth, gelatin, shellac, hydroxypropyl methyl cellulose, hydroxypropyl cellulose, polyvinylpyrrolidone, polypropylene glycol/polyoxyethylene block polymer, and meglumine.

Disintegrating agents include, for example, starch, agar, gelatin powder, crystalline cellulose, calcium carbonate, sodium bicarbonate, calcium citrate, dextran, pectin, and calcium carboxymethyl cellulose.

Lubricants include, for example, magnesium stearate, talc, polyethylene glycol, silica, and hardened vegetable oil.

Coloring agents approved for use as additives for pharmaceuticals are used. Flavoring agents used include, for example, cacao powder, menthol, aromatic powder, peppermint oil, borneol, and cinnamon powder.

Of course, these tablets and granules may be coated with sugar, or if needed, other appropriate coatings. Alternatively, when liquid preparations such as syrups and injections are produced, the compounds of the present invention or pharmacologically acceptable salts thereof are combined with pH adjusting agents, solubilizers, isotonizing agents, or such, and if needed, solubilizing agents, stabilizers, and such, and then formulated using routine methods.

Methods for producing external preparations are not limited, and they can be produced by conventional methods. Various conventional materials for pharmaceuticals, quasi-drags, cosmetics, and such can be used as base materials in the production. Specifically, the base materials used include, for example, animal and vegetable oils, mineral oils, ester oils, waxes, higher alcohols, fatty acids, silicon oils, surfactants, phospholipids, alcohols, polyalcohols, water-soluble polymers, clay minerals, and purified water. Furthermore, as necessary, it is possible to add pH-adjusting agents, antioxidants, chelating agents, preservatives, colorants, flavoring agents, and such. However, the base materials for external preparations of the present invention are not limited thereto.

Furthermore, if needed, the preparations may be combined with components that have an activity of inducing differentiation, or components such as blood flow-enhancing agents, antimicrobial agents, antiphlogistic agents, cell-activating agents, vitamins, amino acids, humectants, and keratolytic agents. The amount of above-described base materials added is a quantity that provides a concentration typically selected in the production of external preparations.

The anticancer agents (granular pharmaceutical compositions for treating cancer) for administering a compound having FGFR inhibitory activity in the present invention are not particularly limited in their dosage form; and the agents may be administered orally or parenterally by commonly used methods. They can be formulated and administered as, for example, tablets, powders, granules, capsules, syrups, troches, inhalants, suppositories, injections, ointments, eye ointments, eye drops, nose drops, ear drops, cataplasms, lotions, etc.

In the present invention, the dosage of an FGFR inhibitor contained in an anticancer agent or a pharmaceutical composition for treating cancer can be appropriately selected according to the severity of symptoms, age, sex, weight, dosage form, salt type, specific type of disease, and such.

The dosage varies considerably depending on the patient's disease type, symptom severity, age, sex, sensitivity to the agent, and such. Typically, the agent is administered to an adult once or several times a day at a daily dose of about 0.03 to 1,000 mg, preferably 0.1 to 500 mg, and more preferably 0.1 to 100 mg. The agents or compositions of the present invention are administered once or several times a day. When an injection is used, the daily dose is generally about 1 µg/kg to 3,000 µg/kg, and preferably about 3 µg/kg to 1,000 µg/kg.

The present invention also relates to pharmaceutical compositions for treating cancer which comprise an above-described compound having FGFR inhibitory activity, and are characterized by their use of being administered to patients expressing a mutant polypeptide of the present invention or carrying a polynucleotide encoding the mutant polypeptide.

The present invention further relates to methods for treating or preventing cancer which comprise administering an effective amount of the above-mentioned compounds having FGFR inhibitory activity or pharmaceutically acceptable salts thereof to patients expressing the mutant polypeptides or carrying the polynucleotides; use of compounds having FGFR inhibitory activity or pharmaceutically acceptable salts thereof in the production of pharmaceutical compositions for cancer treatment for administration to patients expressing the fusion polypeptides or carrying the polynucleotides; compounds having FGFR inhibitory activity or pharmaceutically acceptable salts thereof for use in treatment or prevention for patients expressing the mutant polypeptides or carrying the polynucleotides; and such.

Specifically, use of the pharmaceutical compositions for treating cancer is characterized in that whether a patient expresses the mutant polypeptide or carries a polynucleotide encoding the mutant polypeptide is tested using a mutant polypeptide of the present invention as a biomarker before an above-described anticancer agent comprising an FGFR inhibitor is administered to the patient, and the anticancer agent containing an FGFR inhibitor is administered to the patient only if the patient expresses the mutant polypeptide or carries a polynucleotide encoding the mutant polypeptide. This enables one to avoid side effects in therapies using the agent and control the therapeutic condition to produce the best therapeutic effect, thus enabling personalized medicine.

Whether a patient expresses a mutant polypeptide of the present invention or carries a polynucleotide encoding the mutant polypeptide can be tested by using methods of the present invention described above.

The present invention also relates to methods for identifying compounds having FGFR inhibitory activity.

Specifically, methods for identifying compounds having FGFR inhibitory activity in the present invention include methods comprising the steps of:
(a) culturing cells that express an above-described mutant polypeptide of the present invention in the presence or absence of a test compound and determining the level of cell proliferation;
(b) comparing the proliferation level of cultured cell between in the presence and absence of the test compound; and
(c) judging that the test compound has FGFR inhibitory activity when the proliferation level of the cell cultured in the presence of the test compound is lower than that of the cell cultured in the absence of the test compound.

Cells used for the above method may be primary cultured cells, established cell lines, or recombinant cells, as long as they express a mutant polypeptide of the present invention. Such recombinant cells include those introduced with an above-described vector carrying a polynucleotide encoding a mutant polypeptide of the present invention.

Meanwhile, the primary cultured cells include cells collected from cancer patients. The established cell lines include cancer cell lines established from cancer cells collected from cancer patients.

In the present invention, cancer includes any cancer described above.

Methods for identifying compounds having FGFR inhibitory activity in the present invention also include those comprising the steps of:
(a) administering a test compound to a non-human mammal transplanted with cells that express an above-described mutant polypeptide of the present invention and determining the proliferation level of the cells;
(b) comparing the cell proliferation level determined in step (a) with that determined using a non-human mammal transplanted with the cells but not administered with the test compound; and
(c) judging that the test compound has FGFR inhibitory activity when the cell proliferation level determined in step (a) is lower than that determined using a non-human mammal transplanted with the cells but not administered with the test compound.

Cells used for the above method may be primary cultured cells, established cell lines, or recombinant cells, as long as they express a mutant polypeptide of the present invention. Such recombinant cells include those introduced with an above-described vector carrying a polynucleotide encoding a mutant polypeptide of the present invention.

Meanwhile, the primary cultured cells include cells collected from cancer patients. The established cell lines include cancer cell lines established from cancer cells collected from cancer patients.

In the present invention, cancer includes any cancer described above.

In the methods of the present invention, the cell proliferation level can be tested according to routine methods, for example, by colorimetric methods that measure the enzyme activity of reducing a dye (MTT, XTT, MTS, WST, etc.) to formazan dye (purple).

When the above-described cells are cancer cells, the cell proliferation level can also be determined by measuring the volume or weight of tumor formed as a result of cell proliferation.

In the present invention, methods for identifying compounds having FGFR inhibitory activity also comprise embodiments that use reporter gene assays.

Reporter genes include commonly-used genes encoding arbitrary fluorescent proteins, for example, the green fluorescent protein (GFP) derived from *Aequorea coerulescens*, luciferase derived from *Renilla reniformis* or such, reef coral fluorescent proteins (RCFPs) derived from hermatypic coral, fruit fluorescent proteins, and variants thereof.

In the present invention, reporter gene assay can be carried out, for example, as follows.

Recombinant cells are prepared by transforming cells that are typically used for producing recombinant proteins with an expression vector inserted with a polynucleotide encoding the mutant polypeptide of the present invention and a gene encoding a reporter protein, so that the reporter protein-encoding gene is transcribed into mRNA dependently on the signal that transcribes the mutant polypeptide-encoding polynucleotide into mRNA. A test compound is contacted with the obtained transformed cells. Whether the compound affects the expression of the mutant polypeptide is indirectly analyzed by determining the expression level of the mutant polypeptide, which depends on the compound activity, by measuring the intensity of fluorescence emitted by the reporter protein simultaneously expressed with the mutant polypeptide (for example, U.S. Pat. Nos. 5,436,128; 5,401,629).

Identification of the compounds using the above-described assay can be achieved by manual operation; however, it can also be done readily and simply by so-called "high-throughput screening" using robots automatically (Soshiki Baiyou Kougaku (The Tissue Culture Engineering), Vol. 23, No. 13, p. 521-524; U.S. Pat. No. 5,670,113).

Hereinbelow, the present invention is specifically described using the Examples, but it is not to be construed as being limited thereto.

Unless otherwise specified, each assay step can be performed according to known methods.

Meanwhile, when using commercially available reagents, kits, or such, assays can be performed according to manuals included in the commercial products.

All prior art documents cited herein are incorporated by reference in their entirety.

EXAMPLES

[Example 1] Examination of the V564F Mutant and the V562L Mutant of FGFR2

(1) Evaluation of Phosphorylation-Inhibiting Actions by FGFR Inhibitors

The polynucleotide (SEQ ID NO: 6) encoding the FGFR2 V564F mutant (SEQ ID NO: 9) and the polynucleotide (SEQ ID NO: 7) encoding the FGFR2 V562L mutant (SEQ ID NO: 10) were prepared from the ORF polynucleotide (SEQ ID NO: 5) of the wild-type FGFR2 (SEQ ID NO: 8) by a PCR-based site-directed mutagenesis method. The wild-type FGFR2 ORF polynucleotide and a polynucleotide encoding the FGFR2 V564F mutant or the FGFR2 V562L mutant were subcloned into the pCXND3 vector (Kaketsuken) to prepare vectors for expressing each of the polypeptides. Each of the prepared vectors were introduced into HCT 116 human colon adenocarcinoma cells (ATCC) using a transfection reagent FuGENE® HD (Promega) to transiently express the wild-type FGFR2 polypeptide (SEQ ID NO: 8), the FGFR2 V564F mutant polypeptide (SEQ ID NO: 9), and the FGFR2 V562L mutant polypeptide (SEQ ID NO: 10), respectively. Either Compound A or Compound C was made to act on each of the cells in the presence of 0.1% DMSO, and then the cell lysates from each of the cells were collected by using Cell Lysis Buffer (Cell Signaling Technology). Analysis of each of the cell lysates by Western blotting using the Phospho-FGF Receptor (Tyr653/654) Antibody (Cell Signaling Technology) or the FGFR-2 Antibody (Sigma) revealed that the phosphorylation inhibitory effects of each compound on the FGFR2 V564F mutant polypeptide and the FGFR2 V562L mutant polypeptide showed a great reduction with Compound C, while the effects did not reduce much with Compound A, compared to the phosphorylation inhibitory effects on the wild-type FGFR2 polypeptide, as shown in FIG. 1.

Figure 2:
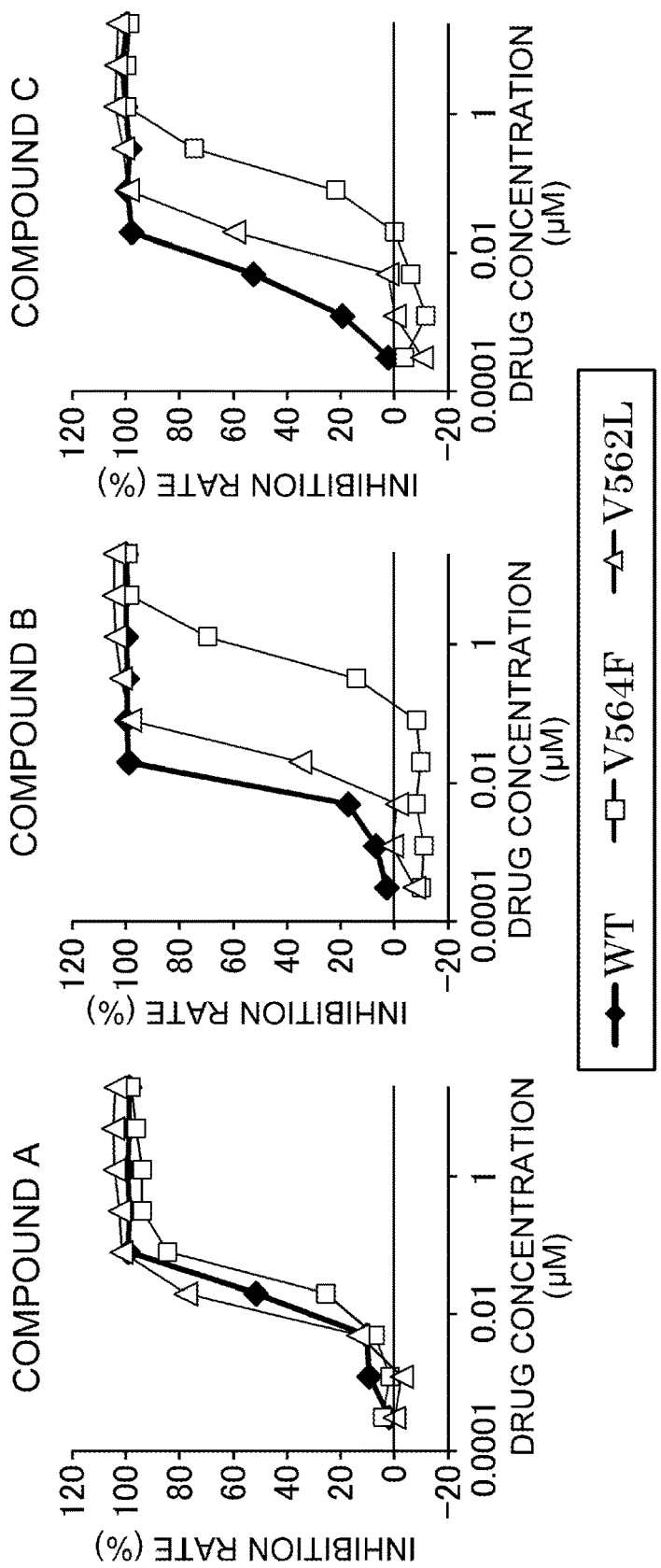
FIG. 2 shows graphs indicating the inhibitory effects of Compounds A, B, and C on proliferation of cells made to express the wild-type FGFR2, the FGFR2 V564F mutant, or the FGFR2 V562L mutant.

(2) Evaluation of In Vitro Cell Proliferation-Inhibiting Effects by FGFR Inhibitors Each polypeptide expression vector for the wild-type FGFR2, the FGFR2 V564F mutant, or the V562L mutant prepared in (1) of Example 1 was introduced into IL-3-dependent mouse pro-B cells Ba/F3 (Riken) by electroporation, the cells were cultured in the absence of IL-3 under conditions in which selection marker G-418 (Life Technology), and FGF1 (Sigma) and heparin (Sigma) was added, and then a Ba/F3 strain that can stably express the wild-type FGFR2 polypeptide, FGFR2 V564F mutant polypeptide, or FGFR2 V562L mutant polypeptide and can proliferate independently from IL-3 was established. Each of the strains seeded onto 96-well plates was added with each compound (Compound A, B, or C) made into a nine-step four-fold dilution series with the maximum concentration of 20 µM, or DMSO (used as the control), and cultured for four days. Cell proliferation after culturing for four days was measured using WST-8 (Dojindo Laboratories). Cell proliferation-inhibiting activity of each compound on each cell was calculated using the equation $(1-T/C) \times 100(\%)$, where T is the absorbance value at 450 nm for a well wherein the cells were added with the compound of each concentration and cultured, and C is the absorbance value at 450 nm wherein the cells were added with DMSO and cultured, and the IC50 was calculated by the least-square method. As a result, the cell proliferation-inhibiting activities of each of the compounds on the strain stably expressing the FGFR2 V564F mutant polypeptide or the FGFR2 V562L mutant polypeptide was greatly weakened with Compound B and Compound C, while the activities showed hardly any change with Compound A, compared to their cell proliferation-inhibiting activities on the strain stably expressing the wild-type FGFR2 polypeptide, as shown in FIG. 2 and Table 2.

TABLE 2

| | IC50 RATIO RELATIVE TO WT FGFR2 | | |
|---|---|---|---|
| MUTATION | COMPOUND A | COMPOUND B | COMPOUND C |
| V564F | 1.9 | 90 | 37 |
| V562L | 0.58 | 3.2 | 3.5 |

Figure 3:
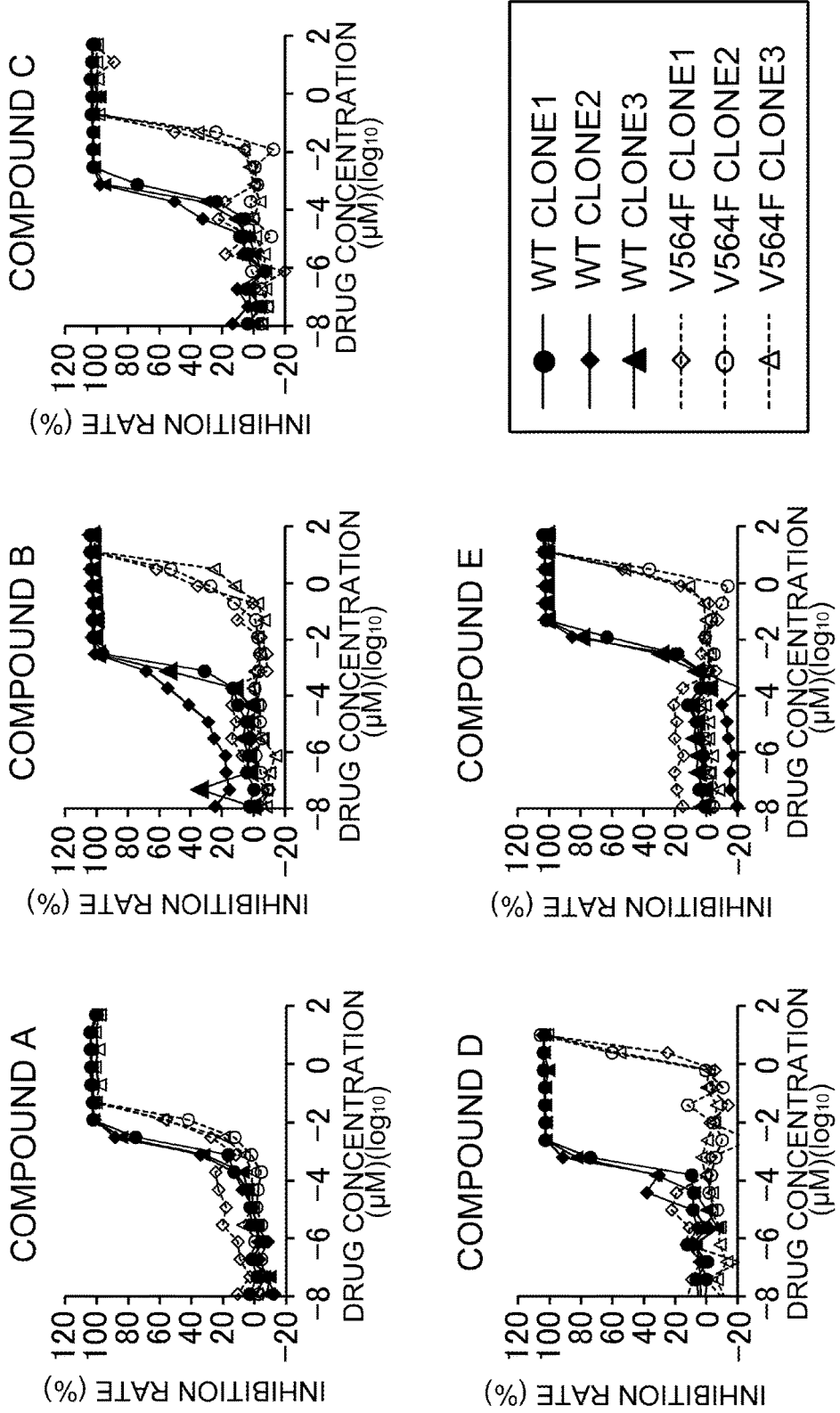
FIG. 3 shows graphs indicating the inhibitory effects of Compounds A, B, C, D, and E on proliferation of cells made to express the TEL-fused wild-type FGFR2 or the TEL-fused FGFR2 V564F mutant.

[Example 2] Examination of the TEL-Fused FGFR2 V564F Mutant (1) Evaluation of In Vitro Cell Proliferation-Inhibiting Effects by FGFR Inhibitors A polynucleotide encoding the dimerization domain of wild-type TEL (SEQ ID NO: 33) and a polynucleotide encoding the intracellular domain of wild-type FGFR2 (SEQ ID NO: 1) were fused by a PCR-based site-directed mutagenesis method to produce a polynucleotide (SEQ ID NO: 11) encoding the TEL-fused wild-type FGFR2 (SEQ ID NO: 34). Using the polynucleotide encoding the TEL-fused wild-type FGFR2 as a template, a polynucleotide (SEQ ID NO: 12) encoding the TEL-fused FGFR2 V564F mutant (SEQ ID NO: 35) was prepared by a PCR-based site-directed mutagenesis method. The polynucleotides encoding the TEL-fused wild-type FGFR2 and the TEL-fused FGFR2 V564F mutant were subcloned into a pCXND3 vector (Kaketsuken) to prepare vectors for expressing each of the polypeptides. Each polypeptide expression vector for the TEL-fused wild-type FGFR2 or the TEL-fused FGFR2 V564F mutant was introduced into IL-3-dependent mouse pro-B cells Ba/F3 by electroporation, and the cells were cultured in the absence of IL-3 with addition of selection marker G-418 to establish a Ba/F3 strain that can stably express the TEL-fused wild-type FGFR2 polypeptide or TEL-fused FGFR2 V564F mutant polypeptide and can proliferate independently of IL-3. Each of the strains seeded onto 96-well plates was added with each compound (Compound A, B, C, or E) made into an 18-step four-fold dilution series with the maximum concentration of 50 µM, a compound (Compound D) made into an 18-step four-fold dilution series with the maximum concentration of 10 µM, or DMSO (used as the control), and cultured for four days. Cell proliferation after culturing for four days was measured using WST-8 (Dojindo Laboratories). Cell proliferation-inhibiting activity of each compound on each cell was calculated using the equation $(1-T/C) \times 100$ (%), where T is the absorbance value at 450 nm for a well wherein the cells were added with the compound of each concentration and cultured, and C is the absorbance value at 450 nm wherein the cells were added with DMSO and cultured. As a result, the cell proliferation-inhibiting activities of each of the compounds on the strain stably expressing the TEL-fused FGFR2 V564F mutant polypeptide were greatly weakened with Compounds B, C, D, and E, while the activities showed hardly any change with Compound A, compared to their cell proliferation-inhibiting activities on the strain stably expressing the TEL-fused wild-type FGFR2 polypeptide, as shown in FIG. 3.

(2) Evaluation of In Vivo Tumor Increase-Inhibiting Effects by FGFR Inhibitors

Figure 4:
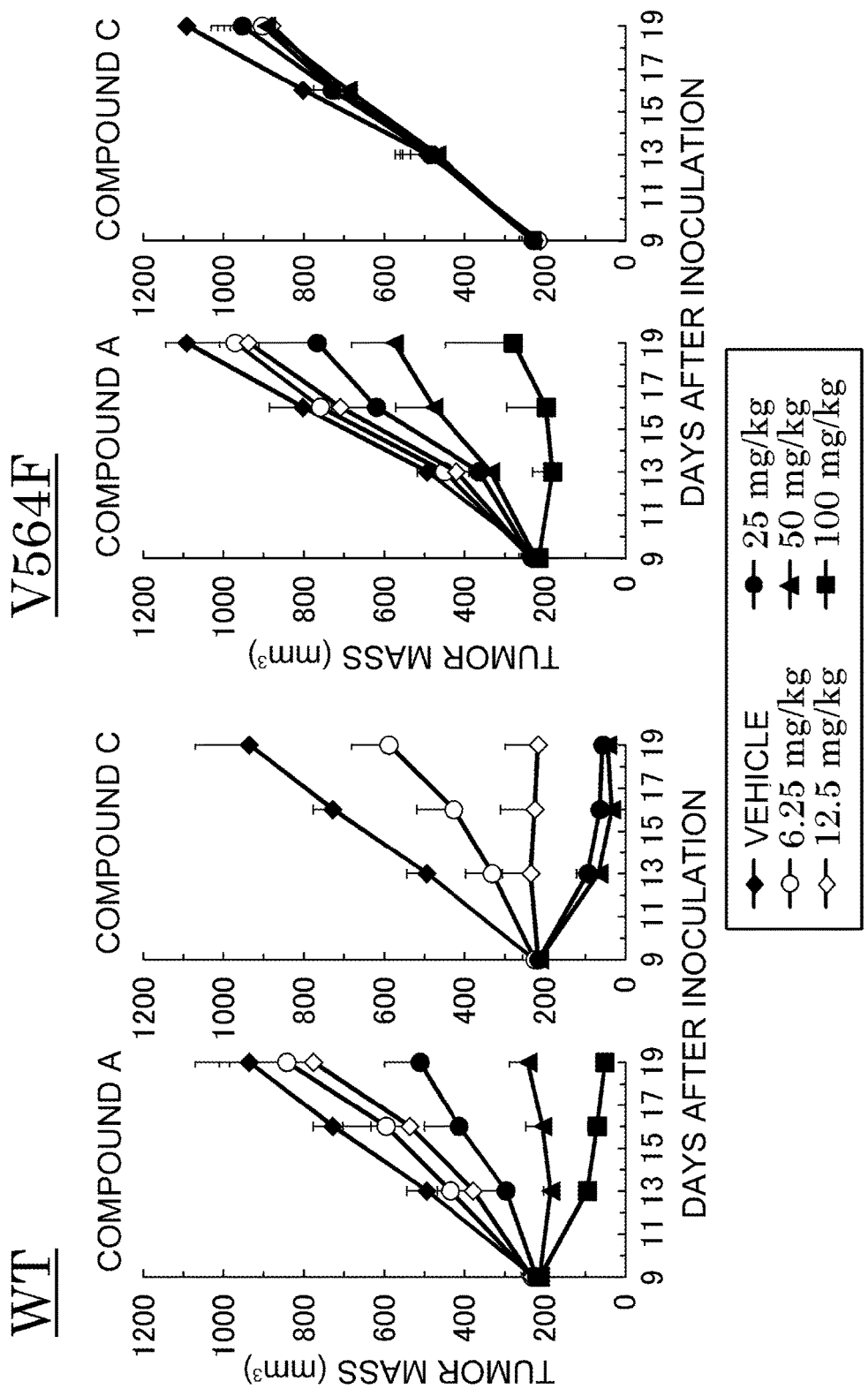
FIG. 4 shows graphs indicating the inhibitory effects of Compounds A and C on tumor proliferation in mice carrying tumor cells expressing the TEL-fused wild-type FGFR2 or the TEL-fused FGFR2 V564F mutant.

The Ba/F3 strain established in (1) of Example 2 that can stably express the TEL-fused wild-type FGFR2 polypeptide or the TEL-fused FGFR2 V564F mutant polypeptide and which can proliferate independently of IL-3, was inoculated subcutaneously in the inguinal region of BALB/c nude mice (Japan Charles River) with $5.0 \times 10^6$ to $5.2 \times 10^6$ cells per inoculation. From nine days after the inoculation, Compound A or Compound C suspended in a solution containing 10% DMSO, 10% Cremophor EL, 15% PEG400, and 15% HPCD, was administered orally once every day to the mice at a concentration of 20 mL/kg. As shown in FIG. 4, the tumor proliferation-inhibiting activities of each of the compounds in mice carrying tumor cells that express the TEL-fused FGFR2 V564F mutant polypeptide showed a great reduction with Compound C, while the activities showed hardly any change with Compound A, compared to the activities in mice carrying tumor cells expressing the TEL-fused wild-type FGFR2 polypeptide.

Figure 5:
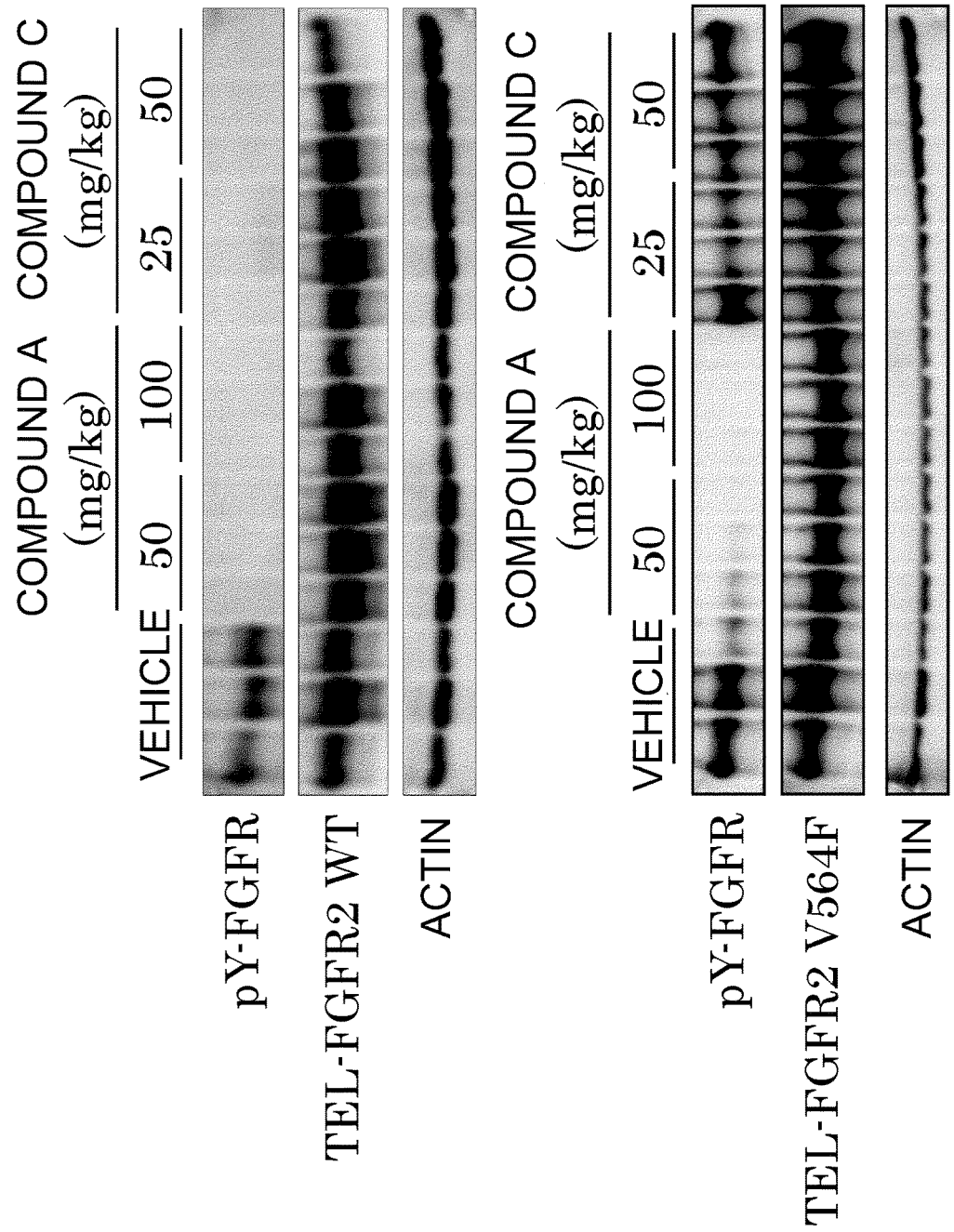
FIG. 5 shows graphs indicating the inhibitory effects of Compound A or Con phosphorylation in tumors in mice carrying tumor cells expressing the TEL-fused wild-type FGFR2 or the TEL-fused FGFR2 V564F mutant.

Furthermore, tumor lysates were collected from tumor samples that have undergone the testing, by using a Cell Lysis Buffer (Cell Signaling Technology), and each of the tumor lysates were analyzed by Western blotting using Phospho-FGF Receptor (Tyr653/654) Antibody (Cell Signaling Technology) or FGFR-2 Antibody (Sigma). As shown in FIG. 5, the inhibitory effects of each of the compounds on phosphorylation in tumors in mice carrying tumor cells that express the TEL-fused FGFR2 V564F mutant polypeptide showed a great reduction with Compound C, while the activities showed hardly any change with Compound A, compared to the activities in mice carrying tumor cells expressing the TEL-fused wild-type FGFR2 polypeptide.

INDUSTRIAL APPLICABILITY

The mutant FGFR polypeptides of the present invention demonstrate resistance to known FGFR inhibitors such as AZD4547, and at the same time demonstrate sensitivity to specific compounds. Therefore, the mutant polypeptides may be used as biomarkers in cancer treatment by various FGFR inhibitors to determine applicability of each type of FGFR inhibitor to each individual patient, to prevent the development of side effects in therapy using conventional FGFR inhibitors, and to control the therapeutic mode for receiving the best therapeutic effect, thus making individualized treatment possible.

The invention claimed is:

1. A method for treating a subject who has cancer involving activated fibroblast growth factor receptor (FGFR), the method comprising:
   a) identifying the subject as having a mutant FGFR polypeptide or a polynucleotide encoding the mutant FGFR polypeptide, wherein the mutant FGFR polypeptide comprises either (i) or (ii):
      (i) SEQ ID NO: 53 with
         (1) a substitution of valine to phenylalanine at position 7, or
         (2) a substitution of valine to leucine at position 5, or
         (3) both (1) and (2); or
      (ii) SEQ ID NO: 54 with
         (4) a substitution of valine to phenylalanine at position 7, or
         (5) a substitution of valine to leucine at position 5, or
         (6) both (4) and (5); and
   b) administering to the subject a pharmaceutical composition comprising an active agent that inhibits function of the mutant FGFR polypeptide in an amount effective to treat cancer in the subject, wherein the active agent is a compound of Formula (I) or a pharmaceutically acceptable salt thereof:

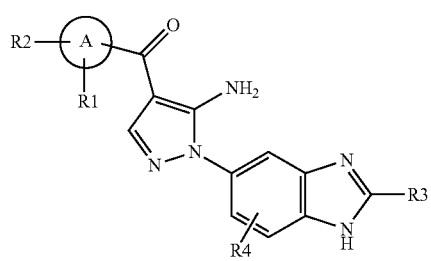

(I)

wherein $R_1$, $R_2$, $R_3$, and $R_4$ are defined as follows:

$R_1$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl, a 5- to 10-membered heteroaryl, a 3- to 10-membered heterocyclyl, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$, wherein the $C_{6-10}$ aryl is optionally substituted by one or more groups independently selected from group P, and the 5- to 10-membered heteroaryl or the 3- to 10-membered heterocyclyl is optionally substituted by one or more groups independently selected from group Q;

$R_2$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl, a 5- to 10-membered heteroaryl, a 3- to 10-membered heterocyclyl, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$, wherein the $C_{6-10}$ aryl is optionally substituted by one or more groups independently selected from group P, and the 5- to 10-membered heteroaryl or the 3- to 10-membered heterocyclyl is optionally substituted by one or more groups independently selected from group Q; or $R_1$ and $R_2$, together with an atom linked thereto, form a 3- to 10-membered heterocyclyl optionally substituted by halogen, or form a 5- to 10-membered heteroaryl optionally substituted by halogen;

$R_3$ represents methyl;

$R_4$ represents hydrogen;

A is indole;

$R_5$ represents $C_{1-5}$ alkyl, $C_{3-7}$ cycloalkyl, $C_{3-7}$ cycloalkyl $C_{1-3}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{1-3}$ alkoxy $C_{1-4}$ alkoxy $C_{1-4}$ alkyl, $C_{1-4}$ aminoalkyl, $C_{1-4}$ alkylamino $C_{1-4}$ alkyl, di($C_{1-4}$ alkyl)amino $C_{1-4}$ alkyl, $C_{6-10}$) aryl, $C_{6-10}$) aryl $C_{1-3}$ alkyl, a 3- to 10-membered heterocyclyl $C_{1-3}$ alkyl, a 3- to 10-membered heterocyclyl, a 5- to 10-membered heteroaryl, a 5- to 10-membered heteroaryl $C_{1-3}$ alkyl, $C_{1-6}$ monohydroxy alkyl, $C_{1-6}$ dihydroxy alkyl, or $C_{1-6}$ trihydroxy alkyl that is optionally substituted by one or more groups independently selected from group Q;

$R_6$ and $R_7$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl $C_{1-3}$ alkyl, a 3- to 10-membered heterocyclyl $C_{1-3}$ alkyl, a 5- to 10-membered heteroaryl $C_{1-3}$ alkyl, $C_{1-6}$ monohydroxy alkyl, $C_{1-6}$ dihydroxy alkyl, $C_{1-6}$ trihydroxy alkyl, a 3- to 10-membered heterocyclyl, $C_{1-4}$ aminoalkyl, $C_{1-4}$ alkylamino $C_{1-4}$ alkyl, di($C_{1-4}$ alkyl)amino $C_{1-4}$ alkyl, or cyano($C_{1-3}$ alkyl); or alternatively $R_6$ and $R_7$, together with a nitrogen atom linked thereto, form a 3- to 10-membered heterocyclyl or a 5- to 10-membered heteroaryl;

n represents 1 to 3;

$R_8$ and $R_9$, which can be the same or different, each represents hydrogen, $C_{1-4}$ alkyl, or halogen; or alternatively $R_8$ and $R_9$, together with a carbon atom linked thereto, form a cycloaliphatic ring;

$Z_1$ represents hydrogen, $NR_{10}R_{11}$, —OH, a 3- to 10-membered heterocyclyl, or a 5- to 10-membered heteroaryl, wherein the 3- to 10-membered heterocyclyl or the 5- to 10-membered heteroaryl is optionally substituted by one or more groups independently selected from group Q;

$R_{10}$ and $R_{11}$, which can be the same or different, each represents $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, cyano($C_{1-3}$ alkyl), or $C_{1-3}$ alkylsulfonyl $C_{1-4}$ alkyl; or alternatively $R_{10}$ and $R_{11}$, together with a nitrogen atom linked thereto, form a 3- to 10-membered heterocyclyl or a 5- to 10-membered heteroaryl;

$R_{12}$ and $R_{13}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl, a 5- to 10-membered heteroaryl, a 3- to 10-membered heterocyclyl, $C_{6-10}$ aryl $C_{1-4}$ alkyl, a 3- to 10-membered heterocyclyl $C_{1-3}$ alkyl, a 5- to 10-membered heteroaryl $C_{1-3}$ alkyl, cyano($C_{1-3}$ alkyl), $C_{1-3}$ alkylsulfonyl $C_{1-4}$ alkyl, a 3- to 10-membered cycloaliphatic ring, a 5- to 10-membered heteroaryl, or a 3- to 10-membered heterocyclyl; or alternatively $R_{12}$ and $R_{13}$, together with a nitrogen atom linked thereto, form a 3- to 10-membered heterocyclyl optionally substituted by one or more groups independently selected from group Q, or form a 5- to 10-membered heteroaryl optionally substituted by one or more groups independently selected from group Q;

$R_{14}$ represents $C_{1-4}$ alkyl, $C_{2-6}$ alkenyl, $C_{2-6}$ alkynyl, $C_{1-4}$ haloalkyl, $C_{6-10}$ aryl, a 5- to 10-membered heteroaryl, or a 3- to 10-membered heterocyclyl, wherein the $C_{6-10}$ aryl is optionally substituted by one or more groups independently selected from group P, and the 5- to 10-membered heteroaryl or the 3- to 10-membered heterocyclyl is optionally substituted by one or more groups independently selected from group Q;

$R_{15}$ represents $C_{1-4}$ alkyl, $C_{2-6}$ alkenyl, $C_{2-6}$ alkynyl, $C_{1-4}$ haloalkyl, $C_{6-10}$ aryl, a 5- to 10-membered heteroaryl, or a 3- to 10-membered heterocyclyl, wherein $C_{6-10}$ aryl is optionally substituted by one or more groups independently selected from group P, and the 5- to 10-membered heteroaryl or the 3- to 10-membered heterocyclyl is optionally substituted by one or more groups independently selected from group Q;

$R_{16}$ represents $C_{1-4}$ alkyl, $C_{2-6}$ alkenyl, $C_{2-6}$ alkynyl, $C_{1-4}$ haloalkyl, $C_{6-10}$ aryl, a 5- to 10-membered heteroaryl, or a 3- to 10-membered heterocyclyl, wherein the $C_{6-10}$ aryl is optionally substituted by one or more groups independently selected from group P, and the 5- to 10-membered heteroaryl or the 3- to 10-membered heterocyclyl is optionally substituted by one or more groups independently selected from group Q;

$R_{17}$ represents hydrogen or $C_{1-4}$ alkyl;

$R_{18}$ represents $C_{1-4}$ alkyl, $C_{2-6}$ alkenyl, $C_{2-6}$ alkynyl, $C_{1-4}$ haloalkyl, $C_{6-10}$ aryl, a 5- to 10-membered heteroaryl, or a 3- to 10-membered heterocyclyl, wherein $C_{6-10}$ aryl is optionally substituted by one or more groups independently selected from group P, and the 5- to 10-membered heteroaryl or the 3- to 10-membered heterocyclyl is optionally substituted by one or more groups independently selected from group Q;

$R_{19}$ represents hydrogen, $C_{1-4}$ alkyl, $C_{3-7}$ cycloalkyl, $C_{1-4}$ haloalkyl, $C_{6-10}$ aryl, a 5- to 10-membered heteroaryl, or a 3- to 10-membered heterocyclyl, wherein the 5- to 10-membered heteroaryl or the 3- to 10-membered heterocyclyl is optionally substituted by one or more groups independently selected from group Q;

$R_{20}$ represents $C_{1-4}$ alkyl, $C_{3-7}$ cycloalkyl, $C_{1-4}$ haloalkyl, $C_{6-10}$ aryl, a 5- to 10-membered heteroaryl, or a 3- to 10-membered heterocyclyl;

$R_{21}$ represents $C_{1-4}$ alkyl, $C_{3-7}$ cycloalkyl, $C_{1-4}$ haloalkyl, $C_{6-10}$ aryl, a 5- to 10-membered heteroaryl, or a 3- to 10-membered heterocyclyl;

$R_{22}$ represents hydrogen, $C_{1-4}$ alkyl, or $C_{1-4}$ haloalkyl;

$R_{23}$ represents hydrogen, $C_{1-4}$ alkyl, $C_{3-7}$ cycloalkyl, $C_{1-4}$ haloalkyl, $C_{6-10}$ aryl, a 5- to 10-membered heteroaryl, or a 3- to 10-membered heterocyclyl;

$R_{24}$ represents hydrogen, $C_{1-4}$ alkyl, or $C_{1-4}$ haloalkyl;

$R_{25}$ represents $C_{1-4}$ alkyl, $C_{3-7}$ cycloalkyl, $C_{1-4}$ haloalkyl, $C_{6-10}$ aryl, a 5- to 10-membered heteroaryl, or a 3- to 10-membered heterocyclyl;

$R_{26}$ and $R_{27}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, a 5- to 10-membered heteroaryl, a 3- to 10-membered heterocyclyl, $C_{6-10}$ aryl $C_{1-4}$ alkyl, a 3- to 10-membered heterocyclyl $C_{1-3}$ alkyl, a 5- to 10-membered heteroaryl $C_{1-3}$ alkyl, cyano($C_{1-3}$ alkyl), $C_{1-3}$ alkylsulfonyl $C_{1-4}$ alkyl, or a 3- to 10-membered cycloaliphatic ring; or alternatively $R_{26}$ and $R_{27}$, together with a nitrogen atom linked thereto, form a 3- to 10-membered heterocyclyl or a 5- to 10-membered heteroaryl;

$R_{28}$ and $R_{29}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, a 5- to 10-membered heteroaryl, a 3- to 10-membered heterocyclyl, $C_{6-10}$ aryl $C_{1-4}$ alkyl, a 3- to 10-membered heterocyclyl $C_{1-3}$ alkyl, a 5- to 10-membered heteroaryl $C_{1-3}$ alkyl, cyano($C_{1-3}$ alkyl), $C_{1-3}$ alkylsulfonyl $C_{1-4}$ alkyl, or a 3- to 10-membered cycloaliphatic ring; or alternatively $R_{28}$ and $R_{29}$, together with a nitrogen atom linked thereto, form a 3- to 10-membered heterocyclyl or a 5- to 10-membered heteroaryl;

$R_{30}$ represents $C_{1-4}$ alkyl, $C_{3-7}$ cycloalkyl, $C_{1-4}$ haloalkyl, $C_{6-10}$ aryl, a 5- to 10-membered heteroaryl, or a 3- to 10-membered heterocyclyl;

$R_{31}$ represents $C_{1-4}$ alkyl, $C_{3-7}$ cycloalkyl, $C_{1-4}$ haloalkyl, $C_{6-10}$ aryl, a 5- to 10-membered heteroaryl, or a 3- to 10-membered heterocyclyl;

$R_{32}$ represents $C_{1-4}$ alkyl or $C_{6-10}$ aryl;

group P consists of: halogen, $C_{1-4}$ alkyl, $C_{1-4}$ haloalkyl, —OH, $C_{1-3}$ alkoxy, $C_{1-3}$ haloalkoxy, 3- to 10-membered heterocyclylamino, —$SO_2R_{16}$, —CN, —$NO_2$, and 3- to 10-membered heterocyclyl;

group Q consists of: halogen, $C_{1-4}$ alkyl, $C_{1-4}$ haloalkyl, —OH, $C_{1-3}$ alkoxy, $C_{1-6}$ monohydroxy alkyl, $C_{1-6}$ dihydroxy alkyl, $C_{1-6}$ trihydroxy alkyl, 3- to 10-membered heterocyclyl amine, —$SO_2R_{16}$, —CN, —$NO_2$, $C_{3-7}$ cycloalkyl, —$COR_{19}$, and 3- to 10-membered heterocyclyl that is optionally substituted by $C_{1-4}$ alkyl.

2. The method of claim 1, wherein $R_1$ represents hydrogen, hydroxy, halogen, cyano, $C_{1-4}$ haloalkyl, $C_{1-6}$ alkyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SO_2R_{16}$, —$NR_{17}SO_2R_{18}$, COOH, an imidazolyl group, a thienyl group, a pyridyl group, a pyridazinyl group, a pyrazolyl group, a morpholinyl group, a tetrahydropyridyl group, a piperidinyl group, or $C_{6-10}$ aryl that is optionally substituted with one or more groups independently selected from group P2;

$R_2$ represents hydrogen, halogen, $C_{1-4}$ haloalkyl, $C_{1-6}$ alkyl, —$OR_5$, a pyridyl group, or $C_{6-10}$ aryl that is optionally substituted with one or more groups independently selected from group P2;

$R_5$ represents $C_{1-5}$ alkyl, $C_{3-7}$ cycloalkyl $C_{1-3}$ alkyl, $C_{1-4}$ haloalkyl, $C_{1-3}$ alkoxy $C_{1-4}$ alkyl, $C_{6-10}$ aryl, $C_{6-10}$ aryl $C_{1-3}$ alkyl, a piperazinylethyl group, an oxetanylmethyl group, a morpholinylethyl group, an oxetanyl group, or a tetrahydropyranyl group;

$R_6$ and $R_7$, which can be the same or different, each represents hydrogen, $C_{1-3}$ alkoxy $C_{1-4}$ alkyl, $C_{1-6}$ dihydroxyalkyl, a morpholinylethyl group, or a pyridylethyl group;

$R_8$ and $R_9$ each represents hydrogen;

$Z_1$ represents $NR_{10}R_{11}$ or —OH, or a 3- to 10-membered heterocyclyl that is optionally substituted with one or more groups independently selected from group Q2;

$R_{10}$ and $R_{11}$, which can be the same or different, each represents $C_{1-4}$ alkyl, $C_{2-6}$ alkynyl, or $C_{1-3}$ alkoxy $C_{2-4}$ alkyl;

$R_{12}$ and $R_{13}$, which can be the same or different, each represents hydrogen, $C_{1-4}$ alkyl, or $C_{1-4}$ haloalkyl;

$R_{14}$ represents $C_{1-4}$ alkyl or $C_{1-4}$ haloalkyl;

$R_{16}$ represents $C_{1-4}$ alkyl;

$R_{17}$ represents hydrogen;

$R_{18}$ represents $C_{1-4}$ alkyl;

$R_{19}$ represents hydrogen, a 5- to 10-membered heteroaryl, or a 3- to 10-membered heterocyclyl, wherein the 5- to 10-membered heteroaryl or the 3- to 10-membered heterocyclyl is optionally substituted with one or more groups independently selected from group Q2;

group P2 consists of: halogen, $C_{1-4}$ haloalkyl, $C_{1-3}$ alkoxy, $C_{1-3}$ haloalkoxy, and a 3- to 10-membered heterocyclyl;

group Q2 consists of: halogen, $C_{1-4}$ alkyl, $C_{1-4}$ haloalkyl, —OH, $C_{1-3}$ alkoxy, $C_{1-6}$ monohydroxyalkyl, —$SO_2R_{16}$, $C_{3-7}$ cycloalkyl, —$COR_{19}$, and a 3- to 10-membered heterocyclyl that is optionally substituted with $C_{1-4}$ alkyl.

3. The method of claim 2, wherein the active agent is a compound having the formula:

or a pharmaceutically acceptable salt thereof.

4. The method of claim 1, wherein the cancer is bladder cancer, brain tumor, head and neck squamous cell carcinoma, lung cancer, lung adenocarcinoma, lung squamous cell carcinoma, skin melanoma, endometrial cancer, breast cancer, prostate cancer, colon cancer, esophageal cancer, gastric cancer, bile duct cancer, biliary tract cancer, or liver cancer.

5. The method of claim 1, wherein the method comprises the step of determining that a sample from the subject comprises the mutant FGFR polypeptide.

6. The method of claim 1, wherein the method comprises the step of determining that a sample from the subject comprises a polynucleotide encoding the mutant FGFR polypeptide.

7. The method of claim 1, wherein the mutant FGFR polypeptide comprises SEQ ID NO: 53 with a substitution of valine to phenylalanine at position 7 of SEQ ID NO: 53.

8. The method of claim 1, wherein the mutant FGFR polypeptide comprises SEQ ID NO: 53 with a substitution of valine to leucine at position 5 of SEQ ID NO: 53.

9. The method of claim 1, wherein the mutant FGFR polypeptide comprises SEQ ID NO: 53 with a substitution of valine to phenylalanine at position 7 and a substitution of valine to leucine at position 5 of SEQ ID NO: 53.

10. The method of claim 1, wherein the mutant FGFR polypeptide comprises SEQ ID NO: 54 with a substitution of valine to phenylalanine at position 7 of SEQ ID NO: 54.

11. The method of claim 1, wherein the mutant FGFR polypeptide comprises SEQ ID NO: 54 with a substitution of valine to leucine at position 5 of SEQ ID NO: 54.

12. The method of claim 1, wherein the mutant FGFR polypeptide comprises SEQ ID NO: 54 with a substitution of valine to phenylalanine at position 7 and a substitution of valine to leucine at position 5 of SEQ ID NO: 54.

* * * * *